(12) United States Patent
Buettelmann et al.

(10) Patent No.: US 11,091,471 B2
(45) Date of Patent: Aug. 17, 2021

(54) ISOXAZOLYL ETHER DERIVATIVES AS GABA$_A$ α5 PAM

(71) Applicant: Hoffmann-La Roche Inc., Little Falls, NJ (US)

(72) Inventors: Bernd Buettelmann, Basel (CH); Giuseppe Cecere, Basel (CH); Bernhard Fasching, Basel (CH); Katrin Groebke Zbinden, Basel (CH); Maria-Clemencia Hernandez, Basel (CH); Henner Knust, Basel (CH); Andreas Koblet, Basel (CH); Emmanuel Pinard, Basel (CH); Andrew Thomas, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/432,584

(22) Filed: Jun. 5, 2019

(65) Prior Publication Data

US 2019/0300516 A1    Oct. 3, 2019

Related U.S. Application Data

(63) Continuation of application No. PCT/EP2017/081768, filed on Dec. 7, 2017.

(30) Foreign Application Priority Data

Dec. 8, 2016   (EP) .................................. 16202889

(51) Int. Cl.
| | | |
|---|---|---|
| *C07D 413/14* | (2006.01) | |
| *A61P 25/28* | (2006.01) | |
| *C07D 471/04* | (2006.01) | |
| *C07D 487/10* | (2006.01) | |

(52) U.S. Cl.
CPC ............ *C07D 413/14* (2013.01); *A61P 25/28* (2018.01); *C07D 471/04* (2013.01); *C07D 487/10* (2013.01)

(58) Field of Classification Search
CPC .................................................... C07D 413/14
USPC ........................................................ 544/238
See application file for complete search history.

(56) References Cited

U.S. PATENT DOCUMENTS

| | | | | |
|---|---|---|---|---|
| 7,943,619 B2 * | 5/2011 | Buettelmann | ........ | C07D 413/12 514/252.05 |
| 8,222,246 B2 * | 7/2012 | Buettelmann | ........ | C07D 413/14 514/227.2 |
| 2009/0143371 A1 * | 6/2009 | Buettelmann | ........ | C07D 487/04 514/227.8 |
| 2009/0143385 A1 * | 6/2009 | Buettelmann | ........ | C07D 413/12 514/236.5 |
| 2010/0286132 A1 | 11/2010 | Jakob-Roetne et al. | | |
| 2019/0300516 A1 | 10/2019 | Buettelmann et al. | | |

FOREIGN PATENT DOCUMENTS

| | | | | |
|---|---|---|---|---|
| WO | 2009/071476 A1 | 6/2009 | | |
| WO | 2010/112475 A1 | 10/2010 | | |
| WO | WO 2010112475 | * 10/2010 | ........... | C07D 413/12 |
| WO | 2009/071477 A1 | 6/2011 | | |
| WO | 2017/029601 | 2/2017 | | |
| WO | 2017/120422 | 7/2017 | | |
| WO | 2017/120508 | 7/2017 | | |
| WO | 2018/104419 | 6/2018 | | |

OTHER PUBLICATIONS

Abrahams, Brett S., et al., "Advances in autism genetics: on the threshold of a new neurobiology" Nat Rev Genet 9(5):341-355 (May 1, 2008).
DeLorey, Timothy M., "GABRB3 Gene Deficient Mice: A Potential Model of Autism Spectrum Disorder" Int Rev Neurobiology 71:359-382 (Feb. 1, 2005).
Dhossche, Dirk, et al., "Elevated plasma gamma-aminobutyric acid (GABA) levels in autistic youngsters: stimulus for a GABA hypothesis of autism" Med Sci Monit 8(8):PR1-PR6 (Aug. 7, 2002).
Fatemi, S. Hossein, et al., "Glutamic Acid Decarboxylase 65 and 67 kDa Proteins are Reduced in Autistic Parietal and Cerebellar Cortices" Biol Psychiatry 52:805-810 (Apr. 10, 2002).
Frye, Richard E., et al., "Neuropathological Mechanisms of Seizures in Autism Spectrum Disorder" Front Neurosci 10(192):1-9 (May 10, 2016).
Gaetz, W., et al., "GABA estimation in the Brains of Children on the Autism Spectrum: Measurement precision and regional cortical variation" Neuroimage 86: 1-9 (Feb. 1, 2014).
Han, Sung, et al., "Autistic behavior in Scn1a+/− mice and rescue by enhanced GABAergic transmission" Nature 489(7416):385-390 (Sep. 20, 2012).
Han, Sung, et al., "Enhancement of Inhibitory Neurotransmission byGABA A Receptors Having α2,3-Subunits Ameliorates Behavioral Deficits in a Mouse Model of Autism" Neuron 81:1282-1289 (Mar. 19, 2014).

(Continued)

*Primary Examiner* — Nizal S Chandrakumar
(74) *Attorney, Agent, or Firm* — Robert C. Hall

(57) ABSTRACT

Compounds having the formula (I)

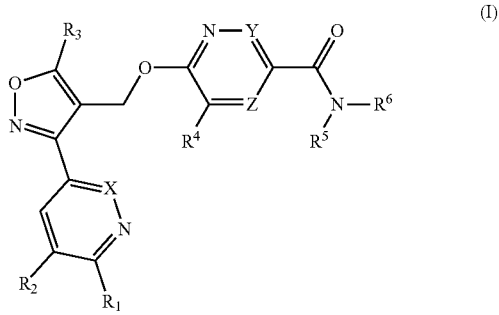

wherein $R^1$, $R^2$, $R^3$, $R^4$, $R^5$, $R^6$, X, Y and Z are as described herein, compositions including the compounds and methods of using the compounds.

12 Claims, No Drawings

(56) References Cited

OTHER PUBLICATIONS

International Preliminary Report on Patentability—PCT/EP2017/081768, dated Jun. 20, 2019, pp. 1-7, dated Jun. 11, 2019.
International Search Report—PCT/EP2017/081768 dated Jan. 28, 2018, pp. 1-7, dated Jan. 12, 2018.
Mendez, Maria A. et al., "The brain GABA-benzodiazepine receptor alpha-5 subtype in autism spectrum disorder: A pilot [11C]Ro15-4513 positron emission tomography study" Neuropharmacology 68:195-201 (Apr. 8, 2012).
Möhler, Hanns, "The rise of a new GABA pharmacology" Neuropharmacology 60:1042-1049 (Jan. 1, 2011).
Mori, Kenji et al., "Decreased benzodiazepine receptor and increased GABA level in cortical tubers in tuberous sclerosis complex" Brain Dev—Jpn 34:478-486 (Sep. 3, 2011).
Pizzarelli, Rocco et al., "Alterations of GABAergic Signaling in Autism Spectrum Disorders" Neural Plasticity 2011:1-12 (Apr. 1, 2011).
!Robertson, Caroline et al., "Reduced GABAergic Action in the Autistic Brain" Curr Biol 26:1-6 (Jan. 11, 2016).
Rojas, Donald C., et al., "Decreased left perisylvian GABA concentration in children with autism and unaffected siblings" Neuroimage 86:28-34 (Feb. 1, 2014).
Rubenstein, J.L.R., et al., "Model of autism: increased ratio of excitation/ inhibition in key neural systems" Gene Brain Behav 2:255-267 (Jul. 9, 2003).
Sieghart, Werner, "Structure, Pharmacology, and Function of GABAA Receptor Subtypes" Adv. Pharmacology 54:231-262 (Jan. 1, 2006).
Soto, Paul L., et al., "Allosteric Modulation of GABAA Receptor Subtypes: Effects on Visual Recognition and Visuospatial Working Memory in Rhesus Monkeys" Neuropharmacology 38:2315-2325 (Jun. 26, 2013).
Sur, Cyrille, et al., "Autoradiographic localization of $\alpha 5$ subunit-containing GABA A receptors in rat brain" Brain Res 822:265-270 (Jan. 1, 1999).
Vithlani, M. et al., "The dynamic modulation of GABAA receptor trafficking and its role in the formation of inhibitory synapses" Physiol Rev 91(3): 1009-1022 (Jul. 1, 2011).

\* cited by examiner

ISOXAZOLYL ETHER DERIVATIVES AS GABA$_A$ α5 PAM

CROSS-REFERENCE TO RELATED APPLICATION

This application is a continuation of International Patent Application No. PCT/EP2017/081768 filed on Dec. 7, 2017, which claims priority to EP Application No. 16202889.8 filed on Dec. 8, 2016, the entire disclosures of which are hereby incorporated by reference in their entirety.

FIELD OF THE INVENTION

This invention relates in particular to GABA$_A$ α5 receptor positive allosteric modulators (PAMs) for the treatment or prophylaxis of GABA$_A$ α5 receptor related diseases and diseases or conditions which can be treated by the modulation of GABA$_A$ α5 receptor activity, such Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder.

BACKGROUND OF THE INVENTION

Receptors for the major inhibitory neurotransmitter, gamma-aminobutyric acid (GABA), are divided into two main classes: (1) GABA$_A$ receptors, which are members of the ligand-gated ion channel superfamily and (2) GABA$_B$ receptors, which are members of the G-protein linked receptor family. The GABA$_A$ receptor complex which is a membrane-bound heteropentameric protein polymer is composed principally of α, β and γ subunits. GABA$_A$ receptors are ligand-gated chloride channels and the principal mediators of inhibitory neurotransmission in the human brain.

There are 19 genes encoding for GABA$_A$ receptor subunits that assemble as pentamers with the most common stoichiometry being two α, two β and one γ subunit. GABA$_A$ subunit combinations give rise to functional, circuit, and behavioral specificity (Sieghart, 2006; Vithlani et al., 2011). GABA$_A$ receptors containing the α5 subunit (GABA$_A$ α5) are of particular interest due to their restricted pattern of expression and unique physiological and pharmacological properties (Sur et al., 1999; Mohler, 2011). The GABA$_A$ α5 subunit-containing receptors are preferentially localized in the hippocampus, prefrontal cortex, nucleus accumbens and amygdala, which are key regions believed to be involved in the neuropathology and pathophysiology of a variety of CNS disorders.

Hippocampal hyperactivity as result of reduced GABA$_A$ α5 expression or GABAergic deficit or other conditions, is the common hallmark of a variety of CNS disorders characterized by cognitive decline (memory and executive functions). In such a disease state, a GABA$_A$ α5 positive allosteric modulator (PAM) and not a negative allosteric modulator (NAM) may be an effective treatment for the cognitive impairment associated with such diseases.

Multiple lines of evidence suggest that an imbalance between excitatory/inhibitory neurotransmission arising from dysfunction of GABAergic signaling system, the main inhibitory neurotransmitter system in the brain, to be at the core of the pathogenesis a variety of CNS disorders. Given the distribution of GABA$_A$ α5 receptors, they are very attractive targets for restoring levels of intracortical inhibition and consequently the (E/I) circuit balance in these conditions. Therefore compounds described herein and their pharmaceutically acceptable salts and esters can be used, alone or in combination with other drugs, as disease-modifying or as symptomatic agents for the treatment or prevention of acute neurological disorders, chronic neurological disorders, cognitive disorders, Alzheimer's disease, memory deficits, schizophrenia, positive, negative and/or cognitive symptoms associated with schizophrenia, bipolar disorders, autism, Angelman syndrome, Prader-Willi syndrome, Rett syndrome, Down syndrome, neurofibromatosis type I, sleep disorders, disorders of circadian rhythms, amyotrophic lateral sclerosis (ALS), fragile-X disorder, dementia caused by AIDS, age-associated memory impairment, psychotic disorders, substance-induced psychotic disorder, anxiety disorders, generalized anxiety disorder, panic disorder, delusional disorder, obsessive/compulsive disorders, acute stress disorder, post-traumatic stress disorder (PTSD), drug addictions, movement disorders, Parkinson's disease, restless leg syndrome, mild cognitive impairment (MCI), cognition deficiency disorders, age-related cognitive decline, multi-infarct dementia, mood disorders, depression, neuropsychiatric conditions, psychosis, attention-deficit/hyperactivity disorder, neuropathic pain, epilepsy, stroke and attentional disorders.

The most preferred indication in accordance with the present invention is autism spectrum disorder (ASD). ASD is a complex, heterogeneous neurodevelopmental disorder characterized by impairments in three core symptoms: social interactions, repetitive behaviors and cognitive deficits. The estimated prevalence of ASD in the United States is 1 in 68 children (CDC, 2014), and it is estimated that 1% of the world's population have ASD (WHO, 2013).

No approved pharmacological treatment exists for the core social communication and repetitive deficits of ASD Autism Spectrum Disorder, and this disorder continues to be an area of high unmet medical need. Current approved treatments for associated symptoms of ASD are limited to the antipsychotics (Risperidone and Aripiprazole) indicated for the treatment of irritability associated with ASD symptoms. Emerging evidence suggests that the GABAergic system, the main inhibitory neurotransmitter system in the brain, plays a key role in the pathophysiology of ASD (Dhossche et al., 2002; Pizzarelli and Cherubini, 2011; Robertson et al., 2016).

Both genetic and imaging studies using positron emission tomography study (PET) and magnetic resonance spectroscopy (MRS) suggest alterations in GABAergic signaling in ASD. GABA$_A$ receptor binding has been reported to be dramatically reduced in the superior and medial frontal cortex of patients with ASD using [$^{123}$I]-iomazenil PET (Mori et al., 2012). Also, a pilot [$^{11}$C]-RO154513 PET study found reduced binding of this tracer suggesting lower levels of GABA$_A$ α5 receptor in ASD (Mendez et al., 2012). MRS studies found altered GABA levels in ASD (Gaetz et al., 2014; Rojas et al., 2014) and in particular some recent studies showed reduced GABA and altered somatosensory function in children with ASD and (Puts et al., 2016; Robertson et al., 2016). In line with these observations, postmortem reduced expression of GABA$_A$ receptor subunits including GABRB3 (DeLorey, 2005; Abrahams and Geschwind, 2008) and the GABA synthesizing enzymes, glutamic acid decarboxylase (GAD) 65 and 67 were found in parietal and cerebellar cortices of patients with autism (Fatemi et al., 2002). Importantly, a reduction of GABAergic inhibitory activity has been proposed to result in hyperexcitability observed in ASD, including the high incidence of seizures and auditory-tactile hypersensitivity (Rubenstein and Merzenich, 2003; Frye et al., 2016). The altered GABAergic function may reduce the threshold for developing seizures as demonstrated by the high comorbidity of epilepsy in ASD, occurring in up to one-third of affected people. Finally, enhancement of $GABA_A$ receptor activity by non-selective BZDs have been shown to ameliorate behavioral deficits in mouse models of ASD, however very narrow therapeutic margins were observed due to sedation mediated by the $GABA_A$ α1 subtype (Han et al., 2012, 2014; Soto et al. 2013). These findings support the notion that rebalancing of GABAergic transmission via $GABA_A$ α5 receptors can improve symptoms in ASD without the side effects of non-selective benzodiazepines.

SUMMARY OF THE INVENTION

The present invention provides novel compounds of formula (I)

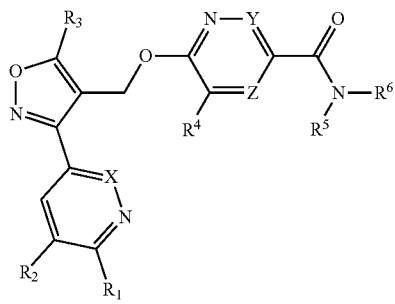

wherein
X is selected from
  i) N, and
  ii) CH;
Y is selected from
  i) N, and
  ii) $CR^{10}$;
Z is selected from
  i) N, and
  ii) $CR^{11}$;
$R^1$ is selected from
  i) $C_{1-6}$-alkyl;
  ii) halo-$C_{1-6}$-alkyl,
  iii) $C_{1-6}$-alkoxy,
  iv) halo-$C_{1-6}$-alkoxy,
  v) hydroxy-$C_{1-6}$-alkyl,
  vi) $C_{3-8}$-cycloalkyl,
  vii) halogen, and
  viii) amino substituted on the nitrogen atom by one or two substituents independently selected from
    a. H,
    b. $C_{1-6}$-alkyl, and
    c. $C_{3-8}$-cycloalkyl;
$R^2$ is selected from
  i) H, and
  ii) halogen;
$R^3$ is selected from
  i) H,
  ii) $C_{1-6}$-alkyl,
  iii) $C_{3-8}$-cycloalkyl,
  iv) hydroxy-$C_{1-6}$-alkyl, and
  v) halo-$C_{1-6}$-alkyl;

$R^4$ is selected from
  i) H,
  ii) $C_{1-6}$-alkyl,
  iii) $C_{1-6}$-alkoxy,
  iv) $C_{3-8}$-cycloalkyl, and
  v) halogen;
$R^5$ is H;
$R^6$ is selected from
  i) H,
  ii) $C_{1-6}$-alkyl,
  iii) $C_{3-8}$-cycloalkyl substituted with $R^7$, $R^8$ and $R^9$,
  iv) $C_{3-8}$-cycloalkyl-$C_{1-6}$-alkyl substituted with $R^7$, $R^8$ and $R^9$,
  v) $C_{1-6}$-alkylsulfonyl-$C_{1-6}$-alkyl,
  vi) cyano-$C_{1-6}$-alkyl,
  vii) hydroxy-$C_{1-6}$-alkyl,
  viii) dihydroxy-$C_{1-6}$-alkyl,
  ix) halo-$C_{1-6}$-alkyl,
  x) heterocycloalkyl substituted with $R^7$, $R^8$ and $R^9$, and
  xi) heterocycloalkyl-$C_{1-6}$-alkyl substituted with $R^7$, $R^8$ and $R^9$;
$R^7$, $R^8$ and $R^9$ are independently selected from
  i) H,
  ii) $C_{1-6}$-alkyl,
  iii) $C_{1-6}$-alkoxy,
  iv) $C_{1-6}$-alkoxyalkyl,
  v) $C_{1-6}$-alkoxycarbonyl,
  vi) cyano,
  vii) $C_{3-8}$-cycloalkoxy,
  viii) $C_{3-8}$-cycloalkyl,
  ix) halo-$C_{1-6}$-alkoxy,
  x) halo-$C_{1-6}$-alkyl,
  xi) halogen,
  xii) hydroxy,
  xiii) hydroxy-$C_{1-6}$-alkyl, and
  xiv) oxo;
$R^{10}$ is selected from
  i) H,
  ii) $C_{1-6}$-alkyl,
  iii) $C_{1-6}$-alkoxy,
  iv) $C_{3-8}$-cycloalkyl, and
  v) halogen;
$R^{11}$ is selected from
  i) H,
  ii) $C_{1-6}$-alkyl,
  iii) $C_{1-6}$-alkoxy,
  iv) $C_{3-8}$-cycloalkyl, and
  v) halogen;
or $R^5$ and $R^{10}$ together form —$(CH_2)_n$—;
or $R^5$ and $R^{11}$ together form —$(CH_2)_n$—;
or $R^5$ and $R^6$ together with the nitrogen atom to which they are attached form a heterocycloalkyl substituted with $R^7$, $R^8$ and $R^9$;
n is selected from 1 and 2;
or pharmaceutically acceptable salts.

Objects of the present invention are compounds of formula (I) and their pharmaceutically acceptable salts and esters, the preparation of the above mentioned compounds, medicaments containing them and their manufacture as well as the use of the above mentioned compounds in the treatment or prevention of diseases related to $GABA_A$ α5 receptor related diseases and diseases or conditions which can be treated by the modulation of $GABA_A$ α5 receptor activity, such as Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder. Compounds of the present invention are selective $GABA_A$ α5 receptor positive allosteric modulators (PAMs) as they enhance the function of α5-containing $GABA_A$ receptors by increasing GABAergic currents (influx of chloride) at a given $EC_{20}$ concentration of gamma amino butyric acid (GABA). Most preferred are compounds with a $K_i$ (nM)<35 towards α5 subunit. In a preferred embodiment the compounds of the invention are binding selective for the α5 subunit relative to the α1, α2 and α3 subunits. Compatible with the α5-subtype brain distribution, selective $GABA_A$ α5 PAMs will restore GABAergic signaling in key brain regions (e.g. hippocampus, amygdala, nucleus accumbens and prefrontal cortex) without the side-effects of non-selective $GABA_A$ modulators (e.g. benzodiazepines).

DETAILED DESCRIPTION OF THE INVENTION

Definitions

The term "$C_{1-6}$-alkoxy" denotes a group of the formula —O—R', wherein R' is an $C_{1-6}$-alkyl group. Examples of $C_{1-6}$-alkoxy groups include methoxy, ethoxy, n-propoxy, isopropoxy, n-butoxy, isobutoxy and tert-butoxy. Particular examples are methoxy and ethoxy. In the case of $R^1$, particular example is methoxy.

The term "$C_{1-6}$-alkoxy-$C_{1-6}$-alkyl" denotes an $C_{1-6}$-alkyl group wherein one of the hydrogen atoms of the $C_{1-6}$-alkyl group has been replaced by an $C_{1-6}$-alkoxy group. Examples of $C_{1-6}$-alkoxy-$C_{1-6}$-alkyl groups include methoxymethyl, ethoxymethyl, methoxymethyl, ethoxyethyl, methoxypropyl and ethoxypropyl. Particular alkoxyalkyl group is methoxyethyl.

The term "$C_{1-6}$-alkoxycarbonyl" denotes a group of the formula —C(O)—R', wherein R' is a $C_{1-6}$-alkoxy group. Examples of $C_{1-6}$-alkoxycarbonyl groups include groups wherein R' is methoxy, ethoxy, n-propoxy, isopropoxy, n-butoxy, isobutoxy or tert-butoxy Particular example of $C_{1-6}$-alkoxycarbonyl is a group wherein R' is ethoxy.

The term "$C_{1-6}$-alkyl" denotes a monovalent linear or branched saturated hydrocarbon group of 1 to 6 carbon atoms. Examples of $C_{1-6}$-alkyl include methyl, ethyl, propyl, isopropyl, n-butyl, iso-butyl, sec-butyl, tert-butyl and pentyl. Particular $C_{1-6}$-alkyl groups are methyl, ethyl, isopropyl and tert-butyl. In the case of $R^1$, more particular example is methyl. In the case of $R^3$, more particular examples are methyl and ethyl. In the case of $R^3$, further more particular example is methyl.

The term "$C_{1-6}$-alkylsulfonyl" denotes a group of the formula —S(O)$_2$—R', wherein R' is a $C_{1-6}$-alkyl group. Examples of $C_{1-6}$-alkylsulfonyl include groups wherein R' is methyl, ethyl, propyl, isopropyl, n-butyl, iso-butyl, sec-butyl, tert-butyl or pentyl.

The term "$C_{1-6}$-alkylsulfonyl-$C_{1-6}$-alkyl" denotes a $C_{1-6}$-alkyl group wherein one of the hydrogen atoms of the $C_{1-6}$-alkyl group has been replaced by a $C_{1-6}$-alkylsulfonyl group. Particular $C_{1-6}$-alkylsulfonyl-$C_{1-6}$-alky is methylsulfonyl(methyl)butanyl.

The term "amino" denotes a —NH$_2$ group.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carbonyl" denotes a —C(O)— group.

The term "cyano" denotes a —C≡N group.

The term "cyano-$C_{1-6}$-alkyl" denotes an —$C_{1-6}$-alkyl group wherein one of the hydrogen atoms of the $C_{1-6}$-alkyl group has been replaced by cyano group. Examples of cyano-$C_{1-6}$-alkyl include cyanomethyl, cyanoethyl, cyanopropyl and cyanobutyl. Particular examples are cyanoethyl and cyanobutyl.

The term "cyano-$C_{1-6}$-alkoxy" denotes an —$C_{1-6}$-alkoxy group wherein one of the hydrogen atoms of the $C_{1-6}$-alkoxy group has been replaced by cyano group.

The term "$C_{3-8}$-cycloalkyl" denotes a monovalent saturated monocyclic or bicyclic hydrocarbon group of 3 to 8 ring carbon atoms. Bicyclic means a ring system consisting of two saturated carbocycles having on or two carbon atoms in common Examples of monocyclic $C_{3-8}$-cycloalkyl are cyclopropyl, cyclobutanyl, cyclopentyl, cyclohexyl or cycloheptyl. Particular monocyclic cycloalkyl groups are cyclopropyl, cyclobutanyl, cyclopentyl and cyclohexyl. More particular monocyclic cycloalkyl group is cyclopropyl. Example of bicyclic $C_{3-8}$-cycloalkyl is spiro[3.3]heptanyl. In the case of $R^1$ and $R^3$, particular example of $C_{3-8}$-cycloalkyl is cyclopropyl.

The term "$C_{3-8}$-cycloalkyl-$C_{1-6}$-alkyl" denotes an —$C_{1-6}$-alkyl group wherein one of the hydrogen atoms of the $C_{1-6}$-alkyl group has been replaced by an $C_{3-8}$-cycloalkyl group. Examples of $C_{3-8}$-cycloalkyl-$C_{1-6}$-alkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Particular example of $C_{3-8}$-cycloalkyl-$C_{1-6}$-alkyl is cyclopropylmethyl.

The term "dihydroxy-$C_{1-6}$-alkyl" denotes an $C_{1-6}$-alkyl group wherein two of the hydrogen atoms of the $C_{1-6}$-alkyl group have been replaced by an hydroxy group. Examples of dihydroxy-$C_{1-6}$-alkyl include dihydroxyethyl, dihydroxypropyl, dihydroxy(methyl)propyl and dihydroxybutyl. Particular example is dihydroxy(methyl)propyl.

The term "halo-$C_{1-6}$-alkoxy" denotes an $C_{1-6}$-alkoxy group wherein at least one of the hydrogen atoms of the $C_{1-6}$-alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, fluoroethoxy, difluoroethoxy, trifluoroethoxy, trifluoromethylethoxy, trifluorodimethylethoxy and pentafluoroethoxy. Particular haloalkoxy groups are difluoromethoxy and difluoroethoxy.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhalo-$C_{1-6}$-alkyl alkyl" denotes an —$C_{1-6}$-alkyl alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular halo-$C_{1-6}$-alkyl 1 group is fluoromethyl, difluoromethyl are trifluoromethyl. More halo-$C_{1-6}$-alkyl 1 group trifluoromethyl.

The term "halogen" and "halo" are used interchangeably herein and denote fluoro, chloro, bromo or iodo. Particular halogen is fluoro. In the case of R', particular halogen is chloro.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having one or two ring atoms in common Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydrothiophenyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl.

Examples for bicyclic saturated heterocycloalkyl are oxabicyclo[2.2.1]heptanyl, oxaspiro[3.3]heptanyl, 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular heterocycloalkyl are oxetanyl, tetrahydrofuranyl, tetrahydropyranyl, oxepanyl, oxabicyclo[2.2.1]heptanyl, oxaspiro[3.3]heptanyl, azetidinyl, tetrahydrothiophenyl and tetrahydrothiopyranyl. More particular heterocycloalkyl is tetrahydropyranyl.

In the case of the heterocycloalkyl formed by $R^5$ and $R^6$ together with the nitrogen atom to which they are attached, particular examples of heterocycloalkyl are azetidinyl, pyrrolidinyl, piperidinyl, morpholinyl, thiomorpholinyl, oxaazabicyclo[3.1.1]heptanyl, oxaazabicyclo[2.2.1]heptanyl, azaspiro[3.3]heptanyl, oxaazaspiro[3.3]heptanyl and thiaazaspiro[3.3]heptanyl.

The term "heterocycloalkyl-$C_{1-6}$-alkyl" denotes an $C_{1-6}$-alkyl group wherein one of the hydrogen atoms of the $C_{1-6}$-alkyl group has been replaced by a heterocycloalkyl group. Particular heterocycloalkyl-$C_{1-6}$-alkyl is oxetanymethyl.

The term "hydroxy" denotes a —OH group.

The term "hydroxy-$C_{1-6}$-alkyl alkyl" denotes an $C_{1-6}$-alkyl alkyl group wherein at least one of the hydrogen atoms of the $C_{1-6}$-alkyl alkyl group has been replaced by a hydroxy group. Examples of hydroxy-$C_{1-6}$-alkyl include hydroxymethyl, hydroxyethyl, hydroxypropyl, hydroxymethylpropyl, hydroxybutyl and hydroxypentyl. Particular example is hydroxypentyl.

The term "oxo" denotes a =O group.

The term "sulfonyl" denotes a —S(O)$_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The invention provides compounds according to formula (I) a

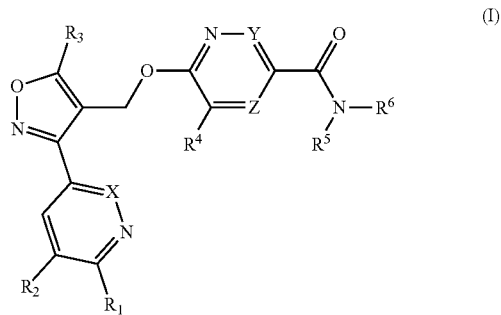

and pharmaceutically acceptable salts or esters thereof.

A particular embodiment of the present invention provides compounds according to formula (I) as described herein, wherein X is CH.

A particular embodiment of the present invention provides compounds according to formula (I) as described herein, wherein Y is N.

A particular embodiment of the present invention provides compounds according to formula (I) as described herein, wherein Z is $CR^{11}$.

A particular embodiment of the present invention provides compounds according to formula (I) as described herein, wherein $R^1$ is selected from
  i) $C_{1-6}$-alkyl,
  ii) halo-$C_{1-6}$-alkyl,
  iii) $C_{1-6}$-alkoxy,
  iv) $C_{3-8}$-cycloalkyl,
  v) halogen, and
  vi) amino substituted on the nitrogen atom by one or two substituents selected from
    a. H,
    b. $C_{1-6}$-alkyl, and
    c. $C_{3-8}$-cycloalkyl.

A further particular embodiment of the present invention provides compounds according to formula (I) as described herein, wherein $R^1$ is selected from
  i) $C_{1-6}$-alkyl,
  ii) halo-$C_{1-6}$-alkyl,
  iii) $C_{1-6}$-alkoxy,
  iv) $C_{3-8}$-cycloalkyl,
  v) halogen, and
  vi) amino substituted on the nitrogen atom by two independently selected $C_{1-6}$-alkyl.

A more particular embodiment of the present invention provides compounds according to formula (I) as described herein, wherein $R^1$ is $C_{1-6}$-alkyl.

A further more particular embodiment of the present invention provides compounds according to formula (I) as described herein, wherein $R^1$ is methyl.

A particular embodiment of the present invention provides compounds according to formula (I) as described herein, wherein $R^2$ is H.

A particular embodiment of the present invention provides compounds according to formula (I) as described herein, wherein $R^3$ is selected from
  i) H,
  ii) $C_{1-6}$-alkyl,
  iii) $C_{3-8}$-cycloalkyl, and
  iv) halo-$C_{1-6}$-alkyl.

A further particular embodiment of the present invention provides compounds according to formula (I) as described herein, wherein $R^3$ is selected from
  i) H,
  ii) $C_{1-6}$-alkyl, and
  iii) $C_{3-8}$-cycloalkyl.

A more particular embodiment of the present invention provides compounds according to formula (I) as described herein, wherein $R^3$ is $C_{1-6}$-alkyl.

A further more particular embodiment of the present invention provides compounds according to formula (I) as described herein, wherein $R^3$ is methyl.

A particular embodiment of the present invention provides compounds according to formula (I) as described herein, wherein $R^4$ is selected from
  i) H, and
  ii) $C_{1-6}$-alkyl.

A particular embodiment of the present invention provides compounds according to formula (I) as described herein, wherein $R^4$ is H.

A particular embodiment of the present invention provides compounds according to formula (I) as described herein, wherein $R^6$ is selected from
  i) H,
  ii) $C_{1-6}$-alkyl,
  iii) $C_{3-8}$-cycloalkyl substituted with $R^7$, $R^8$ and $R^9$, wherein $R^7$, $R^8$ and $R^9$ are independently selected from
    a. H,
    b. $C_{1-6}$-alkyl,
    c. $C_{1-6}$-alkoxy,
    d. $C_{1-6}$-alkoxyalkyl,
    e. $C_{1-6}$-alkoxycarbonyl,
    f. cyano,
    g. $C_{3-8}$-cycloalkoxy,
    h. halo-$C_{1-6}$-alkoxy,
    i. halo-$C_{1-6}$-alkyl,
    j. halogen,
    k. hydroxy, and
    l. hydroxy-$C_{1-6}$-alkyl;
  iv) $C_{3-8}$-cycloalkyl-$C_{1-6}$-alkyl substituted with $R^7$, $R^8$ and $R^9$, wherein $R^7$, $R^8$ and $R^9$ are independently selected from
    a. H,
    b. $C_{1-6}$-alkyl,
    c. $C_{1-6}$-alkoxy,
    d. $C_{1-6}$-alkoxyalkyl,
    e. $C_{1-6}$-alkoxycarbonyl,
    f. cyano,
    g. $C_{3-8}$-cycloalkoxy,
    h. halo-$C_{1-6}$-alkoxy,
    i. halo-$C_{1-6}$-alkyl,
    j. halogen,
    k. hydroxy, and
    l. hydroxy-$C_{1-6}$-alkyl;
  v) $C_{1-6}$-alkylsulfonyl-$C_{1-6}$-alkyl,
  vi) cyano-$C_{1-6}$-alkyl,
  vii) hydroxy-$C_{1-6}$-alkyl,
  viii) dihydroxy-$C_{1-6}$-alkyl,
  ix) halo-$C_{1-6}$-alkyl,
  x) heterocycloalkyl substituted with $R^7$, $R^8$ and $R^9$, wherein $R^7$, $R^8$ and $R^9$ are independently selected from
    a. H,
    b. $C_{1-6}$-alkyl,
    c. hydroxy, and
    d. oxo;
    and wherein the heterocycloalkyl is selected from
    a. oxetanyl,
    b. tetrahydrofuranyl,
    c. tetrahydropyranyl,
    d. oxepanyl,
    e. oxabicyclo[2.2.1]heptanyl,
    f. oxaspiro[3.3]heptanyl,
    g. azetidinyl,
    h. tetrahydrothiophenyl, and
    i. tetrahydrothiopyranyl; and
  xi) oxetanyl-$C_{1-6}$-alkyl substituted with $R^7$, $R^8$ and $R^9$, wherein $R^7$, $R^8$ and $R^9$ are independently selected from
    a. H, and
    b. hydroxy.

A further particular embodiment of the present invention provides compounds according to formula (I) as described herein, wherein $R^6$ is selected from
i) $C_{1-6}$-alkyl,
ii) $C_{3-8}$-cycloalkyl substituted with $R^7$, $R^8$ and $R^9$, wherein $R^7$, $R^8$ and $R^9$ are independently selected from
  a. H,
  b. $C_{1-6}$-alkyl,
  c. $C_{1-6}$-alkoxyalkyl,
  d. halo-$C_{1-6}$-alkyl;
iii) hydroxy-$C_{1-6}$-alkyl,
iv) halo-$C_{1-6}$-alkyl,
v) heterocycloalkyl substituted with $R^7$, $R^8$ and $R^9$, wherein $R^7$, $R^8$ and $R^9$ are independently selected from
  a. H, and
  b. $C_{1-6}$-alkyl,
  and wherein the heterocycloalkyl is selected from
  a. oxetanyl,
  b. tetrahydrofuranyl,
  c. tetrahydropyranyl, and
  d. oxaspiro[3.3]heptanyl.

A particular embodiment of the present invention provides compounds according to formula (I) as described herein, wherein $R^7$, $R^8$ and $R^9$ are independently selected from
i) H,
ii) $C_{1-6}$-alkyl,
iii) $C_{1-6}$-alkoxy,
iv) $C_{1-6}$-alkoxyalkyl,
v) $C_{1-6}$-alkoxycarbonyl,
vi) cyano,
vii) $C_{3-8}$-cycloalkoxy,
viii) halo-$C_{1-6}$-alkoxy,
ix) halo-$C_{1-6}$-alkyl,
x) halogen,
xi) hydroxy,
xii) hydroxy-$C_{1-6}$-alkyl, and
xiii) oxo.

A further particular embodiment of the present invention provides compounds according to formula (I) as described herein, wherein $R^1$ is selected from
i) H,
ii) $C_{1-6}$-alkyl,
iii) $C_{1-6}$-alkoxy,
iv) $C_{1-6}$-alkoxyalkyl,
v) $C_{1-6}$-alkoxycarbonyl,
vi) cyano,
vii) $C_{3-8}$-cycloalkoxy,
viii) halo-$C_{1-6}$-alkoxy,
ix) halo-$C_{1-6}$-alkyl,
x) halogen,
xi) hydroxy,
xii) hydroxy-$C_{1-6}$-alkyl, and
xiii) oxo.

A more particular embodiment of the present invention provides compounds according to formula (I) as described herein, wherein $R^1$ is selected from
i) H,
ii) $C_{1-6}$-alkyl,
iii) $C_{1-6}$-alkoxyalkyl, and
iv) halo-$C_{1-6}$-alkyl.

A further particular embodiment of the present invention provides compounds according to formula (I) as described herein, wherein $R^8$ is selected from
i) H,
ii) $C_{1-6}$-alkyl,
iii) halo-$C_{1-6}$-alkyl,
iv) halogen, and
v) oxo.

A more particular embodiment of the present invention provides compounds according to formula (I) as described herein, wherein $R^8$ is H.

A further particular embodiment of the present invention provides compounds according to formula (I) as described herein, wherein $R^9$ is selected from
i) H, and
ii) halogen.

A more particular embodiment of the present invention provides compounds according to formula (I) as described herein, wherein $R^9$ is H.

A particular embodiment of the present invention provides compounds according to formula (I) as described herein, wherein $R^{10}$ is selected from
i) H, and
ii) halogen.

A further particular embodiment of the present invention provides compounds according to formula (I) as described herein, wherein $R^{10}$ is H.

A particular embodiment of the present invention provides compounds according to formula (I) as described herein, wherein $R^{11}$ is selected from
i) H,
ii) $C_{1-6}$-alkyl, and
iii) $C_{1-6}$-alkoxy.

A further particular embodiment of the present invention provides compounds according to formula (I) as described herein, wherein $R^{11}$ is H.

A particular embodiment of the present invention provides compounds according to formula (I) as described herein, wherein n is 1.

A further particular embodiment of the present invention provides compounds according to formula (I) as described herein, wherein
X is selected from
  i) N, and
  ii) CH;
Y is selected from
  i) N, and
  ii) $CR^{10}$;
Z is selected from
  i) N, and
  ii) $CR^{11}$;
$R^1$ is selected from
  i) $C_{1-6}$-alkyl,
  ii) halo-$C_{1-6}$-alkyl,
  iii) $C_{1-6}$-alkoxy,
  iv) $C_{3-8}$-cycloalkyl,
  v) halogen, and
  vi) amino substituted on the nitrogen atom by two independently selected $C_{1-6}$-alkyl;
$R^2$ is selected from
  i) H,
  ii) halogen;
$R^3$ is selected from
  i) H,
  ii) $C_{1-6}$-alkyl,
  iii) $C_{3-8}$-cycloalkyl, and
  iv) halo-$C_{1-6}$-alkyl;
$R^4$ is selected from
  i) H, and
  ii) $C_{1-6}$-alkyl;

R⁵ is H;
R⁶ is selected from
  i) H,
  ii) $C_{1-6}$-alkyl,
  iii) $C_{3-8}$-cycloalkyl substituted with R⁷, R⁸ and R⁹, wherein R⁷, R⁸ and R⁹ are independently selected from
    a. H,
    b. $C_{1-6}$-alkyl,
    c. $C_{1-6}$-alkoxy,
    d. $C_{1-6}$-alkoxyalkyl,
    e. $C_{1-6}$-alkoxycarbonyl,
    f. cyano,
    g. $C_{3-8}$-cycloalkoxy,
    h. halo-$C_{1-6}$-alkoxy,
    i. halo-$C_{1-6}$-alkyl,
    j. halogen,
    k. hydroxy, and
    l. hydroxy-$C_{1-6}$-alkyl;
  iv) $C_{3-8}$-cycloalkyl-$C_{1-6}$-alkyl substituted with R⁷, R⁸ and R⁹, wherein R⁷, R⁸ and R⁹ are independently selected from
    a. H,
    b. $C_{1-6}$-alkyl,
    c. $C_{1-6}$-alkoxy,
    d. $C_{1-6}$-alkoxyalkyl,
    e. $C_{1-6}$-alkoxycarbonyl,
    f. cyano,
    g. $C_{3-8}$-cycloalkoxy,
    h. halo-$C_{1-6}$-alkoxy,
    i. halo-$C_{1-6}$-alkyl,
    j. halogen,
    k. hydroxy, and
    l. hydroxy-$C_{1-6}$-alkyl;
  v) $C_{1-6}$-alkylsulfonyl-$C_{1-6}$-alkyl,
  vi) cyano-$C_{1-6}$-alkyl,
  vii) dihydroxy-$C_{1-6}$-alkyl,
  viii) halo-$C_{1-6}$-alkyl,
  ix) heterocycloalkyl substituted with R⁷, R⁸ and R⁹, wherein R⁷, R⁸ and R⁹ are independently selected from
    a. H,
    b. $C_{1-6}$-alkyl,
    c. hydroxy, and
    d. oxo;
  and wherein the heterocycloalkyl is selected from
    a. oxetanyl,
    b. tetrahydrofuranyl,
    c. tetrahydropyranyl,
    d. oxepanyl,
    e. oxabicyclo[2.2.1]heptanyl,
    f. oxaspiro[3.3]heptanyl,
    g. azetidinyl,
    h. tetrahydrothiophenyl, and
    i. tetrahydrothiopyranyl; and
  x) oxetanyl-$C_{1-6}$-alkyl substituted with R⁷, R⁸ and R⁹, wherein R⁷, R⁸ and R⁹ are independently selected from
    a. H,
    b. hydroxy;
R¹⁰ is selected from
  i) H, and
  ii) halogen;
R¹¹ is selected from
  i) H,
  ii) $C_{1-6}$-alkyl, and
  iii) $C_{1-6}$-alkoxy;
or R⁵ and R¹⁰ together form —(CH₂)ₙ—;
or R⁵ and R¹¹ together form —(CH₂)ₙ—;
or R⁵ and R⁶ together with the nitrogen atom to which they are attached form a heterocycloalkyl substituted with R⁷, R⁸ and R⁹, wherein R⁷, R⁸ and R⁹ are independently selected from
  a. H,
  b. $C_{1-6}$-alkyl,
  c. $C_{1-6}$-alkoxy,
  d. cyano,
  e. halogen,
  f. hydroxy, and
  g. oxo;
and wherein the heterocycloalkyl is selected from
  a. azetidinyl,
  b. pyrrolidinyl,
  c. piperidinyl,
  d. morpholinyl,
  e. thiomorpholinyl,
  f. oxaazabicyclo[3.1.1]heptanyl,
  g. oxaazabicyclo[2.2.1]heptanyl,
  h. azaspiro[3.3]heptanyl,
  i. oxaazaspiro[3.3]heptanyl,
  j. thiaazaspiro[3.3]heptanyl;
n is 1;
or pharmaceutically acceptable salts.

A particular embodiment of the present invention provides compounds according to formula (I) as described herein, wherein
X is selected from
  i) N, and
  ii) CH;
Y is selected from
  i) N, and
  ii) CR¹⁰;
Z is selected from
  i) N, and
  ii) CR¹¹;
R¹ is selected from
  i) $C_{1-6}$-alkyl,
  ii) halo-$C_{1-6}$-alkyl,
  iii) $C_{1-6}$-alkoxy,
  iv) $C_{3-8}$-cycloalkyl,
  v) halogen, and
  vi) amino substituted on the nitrogen atom by two independently selected $C_{1-6}$-alkyl;
R² is selected from
  i) H,
  ii) halogen;
R³ is selected from
  i) H,
  ii) $C_{1-6}$-alkyl,
  iii) $C_{3-8}$-cycloalkyl, and
  iv) halo-$C_{1-6}$-alkyl;
R⁴ is selected from
  i) H, and
  ii) $C_{1-6}$-alkyl;
R⁵ is H;
R⁶ is selected from
  i) H,
  ii) $C_{1-6}$-alkyl,
  iii) $C_{3-8}$-cycloalkyl substituted with R⁷, R⁸ and R⁹, wherein R⁷, R⁸ and R⁹ are independently selected from
    a. H,
    b. $C_{1-6}$-alkyl,
    c. $C_{1-6}$-alkoxy,
    d. $C_{1-6}$-alkoxyalkyl, e. $C_{1-6}$-alkoxycarbonyl,
f. cyano,
g. $C_{3-8}$-cycloalkoxy,
h. halo-$C_{1-6}$-alkoxy,
i. halo-$C_{1-6}$-alkyl,
j. halogen,
k. hydroxy, and
l. hydroxy-$C_{1-6}$-alkyl;
iv) $C_{3-8}$-cycloalkyl-$C_{1-6}$-alkyl substituted with $R^7$, $R^8$ and $R^9$, wherein $R^7$, $R^8$ and $R^9$ are independently selected from
a. H,
b. $C_{1-6}$-alkyl,
c. $C_{1-6}$-alkoxy,
d. $C_{1-6}$-alkoxyalkyl,
e. $C_{1-6}$-alkoxycarbonyl,
f. cyano,
g. $C_{3-8}$-cycloalkoxy,
h. halo-$C_{1-6}$-alkoxy,
i. halo-$C_{1-6}$-alkyl,
j. halogen,
k. hydroxy, and
l. hydroxy-$C_{1-6}$-alkyl;
v) $C_{1-6}$-alkylsulfonyl-$C_{1-6}$-alkyl,
vi) cyano-$C_{1-6}$-alkyl,
vii) dihydroxy-$C_{1-6}$-alkyl,
viii) halo-$C_{1-6}$-alkyl,
ix) heterocycloalkyl substituted with $R^7$, $R^8$ and $R^9$, wherein $R^7$, $R^8$ and $R^9$ are independently selected from
a. H,
b. $C_{1-6}$-alkyl,
c. hydroxy, and
d. oxo;
and wherein the heterocycloalkyl is selected from
a. oxetanyl,
b. tetrahydrofuranyl,
c. tetrahydropyranyl,
d. oxepanyl,
e. oxabicyclo[2.2.1]heptanyl,
f. oxaspiro[3.3]heptanyl,
g. azetidinyl,
h. tetrahydrothiophenyl, and
i. tetrahydrothiopyranyl; and
x) oxetanyl-$C_{1-6}$-alkyl substituted with $R^7$, $R^8$ and $R^9$, wherein $R^7$, $R^8$ and $R^9$ are independently selected from
a. H,
b. hydroxy;
$R^{10}$ is selected from
i) H, and
ii) halogen;
$R^{11}$ is selected from
i) H,
ii) $C_{1-6}$-alkyl, and
iii) $C_{1-6}$-alkoxy;
or pharmaceutically acceptable salts.

A particular embodiment of the present invention provides compounds according to formula (I) as described herein, wherein
X is selected from
i) N, and
ii) CH;
Y is selected from
i) N, and
ii) $CR^{10}$;
Z is $CR^{11}$;
$R^1$ is $C_{1-6}$-alkyl;
$R^2$ is selected from
i) H,
ii) halogen;
$R^3$ is selected from
i) $C_{1-6}$-alkyl,
ii) $C_{3-8}$-cycloalkyl, and
iii) halo-$C_{1-6}$-alkyl;
$R^4$ is selected from
i) H, and
ii) $C_{1-6}$-alkyl;
$R^5$ is H;
$R^6$ is selected from
i) $C_{1-6}$-alkyl,
ii) $C_{3-8}$-cycloalkyl substituted with $R^7$, $R^8$ and $R^9$, wherein $R^7$, $R^8$ and $R^9$ are independently selected from
a. H,
b. $C_{1-6}$-alkyl,
c. $C_{1-6}$-alkoxyalkyl, and
d. halo-$C_{1-6}$-alkyl;
iii) hydroxy-$C_{1-6}$-alkyl,
iv) halo-$C_{1-6}$-alkyl,
v) heterocycloalkyl substituted with $R^7$, $R^8$ and $R^9$, wherein $R^7$, $R^8$ and $R^9$ are independently selected from
a. H, and
b. $C_{1-6}$-alkyl;
and wherein the heterocycloalkyl is selected from
a. oxetanyl,
b. tetrahydrofuranyl,
c. tetrahydropyranyl,
d. oxepanyl, and
e. oxaspiro[3.3]heptanyl;
$R^{10}$ is H;
$R^{11}$ is H;
or pharmaceutically acceptable salts.

A particular embodiment of the present invention provides compounds according to formula (I) as described herein, wherein
X is CH;
Y is N;
Z is $CR^{11}$;
$R^1$ is $C_{1-6}$-alkyl;
$R^2$ is H;
$R^3$ is $C_{1-6}$-alkyl;
$R^4$ is H;
$R^5$ is H;
$R^6$ is heterocycloalkyl substituted with $R^7$, $R^8$ and $R^9$;
$R^7$, $R^8$ and $R^9$ are H;
$R^{11}$ is H;
or pharmaceutically acceptable salts.

A particular embodiment of the present invention provides compounds according to formula (I) as described herein, wherein
X is CH;
Y is N;
Z is $CR^{11}$;
$R^1$ is $C_{1-6}$-alkyl;
$R^2$ is H;
$R^3$ is $C_{1-6}$-alkyl;
$R^4$ is H;
$R^5$ is H;
$R^6$ is tetrahydropyranyl substituted with $R^7$, $R^8$ and $R^9$;
$R^7$, $R^8$ and $R^9$ are H;
$R^{11}$ is H;
or pharmaceutically acceptable salts.

Particular examples of compounds of formula (I) as described herein are selected from 6-((5-methyl-3-(6-methyl-3-pyridyl)isoxazol-4-yl)methoxy)-N-tetrahydropyran-4-yl-pyridine-3-carboxamide;

N-(cyclopropylmethyl)-6-((5-methyl-3-(6-methyl-3-pyridyl)isoxazol-4-yl)methoxy)pyridine-3-carboxamide;

N-ethyl-6-((5-methyl-3-(6-methyl-3-pyridyl)isoxazol-4-yl)methoxy)pyridine-3-carboxamide;

N-((1S)-1-(hydroxymethyl)butyl)-6-((5-methyl-3-(6-methyl-3-pyridyl)isoxazol-4-yl)methoxy)pyridine-3-carboxamide;

6-((5-cyclopropyl-3-(6-methyl-3-pyridyl)isoxazol-4-yl)methoxy)-N-((1S)-1-(hydroxymethyl)butyl)pyridine-3-carboxamide;

6-((5-cyclopropyl-3-(6-methyl-3-pyridyl)isoxazol-4-yl)methoxy)-N-tetrahydropyran-4-yl-pyridine-3-carboxamide;

(S)—N-(1-hydroxypentan-2-yl)-6-((5-methyl-3-(6-methylpyridin-3-yl)isoxazol-4-yl)methoxy)pyridazine-3-carboxamide;

6-((5-methyl-3-(6-methylpyridin-3-yl)isoxazol-4-yl)methoxy)-N-(tetrahydro-2H-pyran-4-yl)pyridazine-3-carboxamide;

2-isobutyl-6-((5-methyl-3-(6-methylpyridin-3-yl)isoxazol-4-yl)methoxy)-1H-pyrrolo[3,4-c]pyridin-3(2H)-one;

2-methyl-6-((5-methyl-3-(6-methylpyridin-3-yl)isoxazol-4-yl)methoxy)-1H-pyrrolo[3,4-c]pyridin-3(2H)-one;

N-isobutyl-6-((5-methyl-3-(6-methylpyridin-3-yl)isoxazol-4-yl)methoxy)nicotinamide;

2-(2-hydroxyethyl)-6-((5-methyl-3-(6-methylpyridin-3-yl)isoxazol-4-yl)methoxy)-1H-pyrrolo[3,4-c]pyridin-3(2H)-one;

(S)-2-(1-hydroxypentan-2-yl)-6-((5-methyl-3-(6-methylpyridin-3-yl)isoxazol-4-yl)methoxy)-1H-pyrrolo[3,4-c]pyridin-3(2H)-one;

(S)—N-(1-hydroxypentan-2-yl)-5-((5-methyl-3-(6-methylpyridin-3-yl)isoxazol-4-yl)methoxy)pyrazine-2-carboxamide;

5-((5-methyl-3-(6-methylpyridin-3-yl)isoxazol-4-yl)methoxy)-N-(tetrahydro-2H-pyran-4-yl)pyrazine-2-carboxamide;

N-(1,1-dioxothiolan-3-yl)-6-((5-methyl-3-(6-methyl-3-pyridyl)isoxazol-4-yl)methoxy)pyridine-3-carboxamide;

6-((5-methyl-3-(6-methylpyridin-3-yl)isoxazol-4-yl)methoxy)nicotinamide;

6-((5-methyl-3-(6-methylpyridin-3-yl)isoxazol-4-yl)methoxy)pyridazine-3-carboxamide;

N-((3S)-1,1-dioxothiolan-3-yl)-6-((5-methyl-3-(6-methylpyridin-3-yl)-1,2-oxazol-4-yl)methoxy)pyridine-3-carboxamide;

N-((3R)-1,1-dioxothiolan-3-yl)-6-((5-methyl-3-(6-methylpyridin-3-yl)-1,2-oxazol-4-yl)methoxy)pyridine-3-carboxamide;

N-(1,1-dioxothian-4-yl)-6-((5-methyl-3-(6-methylpyridin-3-yl)-1,2-oxazol-4-yl)methoxy)pyridine-3-carboxamide;

6-((5-methyl-3-(6-methylpyridin-3-yl)isoxazol-4-yl)methoxy)-2-(tetrahydro-2H-pyran-4-yl)-1H-pyrrolo[3,4-c]pyridin-3(2H)-one;

N-((1S,2R)-2-Hydroxycyclohexyl)-6-((5-methyl-3-(6-methylpyridin-3-yl)isoxazol-4-yl)methoxy)pyridazine-3-carboxamide;

N-((1S,2S)-2-Hydroxycyclohexyl)-6-((5-methyl-3-(6-methylpyridin-3-yl)isoxazol-4-yl)methoxy)pyridazine-3-carboxamide;

N-((1R,2R)-2-Hydroxycyclohexyl)-6-((5-methyl-3-(6-methylpyridin-3-yl)isoxazol-4-yl)methoxy)pyridazine-3-carboxamide;

N-cyclopropyl-6-((5-methyl-3-(6-methylpyridin-3-yl)isoxazol-4-yl)methoxy)pyridazine-3-carboxamide;

N-((1R,2S)-2-hydroxycyclohexyl)-6-((5-methyl-3-(6-methylpyridin-3-yl)isoxazol-4-yl)methoxy)pyridazine-3-carboxamide;

N-((3S,4R)-3-hydroxytetrahydropyran-4-yl)-6-((5-methyl-3-(6-methylpyridin-3-yl)isoxazol-4-yl)methoxy)pyridazine-3-carboxamide;

N-(2-hydroxyethyl)-6-((5-methyl-3-(6-methylpyridin-3-yl)isoxazol-4-yl)methoxy)pyridazine-3-carboxamide;

N-(1,1-dioxothian-4-yl)-6-((5-methyl-3-(6-methylpyridin-3-yl)-1,2-oxazol-4-yl)methoxy)pyridazine-3-carboxamide;

N-(cyclopropylmethyl)-6-((5-methyl-3-(6-methylpyridin-3-yl)isoxazol-4-yl)methoxy)pyridazine-3-carboxamide;

N-(cyclopropylmethyl)-6-((5-methyl-3-(6-methylpyridin-3-yl)isoxazol-4-yl)methoxy)pyridazine-3-carboxamide;

N-(2-cyanoethyl)-6-((5-methyl-3-(6-methylpyridin-3-yl)isoxazol-4-yl)methoxy)pyridazine-3-carboxamide;

(RS)-6-((5-methyl-3-(6-methylpyridin-3-yl)isoxazol-4-yl)methoxy)-N-(1,1,1-trifluoropropan-2-yl)pyridazine-3-carboxamide;

6-((5-methyl-3-(6-methylpyridin-3-yl)isoxazol-4-yl)methoxy)-N-(oxetan-3-yl)pyridazine-3-carboxamide;

(RS)—N-(1,1-dioxothiolan-3-yl)-6-((5-methyl-3-(6-methylpyridin-3-yl)-1,2-oxazol-4-yl)methoxy)pyridazine-3-carboxamide;

N-ethyl-6-((5-methyl-3-(6-methylpyridin-3-yl)isoxazol-4-yl)methoxy)pyridazine-3-carboxamide;

N-isopropyl-6-((5-methyl-3-(6-methylpyridin-3-yl)isoxazol-4-yl)methoxy)pyridazine-3-carboxamide;

N-isobutyl-6-((5-methyl-3-(6-methylpyridin-3-yl)isoxazol-4-yl)methoxy)pyridazine-3-carboxamide;

6-((5-methyl-3-(6-methylpyridin-3-yl)isoxazol-4-yl)methoxy)-N-(2,2,2-trifluoroethyl)pyridazine-3-carboxamide;

N-tert-butyl-6-((5-methyl-3-(6-methylpyridin-3-yl)isoxazol-4-yl)methoxy)pyridazine-3-carboxamide;

N-(3,3-difluorocyclobutyl)-6-((5-methyl-3-(6-methylpyridin-3-yl)isoxazol-4-yl)methoxy)pyridazine-3-carboxamide;

N-(4,4-difluorocyclohexyl)-6-((5-methyl-3-(6-methylpyridin-3-yl)isoxazol-4-yl)methoxy)pyridazine-3-carboxamide;

6-((3-(6-methyl-3-pyridyl)isoxazol-4-yl)methoxy)-N-tetrahydropyran-4-yl-pyridine-3-carboxamide;

(RS)-6-((5-methyl-3-(6-methylpyridin-3-yl)isoxazol-4-yl)methoxy)-N-(tetrahydrofuran-3-yl)pyridazine-3-carboxamide;

N-methyl-6-((5-methyl-3-(6-methylpyridin-3-yl)isoxazol-4-yl)methoxy)pyridazine-3-carboxamide;

(3,3-difluoroazetidin-1-yl)(6-((5-methyl-3-(6-methylpyridin-3-yl)isoxazol-4-yl)methoxy)pyridazin-3-yl)methanone;

(3,3-difluoropyrrolidin-1-yl)(6-((5-methyl-3-(6-methylpyridin-3-yl)isoxazol-4-yl)methoxy)pyridazin-3-yl)methanone;

6-((5-methyl-3-(6-methylpyridin-3-yl)isoxazol-4-yl)methoxy)-N-((3-methyloxetan-3-yl)methyl)pyridazine-3-carboxamide;

6-((5-methyl-3-(6-methyl-3-pyridyl)isoxazol-4-yl)methoxy)-N-(oxetan-3-ylmethyl)pyridazine-3-carboxamide;

N-((3-hydroxyoxetan-3-yl)methyl)-6-((5-methyl-3-(6-methylpyridin-3-yl)isoxazol-4-yl)methoxy)pyridazine-3-carboxamide;

6-((5-methyl-3-(6-methylpyridin-3-yl)isoxazol-4-yl)methoxy)-N-((3R,4R)-3-methyltetrahydropyran-4-yl)pyridazine-3-carboxamide;

(4,4-difluoropiperidin-1-yl)(6-((5-methyl-3-(6-methylpyridin-3-yl)isoxazol-4-yl)methoxy)pyridazin-3-yl)methanone;

N-(1-(methoxymethyl)cyclopropyl)-6-((5-methyl-3-(6-methylpyridin-3-yl)isoxazol-4-yl)methoxy)pyridazine-3-carboxamide;

(3-methoxyazetidin-1-yl)(6-((5-methyl-3-(6-methylpyridin-3-yl)isoxazol-4-yl)methoxy)pyridazin-3-yl)methanone;

(3-hydroxy-3-methylazetidin-1-yl)(6-((5-methyl-3-(6-methylpyridin-3-yl)isoxazol-4-yl)methoxy)pyridazin-3-yl)methanone;

azetidin-1-yl(6-((5-methyl-3-(6-methylpyridin-3-yl)isoxazol-4-yl)methoxy)pyridazin-3-yl)methanone;

(RS)—N-(2,2-dimethyltetrahydropyran-4-yl)-6-((5-methyl-3-(6-methylpyridin-3-yl)isoxazol-4-yl)methoxy)pyridazine-3-carboxamide;

6-((5-methyl-3-(6-methylpyridin-3-yl)isoxazol-4-yl)methoxy)-N-(1-(trifluoromethyl)cyclopropyl)pyridazine-3-carboxamide;

(6-((5-methyl-3-(6-methylpyridin-3-yl)isoxazol-4-yl)methoxy)pyridazin-3-yl)(morpholino)methanone;

(6-((5-methyl-3-(6-methylpyridin-3-yl)isoxazol-4-yl)methoxy)pyridazin-3-yl)(2-oxa-6-azaspiro[3.3]heptan-6-yl)methanone;

4-methyl-6-((5-methyl-3-(6-methylpyridin-3-yl)isoxazol-4-yl)methoxy)-N-(tetrahydropyran-4-yl)pyridazine-3-carboxamide;

(6-((5-methyl-3-(6-methylpyridin-3-yl)isoxazol-4-yl)methoxy)pyridazin-3-yl)(6-oxa-1-azaspiro[3.3]heptan-1-yl)methanone;

6-((5-methyl-3-(6-methylpyridin-3-yl)isoxazol-4-yl)methoxy)-N-(1,1,1-trifluoro-2-methylpropan-2-yl)pyridazine-3-carboxamide;

(3-fluoroazetidin-1-yl)(6-((5-methyl-3-(6-methylpyridin-3-yl)isoxazol-4-yl)methoxy)pyridazin-3-yl)methanone;

(3-hydroxyazetidin-1-yl)(6-((5-methyl-3-(6-methylpyridin-3-yl)isoxazol-4-yl)methoxy)pyridazin-3-yl)methanone;

(3-fluoro-3-methylazetidin-1-yl)(6-((5-methyl-3-(6-methylpyridin-3-yl)isoxazol-4-yl)methoxy)pyridazin-3-yl)methanone;

ethyl 1-(6-((5-methyl-3-(6-methylpyridin-3-yl)isoxazol-4-yl)methoxy)pyridazine-3-carboxamido)cyclopropanecarboxylate;

N-(1-cyanocyclopropyl)-6-((5-methyl-3-(6-methylpyridin-3-yl)isoxazol-4-yl)methoxy)pyridazine-3-carboxamide;

5-methyl-6-((5-methyl-3-(6-methylpyridin-3-yl)isoxazol-4-yl)methoxy)pyridazine-3-carboxamide;

5-methyl-6-((5-methyl-3-(6-methylpyridin-3-yl)isoxazol-4-yl)methoxy)-N-(tetrahydropyran-4-yl)pyridazine-3-carboxamide;

N-(1,1-dioxothian-4-yl)-5-((5-methyl-3-(6-methyl-3-pyridyl)isoxazol-4-yl)methoxy)pyrazine-2-carboxamide;

N-(2-hydroxy-1,1-dimethyl-ethyl)-5-((5-methyl-3-(6-methyl-3-pyridyl)isoxazol-4-yl)methoxy)pyrazine-2-carboxamide;

N-cyclopropyl-5-((5-methyl-3-(6-methyl-3-pyridyl)isoxazol-4-yl)methoxy)pyrazine-2-carboxamide;

(RS)-6-((5-methyl-3-(6-methylpyridin-3-yl)isoxazol-4-yl)methoxy)-N-(3-methyltetrahydrofuran-3-yl)pyridazine-3-carboxamide;

6-((5-methyl-3-(6-methylpyridin-3-yl)isoxazol-4-yl)methoxy)-N-(1-methylcyclopropyl)pyridazine-3-carboxamide;

5-((5-methyl-3-(6-methyl-3-pyridyl)isoxazol-4-yl)methoxy)-N-(oxetan-3-yl)pyrazine-2-carboxamide;

5-((5-methyl-3-(6-methyl-3-pyridyl)isoxazol-4-yl)methoxy)-N-(2,2,2-trifluoroethyl)pyrazine-2-carboxamide;

N-(4-hydroxy-2-methylbutan-2-yl)-6-((5-methyl-3-(6-methylpyridin-3-yl)isoxazol-4-yl)methoxy)pyridazine-3-carboxamide;

6-((5-methyl-3-(6-methylpyridin-3-yl)isoxazol-4-yl)methoxy)-N-(2-methyl-4-(methylsulfonyl)butan-2-yl)pyridazine-3-carboxamide;

(S)-6-((5-methyl-3-(6-methylpyridin-3-yl)isoxazol-4-yl)methoxy)-N-(3-methyltetrahydrofuran-3-yl)pyridazine-3-carboxamide;

(R)-6-((5-methyl-3-(6-methylpyridin-3-yl)isoxazol-4-yl)methoxy)-N-(3-methyltetrahydrofuran-3-yl)pyridazine-3-carboxamide;

6-((5-methyl-3-(6-methylpyridin-3-yl)isoxazol-4-yl)methoxy)-N-(3-methyloxetan-3-yl)pyridazine-3-carboxamide;

1-(6-((5-methyl-3-(6-methylpyridin-3-yl)isoxazol-4-yl)methoxy)pyridazine-3-carbonyl)azetidine-3-carbonitrile;

N-(1-(hydroxymethyl)cyclopropyl)-6-((5-methyl-3-(6-methylpyridin-3-yl)isoxazol-4-yl)methoxy)pyridazine-3-carboxamide;

N-(4,4-difluorocyclohexyl)-5-((5-methyl-3-(6-methyl-3-pyridyl)isoxazol-4-yl)methoxy)pyrazine-2-carboxamide;

(S)-6-((5-methyl-3-(6-methylpyridin-3-yl)isoxazol-4-yl)methoxy)-N-(tetrahydrofuran-3-yl)pyridazine-3-carboxamide;

(S)—N-(1-cyanobutan-2-yl)-6-((5-methyl-3-(6-methylpyridin-3-yl)isoxazol-4-yl)methoxy)pyridazine-3-carboxamide;

(R)-5-((5-Methyl-3-(6-methylpyridin-3-yl)isoxazol-4-yl)methoxy)-N-(tetrahydrofuran-3-yl)pyrazine-2-carboxamide;

N-(2-Hydroxyethyl)-5-((5-methyl-3-(6-methylpyridin-3-yl)isoxazol-4-yl)methoxy)pyrazine-2-carboxamide;

2-(1,1-Dioxothian-4-yl)-6-[[5-methyl-3-(6-methylpyridin-3-yl)-1,2-oxazol-4-yl]methoxy]-1#H!-pyrrolo[3,4-c]pyridin-3-one;

(S)-5-((5-Methyl-3-(6-methylpyridin-3-yl)isoxazol-4-yl)methoxy)-N-(tetrahydrofuran-3-yl)pyrazine-2-carboxamide;

2-((5-methyl-3-(6-methyl-3-pyridyl)isoxazol-4-yl)methoxy]-6-tetrahydropyran-4-yl-7H-pyrrolo[3,4-b]pyridin-5-one;

N-(1,1-Dioxothiolan-3-yl)-5-((5-methyl-3-(6-methylpyridin-3-yl)-1,2-oxazol-4-yl)methoxy)pyrazine-2-carboxamide;

N-(Cyclopropylmethyl)-5-((5-methyl-3-(6-methylpyridin-3-yl)isoxazol-4-yl)methoxy)pyrazine-2-carboxamide;

2-(4,4-Difluorocyclohexyl)-6-((5-methyl-3-(6-methylpyridin-3-yl)isoxazol-4-yl)methoxy)-1H-pyrrolo[3,4-c]pyridin-3(2H)-one;

6-((5-Methyl-3-(6-methylpyridin-3-yl)isoxazol-4-yl)methoxy)-N-(4-methyltetrahydro-2H-pyran-4-yl)pyridazine-3-carboxamide;

(R)-5-((5-Methyl-3-(6-methylpyridin-3-yl)isoxazol-4-yl)methoxy)-N-(tetrahydro-2H-pyran-3-yl)pyrazine-2-carboxamide;

(R)-6-((5-methyl-3-(6-methylpyridin-3-yl)isoxazol-4-yl)methoxy)-N-(tetrahydropyran-3-yl)pyridazine-3-carboxamide;

6-((5-methyl-3-(6-methylpyridin-3-yl)isoxazol-4-yl)
methoxy)-N-(2-oxaspiro[3.3]heptan-6-yl)pyridazine-3-
carboxamide;

5-((5-Methyl-3-(6-methylpyridin-3-yl)isoxazol-4-yl)
methoxy)-N-(2-oxaspiro[3.3]heptan-6-yl)pyrazine-2-car-
boxamide;

5-((5-Methyl-3-(6-methylpyridin-3-yl)isoxazol-4-yl)
methoxy)-N-((cis)-4-(trifluoromethyl)cyclohexyl)pyra-
zine-2-carboxamide;

(S)-6-((5-methyl-3-(6-methylpyridin-3-yl)isoxazol-4-yl)
methoxy)-N-(tetrahydropyran-3-yl)pyridazine-3-carbox-
amide;

N-((cis)-4-Hydroxy-4-methylcyclohexyl)-5-((5-methyl-3-
(6-methylpyridin-3-yl)isoxazol-4-yl)methoxy)pyrazine-
2-carboxamide;

N-((trans)-4-Hydroxy-4-methylcyclohexyl)-5-((5-methyl-3-
(6-methylpyridin-3-yl)isoxazol-4-yl)methoxy)pyrazine-
2-carboxamide;

6-((5-methyl-3-(6-methylpyridin-3-yl)isoxazol-4-yl)
methoxy)-N-(4-methyltetrahydro-2H-pyran-4-yl)nicoti-
namide;

6-((5-Methyl-3-(6-methylpyridin-3-yl)isoxazol-4-yl)
methoxy)-2-(tetrahydro-2H-thiopyran-4-yl)-1H-pyrrolo
[3,4-c]pyridin-3(2H)-one;

6-((5-methyl-3-(6-methylpyridazin-3-yl)isoxazol-4-yl)
methoxy)-N-tetrahydropyran-4-yl-pyridine-3-carboxam-
ide;

N-((1S)-1-(hydroxymethyl)butyl)-6-((5-methyl-3-(6-meth-
ylpyridazin-3-yl)isoxazol-4-yl)methoxy)pyridine-3-car-
boxamide;

6-((5-methyl-3-(6-methylpyridin-3-yl)isoxazol-4-yl)
methoxy)-N-(4-methyltetrahydrothiopyran-4-yl)
pyridazine-3-carboxamide;

N-(4-methyl-1,1-dioxidotetrahydro-2H-thiopyran-4-yl)-6-
((5-methyl-3-(6-methylpyridin-3-yl)isoxazol-4-yl)
methoxy)pyridazine-3-carboxamide;

(2,2-dioxido-2-thia-6-azaspiro[3.3]heptan-6-yl)(6-((5-
methyl-3-(6-methylpyridin-3-yl)isoxazol-4-yl)methoxy)
pyridazin-3-yl)methanone;

(2,2-Dioxido-2-thia-6-azaspiro[3.3]heptan-6-yl)(5-((5-
methyl-3-(6-methylpyridin-3-yl)isoxazol-4-yl)methoxy)
pyrazin-2-yl)methanone;

6-((5-methyl-3-(6-methylpyridin-3-yl)isoxazol-4-yl)
methoxy)-N-(1-methylcyclopentyl)pyridazine-3-carbox-
amide;

5-((5-Methyl-3-(6-methylpyridin-3-yl)isoxazol-4-yl)
methoxy)-N-(4,4,4-trifluorobutyl)pyrazine-2-carboxam-
ide;

N-(1-isopropylazetidin-3-yl)-6-((5-methyl-3-(6-methylpyri-
din-3-yl)isoxazol-4-yl)methoxy)pyridazine-3-carboxam-
ide;

6-((5-Methyl-3-(6-methylpyridin-3-yl)isoxazol-4-yl)
methoxy)-2-(2-oxaspiro[3.3]heptan-6-yl)-1H-pyrrolo[3,
4-c]pyridin-3(2H)-one;

6-((5-methyl-3-(6-methylpyridin-3-yl)isoxazol-4-yl)
methoxy)-N-(1-methylcyclobutyl)pyridazine-3-carbox-
amide;

6-((5-Ethyl-3-(6-methylpyridin-3-yl)isoxazol-4-yl)
methoxy)-N-(tetrahydro-2H-pyran-4-yl)nicotinamide;

N-(1,1-Dioxidotetrahydro-2H-thiopyran-4-yl)-6-((5-ethyl-
3-(6-methylpyridin-3-yl)isoxazol-4-yl)methoxy)nicotina-
mide;

6-((5-ethyl-3-(6-methylpyridin-3-yl)isoxazol-4-yl)
methoxy)-N-(tetrahydropyran-4-yl)pyridazine-3-carbox-
amide;

6-((5-ethyl-3-(6-methylpyridin-3-yl)isoxazol-4-yl)
methoxy)-N-(3-methyloxetan-3-yl)pyridazine-3-carbox-
amide;

N-cyclopropyl-6-((5-ethyl-3-(6-methylpyridin-3-yl)isoxa-
zol-4-yl)methoxy)pyridazine-3-carboxamide;

(R)—N-(1-hydroxypentan-2-yl)-6-((5-methyl-3-(6-meth-
ylpyridin-3-yl)isoxazol-4-yl)methoxy)nicotinamide;

6-((5-(difluoromethyl)-3-(6-methyl-3-pyridyl)isoxazol-4-
yl)methoxy)-N-((1S)-1-(hydroxymethyl)butyl)pyridine-
3-carboxamide;

6-((5-(difluoromethyl)-3-(6-methyl-3-pyridyl)isoxazol-4-
yl)methoxy)-N-tetrahydropyran-4-yl-pyridine-3-carbox-
amide;

N-((3R,4S)-3-hydroxytetrahydropyran-4-yl)-6-((5-methyl-
3-(6-methyl-3-pyridyl)isoxazol-4-yl)methoxy)pyridine-
3-carboxamide;

6-((3-(6-cyclopropyl-3-pyridyl)-5-methyl-isoxazol-4-yl)
methoxy)-N-tetrahydropyran-4-yl-pyridine-3-carboxam-
ide;

6-((3-(6-cyclopropyl-3-pyridyl)-5-methyl-isoxazol-4-yl)
methoxy)-N-((1S)-1-(hydroxymethyl)butyl)pyridine-3-
carboxamide;

6-((3-(6-cyclopropyl-3-pyridyl)-5-methyl-isoxazol-4-yl)
methoxy)-N-(1,1-dioxothian-4-yl)pyridine-3-carboxam-
ide;

N-((1R,2S)-3,3-difluoro-2-hydroxycyclohexyl)-6-((5-
methyl-3-(6-methylpyridin-3-yl)isoxazol-4-yl)methoxy)
nicotinamide;

N-((1R,2R)-2-hydroxycyclohexyl)-6-((5-methyl-3-(6-meth-
ylpyridin-3-yl)isoxazol-4-yl)methoxy)nicotinamide;

N-((1S,2R)-3,3-difluoro-2-hydroxycyclohexyl)-6-((5-
methyl-3-(6-methylpyridin-3-yl)isoxazol-4-yl)methoxy)
nicotinamide;

N-((3S,4R)-3-hydroxytetrahydro-2H-pyran-4-yl)-6-((5-
methyl-3-(6-methylpyridin-3-yl)isoxazol-4-yl)methoxy)
nicotinamide;

N-((1S,2S)-2-hydroxycyclohexyl)-6-((5-methyl-3-(6-meth-
ylpyridin-3-yl)isoxazol-4-yl)methoxy)nicotinamide;

2-fluoro-N-methyl-6-((5-methyl-3-(6-methylpyridin-3-yl)
isoxazol-4-yl)methoxy)nicotinamide;

6-((3-(6-methoxypyridin-3-yl)-5-methylisoxazol-4-yl)
methoxy)-N-(tetrahydro-2H-pyran-4-yl)nicotinamide;

N-isopropyl-6-((3-(6-methoxypyridin-3-yl)-5-methylisoxa-
zol-4-yl)methoxy)nicotinamide;

(S)—N-(1-hydroxypentan-2-yl)-6-((3-(6-methoxypyridin-
3-yl)-5-methylisoxazol-4-yl)methoxy)nicotinamide;

(1,1-dioxidothiomorpholino)(6-((3-(6-methoxypyridin-3-
yl)-5-methylisoxazol-4-yl)methoxy)pyridin-3-yl)metha-
none;

(S)-6-((3-(6-(dimethylamino)pyridin-3-yl)-5-methylisoxa-
zol-4-yl)methoxy)-N-(1-hydroxypentan-2-yl)nicotina-
mide;

4-methoxy-6-((5-methyl-3-(6-methylpyridin-3-yl)isoxazol-
4-yl)methoxy)-N-(tetrahydro-2H-pyran-4-yl)nicotina-
mide;

6-((3-(5-fluoro-6-methyl-3-pyridyl)-5-methyl-isoxazol-4-
yl)methoxy)-N-tetrahydropyran-4-yl-pyridine-3-carbox-
amide;

6-((3-(5-fluoro-6-methyl-3-pyridyl)-5-methyl-isoxazol-4-yl)
methoxy)-N-isopropyl-pyridine-3-carboxamide;

6-((3-(5-fluoro-6-methyl-3-pyridyl)-5-methyl-isoxazol-4-
yl)methoxy)-N-((1S)-1-(hydroxymethyl)butyl)pyridine-
3-carboxamide;

N-((1r,4r)-4-hydroxy-4-methylcyclohexyl)-6-((5-methyl-3-
(6-methylpyridin-3-yl)isoxazol-4-yl)methoxy)
pyridazine-3-carboxamide;

N-(1,3-dihydroxy-2-methylpropan-2-yl)-6-((5-methyl-3-(6-methylpyridin-3-yl)isoxazol-4-yl)methoxy)pyridazine-3-carboxamide;

N-((1s,4s)-4-hydroxy-4-methylcyclohexyl)-6-((5-methyl-3-(6-methylpyridin-3-yl)isoxazol-4-yl)methoxy)pyridazine-3-carboxamide;

N-((1R,3S)-3-hydroxy-3-(trifluoromethyl)cyclopentyl)-6-((5-methyl-3-(6-methylpyridin-3-yl)isoxazol-4-yl)methoxy)pyridazine-3-carboxamide;

N-((1S,3R)-3-hydroxy-3-(trifluoromethyl)cyclopentyl)-6-((5-methyl-3-(6-methylpyridin-3-yl)isoxazol-4-yl)methoxy)pyridazine-3-carboxamide;

(1S,4S)-2-oxa-5-azabicyclo[2.2.1]heptan-5-yl(6-((5-methyl-3-(6-methylpyridin-3-yl)isoxazol-4-yl)methoxy)pyridazin-3-yl)methanone;

N-((1RS,3RS)-3-hydroxycyclopentyl)-6-((5-methyl-3-(6-methylpyridin-3-yl)isoxazol-4-yl)methoxy)pyridazine-3-carboxamide;

trans-N-(4-hydroxycyclohexyl)-6-((5-methyl-3-(6-methylpyridin-3-yl)isoxazol-4-yl)methoxy)pyridazine-3-carboxamide;

trans-N-(4-methoxy cyclohexyl)-6-((5-methyl-3-(6-methylpyridin-3-yl)isoxazol-4-yl)methoxy)pyridazine-3-carboxamide;

(6,6-difluoro-2-azaspiro[3.3]heptan-2-yl)(6-((5-methyl-3-(6-methylpyridin-3-yl)isoxazol-4-yl)methoxy)pyridazin-3-yl)methanone;

N-(3-hydroxycyclohexyl)-6-((5-methyl-3-(6-methylpyridin-3-yl)isoxazol-4-yl)methoxy)pyridazine-3-carboxamide;

3-oxa-6-azabicyclo[3.1.1]heptan-6-yl(6-((5-methyl-3-(6-methylpyridin-3-yl)isoxazol-4-yl)methoxy)pyridazin-3-yl)methanone;

cis-N-(4-methoxycyclohexyl)-6-((5-methyl-3-(6-methylpyridin-3-yl)isoxazol-4-yl)methoxy)pyridazine-3-carboxamide;

6-((3-(6-chloropyridin-3-yl)-5-methylisoxazol-4-yl)methoxy)-N-(tetrahydro-2H-pyran-4-yl)pyridazine-3-carboxamide;

(S)-6-((3-(6-chloropyridin-3-yl)-5-methylisoxazol-4-yl)methoxy)-N-(tetrahydrofuran-3-yl)pyridazine-3-carboxamide;

6-((3-(6-chloropyridin-3-yl)-5-methylisoxazol-4-yl)methoxy)-N-(3-methyloxetan-3-yl)pyridazine-3-carboxamide;

6-((3-(6-chloropyridin-3-yl)-5-methylisoxazol-4-yl)methoxy)-N-(2-oxaspiro[3.3]heptan-6-yl)pyridazine-3-carboxamide;

trans-N-(3-methoxycyclobutyl)-6-((5-methyl-3-(6-methyl-3-pyridyl)isoxazol-4-yl)methoxy)pyridazine-3-carboxamide;

cis-N-(3-methoxycyclobutyl)-6-((5-methyl-3-(6-methyl-3-pyridyl)isoxazol-4-yl)methoxy)pyridazine-3-carboxamide;

6-((5-cyclopropyl-3-(6-methylpyridazin-3-yl)isoxazol-4-yl)methoxy)-N-(tetrahydro-2H-pyran-4-yl)pyridazine-3-carboxamide;

trans-N-((1RS,3RS)-3-methoxycyclopentyl)-6-((5-methyl-3-(6-methylpyridin-3-yl)isoxazol-4-yl)methoxy)pyridazine-3-carboxamide;

N-(6,6-difluorospiro[3.3]heptan-2-yl)-6-((5-methyl-3-(6-methylpyridin-3-yl)isoxazol-4-yl)methoxy)pyridazine-3-carboxamide;

6-((5-(fluoromethyl)-3-(6-methylpyridin-3-yl)isoxazol-4-yl)methoxy)-N-(tetrahydropyran-4-yl)pyridazine-3-carboxamide;

cis-N-3-((2,2-difluoroethoxy)cyclobutyl)-6-((5-methyl-3-(6-methylpyridin-3-yl)isoxazol-4-yl)methoxy)pyridazine-3-carboxamide;

trans-N-3-((2,2-difluoroethoxy)cyclobutyl)-6-((5-methyl-3-(6-methylpyridin-3-yl)isoxazol-4-yl)methoxy)pyridazine-3-carboxamide;

cis-N-(3-ethoxycyclobutyl)-6-((5-methyl-3-(6-methylpyridin-3-yl)isoxazol-4-yl)methoxy)pyridazine-3-carboxamide;

trans-N-(3-ethoxycyclobutyl)-6-((5-methyl-3-(6-methylpyridin-3-yl)isoxazol-4-yl)methoxy)pyridazine-3-carboxamide;

cis-N-(3-(difluoromethoxy)cyclobutyl)-6-((5-methyl-3-(6-methylpyridin-3-yl)isoxazol-4-yl)methoxy)pyridazine-3-carboxamide;

trans-N-(3-(difluoromethoxy)cyclobutyl)-6-((5-methyl-3-(6-methylpyridin-3-yl)isoxazol-4-yl)methoxy)pyridazine-3-carboxamide;

trans-N-(3-cyclopropoxycyclobutyl)-6-((5-methyl-3-(6-methylpyridin-3-yl)isoxazol-4-yl)methoxy)pyridazine-3-carboxamide;

cis-N-(3-cyclopropoxycyclobutyl)-6-((5-methyl-3-(6-methylpyridin-3-yl)isoxazol-4-yl)methoxy)pyridazine-3-carboxamide;

6-((3-(6-chloropyridin-3-yl)-5-cyclopropylisoxazol-4-yl)methoxy)-N-(3-methyloxetan-3-yl)pyridazine-3-carboxamide;

6-((3-(6-chloropyridin-3-yl)-5-cyclopropylisoxazol-4-yl)methoxy)-N-(2-oxaspiro[3.3]heptan-6-yl)pyridazine-3-carboxamide;

(S)-6-((3-(6-chloropyridin-3-yl)-5-cyclopropylisoxazol-4-yl)methoxy)-N-(tetrahydrofuran-3-yl)pyridazine-3-carboxamide;

6-((5-cyclopropyl-3-(6-methylpyridin-3-yl)isoxazol-4-yl)methoxy)-N-(3-methyloxetan-3-yl)pyridazine-3-carboxamide;

6-((5-cyclopropyl-3-(6-methylpyridin-3-yl)isoxazol-4-yl)methoxy)-N-(2-oxaspiro[3.3]heptan-6-yl)pyridazine-3-carboxamide;

(S)-6-((5-cyclopropyl-3-(6-methylpyridin-3-yl)isoxazol-4-yl)methoxy)-N-(tetrahydrofuran-3-yl)pyridazine-3-carboxamide;

6-((5-cyclopropyl-3-(6-methylpyridin-3-yl)isoxazol-4-yl)methoxy)-N-(tetrahydropyran-4-yl)pyridazine-3-carboxamide;

6-((5-(fluoromethyl)-3-(6-methylpyridin-3-yl)isoxazol-4-yl)methoxy)-N-(1-(trifluoromethyl)cyclopropyl)pyridazine-3-carboxamide;

6-((5-methyl-3-(6-(trifluoromethyl)pyridin-3-yl)isoxazol-4-yl)methoxy)-N-(tetrahydropyran-4-yl)pyridazine-3-carboxamide;

N-((2S)-7-oxabicyclo[2.2.1]heptan-2-yl)-6-((5-methyl-3-(6-methylpyridin-3-yl)isoxazol-4-yl)methoxy)pyridazine-3-carboxamide;

(RS)-6-((5-methyl-3-(6-methylpyridin-3-yl)isoxazol-4-yl)methoxy)-N-(oxepan-4-yl)pyridazine-3-carboxamide;

6-((5-methyl-3-(6-methyl-3-pyridyl)isoxazol-4-yl)methoxy)-N-((1R,3S,4R)-7-oxabicyclo[2.2.1]heptan-3-yl)pyridazine-3-carboxamide;

N-((2R)-7-oxabicyclo[2.2.1]heptan-2-yl)-6-((5-methyl-3-(6-methylpyridin-3-yl)isoxazol-4-yl)methoxy)pyridazine-3-carboxamide;

N-((1R,3R)-3-ethoxycyclopentyl)-6-((5-methyl-3-(6-methylpyridin-3-yl)isoxazol-4-yl)methoxy)pyridazine-3-carboxamide;

N-((1R,3R)-3-(2,2-difluoroethoxy)cyclopentyl)-6-((5-methyl-3-(6-methylpyridin-3-yl)isoxazol-4-yl)methoxy)pyridazine-3-carboxamide;

6-((5-(fluoromethyl)-3-(6-methylpyridazin-3-yl)isoxazol-4-yl)methoxy)-N-(tetrahydro-2H-pyran-4-yl)pyridazine-3-carboxamide;

6-((5-methyl-3-(6-methylpyridazin-3-yl)isoxazol-4-yl)methoxy)-N-(tetrahydro-2H-pyran-4-yl)pyridazine-3-carboxamide;

N-[4-(2,2-difluoroethoxy)cyclohexyl]-6-[[5-methyl-3-(6-methylpyridin-3-yl)-1,2-oxazol-4-yl]methoxy]pyridazine-3-carboxamide;

N-(4-ethoxycyclohexyl)-6-[[5-methyl-3-(6-methylpyridin-3-yl)-1,2-oxazol-4-yl]methoxy]pyridazine-3-carboxamide;

or pharmaceutically acceptable salts thereof.

Further particular examples of compounds of formula (I) as described herein are selected from N-((1S)-1-(hydroxymethyl)butyl)-6-((5-methyl-3-(6-methyl-3-pyridyl)isoxazol-4-yl)methoxy)pyridine-3-carboxamide;

6-((5-methyl-3-(6-methylpyridin-3-yl)isoxazol-4-yl)methoxy)-N-(tetrahydro-2H-pyran-4-yl)pyridazine-3-carboxamide;

N-cyclopropyl-6-((5-methyl-3-(6-methylpyridin-3-yl)isoxazol-4-yl)methoxy)pyridazine-3-carboxamide;

(RS)-6-((5-methyl-3-(6-methylpyridin-3-yl)isoxazol-4-yl)methoxy)-N-(1,1,1-trifluoropropan-2-yl)pyridazine-3-carboxamide;

N-isopropyl-6-((5-methyl-3-(6-methylpyridin-3-yl)isoxazol-4-yl)methoxy)pyridazine-3-carboxamide;

N-tert-butyl-6-((5-methyl-3-(6-methylpyridin-3-yl)isoxazol-4-yl)methoxy)pyridazine-3-carboxamide;

N-(1-(methoxymethyl)cyclopropyl)-6-((5-methyl-3-(6-methylpyridin-3-yl)isoxazol-4-yl)methoxy)pyridazine-3-carboxamide;

6-((5-methyl-3-(6-methylpyridin-3-yl)isoxazol-4-yl)methoxy)-N-(1-(trifluoromethyl)cyclopropyl)pyridazine-3-carboxamide;

5-methyl-6-((5-methyl-3-(6-methylpyridin-3-yl)isoxazol-4-yl)methoxy)-N-(tetrahydropyran-4-yl)pyridazine-3-carboxamide;

6-((5-methyl-3-(6-methylpyridin-3-yl)isoxazol-4-yl)methoxy)-N-(1-methylcyclopropyl)pyridazine-3-carboxamide;

(S)-6-((5-methyl-3-(6-methylpyridin-3-yl)isoxazol-4-yl)methoxy)-N-(3-methyltetrahydrofuran-3-yl)pyridazine-3-carboxamide;

(R)-6-((5-methyl-3-(6-methylpyridin-3-yl)isoxazol-4-yl)methoxy)-N-(3-methyltetrahydrofuran-3-yl)pyridazine-3-carboxamide;

6-((5-methyl-3-(6-methylpyridin-3-yl)isoxazol-4-yl)methoxy)-N-(3-methyloxetan-3-yl)pyridazine-3-carboxamide;

(S)-6-((5-methyl-3-(6-methylpyridin-3-yl)isoxazol-4-yl)methoxy)-N-(tetrahydrofuran-3-yl)pyridazine-3-carboxamide;

6-((5-Methyl-3-(6-methylpyridin-3-yl)isoxazol-4-yl)methoxy)-N-(4-methyltetrahydro-2H-pyran-4-yl)pyridazine-3-carboxamide;

(R)-6-((5-methyl-3-(6-methylpyridin-3-yl)isoxazol-4-yl)methoxy)-N-(tetrahydropyran-3-yl)pyridazine-3-carboxamide;

6-((5-methyl-3-(6-methylpyridin-3-yl)isoxazol-4-yl)methoxy)-N-(2-oxaspiro[3.3]heptan-6-yl)pyridazine-3-carboxamide;

6-((5-methyl-3-(6-methylpyridin-3-yl)isoxazol-4-yl)methoxy)-N-(1-methylcyclobutyl)pyridazine-3-carboxamide;

6-((3-(5-fluoro-6-methyl-3-pyridyl)-5-methyl-isoxazol-4-yl)methoxy)-N-((1S)-1-(hydroxymethyl)butyl)pyridine-3-carboxamide;

6-((5-cyclopropyl-3-(6-methylpyridazin-3-yl)isoxazol-4-yl)methoxy)-N-(tetrahydro-2H-pyran-4-yl)pyridazine-3-carboxamide;

6-((5-(fluoromethyl)-3-(6-methylpyridin-3-yl)isoxazol-4-yl)methoxy)-N-(tetrahydropyran-4-yl)pyridazine-3-carboxamide;

6-((5-cyclopropyl-3-(6-methylpyridin-3-yl)isoxazol-4-yl)methoxy)-N-(3-methyloxetan-3-yl)pyridazine-3-carboxamide;

(RS)-6-((5-methyl-3-(6-methylpyridin-3-yl)isoxazol-4-yl)methoxy)-N-(oxepan-4-yl)pyridazine-3-carboxamide;

6-((5-(fluoromethyl)-3-(6-methylpyridazin-3-yl)isoxazol-4-yl)methoxy)-N-(tetrahydro-2H-pyran-4-yl)pyridazine-3-carboxamide;

6-((5-methyl-3-(6-methylpyridazin-3-yl)isoxazol-4-yl)methoxy)-N-(tetrahydro-2H-pyran-4-yl)pyridazine-3-carboxamide;

or pharmaceutically acceptable salts thereof.

Further particular examples of compounds of formula (I) as described herein are selected from 6-((5-methyl-3-(6-methylpyridin-3-yl)isoxazol-4-yl)methoxy)-N-(tetrahydro-2H-pyran-4-yl)pyridazine-3-carboxamide or pharmaceutically acceptable salts thereof.

Processes for the manufacture of compounds of formula (I) as described herein are also an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. The reaction sequence is not limited to the one displayed in schemes 1-7, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula (I) and their pharmaceutically acceptable salts can be prepared by a process described below (Scheme 1)
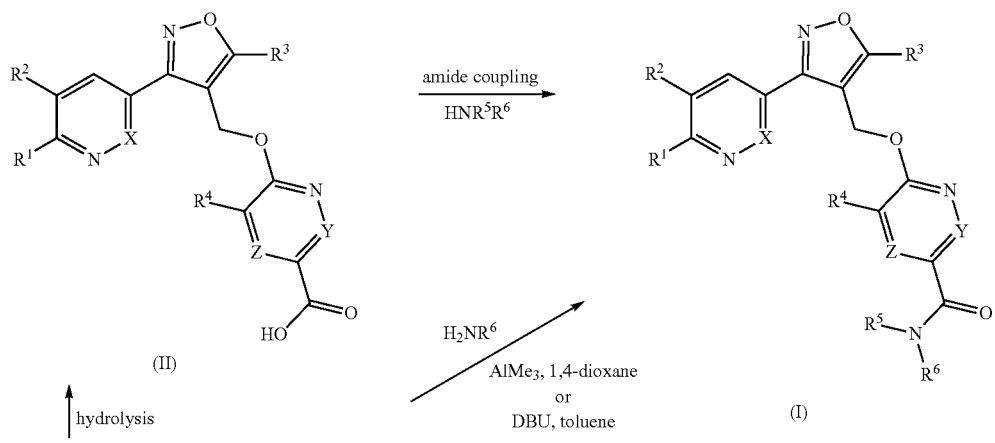
Scheme 1 wherein Y is CH or N; Z is CH or N; with the proviso that not more than one of Y and Z is N; all other definitions are as described above in the claims
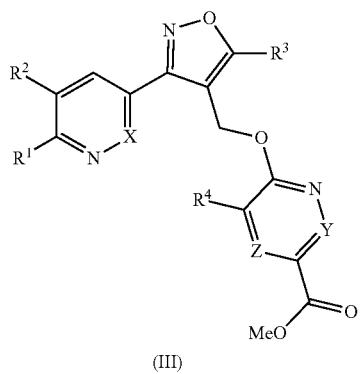

According to Scheme 1, a compound of formula (I) can be prepared by standard amide coupling reaction between a primary ($R^5$=H) or a secondary amine $HNR^5R^6$ and a carboxylic acid of formula (II). Carboxylic acids (II) can be conveniently prepared by hydrolysis of the corresponding methyl esters (III) under standard conditions. In alternative, a compound of formula (I) can be prepared in one step from methyl esters (III) and a primary amine ($H_2NR^6$) by treatment with $Me_3Al$ in 1,4-dioxane or DBU in toluene.

Alternatively, according to Scheme 2, compounds of formula (I) can be prepared by nucleophilic aromatic substitution reaction between a primary alcohol (IV) and an aryl chloride (V) in presence of base ($Cs_2CO_3$).

Scheme 2 wherein Y is CH or N; Z is CH or N;
with the proviso that not more than one of Y and Z is N;
all other definitions are described above and in the claims

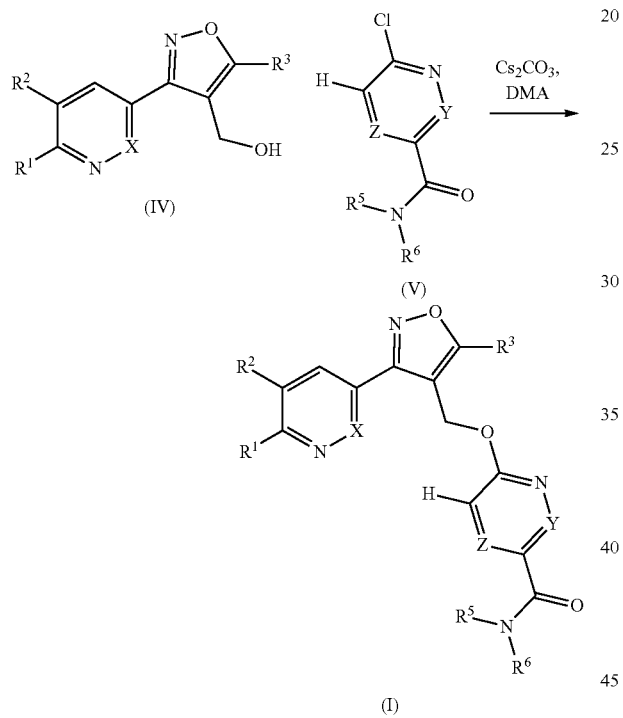

In certain embodiments of the invention, $R^z$ or $R^y$ and $R^5$ are joined together to form —$CH_2$— thereby forming a 5-membered heterocycloalkyl together with the interconnecting atoms. In such a case, compounds of formula (I-a) can be prepared by a process described in Scheme 3.

Scheme 3 wherein all definitions are as described above and in the claims

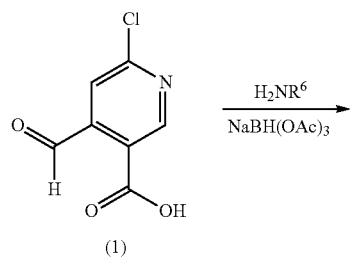

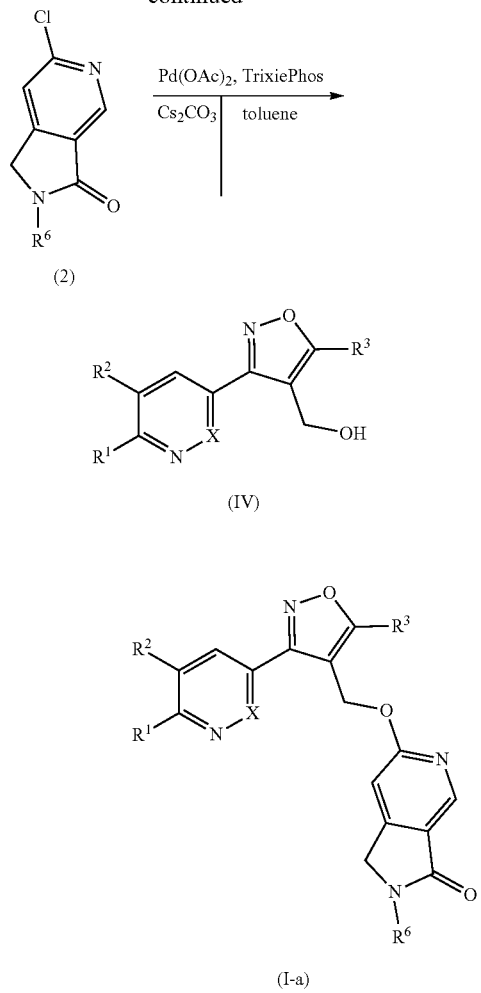

Intermediate γ-lactams (2) can be prepared in a one-pot two-step procedure involving a reductive amination between commercially available 6-chloro-4-formylnicotinic acid and a primary amine ($H_2NR^6$) followed by intramolecular lactam formation. Etherification reaction between γ-lactams (5) and alcohols (IV) can be accomplished by a palladium-mediated process in presence of a base ($Cs_2CO_3$) to form compounds of formula (I-a).

Conversely, regioisomeric compounds of formula (I-b) can be prepared by a process described in Scheme 4.

Scheme 4 wherein all definitions are as described above and in the claims

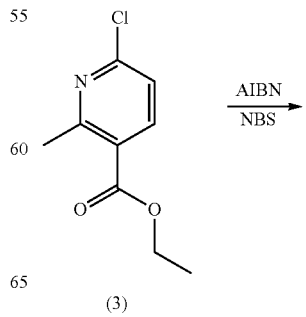

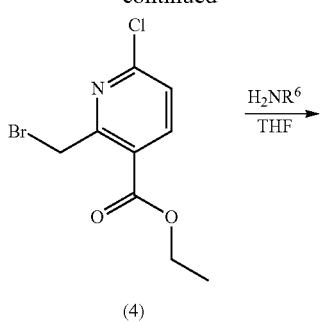

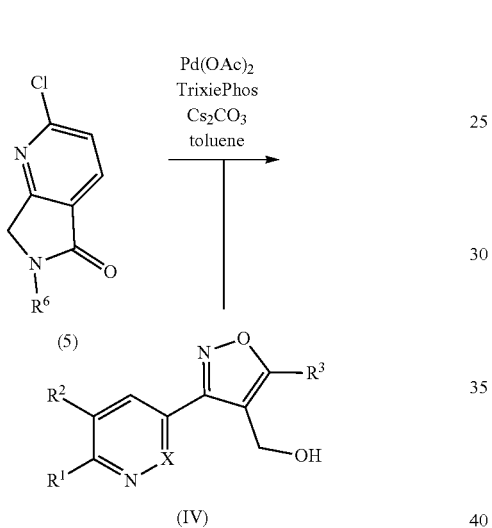

Intermediate γ-lactams (5) can be prepared in two steps from commercially available ethyl 6-chloro-2-methylnicotinate by a radical bromination reaction to form bromide (4). Its subsequent reaction with a primary amine ($H_2NR^6$) followed by intramolecular lactam formation afforded γ-lactams (5). Final etherification between γ-lactams (5) and alcohols (IV) can be accomplished again by a palladium-mediated process in presence of a base ($Cs_2CO_3$) to form compounds of formula (I-b).

Scheme 5 wherein Y is CH or N; Z is CH or N;
with the proviso that not more than one of Y and Z is N;
all other definitions are as described above and in the claims

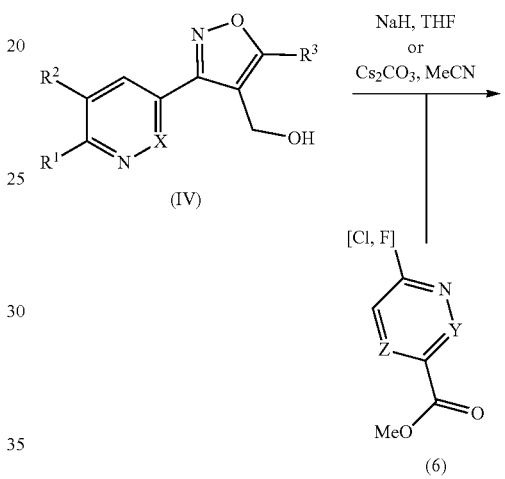

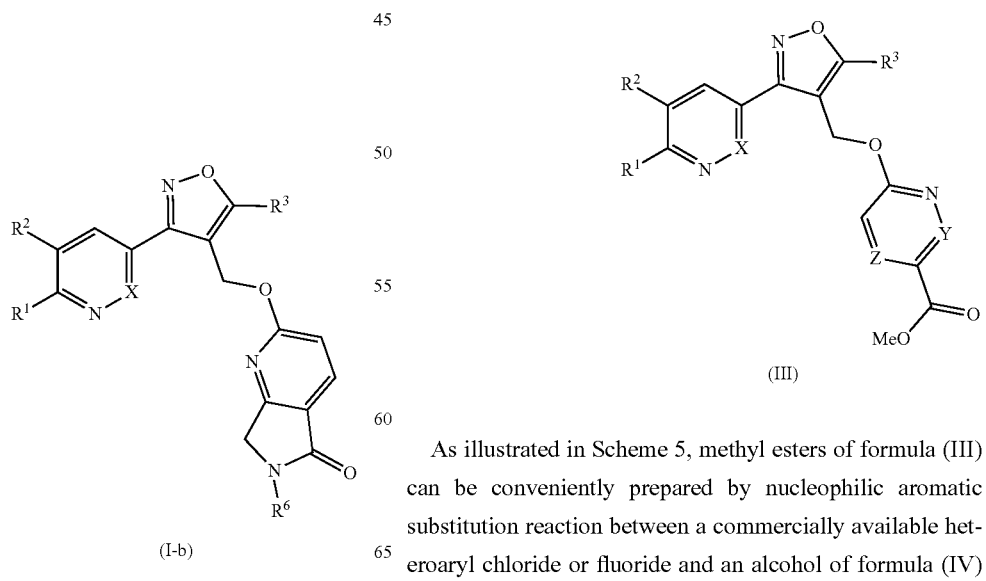

As illustrated in Scheme 5, methyl esters of formula (III) can be conveniently prepared by nucleophilic aromatic substitution reaction between a commercially available heteroaryl chloride or fluoride and an alcohol of formula (IV) in presence of a base (NaH or $Cs_2CO_3$).

Scheme 6 wherein all definitions are as described above and in the claims

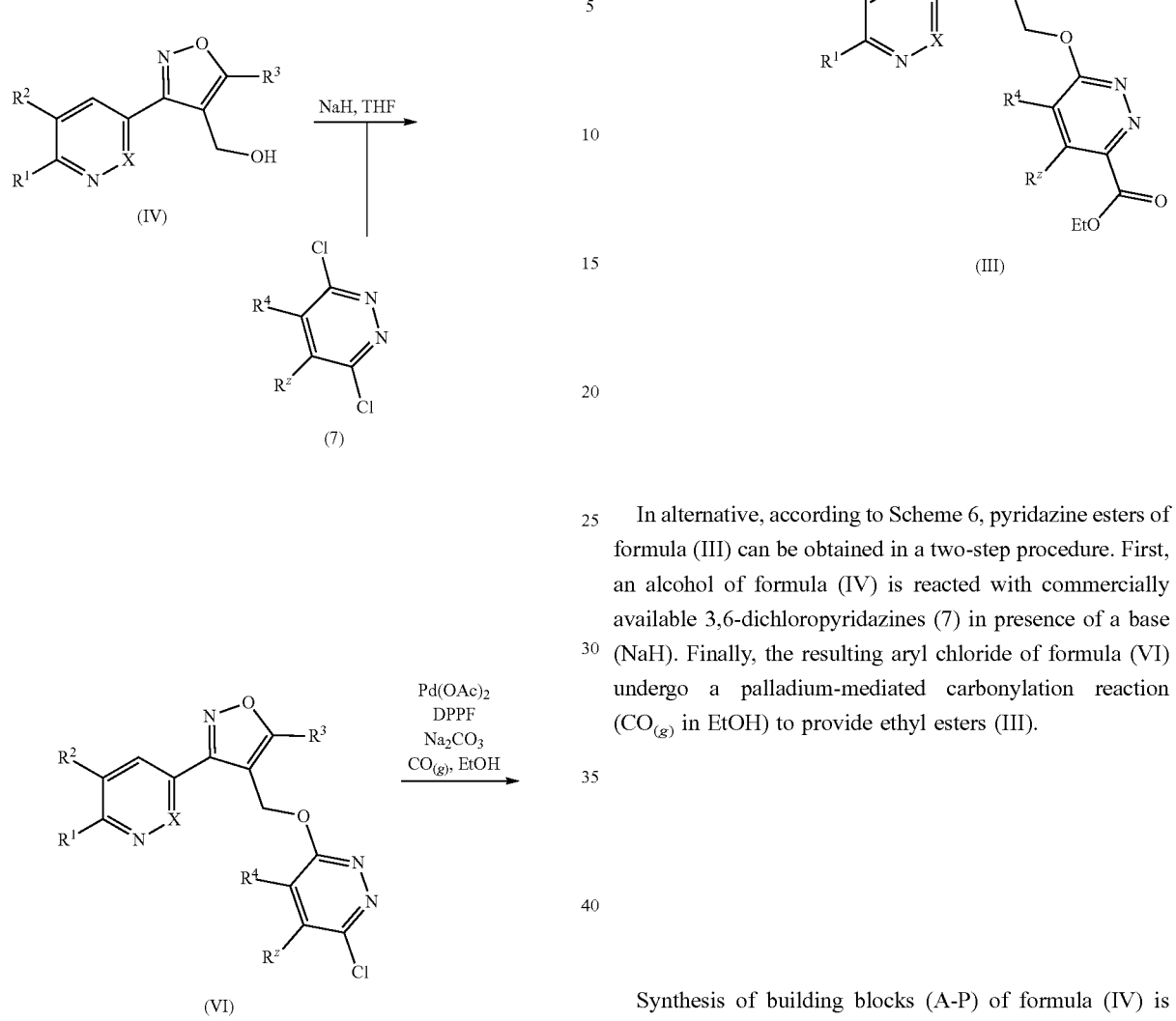

In alternative, according to Scheme 6, pyridazine esters of formula (III) can be obtained in a two-step procedure. First, an alcohol of formula (IV) is reacted with commercially available 3,6-dichloropyridazines (7) in presence of a base (NaH). Finally, the resulting aryl chloride of formula (VI) undergo a palladium-mediated carbonylation reaction ($CO_{(g)}$ in EtOH) to provide ethyl esters (III).

Synthesis of building blocks (A-P) of formula (IV) is highlighted in Scheme 7.

Scheme 7 synthesis of building blocks (A-P); wherein all definitions are as described above and in the claims

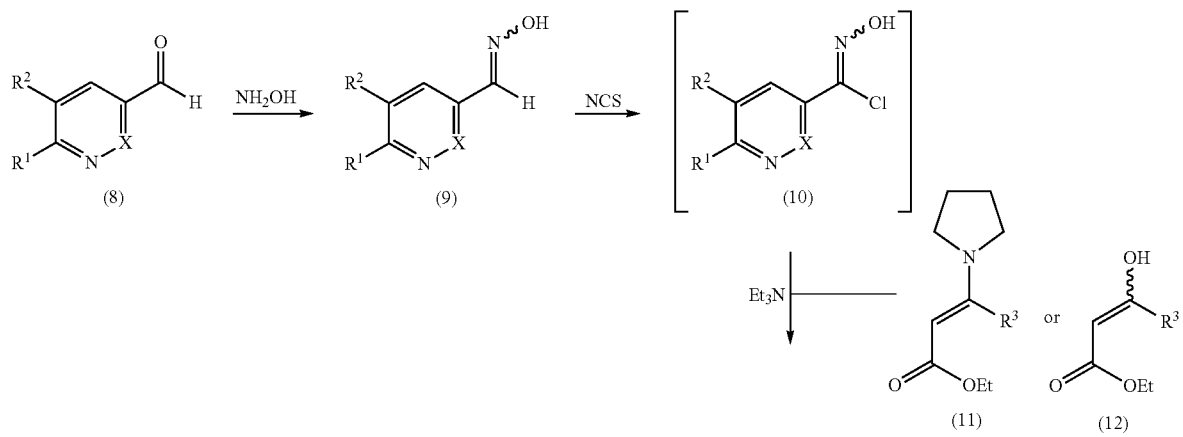

-continued

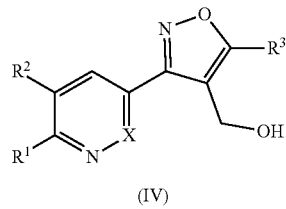
(IV)

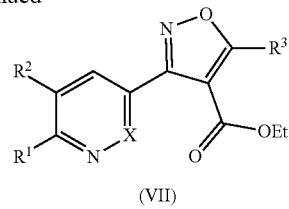
(VII)

LiAlH₄ or DIBAL-H hydrolysis | LiOH

ClC(O)OEt
Et₃N, NaBH₄

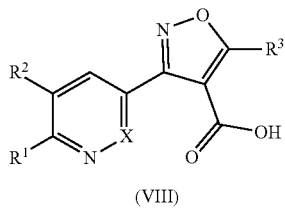
(VIII)

Commercially available aldehydes (8) are converted into corresponding oximes (9) by treatment with hydroxylamine hydrochloride in presence of a base (NaOH). Following electrophilic chlorination with N-chlorosuccinimide, the intermediate chloro-oximes (10), in presence of a base (Et₃N), undergo a 1,3-dipolar cycloaddition reaction with readily available enamines (11) or enols (12) to afford isoxazoles of formula (VII). Their final reduction with LiAlH₄ or DIBAL-H at controlled temperature provides the desired alcohols (IV). In alternative alcohols of formula (IV) can be obtained in a two-step synthetic route from ethyl esters (VII). Saponification reaction (LiOH, water) of ethyl esters (VII) to the corresponding carboxylates (VIII), followed by their reduction by treatment with ethyl chloroformate in presence of a base (Et₃N) and NaBH₄, provide building blocks (A-P) of formula (IV).

Also an embodiment of the present invention is a process to prepare a compound of formula (I) as defined above comprising
  i) the reaction of a compound of formula (II) with a compound of formula (III)

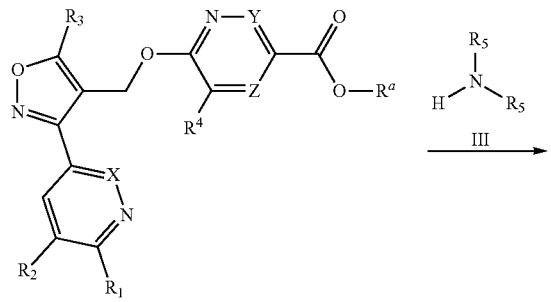

-continued

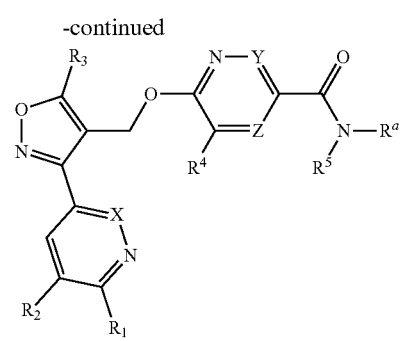
I or ii) the reaction of a compound of formula (IV) with a compound of formula (V)

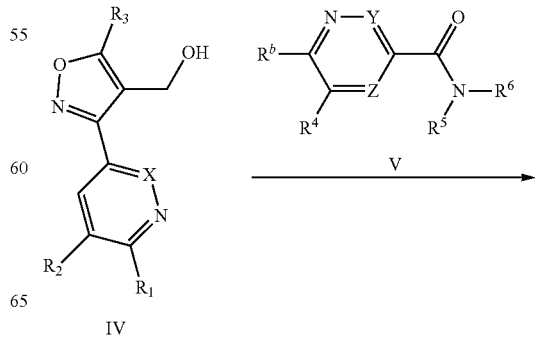

-continued

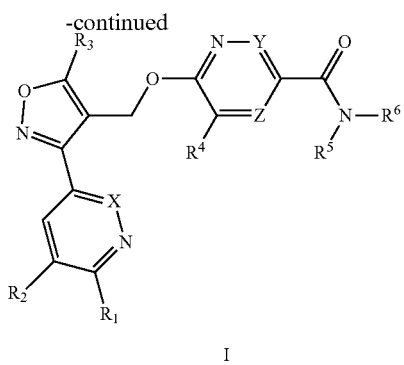

I wherein $R^1$, $R^2$, $R^3$, $R^4$, $R^5$, $R^6$, X, Y and Z are as defined herein and $R^a$ is $C_{1-6}$-alkyl and $R^b$ is bromo, chloro or iodo.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

A particular embodiment of the present invention is a compound according to formula (I) as described herein for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD).

The present invention also relates to the use of a compound according to formula (I) as described herein for the preparation of a medicament for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD).

Also an object of the invention is a method for the treatment or prophylaxis, more particularly the treatment, of Alzheimer's disease, mild cognitive impairment (MCI), age-related cognitive decline, negative and/or cognitive symptoms associated with schizophrenia, bipolar disorders, autism spectrum disorder (ASD), Angelman syndrome, Rett syndrome, Prader-Willi syndrome, epilepsy, post-traumatic stress disorder (PTSD), amyotrophic lateral sclerosis (ALS), fragile-X disorder, more particularly autism spectrum disorder (ASD), Angelman syndrome, Alzheimer's disease, negative and/or cognitive symptoms associated with schizophrenia and post-traumatic stress disorder (PTSD), which method comprises administering an effective amount of a compound according to formula (I) as described herein.

Also an embodiment of the present invention are compounds of formula (I) as described herein, when manufactured according to any one of the described processes.

Assay Procedures

Membrane Preparation and Binding Assay

The affinity of compounds at $GABA_A$ receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at 80° C.

Radioligand binding assays were carried out in a volume of 200 mL (96-well plates) which contained 100 mL of cell membranes, [$^3$H]-Flumazenil at a concentration of 1 nM for α1, α2, α3 subunits and 0.5 nM for α5 subunits and the test compound in the range of $10$-$10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. $K_i$ values were calculated using Excel-Fit (Microsoft) and are the means of two determinations.

The compounds of the accompanying examples were tested in the above described assay, and the preferred compounds were found to possess a $K_i$ value for displacement of [$^3$H]-Flumazenil from α5 subunits of the human $GABA_A$ receptor of 100 nM or less. Most preferred are compounds with a $K_i$ (nM)<35. In a preferred embodiment the compounds of the invention are binding selective for the α5 subunit relative to the α1, α2 and α3 subunit. Representative test results, obtained by the above described assay measuring binding affinity to HEK293 cells expressing human (h) receptors, are shown in the Table below.

Functional Expression of $GABA_A$ Receptors:

*Xenopus* Oocytes Preparation

*Xenopus laevis* oocytes at maturation stages V-VI were used for the expression of cloned mRNA encoding $GABA_A$ receptor subunits. Oocytes ready for RNA micro-injection were bought from Ecocyte, Castrop-Rauxel, Germany and stored in modified Barth's medium (composition in mM: NaCl 88, KCl 1, $NaHCO_3$ 2.4, HEPES 10, $MgSO_4$ 0.82, $CaNO_3$ 0.33, $CaCl_2$ 0.33, pH=7.5) at 20° C. until the experiment.

*Xenopus* Oocytes Microinjection

Oocytes were plated in 96-well plates to be used in an automated instrument (Robo-ocyte, MultiChannelSystems, Reutlingen, Germany) for microinjection and electrophysiological recordings. Approximately 50 nl of an aqueous solution containing the RNA transcripts for the subunits of the desired $GABA_A$ receptor was injected into each oocyte. RNA concentrations ranged between 0.3 and 16 ng/μl/subunit and were adjusted in pilot experiments to obtain GABA responses of a suitable size and a maximal effect of the reference modulator, Beta-CCM ((3-CCM), a betacarboline negative allosteric modulator (NAM) at the GABA$_A$ receptor benzodiazepine (BZD) binding site or Midazolam, a benzodiazepine positive allosteric modulator (PAM) at the GABA$_A$ receptor benzodiazepine (BZD) binding site. The concentration of the γ2 subunit encoding RNA usually was 5 to 10-fold higher than the RNAs encoding the other subunits. Oocytes were kept in modified Barth's medium (composition in mM: NaCl 88, KCl 1, NaHCO$_3$ 4, HEPES 10, MgSO$_4$ 0.82, CaNO$_3$ 0.33, CaCl$_2$ 0.33, pH=7.5) at 20° C. until the experiment.

Electrophysiology

Electrophysiological experiments were performed on days 3 to 5 after the micro-injection of mRNA. During the experiment the oocytes were constantly superfused by a solution containing (in mM) NaCl 90, KCl 1, HEPES 5, MgCl$_2$ 1, CaCl$_2$ 1 (pH 7.4). Oocytes were impaled by two glass microelectrodes (resistance: 0.4 MΩ) which were filled with a solution containing KCl 1M+K-acetate 1.5 M and voltage-clamped to −80 mV. The recordings were performed at room temperature using the Roboocyte two-electrode voltage clamp system (Multichannelsystem). After an initial equilibration period of 1.5 min GABA was added for 1.5 min at a concentration evoking approximately 20% of a maximal current response (EC$_{20}$). After another rest interval of 2.5 min GABA was again added evoking a response of similar amplitude and shape. 0.5 min after the onset of this second GABA application the test compound, at a concentration corresponding to approximately 30 fold its Ki, was added while GABA was still present. Current traces were recorded at a digitization rate of 10 Hz during and shortly before and after the GABA application.

Each compound and concentration was tested on at least 3 oocytes. Different oocytes were used for different compound concentrations. β-CCM, a negative allosteric modulator, or Midazolam, a positive allosteric modulators, were tested on a few (3-6) oocytes on each 96-well plate for a positive control at a maximally effective. β-CCM inhibited the GABA-evoked current by approximatively 50% (Fold increase~0.5), while Midazolam potentiated the GABA-induced current by approximatively 150% (Fold increase~2.5).

Data Analysis

For the analysis, the digitized current traces of the first and second GABA response were superimposed and, if necessary, rescaled to equal maximal amplitudes. The ratio between the two responses during the time interval of test compound application was calculated point by point. The extremum of the resulting "ratio trace" was taken as the efficacy ("Fold increase") of the compound expressed as "% modulation of GABA EC$_{20}$" (100*(Fold increase−1)). The results are shown in Table 1.

TABLE 1

| Example | Ki h-GABA-A α5β3γ2 (μM) | Fold increase h-GABA-A α5β3γ2 oocyte | Efficacy (GABA) % |
| --- | --- | --- | --- |
| 1 | 0.0048 | 1.42 | 42 |
| 2 | 0.0083 | 1.63 | 63 |
| 3 | 0.0014 | 1.41 | 41 |
| 4 | 0.0073 | 2.5 | 150 |
| 5 | 0.0586 | 3.45 | 245 |
| 6 | 0.0541 | 2.67 | 167 |
| 7 | 0.0256 | 2.02 | 102 |
| 8 | 0.0087 | 1.97 | 97 |
| 9 | 0.0137 | 1.62 | 62 |
| 10 | 0.0189 | 1.8 | 80 |

TABLE 1-continued

| Example | Ki h-GABA-A α5β3γ2 (μM) | Fold increase h-GABA-A α5β3γ2 oocyte | Efficacy (GABA) % |
| --- | --- | --- | --- |
| 11 | 0.0112 | 1.55 | 55 |
| 12 | 0.0163 | 1.74 | 74 |
| 13 | 0.0144 | 2.58 | 158 |
| 14 | 0.0745 | 2.6 | 160 |
| 15 | 0.0198 | 1.55 | 55 |
| 16 | 0.0192 | 1.85 | 85 |
| 17 | 0.0098 | 1.6 | 60 |
| 18 | 0.0102 | 1.59 | 59 |
| 19 | 0.0052 | 1.77 | 77 |
| 20 | 0.0118 | 1.95 | 95 |
| 21 | 0.0054 | 2.19 | 119 |
| 22 | 0.0108 | 1.44 | 44 |
| 23 | 0.0204 | 1.89 | 89 |
| 24 | 0.0416 | 1.63 | 63 |
| 25 | 0.0094 | 1.59 | 59 |
| 26 | 0.0052 | 1.8 | 80 |
| 27 | 0.0123 | 1.54 | 54 |
| 28 | 0.008 | 1.52 | 52 |
| 29 | 0.008 | 1.81 | 81 |
| 30 | 0.0124 | 1.94 | 94 |
| 31 | 0.0142 | 2.02 | 102 |
| 32 | 0.0085 | 1.79 | 79 |
| 33 | 0.0116 | 1.76 | 76 |
| 34 | 0.0132 | 1.84 | 84 |
| 35 | 0.0044 | 1.82 | 82 |
| 36 | 0.0058 | 1.65 | 65 |
| 37 | 0.0076 | 1.73 | 73 |
| 38 | 0.0075 | 1.84 | 84 |
| 39 | 0.0146 | 1.89 | 89 |
| 40 | 0.0106 | 1.91 | 91 |
| 41 | 0.0194 | 2.04 | 104 |
| 42 | 0.0089 | 1.81 | 81 |
| 43 | 0.0164 | 1.82 | 82 |
| 44 | 0.0761 | 1.54 | 54 |
| 45 | 0.0066 | 1.84 | 84 |
| 46 | 0.0035 | 1.63 | 63 |
| 47 | 0.013 | 1.68 | 68 |
| 48 | 0.0316 | 1.74 | 74 |
| 49 | 0.0136 | 1.7 | 70 |
| 50 | 0.0076 | 1.72 | 72 |
| 51 | 0.0108 | 1.57 | 57 |
| 52 | 0.0289 | 1.67 | 67 |
| 53 | 0.0958 | 1.8 | 80 |
| 54 | 0.0199 | 1.86 | 86 |
| 55 | 0.0086 | 1.57 | 57 |
| 56 | 0.0079 | 1.64 | 64 |
| 57 | 0.0072 | 1.64 | 64 |
| 58 | 0.0161 | 1.71 | 71 |
| 59 | 0.0104 | 1.93 | 93 |
| 60 | 0.0934 | 1.99 | 99 |
| 61 | 0.0071 | 1.58 | 58 |
| 62 | 0.0208 | 1.42 | 42 |
| 63 | 0.0046 | 1.79 | 79 |
| 64 | 0.0176 | 1.86 | 86 |
| 65 | 0.0072 | 1.62 | 62 |
| 66 | 0.0058 | 1.69 | 69 |
| 67 | 0.0118 | 1.59 | 59 |
| 68 | 0.0562 | 1.72 | 72 |
| 69 | 0.0077 | 1.86 | 86 |
| 70 | 0.0012 | 1.54 | 54 |
| 71 | 0.0024 | 1.61 | 61 |
| 72 | 0.0114 | 2.3 | 130 |
| 73 | 0.0528 | 1.45 | 45 |
| 74 | 0.0092 | 1.28 | 28 |
| 75 | 0.0174 | 1.89 | 89 |
| 76 | 0.009 | 1.92 | 92 |
| 77 | 0.0052 | 1.11 | 11 |
| 78 | 0.0243 | 1.42 | 42 |
| 79 | 0.0113 | 1.96 | 96 |
| 80 | 0.0132 | 2.08 | 108 |
| 81 | 0.0104 | 1.8 | 80 |
| 82 | 0.0124 | 2.01 | 101 |
| 83 | 0.005 | 1.96 | 96 |
| 84 | 0.019 | 1.54 | 54 |
| 85 | 0.0063 | 1.76 | 76 |

TABLE 1-continued
| Example | Ki h-GABA-A α5β3γ2 (μM) | Fold increase h-GABA-A α5β3γ2 oocyte | Efficacy (GABA) % |
|---|---|---|---|
| 86 | 0.017 | 2.2 | 120 |
| 87 | 0.0081 | 1.8 | 80 |
| 88 | 0.0409 | 1.68 | 68 |
| 89 | 0.0131 | 1.31 | 31 |
| 90 | 0.0167 | 1.37 | 37 |
| 91 | 0.0055 | 2.4 | 140 |
| 92 | 0.0132 | 1.67 | 67 |
| 93 | 0.0062 | 1.35 | 35 |
| 94 | 0.01 | 1.92 | 92 |
| 95 | 0.0134 | 1.67 | 67 |
| 96 | 0.0072 | 1.88 | 88 |
| 97 | 0.0136 | 1.71 | 71 |
| 98 | 0.0622 | 1.76 | 76 |
| 99 | 0.0068 | 1.73 | 73 |
| 100 | 0.0085 | 1.7 | 70 |
| 101 | 0.0506 | 1.82 | 82 |
| 102 | 0.0207 | 1.21 | 21 |
| 103 | 0.079 | 1.81 | 81 |
| 104 | 0.0663 | 1.43 | 43 |
| 105 | 0.0227 | 2.01 | 101 |
| 106 | 0.0603 | 1.64 | 64 |
| 107 | 0.0096 | 1.69 | 69 |
| 108 | 0.0004 | 1.2 | 20 |
| 109 | 0.0008 | 1.42 | 42 |
| 110 | 0.0155 | 1.65 | 65 |
| 111 | 0.0046 | 1.89 | 89 |
| 112 | 0.0065 | 1.43 | 43 |
| 113 | 0.0338 | 1.28 | 28 |
| 114 | 0.0281 | 1.74 | 74 |
| 115 | 0.0516 | 2.39 | 139 |
| 116 | 0.0049 | 1.59 | 59 |
| 117 | 0.0156 | 1.99 | 99 |
| 118 | 0.0123 | 1.88 | 88 |
| 119 | 0.031 | 2.02 | 102 |
| 120 | 0.0521 | 2.6 | 160 |
| 121 | 0.0403 | 2.09 | 109 |
| 122 | 0.0264 | 2.26 | 126 |
| 123 | 0.0221 | 2.06 | 106 |
| 124 | 0.0366 | 1.47 | 47 |
| 125 | 0.059 | 2.42 | 142 |
| 126 | 0.0498 | 1.49 | 49 |
| 127 | 0.0228 | 1.5 | 50 |
| 128 | 0.0061 | 2.07 | 107 |
| 129 | 0.0256 | 2.56 | 156 |
| 130 | 0.0304 | 2.28 | 128 |
| 131 | 0.026 | 1.51 | 51 |
| 132 | 0.0377 | 1.64 | 64 |
| 133 | 0.0431 | 1.95 | 95 |
| 134 | 0.0208 | 1.66 | 66 |
| 135 | 0.0304 | 1.92 | 92 |
| 136 | 0.0148 | 1.54 | 54 |
| 137 | 0.0254 | 1.55 | 55 |
| 138 | 0.0938 | 1.46 | 46 |
| 139 | 0.0194 | 2.52 | 152 |
| 140 | 0.056 | 1.13 | 13 |
| 141 | 0.0495 | 3.43 | 243 |
| 142 | 0.0047 | 1.44 | 44 |
| 143 | 0.0145 | 1.2 | 20 |
| 144 | 0.0136 | 1.15 | 15 |
| 145 | 0.029 | 2.44 | 144 |
| 146 | 0.01 | 1.78 | 78 |
| 147 | 0.0096 | 1.48 | 48 |
| 148 | 0.0138 | 1.77 | 77 |
| 149 | 0.005 | 1.37 | 37 |
| 150 | 0.0167 | 1.69 | 69 |
| 151 | 0.0458 | 1.68 | 68 |
| 152 | 0.0053 | 1.85 | 85 |
| 153 | 0.0055 | 1.84 | 84 |
| 154 | 0.01 | 1.97 | 97 |
| 155 | 0.0154 | 1.46 | 46 |
| 156 | 0.0078 | 1.98 | 98 |
| 157 | 0.006 | 1.76 | 76 |
| 158 | 0.0182 | 1.79 | 79 |
| 159 | 0.0237 | 1.55 | 55 |
| 160 | 0.0093 | 1.42 | 42 |
| 161 | 0.008 | 1.6 | 60 |
| 162 | 0.0112 | 1.37 | 37 |
| 163 | 0.0086 | 1.98 | 98 |
| 164 | 0.0115 | 1.95 | 95 |
| 165 | 0.0026 | 2.74 | 174 |
| 166 | 0.0076 | 1.7 | 70 |
| 167 | 0.0191 | 1.64 | 64 |
| 168 | 0.0324 | 2.02 | 102 |
| 169 | 0.0189 | 1.66 | 66 |
| 170 | 0.0088 | 1.6 | 60 |
| 171 | 0.0181 | 1.72 | 72 |
| 172 | 0.0088 | 1.65 | 65 |
| 173 | 0.0156 | 1.68 | 68 |
| 174 | 0.0088 | 1.55 | 55 |
| 175 | 0.0101 | 1.82 | 82 |
| 176 | 0.0127 | 1.64 | 64 |
| 177 | 0.0397 | 2.09 | 109 |
| 178 | 0.0429 | 1.73 | 73 |
| 179 | 0.043 | 1.82 | 82 |
| 180 | 0.0326 | 2.73 | 173 |
| 181 | 0.068 | 2.47 | 147 |
| 182 | 0.0596 | 2.41 | 141 |
| 183 | 0.0567 | 3.13 | 213 |
| 184 | 0.0512 | 1.96 | 96 |
| 185 | 0.0707 | 2.24 | 124 |
| 186 | 0.0166 | 1.72 | 72 |
| 187 | 0.0148 | 1.88 | 88 |
| 188 | 0.0207 | 1.71 | 71 |
| 189 | 0.0188 | 1.86 | 86 |
| 190 | 0.0127 | 1.63 | 63 |
| 191 | 0.0112 | 1.6 | 60 |
| 192 | 0.003 | 1.56 | 56 |
| 193 | 0.001 | 1.64 | 64 |
| 194 | 0.0133 | 1.84 | 84 |
| 195 | 0.0173 | 1.78 | 78 |
WO2009/071476 discloses reference compounds RO-159 as example 159, RO-251 as example 251, RO-272 as example 272 and RO-301 as example 301.
WO2009/071477 discloses reference compound RO-094 as example 94.
Reference examples RE-A and RE-B have been prepared as described herein.
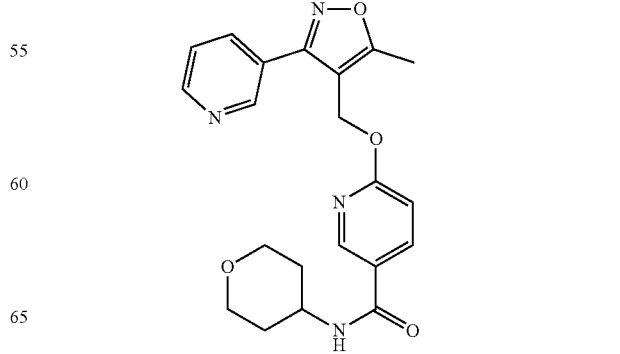
RO-159

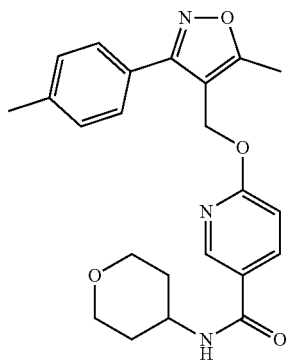

RO-251

RO-301

RO-094

RE-A

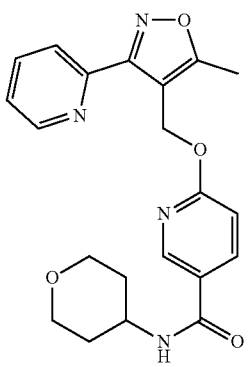

RO-272

RE-B

The reference compounds were also tested for their affinity towards the GABA$_A$ receptor α5β3γ2 subtypes as well as for their efficacy in GABA$_A$ α5β3γ2 overexpressing oocytes. The results are shown in Table 2.

TABLE 2

| Example | Ki α5-human (μM) | Fold increase h-GABA-A α5β3γ2 oocyte | Efficacy (GABA) % |
|---|---|---|---|
| RO-159 | 0.028 | 0.88 | −12% |
| RO-251 | 0.001 | 0.82 | −18% |
| RO-272 | 0.001 | 0.68 | −32% |
| RO-301 | 0.0002 | 0.82 | −18% |
| RO-094 | 0.0029 | 0.82 | −18% |
| RE-A | 0.065 | 0.97 | −3% |
| RE-B | 0.0004 | 1.03 | +3% |

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Preparation of Pharmaceutical Compositions Comprising Compounds of the Invention:

Tablets of the following composition are manufactured in the usual manner:

|  | mg/tablet | | | |
|---|---|---|---|---|
| Ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

|  | mg/capsule | | | |
|---|---|---|---|---|
| ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoapproximatively. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

Building Block A (5-methyl-3-(6-methylpyridin-3-yl)isoxazol-4-yl)methanol

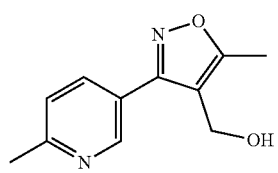

a) (3E)-6-methylpyridine-3-carbaldehyde Oxime

To a solution of 6-methylnicotinaldehyde (9.86 g, 77.3 mmol) in methanol (35 mL) was added under nitrogen hydroxylamine (50 wt. % in water, 5.93 mL, 101 mmol). The resulting suspension was stirred for 3 hours at 40° C. and for 20 hours at room temperature. Concentration by rotary evaporation under reduced pressure afforded the title compound (10.89 g, 98%) as an off-white solid. MS (ESI): 137.0 ([M+H]$^+$).

b) ethyl 5-methyl-3-(6-methylpyridin-3-yl)isoxazole-4-carboxylate

To a solution of (E)-6-methylnicotinaldehyde oxime (10.89 g, 80.0 mmol) in DMF (95 mL) at 6° C. was added N-chlorosuccinimide (11.7 g, 88.0 mmol). Upon addition, the color of the reaction mixture changed from yellow to orange and the reaction was allowed to warm to room temperature. After 1 hour, the mixture was heated to 50° C. for 2 hours. The resulting brown suspension was re-cooled to 6° C. then (E)-ethyl 3-(pyrrolidin-1-yl)but-2-enoate (17.6 g, 96.0 mmol) was added and the reaction mixture was stirred at 50° C. overnight. After cooling to room temperature, water (95 mL) was added dropwise and the resulting brown suspension was filtered through a sintered funnel. The residue was washed with water then dried at high vacuum to afford the title compound (11.80 g, 60%) as a brown solid. MS (ESI): 247.1 ([M+H]$^+$).

c) (5-methyl-3-(6-methylpyridin-3-yl)isoxazol-4-yl)methanol

To a solution of ethyl 5-methyl-3-(6-methylpyridin-3-yl)isoxazole-4-carboxylate (11.8 g, 47.9 mmol) in THF (160 mL) at 2° C. was added under nitrogen over a period of 20 min LiAlH$_4$ (2.55 g, 67.1 mmol). After stirring at 4° C. for 1.5 hours, water (2.61 mL) was carefully added and the mixture was stirred for further 50 min before being quenched by addition of aqueous NaOH (15 wt. %, 2.61 mL). The reaction mixture was stirred for 30 min at room temperature before addition of water (7.8 mL). After stirring for 1 hour, the resulting suspension was filtered through a sintered funnel and the residue was washed with THF (20 mL) to afford the title compound (9.08 g, 93%) as an orange solid. MS (ESI): 205.1 ([M+H]$^+$).

Building Block B (5-ethyl-3-(6-methylpyridin-3-yl)isoxazol-4-yl)methanol

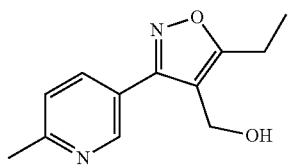 [SMILES: CCc1onc(-c2ccc(C)nc2)c1CO]

a) ethyl 5-ethyl-3-(6-methylpyridin-3-yl)isoxazole-4-carboxylate

In analogy to experiment of building block A b, (E)-6-methylnicotinaldehyde oxime, using ethyl 3-(pyrrolidin-1-yl)pent-2-enoate instead of (E)-ethyl 3-(pyrrolidin-1-yl)but-2-enoate, was converted into the title compound (1.81 g, 63%) which was obtained as a yellow oil. MS (ESI): 261.3 ([M+H]$^+$).

b) (5-ethyl-3-(6-methylpyridin-3-yl)isoxazol-4-yl)methanol

In analogy to experiment of building block A c, ethyl 5-ethyl-3-(6-methylpyridin-3-yl)isoxazole-4-carboxylate instead of ethyl 5-methyl-3-(6-methylpyridin-3-yl)isoxazole-4-carboxylate was converted into the title compound (1.44 g, 95%) which was obtained as an orange solid. MS (ESI): 219.2 ([M+H]$^+$).

Building Block C (5-(fluoromethyl)-3-(6-methylpyridin-3-yl)isoxazol-4-yl)methanol

a) ethyl 4-fluoro-3-oxo-butanoate

To a stirred solution of ethyl acetate (9.59 g, 10.7 mL, 109 mmol) in anhydrous Et$_2$O (100 mL) under argon at −78° C. (CO$_2$-acetone bath) was added over 30 min LDA (2.0 m solution in cyclohexane/ethylbenzene/THF, 59 mL, 118 mmol). The reaction mixture was stirred for 2 hours at −78° C. then ethyl 2-fluoroacetate (10.5 g, 9.62 mL, 99 mmol) was added over 15 min. The CO2-Acetone bath was removed and the reaction was allowed to warm to room temperature and stirred overnight. The reaction was slowly poured into cold aqueous HCl (10 wt. %, 100 mL) and extracted with Et$_2$O (3×50 mL). The combined organic extracts were washed with brine (30 mL), dried (Na$_2$SO$_4$), filtered and evaporated at 35° C. by rotary evaporation under reduced pressure (650 mbar-200 mbar). The resulting colourless liquid was purified by distillation at reduced pressure using a 30 cm Vigreux column. Fractions collected at 13 mbar at 71° C. (vapor temperature) afforded the title compound (12.67 g, 86.4%) as a colourless liquid. MS (ESI): 149.1 ([M+H]$^+$).

b) ethyl 5-(fluoromethyl)-3-(6-methylpyridin-3-yl)isoxazole-4-carboxylate

To a stirred solution of (E)-6-methylnicotinaldehyde oxime (1.00 g, 7.34 mmol) in anhydrous THF (6.7 mL) at 6° C. was added N-chlorosuccinimide (1.10 g, 8.08 mmol). After 30 min, the mixture was heated to 50° C. for 1 hour then all the solvent was removed under reduced pressure. The resulting residue (chloro-oxime) was dissolved in EtOH (6.7 mL) and stirred at room temperature for 30 min. In a separate flask, Et$_3$N (2.05 mL, 14.7 mmol) was added to a solution of ethyl 4-fluoro-3-oxobutanoate (1.65 g, 7.34 mmol) in THF (6.6 mL) and the resulting suspension was stirred at room temperature. After 30 min, the suspension was cooled to 0° C. and the previously prepared suspension of chloro-oxime in EtOH was slowly added via cannula. The resulting yellow suspension was stirred for 3 hours at room temperature. The reaction was diluted with EtOAc (100 mL) and the organic phase washed with water and brine, dried (Na$_2$SO$_4$) and concentrated in vacuo. Purification by flash chromatography (silica, gradient: 0% to 50% EtOAc in heptane) afforded the title compound (1.1 g, 57%) as a white solid. MS (ESI): 265.2 ([M+H]$^+$).

c) (5-(fluoromethyl)-3-(6-methylpyridin-3-yl)isoxazol-4-yl)methanol

To a stirred suspension of ethyl 5-(fluoromethyl)-3-(6-methylpyridin-3-yl)isoxazole-4-carboxylate (404 mg, 1.53 mmol) in anhydrous toluene (4 mL) at −78° C. was added dropwise DIBAL-H (1.0 m in toluene, 1.84 mL, 1.84 mmol). The reaction was stirred at −78° C. for 30 min before being quenched by the addition of EtOAc (0.5 mL). After 15 min, the reaction was allowed to warm to 0° C. and saturated aqueous $NaHCO_3$ (5 mL) was added. The mixture was stirred vigorously for 20 min then diluted with EtOAc (30 mL) and the organic phase washed with brine, dried ($Na_2SO_4$) and concentrated in vacuo. Purification by flash chromatography (silica, gradient: 0% to 100% EtOAc in heptane) afforded the title compound (193 mg, 57%) as a white solid. MS (ESI): 223.2 ([M+H]$^+$).

Building Block D

(5-cyclopropyl-3-(6-methyl-3-pyridyl)isoxazol-4-yl)methanol

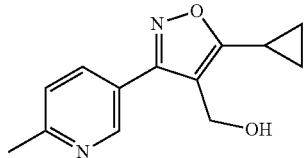 [SMILES: Cc1ccc(-c2noc(C3CC3)c2CO)cn1]

a) ethyl 5-cyclopropyl-3-(6-methylpyridin-3-yl)isoxazole-4-carboxylate

In analogy to experiment of building block A b, (E)-6-methylnicotinaldehyde oxime, using (Z)-ethyl 3-cyclopropyl-3-(pyrrolidin-1-yl)acrylate instead of (E)-ethyl 3-(pyrrolidin-1-yl)but-2-enoate, was converted into the title compound (0.215 g, 43%) which was obtained as a yellow oil. MS (ESI): 273.2 ([M+H]$^+$).

b) (5-cyclopropyl-3-(6-methyl-3-pyridyl)isoxazol-4-yl)methanol

In analogy to experiment of building block A c, ethyl 5-cyclopropyl-3-(6-methylpyridin-3-yl)isoxazole-4-carboxylate instead of ethyl 5-methyl-3-(6-methylpyridin-3-yl)isoxazole-4-carboxylate was converted into the title compound (0.52 g, 83%) which was obtained as a yellow solid. MS (ESI): 231.2 ([M+H]$^+$).

Building Block E

(5-methyl-3-(6-(trifluoromethyl)-3-pyridyl)isoxazol-4-yl)methanol

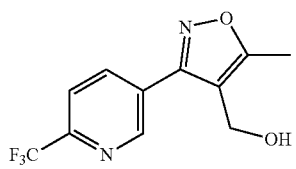 [SMILES: Cc1onc(-c2ccc(C(F)(F)F)nc2)c1CO]

a) (3E)-6-(trifluoromethyl)pyridine-3-carbaldehyde Oxime

In analogy to experiment of building block A a, 6-(trifluoromethyl)pyridine-3-carboxaldehyde instead of 6-methylnicotinaldehyde was converted into the title compound (10.94 g, 96%) which was obtained as a light yellow solid. MS (ESI): 191.1 ([M+H]$^+$).

b) ethyl 5-methyl-3-(6-(trifluoromethyl)-3-pyridyl)isoxazole-4-carboxylate

In analogy to experiment of building block A b, (E)-ethyl 3-(pyrrolidin-1-yl)but-2-enoate, using (3E)-6-(trifluoromethyl)pyridine-3-carbaldehyde oxime instead of (E)-6-methylnicotinaldehyde oxime, was converted into the title compound (7.95 g, 96%) which was obtained as a yellow solid. MS (ESI): 301.1 ([M+H]$^+$).

c) 5-methyl-3-(6-(trifluoromethyl)-3-pyridyl)isoxazole-4-carboxylic Acid

To a stirred solution of ethyl 5-methyl-3-(6-(trifluoromethyl)pyridin-3-yl)isoxazole-4-carboxylate (5.91 g, 19.7 mmol) in a mixture of THF (21 mL), MeOH (21 mL) and water (21 mL) at 0° C. was added LiOH.$H_2O$ monohydrate (2.03 g, 48.4 mmol). The ice bath was removed and the reaction mixture was stirred at room temperature for 2.5 hours. The reaction mixture was re-cooled to 0° C. then acidified with aqueous citric acid (5 wt. %) to pH-5 (a precipitate was formed). The organic solvents were removed by rotary evaporation under reduced pressure. The resulting aqueous suspension was cooled to 0° C. then filtered on a sintered funnel. The collected solid was rinsed with ice cold water (50 mL) and dried under high vacuum to afford the title compound (4.88 g, 91% yield) as a light yellow solid. MS (ESI): 273.1 ([M+H]$^+$).

d) (5-methyl-3-(6-(trifluoromethyl)-3-pyridyl)isoxazol-4-yl)methanol

In analogy to experiment of building block H c, 5-methyl-3-(6-(trifluoromethyl)-3-pyridyl)isoxazole-4-carboxylic acid instead of 3-(6-methyl-3-pyridyl)isoxazole-4-carboxylic acid was converted into the title compound (3.87 g, 84%) which was obtained as a light yellow solid. MS (ESI): 259.1 ([M+H]$^+$).

Building Block F

(3-(6-chloro-3-pyridyl)-5-methyl-isoxazol-4-yl)methanol

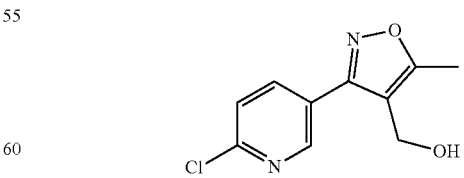

a) (E)-6-chloronicotinaldehyde Oxime

To a solution of 6-chloronicotinaldehyde (100 mg, 0.706 mmol) in acetonitrile (1 mL) were added hydroxylamine hydrochloride (73.6 mg, 1.06 mmol) and potassium phosphate tribasic (75 mg, 0.353 mmol). The mixture was stirred at room temperature for 30 min before addition of water (0.2 mL). After 1 hour, the resulting suspension was diluted with water (5 mL) and the solid was collected through filtration on a sintered funnel then dried in vacuo to afford the title compound (57 mg, 51%) as a white solid. MS (ESI): 157.0 ([M+H]$^+$).

b) ethyl 3-(6-chloropyridin-3-yl)-5-methylisoxazole-4-carboxylate

In analogy to experiment of building block A b, (E)-ethyl 3-(pyrrolidin-1-yl)but-2-enoate, using (E)-6-chloronicotinaldehyde oxime instead of (E)-6-methylnicotinaldehyde oxime, was converted into the title compound (92 mg, 78%) which was obtained as a white solid. MS (ESI): 267.1 ([M+H]$^+$).

c) (3-(6-chloropyridin-3-yl)-5-methylisoxazol-4-yl)methanol

To a stirred solution of ethyl 3-(6-chloropyridin-3-yl)-5-methylisoxazole-4-carboxylate (77 mg, 0.289 mmol) in anhydrous THF (2 mL) at 0° C. was added dropwise DIBAL-H (1.0 m in hexane, 0.924 mL, 0.924 mmol). The resulting light yellow solution was allowed to warm to room temperature and stirred for 4.5 hours before being re-cooled to 0° C. (ice bath) and quenched by addition of aqueous Na/K tartrate (10 wt. %, 7 mL). The mixture was vigorously stirred at room temperature (ice bath removed) for 30 min then diluted with EtOAc (10 mL). Upon addition of aqueous NH$_4$Cl (20 wt. %, 3 mL) and aqueous HCl (1.0 m, 1 mL) the aqueous layer was separated and extracted with EtOAc (2×15 mL). The combined organic extracts were dried (Na$_2$SO$_4$), filtered and concentrated in vacuo. Purification by flash chromatography (silica, gradient: 0% to 100% EtOAc in heptane) afforded the title compound (48 mg, 74%) as a white solid. MS (ESI): 225.0 ([M+H]$^+$).

Building Block G (3-(6-chloro-3-pyridyl)-5-cyclopropyl-isoxazol-4-yl)methanol

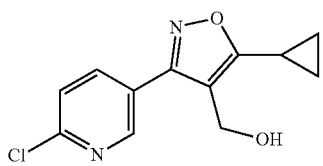 [SMILES: OCc1c(-c2ccc(Cl)nc2)noc1C1CC1]

a) ethyl 3-(6-chloropyridin-3-yl)-5-cyclopropylisoxazole-4-carboxylate

In analogy to experiment of building block A b, (E)-6-chloronicotinaldehyde oxime, using (Z)-ethyl 3-cyclopropyl-3-(pyrrolidin-1-yl)acrylate instead of (E)-ethyl 3-(pyrrolidin-1-yl)but-2-enoate, was converted into the title compound (317 mg, 85%) which was obtained as a light yellow solid. MS (ESI): 293.1 ([M+H]$^+$).

b) (3-(6-chloro-3-pyridyl)-5-cyclopropyl-isoxazol-4-yl)methanol

In analogy to experiment of building block F c, ethyl 3-(6-chloropyridin-3-yl)-5-cyclopropylisoxazole-4-carboxylate instead of ethyl 3-(6-chloropyridin-3-yl)-5-methylisoxazole-4-carboxylate was converted into the title compound (177 mg, 82%) which was obtained as a light yellow solid. MS (ESI): 251.1 ([M+H]$^+$).

Building Block H (3-(6-methyl-3-pyridyl)isoxazol-4-yl)methanol

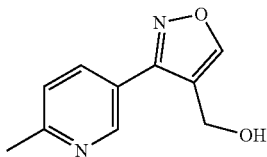

a) ethyl 3-(6-methyl-3-pyridyl)isoxazole-4-carboxylate

In analogy to experiment of building block A b, (E)-6-methylnicotinaldehyde oxime, using ethyl (E)-3-(dimethylamino)prop-2-enoate instead of (E)-ethyl 3-(pyrrolidin-1-yl)but-2-enoate, was converted into the title compound (2.45 g, 57%) which was obtained as a light brown oil. MS (ESI): 233.1 ([M+H]$^+$).

b) 3-(6-methyl-3-pyridyl)isoxazole-4-carboxylic Acid

In analogy to experiment of building block E c, ethyl 3-(6-methyl-3-pyridyl)isoxazole-4-carboxylate instead of ethyl 5-methyl-3-(6-(trifluoromethyl)pyridin-3-yl)isoxazole-4-carboxylate was converted into the title compound (1.48 g, 70%) which was obtained as an off white solid. MS (ESI): 205.0 ([M+H]$^+$).

c) (3-(6-methyl-3-pyridyl)isoxazol-4-yl)methanol

To a stirred suspension of 3-(6-methyl-3-pyridyl)isoxazole-4-carboxylic acid (1.48 g, 7.25 mmol) in anhydrous THF (24 mL) was added triethylamine (1.1 mL, 7.9 mmol). The resulting solution was cooled to −15° C. (NaCl/ice bath) before a solution of ethyl chloroformate (0.73 mL, 7.6 mmol) in THF (4 mL) was added dropwise. After 2 hours, the resulting white precipitate was filtered through a sintered funnel and the collected solid rinsed with a minimal amount of THF. The filtrate was re-cooled to −15° C. (NaCl/ice bath) and a solution of NaBH$_4$ (686 mg, 18.1 mmol) in water (16 mL) was added dropwise. Upon addition, the reaction mixture was allowed to warm to room temperature and stirred for 3 hours. A further amount of NaBH$_4$ (137 mg, 3.62 mmol) was added and the mixture was stirred at room temperature for 1 hour. The reaction was quenched by the addition of aqueous NaOH (2.0 m, 30 mL) then extracted with EtOAc (2×160 mL). The combined organic extracts were dried (Na$_2$SO$_4$) and concentrated in vacuo. Purification by flash chromatography (silica, gradient: 0% to 100%

EtOAc in heptane) afforded the title compound (606 mg, 44%) as an off-white solid. MS (ESI): 191.1 ([M+H]⁺).

Building Block I (5-methyl-3-(6-methylpyridazin-3-yl)isoxazol-4-yl)methanol

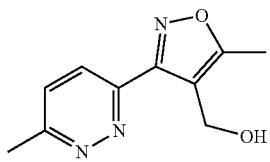

a) (E)-6-methylpyridazine-3-carbaldehyde Oxime

To a stirred solution of 6-methylpyridazine-3-carbaldehyde (880 mg, 7.21 mmol) in EtOH (1.25 mL) were added hydroxylamine hydrochloride (551 mg, 7.93 mmol) followed by aqueous NaOH (2.0 m, 9.2 mL, 18.4 mmol). The reaction mixture was stirred at room temperature for 3 hours then treated with acetic acid to 5. The resulting precipitate was collected by filtration and dried at high vacuum to afford the title compound (943 mg, 95%) as an off-white solid. MS (ESI): 138.1 ([M+H]⁺).

b) ethyl 5-methyl-3-(6-methylpyridazin-3-yl)isoxazole-4-carboxylate

In analogy to experiment of building block A b, (E)-6-methylpyridazine-3-carbaldehyde oxime instead of (E)-6-methylnicotinaldehyde oxime was converted into the title compound (1.15 g, 67%) which was obtained as a brown oil. MS (ESI): 248.1 ([M+H]⁺).

c) (5-methyl-3-(6-methylpyridazin-3-yl)isoxazol-4-yl)methanol

To a stirred suspension of calcium chloride (1.8 g, 16.2 mmol) in a mixture of anhydrous THF (50 mL) and EtOH (33 mL) at 0° C. were added ethyl 5-methyl-3-(6-methylpyridazin-3-yl)isoxazole-4-carboxylate (1.0 g, 4.04 mmol) followed by NaBH₄ (1.22 g, 32.4 mmol, portion-wise addition). The mixture was stirred at 0° C. for 30 min then allowed to warm to room temperature and stirred for further 1 hour. The reaction mixture was re-cooled to 0° C. and quenched by addition of saturated aqueous NH₄Cl. The organic solvents were removed by rotary evaporation under reduced pressure and the resulting aqueous layer was extracted with CH₂Cl₂ (2×50 mL). The combined organic extracts were washed with brine, dried (MgSO4) and concentrated in vacuo. Purification by flash chromatography (silica, gradient: 20% to 100% EtOAc in heptane) afforded the title compound (407 mg, 49%) as a yellow solid. MS (ESI): 206.1 ([M+H]⁺).

Building Block J (5-(difluoromethyl)-3-(6-methyl-3-pyridyl)isoxazol-4-yl)methanol

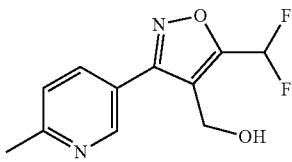 [SMILES: Cc1ccc(-c2noc(C(F)F)c2CO)cn1]

a) (Z)-4,4-difluoro-3-pyrrolidin-1-yl-but-2-enoate

To a stirred solution of ethyl 4,4-difluoro-3-oxobutanoate (1.6 mL, 15.5 mmol) in cyclohexane (11 mL) was added pyrrolidine (1.4 mL, 16.9 mmol). The reaction was heated to 110° C. overnight using a Dean-Stark trap before being cooled to room temperature. The reaction mixture was filtered directly through a pad of Na₂SO₄ and the filtrate concentrated in vacuo to afford the title compound (2.49 g, 62%) as a brown oil. MS (ESI): 220.2 ([M+H]⁺).

b) ethyl 5-(difluoromethyl)-3-(6-methyl-3-pyridyl)isoxazole-4-carboxylate

In analogy to experiment of building block A b, (3E)-6-methylpyridine-3-carbaldehyde oxime, using ethyl (Z)-4,4-difluoro-3-pyrrolidin-1-yl-but-2-enoate instead of (E)-ethyl 3-(pyrrolidin-1-yl)but-2-enoate, was converted into the title compound (362 mg, 58%) which was obtained as an orange oil. MS (ESI): 283.2 ([M+H]⁺).

c) (5-(difluoromethyl)-3-(6-methyl-3-pyridyl)isoxazol-4-yl)methanol

To a stirred solution of ethyl 5-(difluoromethyl)-3-(6-methylpyridin-3-yl)isoxazole-4-carboxylate (0.490 g, 1.56 mmol) in anhydrous toluene (16 mL) at −78° C. was added dropwise DIBAL-H (1.0 m in toluene, 3.2 mL, 3.2 mmol). The reaction was stirred at −78° C. for 3.5 hours before the addition of a further amount of DIBAL-H (1.0 m in toluene, 0.78 mL, 0.78 mmol). After 1.5 hours, the reaction mixture was carefully quenched by the addition of aqueous Na/K tartrate (10 wt. %, 10 mL). The biphasic mixture was allowed to warm to room temperature and stirred vigorously for 1 hour before being extracted with EtOAc (2×40 mL). The combined organic extracts were washed with water (5 mL) and brine (5 mL), dried (Na₂SO₄) and concentrated in vacuo. Purification by flash chromatography (silica, gradient: 0% to 70% EtOAc in heptane) afforded the title compound (165 mg, 44%) as a light yellow solid. MS (ESI): 241.1 ([M+H]⁺).

Building Block K (3-(6-cyclopropyl-3-pyridyl)-5-methyl-isoxazol-4-yl)methanol

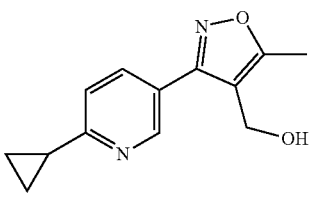 [SMILES: Cc1onc(-c2ccc(C3CC3)nc2)c1CO]

a) (Z)—N-((6-bromopyridin-3-yl)methylidene)hydroxylamine

To a stirred solution of hydroxylamine hydrochloride (11.0 g, 161 mmol) in EtOH (300 mL) was added triethylamine (33.0 mL, 242 mmol) and the reaction was stirred at room temperature for 30 min before addition of 6-bromopyridine-3-carbaldehyde (15.0 g, 80.6 mmol). The reaction mixture was heated at reflux for 1 hour then all the volatiles were removed by rotary evaporation under reduced pressure. The resulting residue was diluted with water and extracted with ethyl acetate (2×200 mL). The combined organic extracts were washed with brine, dried ($Na_2SO_4$) and concentrated in vacuo. Purification by flash chromatography (silica, 10% EtOAc in hexane) afforded the title compound (12.5 g, 77%) as a white solid. MS (ESI): 201.3 ([M+H]$^+$).

b) ethyl 3-(6-bromo-3-pyridyl)-5-methyl-isoxazole-4-carboxylate

In analogy to experiment of building block A b, (Z)—N-((6-bromopyridin-3-yl)methylidene)hydroxylamine instead of (E)-6-methylnicotinaldehyde oxime, was converted into the title compound (16 g, 86%) which was obtained as a brown oil. MS (ESI): 311.0 ([M+H]$^+$).

c) ethyl 3-(6-cyclopropyl-3-pyridyl)-5-methyl-isoxazole-4-carboxylate

A round-bottomed flask was charged with ethyl 3-(6-bromo-3-pyridyl)-5-methyl-isoxazole-4-carboxylate (8.00 g, 25.7 mmol), cyclopropyl boronic acid (8.80 g, 102 mmol), $K_3PO_4$ (19.0 g, 90 mmol), tricyclohexylphosphine (2.89 g, 10.2 mmol) and Pd(OAc)$_2$ (1.16 g, 5.14 mmol). The flask was degassed by alternative evacuation and back filling with argon. A previously degassed 10:1 solution of toluene/water (264 mL) was added and the resulting mixture was flushed with argon for 15 min. The reaction mixture was stirred at 100° C. for 3 hours before being cooled to room temperature and filtered directly through a plug of celite. The filter cake was rinsed with EtOAc and the filtrate concentrated in vacuo. Purification by flash chromatography (silica, 10% EtOAc in hexanes) afforded the title compound (5.5 g, 78%) as a yellow solid. MS (ESI): 272.7 ([M+H]$^+$).

d) (3-(6-cyclopropyl-3-pyridyl)-5-methyl-isoxazol-4-yl)methanol

To a stirred solution of ethyl 3-(6-cyclopropyl-3-pyridyl)-5-methyl-isoxazole-4-carboxylate (2.7 g, 11.4 mmol) in anhydrous THF (20 mL) at −10° C. was added dropwise LiAlH$_4$ (1.0 m in THF, 13.7 mL, 13.7 mmol). After 30 min, the reaction mixture was allowed to warm to 0° C. before being quenched by the addition of sodium sulfate decahydrate. The reaction was filtered directly through a plug of celite. The filter cake was rinsed with EtOAc and the filtrate concentrated in vacuo to afford the title compound (1.8 g, 81%) as an off white solid. MS (ESI): 236.1 ([M+H]$^+$).

Building Block L (5-cyclopropyl-3-(6-methylpyridazin-3-yl)isoxazol-4-yl)methanol

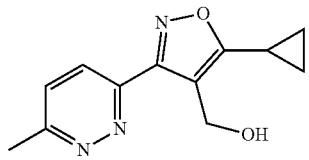 [SMILES: Cc1ccc(-c2noc(C3CC3)c2CO)nn1]

ethyl 5-cyclopropyl-3-(6-methylpyridazin-3-yl)isoxazole-4-carboxylate

In analogy to experiment of building block A b, 6-methylpyridazine-3-carbaldehyde oxime, using ethyl 3-cyclopropyl-3-(pyrrolidin-1-yl)acrylate instead of (E)-ethyl 3-(pyrrolidin-1-yl)but-2-enoate, was converted into the title compound (352 mg, 42%) which was obtained as an orange oil. MS (ESI): 274.1 ([M+H]$^+$).

5-cyclopropyl-3-(6-methylpyridazin-3-yl)isoxazole-4-carboxylic Acid

In analogy to experiment of building block E c, ethyl 5-cyclopropyl-3-(6-methylpyridazin-3-yl)isoxazole-4-carboxylate instead of ethyl 5-methyl-3-(6-(trifluoromethyl)pyridin-3-yl)isoxazole-4-carboxylate was converted into the title compound (260 mg, 95%) which was obtained as an orange solid. MS (ESI): 246.1 ([M+H]$^+$).

(5-cyclopropyl-3-(6-methylpyridazin-3-yl)isoxazol-4-yl)methanol

In analogy to experiment of building block H c, 5-cyclopropyl-3-(6-methylpyridazin-3-yl)isoxazole-4-carboxylic acid instead of 3-(6-methyl-3-pyridyl)isoxazole-4-carboxylic acid was converted into the title compound (85 mg, 47%) which was obtained as an orange solid. MS (ESI): 232.1 ([M+H]$^+$).

Building Block M (3-(6-methoxy-3-pyridyl)-5-methyl-isoxazol-4-yl)methanol

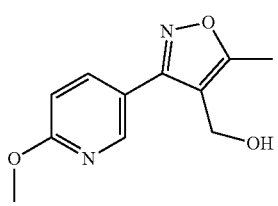 [SMILES: COc1ccc(-c2noc(C)c2CO)cn1]

a) (3E)-6-methoxypyridine-3-carbaldehyde Oxime

To a stirred suspension of 6-methoxypyridine-3-carbaldehyde (1.50 g, 10.9 mmol) in ethanol (2 mL) was added under argon ice-cold water (11 mL) and hydroxylamine hydrochloride (836 mg, 12 mmol). After 10 min, aqueous NaOH (2.0 m, 13.9 mL, 27.9 mmol) was added dropwise and the reaction mixture was stirred at room temperature for 3 hours. The resulting colourless solution was treated with acetic acid to pH-5 (a white precipitate was formed). The resulting precipitate was collected by filtration and dried at high vacuum to afford the title compound (1.47 g, 88%) as a white solid. MS (ESI): 153.1 ([M+H]$^+$).

b) ethyl 3-(6-methoxy-3-pyridyl)-5-methyl-isoxazole-4-carboxylate

To a stirred solution of (3E)-6-methoxypyridine-3-carbaldehyde oxime (1.45 g, 9.53 mmol) in DMF (20 mL) at room temperature was added N-chlorosuccinimide (1.4 g, 10.5 mmol). The reaction was stirred at room temperature for 3.5 hours before addition of (E)-ethyl 3-(pyrrolidin-1-yl)but-2-enoate (2.1 g, 11.4 mmol). The mixture was heated to 50° C. overnight to obtain a clear brown solution then cooled to room temperature. The reaction mixture was diluted with EtOAc (75 mL) and washed with water (75 mL) and brine (75 mL), dried (MgSO$_4$) and concentrated in vacuo. Purification by flash chromatography (silica, gradient: 0% to 30% EtOAc in heptane) afforded the title compound (2.31 g, 92%) as a light brown solid. MS (ESI): 263.1 ([M+H]$^+$).

c) (3-(6-methoxy-3-pyridyl)-5-methyl-isoxazol-4-yl)methanol

To a stirred solution of ethyl 3-(6-methoxy-3-pyridyl)-5-methyl-isoxazole-4-carboxylate (2.3 g, 8.77 mmol) in anhydrous THF (30 mL) at 0° C. was added under argon and portionwise LiAlH$_4$ (466 mg, 12.3 mmol). The reaction mixture was allowed to warm to room temperature for 2 hours before being re-cooled to 0° C. and carefully quenched by addition of water (0.5 mL). After gas evolution had ceased, aqueous NaOH (4.0 m, 0.5 mL) was added followed by water (1.5 mL) and the mixture was stirred at 0° C. for 1 hours. The resulting light yellow suspension was filtered on a sintered funnel and the residue was washed with THF. The filtrate was concentrated in vacuo and purified by flash chromatography (silica, gradient: 0% to 5% MeOH in CH$_2$Cl$_2$) to afford the title compound (1.44 g, 75%) as a yellow solid. MS (ESI): 221.2 ([M+H]$^+$).

Building Block N (3-(6-(dimethylamino)-3-pyridyl)-5-methyl-isoxazol-4-yl)methanol a) (3E)-6-(dimethylamino)pyridine-3-carbaldehyde Oxime

To a stirred suspension of 6-(dimethylamino)pyridine-3-carbaldehyde (1.71 g, 11.4 mmol) in ethanol (2 mL) was added under argon ice-cold water (11 mL) and hydroxylamine hydrochloride (871 mg, 12.5 mmol). After 10 min, aqueous NaOH (2.0 m, 14.5 mL, 29.1 mmol) was added dropwise and the reaction mixture was stirred at room temperature for 3 hours. The resulting colourless solution was treated with acetic acid to pH-5 (a white precipitate was formed) then diluted with water (15 mL). After stirring for 15 min, the precipitate was collected by filtration on a sintered funnel, washed with water and dried at high vacuum. The resulting solid was triturated in a 1:1 mixture of CH$_2$Cl$_2$ and heptane (30 mL) then filtered and dried to obtain the title compound (1.54 g, 82%) as an off-white solid. MS (ESI): 166.2 ([M+H]$^+$).

b) ethyl 3-(6-(dimethylamino)-3-pyridyl)-5-methyl-isoxazole-4-carboxylate

To a stirred solution of (3E)-6-(dimethylamino)pyridine-3-carbaldehyde oxime (1.09 g, 6.58 mmol) in DMF (15 mL) at room temperature was added N-chlorosuccinimide (0.967 g, 7.24 mmol). The reaction was heated to 50° C. for 3 hours before being re-cooled to room temperature and (E)-ethyl 3-(pyrrolidin-1-yl)but-2-enoate (1.45 g, 7.9 mmol) was added in one portion. The mixture was heated again to 50° C. overnight to obtain a clear brown solution. After cooling to room temperature, the reaction was diluted with EtOAc (50 mL) and washed with water (50 mL) and brine (50 mL), dried (MgSO$_4$) and concentrated in vacuo. Purification by flash chromatography (silica, gradient: 0% to 50% EtOAc in heptane) afforded the title compound (0.632 g, 33%) as a yellow solid. MS (ESI): 276.2 ([M+H]$^+$).

c) (3-(6-(dimethylamino)-3-pyridyl)-5-methyl-isoxazol-4-yl)methanol

To a stirred solution of ethyl 3-(6-(dimethylamino)-3-pyridyl)-5-methyl-isoxazole-4-carboxylate (220 mg, 0.799 mmol) in anhydrous THF (5 mL) at 0° C. was carefully added under argon LiAlH$_4$ (42.5 mg, 1.12 mmol). The reaction mixture was stirred for 2 hours before being quenched carefully by addition of water (0.05 mL). After gas evolution had ceased, aqueous NaOH (4.0 m, 0.05 mL) was added followed by water (0.150 mL) and the mixture was allowed to warm to room temperature and stirred for 1 hour. The resulting light yellow slurry was filtered off and the cake was rinsed with THF. The filtrate was concentrated in vacuo and purified by flash chromatography (silica, gradient: 0% to 10% MeOH in CH$_2$Cl$_2$) to afford the title compound (140 mg, 75%) as an off-white solid. MS (ESI): 234.2 ([M+H]$^+$).

Building Block O (3-(5-fluoro-6-methylpyridin-3-yl)-5-methyl-1,2-oxazol-4-yl)methanol

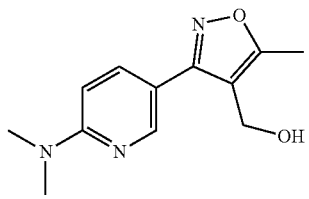

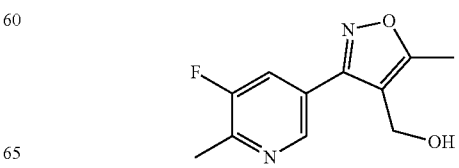

a) (3E)-5-fluoro-6-methyl-pyridine-3-carbaldehyde Oxime

To a stirred suspension of 5-fluoro-6-methyl-pyridine-3-carbaldehyde (450 mg, 3.23 mmol) in ethanol (0.7 mL) was added under argon ice-cold water (4.3 mL) and hydroxylamine hydrochloride (247 mg, 3.56 mmol). After 10 min, aqueous NaOH (2.0 m, 4.12 mL, 8.25 mmol) was added dropwise and the reaction mixture was stirred at room temperature for 3 hours. The resulting colourless solution was treated with acetic acid to pH-5 (a white precipitate was formed). After stirring for 15 min, the precipitate was collected by filtration on a sintered funnel, washed with water and dried at high vacuum to afford the title compound (383 mg, 77%) as a white solid. MS (ESI): 155.1 ([M+H]$^+$).

b) ethyl 3-(5-fluoro-6-methyl-3-pyridyl)-5-methyl-isoxazole-4-carboxylate

To a stirred solution of (3E)-5-fluoro-6-methyl-pyridine-3-carbaldehyde oxime (380 mg, 2.47 mmol) in DMF (5 mL) at room temperature was added N-chlorosuccinimide (329 mg, 2.47 mmol). The reaction was stirred at room temperature for 3.5 hours before addition of (E)-ethyl 3-(pyrrolidin-1-yl)but-2-enoate (452 mg, 2.47 mmol). The mixture was heated to 50° C. overnight to obtain a clear brown solution. After cooling to room temperature, the reaction was diluted with EtOAc (50 mL) and washed with water (50 mL) and brine (50 mL), dried (MgSO$_4$) and concentrated in vacuo. Purification by flash chromatography (silica, gradient: 0% to 30% EtOAc in heptane) afforded the title compound (475 mg, 73%) as a light brown solid. MS (ESI): 265.2 ([M+H]$^+$).

c) (3-(5-fluoro-6-methylpyridin-3-yl)-5-methyl-1,2-oxazol-4-yl)methanol

To a stirred solution of ethyl 3-(5-fluoro-6-methyl-3-pyridyl)-5-methyl-isoxazole-4-carboxylate (470 mg, 1.78 mmol) in anhydrous THF (10 mL) at 0° C. was carefully added under argon LiAlH$_4$ (94.5 mg, 2.49 mmol). The reaction mixture was allowed to warm to room temperature for 2 hours before being re-cooled to 0° C. and carefully quenched by addition of water (0.1 mL). After gas evolution had ceased, aqueous NaOH (4.0 m, 0.1 mL) was added followed by water (0.35 mL) and the mixture was stirred at 0° C. for 30 min. The resulting light yellow suspension was filtered off and the cake was rinsed with THF. The filtrate was concentrated in vacuo and purified by flash chromatography (silica, gradient: 0% to 5% MeOH in CH$_2$Cl$_2$) to afford the title compound (221 mg, 56%) as a yellow solid. MS (ESI): 223.2 ([M+H]$^+$).

Building Block P (5-(fluoromethyl)-3-(6-methylpyridazin-3-yl)isoxazol-4-yl)methanol

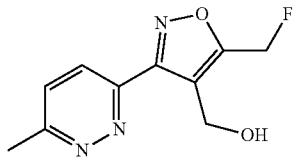 [SMILES: Cc1ccc(-c2noc(CF)c2CO)nn1]

a) ethyl (E)-4-fluoro-3-pyrrolidin-1-yl-but-2-enoate

To a stirred solution of ethyl 4-fluoro-3-oxo-butanoate (1.0 g, 6.75 mmol) in cyclohexane (10 mL) was added dropwise (caution exothermic) pyrrolidine (0.60 mL, 7.22 mmol) followed by a catalytic amount of p-toluenesulfonic acid monohydrate (64.2 mg, 0.338 mmol). The mixture was stirred at room temperature for 30 min then the bottom flask was equipped with a Dean-Stark trap and heated at reflux overnight. The reaction mixture was cooled to room temperature then all the volatiles were removed by rotary evaporation under reduced pressure. The resulting crude residue (orange oil) was used directly in the following step without further purification.

b) ethyl 5-(fluoromethyl)-3-(6-methylpyridazin-3-yl)isoxazole-4-carboxylate

To a stirred suspension of (E)-6-methylpyridazine-3-carbaldehyde oxime (350 mg, 2.55 mmol) in DMF (5 mL) at 6° C. was added N-chlorosuccinimide (375 mg, 2.81 mmol). Upon addition, the color of the reaction mixture changed from yellow to orange and the reaction was allowed to warm to room temperature. After 1 hour, the mixture was heated to 50° C. for 2 hours. The resulting brown suspension was re-cooled to 6° C. then a solution of ethyl (E)-4-fluoro-3-pyrrolidin-1-yl-but-2-enoate (685 mg, 3.06 mmol, purity 90%) in DMF (1.0 mL) was added dropwise and the reaction mixture was stirred at 50° C. overnight. After cooling to room temperature, the reaction was diluted with water (20 mL) and extracted with EtOAc (3×40 mL). The combined organic extracts were washed with brine, dried (Na$_2$SO$_4$) and concentrated in vacuo. Purification by flash chromatography (silica, gradient: 0% to 50% EtOAc in heptane) afforded the title compound (498 mg, 74%) as an orange oil. MS (ESI): 266.1 ([M+H]$^+$).

c) (5-(fluoromethyl)-3-(6-methylpyridazin-3-yl)isoxazol-4-yl)methanol

To a stirred suspension of ethyl 5-(fluoromethyl)-3-(6-methylpyridazin-3-yl)isoxazole-4-carboxylate (498 mg, 1.88 mmol) in anhydrous toluene (16 mL) at −78° C. was added dropwise DIBAL-H (1.0 m in toluene, 5.63 mL, 5.63 mmol). The reaction was stirred at −78° C. for 1 hour then allowed to warm to room temperature and stirred overnight. The reaction mixture was cooled to 0° C. then quenched by addition of aqueous NaOH (1.0 m, 15 mL) followed by EtOAc (20 mL). The mixture was diluted with water (20 mL) and extracted with EtOAc (3×40 mL). The combined organic extracts were washed with brine, dried (Na$_2$SO$_4$) and concentrated in vacuo. Purification by flash chromatography (silica, gradient: 0% to 100% EtOAc in heptane) afforded the title compound (105 mg, 25%) as a light yellow powder. MS (ESI): 224.2 ([M+H]$^+$).

Example 1

6-((5-methyl-3-(6-methyl-3-pyridyl)isoxazol-4-yl)methoxy)-N-tetrahydropyran-4-yl-pyridine-3-carboxamide

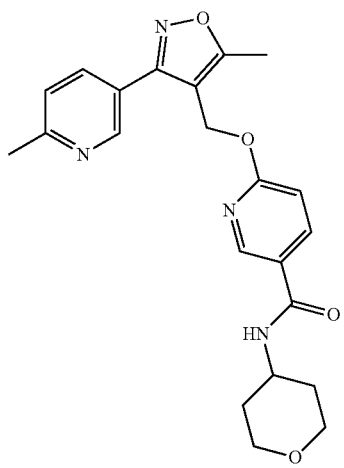 [SMILES: Cc1ccc(-c2noc(C)c2COc2ccc(C(=O)NC3CCOCC3)cn2)cn1]

a) Methyl 6-((5-methyl-3-(6-methyl-3-pyridyl)isoxazol-4-yl)methoxy)pyridine-3-carboxylate To a stirred solution of (5-methyl-3-(6-methylpyridin-3-yl)isoxazol-4-yl)methanol (building block A, 1.39 g, 6.81 mmol) in anhydrous THF (30 mL) at 0° C. was added NaH (60% dispersion in mineral oil, 286 mg, 7.15 mmol). The reaction mixture was allowed to warm to room temperature and stirred for 30 min before being re-cooled to 0° C. Methyl 6-chloronicotinate (1.28 g, 7.49 mmol) was added over a period of 5 min and the reaction mixture was stirred for 5 hours. The reaction was poured into a mixture of aqueous citric acid (5 wt. %, 30 mL) and ice then extracted with EtOAc (2×30 mL). The combined organic extracts were washed with brine, dried (MgSO$_4$) and concentrated in vacuo. Purification by flash chromatography (silica, gradient: 30% to 100% EtOAc in heptane) afforded the title compound (2.07 g, 90%) as a light yellow solid. MS (ESI): 340.2 ([M+H]$^+$).

b) 6-((5-methyl-3-(6-methyl-3-pyridyl)isoxazol-4-yl)methoxy)-N-tetrahydropyran-4-yl-pyridine-3-carboxamide To a stirred solution of tetrahydropyran-4-amine (119 mg, 1.18 mmol) in anhydrous 1,4-dioxane (10 mL) at room temperature was added dropwise trimethylaluminium (2.0 m solution in heptane, 0.60 mL, 1.2 mmol). After 1 hour, a solution of methyl 6-((5-methyl-3-(6-methyl-3-pyridyl)isoxazol-4-yl)methoxy)pyridine-3-carboxylate (100 mg, 0.295 mmol) in anhydrous 1,4-dioxane (5 mL) was added dropwise. The reaction mixture was heated to 90° C. four 2 hours before being cooled to room temperature and poured into a mixture of ice and aqueous Na/K tartrate (10 wt. %, 20 mL). After 20 min vigorous stirring, the mixture was extracted with dichloromethane (2×30 mL). The combined organic extracts were dried (Na$_2$SO$_4$), filtered and concentrated in vacuo. Purification by flash chromatography (silica, gradient: 0% to 3% MeOH in CH$_2$Cl$_2$) afforded the title compound (89 mg, 74%) as a white solid MS (ESI): 409.4 ([M+H]$^+$).

Example 2

N-(cyclopropylmethyl)-6-((5-methyl-3-(6-methyl-3-pyridyl)isoxazol-4-yl)methoxy)pyridine-3-carboxamide

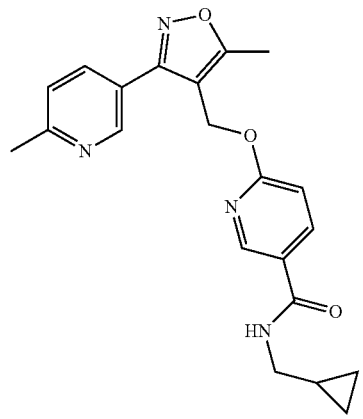 [SMILES: Cc1ccc(-c2noc(C)c2COc2ccc(C(=O)NCC3CC3)cn2)cn1]

In analogy to experiment of example 1b, methyl 6-((5-methyl-3-(6-methyl-3-pyridyl)isoxazol-4-yl)methoxy)pyridine-3-carboxylate, using cyclopropylmethanamine instead of tetrahydropyran-4-amine, was converted into the title compound (60 mg, 54%) which was obtained as a white solid. MS (ESI): 379.4 ([M+H]$^+$).

Example 3

N-ethyl-6-((5-methyl-3-(6-methyl-3-pyridyl)isoxazol-4-yl)methoxy)pyridine-3-carboxamide

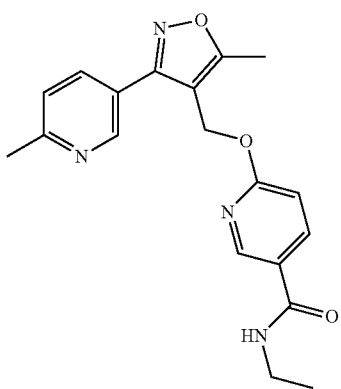 [SMILES: CCNC(=O)c1ccc(OCc2c(-c3ccc(C)nc3)noc2C)nc1]

In analogy to experiment of example 1b, methyl 6-((5-methyl-3-(6-methyl-3-pyridyl)isoxazol-4-yl)methoxy)pyridine-3-carboxylate, using ethylamine instead of tetrahydropyran-4-amine, was converted into the title compound (62 mg, 60%) which was obtained as a white solid. MS (ESI): 353.3 ([M+H]$^+$).

Example 4

(S)—N-(1-hydroxypentan-2-yl)-6-((5-methyl-3-(6-methylpyridin-3-yl)isoxazol-4-yl)methoxy)nicotinamide

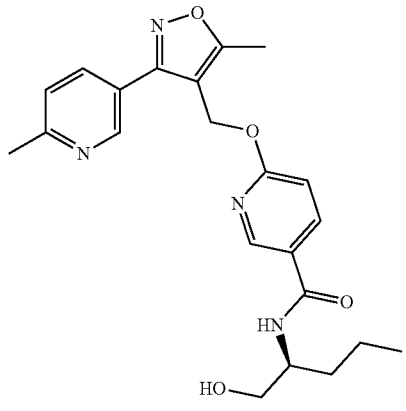

a) 6-((5-methyl-3-(6-methyl-3-pyridyl)isoxazol-4-yl)methoxy)pyridine-3-carboxylic Acid To a stirred solution of methyl 6-((5-methyl-3-(6-methyl-3-pyridyl)isoxazol-4-yl)methoxy)pyridine-3-carboxylate (1.43 g, 3.49 mmol, purity 83%) in a mixture of THF (10 mL), MeOH (10 mL) and water (10 mL) was added LiOH (335 mg, 14.0 mmol). The reaction was stirred at room temperature for 2 hours before being quenched by the addition of aqueous citric acid (5 wt. %, 20 mL). The mixture was diluted with water (20 mL) and stirred at 0° C. for 1 hour. The resulting suspension was filtered on a sintered funnel and the collected solid was rinsed with ice cold water (2×10 mL) and dried under high vacuum to afford the title compound (1.08 g, 95%) as a white solid. MS (ESI): 326.1 ([M+H]$^+$).

b) (S)—N-(1-hydroxypentan-2-yl)-6-((5-methyl-3-(6-methylpyridin-3-yl)isoxazol-4-yl)methoxy)nicotinamide To a stirred solution of 6-((5-methyl-3-(6-methyl-3-pyridyl)isoxazol-4-yl)methoxy)pyridine-3-carboxylic acid (92 mg, 0.284 mmol) and (S)-2-aminopentan-1-ol (44 mg, 0.426 mmol) in anhydrous DMF (3 mL) was added N,N-diisopropylethylamine (0.248 mL, 1.42 mmol) followed by TBTU (109 mg, 0.341 mmol). The resulting light yellow solution was stirred overnight at room temperature then poured into water (20 mL) and extracted with EtOAc (2×20 mL). The combined organic extracts were washed with brine (20 mL), dried (MgSO$_4$) and concentrated in vacuo. The crude residue was purified by flash chromatography (silica, gradient: 95% to 100% EtOAc in heptane then 5% MeOH in EtOAc) to afford the title compound (67 mg, 57%) as an off-white solid. MS (ESI): 411.3 ([M+H]$^+$).

Example 5

6-((5-cyclopropyl-3-(6-methyl-3-pyridyl)isoxazol-4-yl)methoxy)-N-((1S)-1-(hydroxymethyl)butyl)pyridine-3-carboxamide

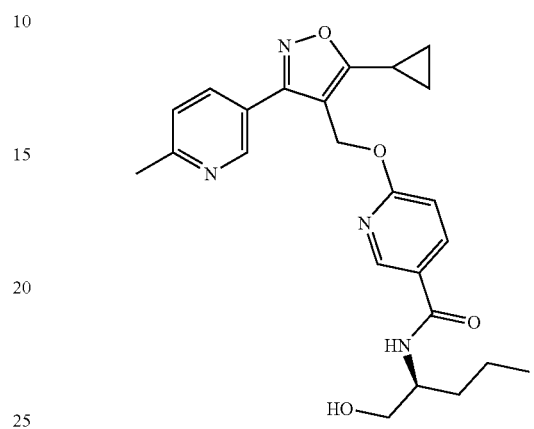

a) Methyl 6-((5-cyclopropyl-3-(6-methyl-3-pyridyl)isoxazol-4-yl)methoxy)pyridine-3-carboxylate In analogy to experiment of example 1a, (5-cyclopropyl-3-(6-methyl-3-pyridyl)isoxazol-4-yl)methanol (building block D) instead of (5-methyl-3-(6-methylpyridin-3-yl)isoxazol-4-yl)methanol (building block A) was converted into the title compound (632 mg, 71%) which was obtained as a light yellow oil. MS (ESI): 366.2 ([M+H]$^+$).

b) 6-((5-cyclopropyl-3-(6-methyl-3-pyridyl)isoxazol-4-yl)methoxy)pyridine-3-carboxylic Acid In analogy to experiment of example 4a, methyl 6-((5-cyclopropyl-3-(6-methyl-3-pyridyl)isoxazol-4-yl)methoxy)pyridine-3-carboxylate instead of methyl 6-((5-methyl-3-(6-methyl-3-pyridyl)isoxazol-4-yl)methoxy)pyridine-3-carboxylate was converted into the title compound (632 mg, 71%) which was obtained as a white solid. MS (ESI): 352.2 ([M+H]$^+$).

c) 6-((5-cyclopropyl-3-(6-methyl-3-pyridyl)isoxazol-4-yl)methoxy)-N-((1S)-1-(hydroxymethyl)butyl)pyridine-3-carboxamide In analogy to experiment 4b, 6-((5-cyclopropyl-3-(6-methyl-3-pyridyl)isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid was converted into the title compound (96 mg, 96%) which was obtained as a white solid. MS (ESI): 437.2 ([M+H]$^+$).

Example 6

6-((5-cyclopropyl-3-(6-methyl-3-pyridyl)isoxazol-4-yl)methoxy)-N-tetrahydropyran-4-yl-pyridine-3-carboxamide

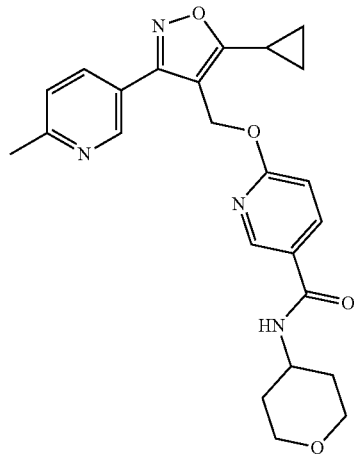

In analogy to experiment of example 4b, 6-((5-cyclopropyl-3-(6-methyl-3-pyridyl)isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid, using tetrahydropyran-4-amine instead of (S)-2-aminopentan-1-ol, was converted into the title compound (64 mg, 63%) which was obtained as a white solid. MS (ESI): 435.3 ([M+H]$^+$).

Example 7

(S)—N-(1-hydroxypentan-2-yl)-6-((5-methyl-3-(6-methylpyridin-3-yl)isoxazol-4-yl)methoxy)pyridazine-3-carboxamide

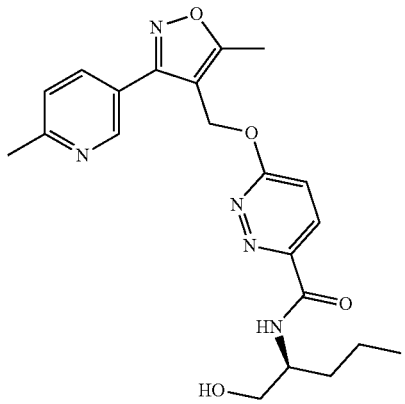 [SMILES: CCC[C@@H](CO)NC(=O)c1ccc(OCc2c(-c3ccc(C)nc3)noc2C)nc1]

a) Methyl 6-((5-methyl-3-(6-methylpyridin-3-yl)isoxazol-4-yl)methoxy)pyridazine-3-carboxylate To a solution of (5-methyl-3-(6-methylpyridin-3-yl)isoxazol-4-yl)methanol (building block A, 170 mg, 0.832 mmol) in anhydrous THF (6 mL) at 0° C. was added NaH (55% in mineral oil, 40.0 mg, 0.999 mmol). The reaction mixture was warmed to room temperature and stirred for 4 hours. After cooling to 0° C., methyl 6-chloropyridazine-3-carboxylate (187 mg, 1.08 mmol) was added and the reaction was maintained at 0° C. overnight using a thawing ice bath. Upon addition of a further amount of methyl 6-chloropyridazine-3-carboxylate (187 mg, 1.08 mmol) and NaH (55% in mineral oil, 40.0 mg, 0.999 mmol), the reaction mixture was heated to 80° C. overnight. The reaction mixture was re-cooled to room temperature then poured into water and ice and extracted with EtOAc (2×30 mL). The combined organic extracts were washed with brine, dried (Na$_2$SO$_4$) and concentrated in vacuo. The crude residue was purified by flash chromatography (silica, gradient: 5% to 100% EtOAc in heptane then 5% MeOH in EtOAc) to afford the title compound (132 mg, 47%) as an off-white solid. MS (ESI): 341.1 ([M+H]$^+$).

b) (S)—N-(1-hydroxypentan-2-yl)-6-((5-methyl-3-(6-methylpyridin-3-yl)isoxazol-4-yl)methoxy)pyridazine-3-carboxamide To a stirred solution of methyl 6-((5-methyl-3-(6-methylpyridin-3-yl)isoxazol-4-yl)methoxy)pyridazine-3-carboxylate (70 mg, 0.206 mmol) in toluene (0.5 mL) was added under argon (S)-2-aminopentan-1-ol (25.5 mg, 0.247 mmol) and 1,5,7-triazabicyclo[4.4.0]dec-5-ene (17.2 mg, 0.123 mmol). The reaction mixture was stirred at room temperature for 6 hours before the addition of a further amount of (S)-2-aminopentan-1-ol (25.5 mg, 0.247 mmol). After 16 hours, the resulting solution was concentrated in vacuo to provide a brown oil which was purified by flash chromatography (silica, gradient: 0% to 10% MeOH in CH$_2$Cl$_2$) to afford the title compound (45 mg, 43%) as an off-white solid. MS (ESI): 412.3 ([M+H]$^+$).

Example 8

6-((5-methyl-3-(6-methylpyridin-3-yl)isoxazol-4-yl)methoxy)-N-(tetrahydropyran-4-yl)pyridazine-3-carboxamide

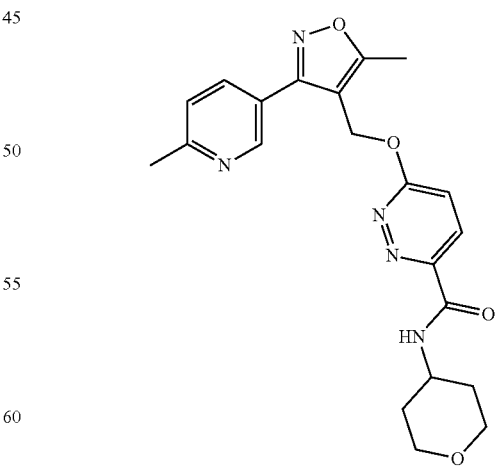

In analogy to experiment of example 4b, methyl 6-((5-methyl-3-(6-methylpyridin-3-yl)isoxazol-4-yl)methoxy)pyridazine-3-carboxylate instead of 6-((5-methyl-3-(6-methyl-3-pyridyl)isoxazol-4-yl)methoxy)pyridine-3- carboxylic acid, using tetrahydropyran-4-amine instead of (S)-2-aminopentan-1-ol, was converted into the title compound (6 mg, 8%) which was obtained as an off-white solid. MS (ESI): 410.3 ([M+H]⁺).

Example 9

2-isobutyl-6-((5-methyl-3-(6-methylpyridin-3-yl)isoxazol-4-yl)methoxy)-1H-pyrrolo[3,4-c]pyridin-3(2H)-one

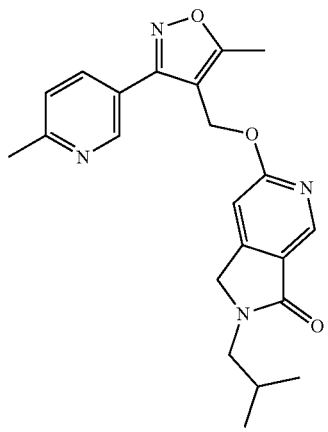 [SMILES: Cc1ccc(-c2noc(C)c2COc2cc3c(cn2)C(=O)N(CC(C)C)C3)cn1]

a) 6-chloro-2-isobutyl-1H-pyrrolo[3,4-c]pyridin-3-one

To a suspension of 6-chloro-4-formylnicotinic acid (520 mg, 2.8 mmol) in acetic acid (1.12 mL, 19.6 mmol) was added under nitrogen isobutylamine (0.323 mL, 3.22 mmol), hydrochloric acid (4.0 m solution in 1,4-dioxane, 0.771 mL, 3.08 mmol) and sodium triacetoxyborohydride (891 mg, 4.2 mmol). The reaction mixture was stirred at room temperature for 18 hours then heated to 60° C. for 5 hours. After this time, a second portion of isobutylamine (0.225 mL, 2.24 mmol) and sodium triacetoxyborohydride (475 mg, 2.24 mmol) were added and the reaction mixture was stirred at room temperature for further 18 hours. The mixture was diluted with EtOAc (30 mL) and the organic layer was washed with aqueous $Na_2CO_3$ (1.0 m solution, 30 mL), water (30 mL) and brine (30 mL). The combined organic extracts were dried ($MgSO_4$) and concentrated in vacuo to afford the title compound as a white solid (438 mg, 70%). MS (ESI): 410.3 ([M+H]⁺).

b) 2-isobutyl-6-((5-methyl-3-(6-methylpyridin-3-yl)isoxazol-4-yl)methoxy)-1H-pyrrolo[3,4-c]pyridin-3(2H)-one A round-bottomed flask was charged with (5-methyl-3-(6-methylpyridin-3-yl)isoxazol-4-yl)methanol (building block A, 107 mg, 0.524 mmol), 6-chloro-2-isobutyl-1H-pyrrolo[3,4-c]pyridin-3(2H)-one (177 mg, 0.786 mmol), $Cs_2CO_3$ (333 mg, 1.02 mmol), rac-2-(di-tert-butylphosphino)-1,1'-binaphthyl (20.9 mg, 52.4 μmop) and $Pd(OAc)_2$ (9.41 mg, 41.9 μmop. The flask was degassed by alternative evacuation and back filling with argon before addition of anhydrous toluene (2.0 mL). The mixture was flushed with argon for 15 min then stirred at 90° C. for 18 hours before being concentrated in vacuo. The resulting brown oil crude residue was purified by flash chromatography (silica, gradient: 30% to 100% EtOAc in heptane) to afford the title compound (166 mg, 81%) as a white solid. MS (ESI): 393.2 ([M+H]⁺).

Example 10

2-methyl-6-((5-methyl-3-(6-methylpyridin-3-yl)isoxazol-4-yl)methoxy)-1H-pyrrolo[3,4-c]pyridin-3(2H)-one

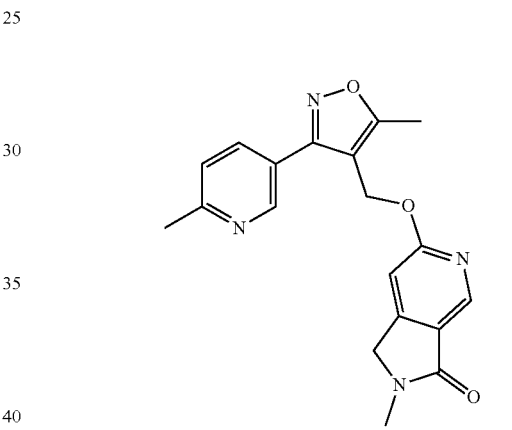

a) 6-chloro-2-methyl-1H-pyrrolo[3,4-c]pyridin-3-one

In analogy to experiment of example 9a, 6-chloro-4-formylnicotinic acid, using methylamine instead of isobutylamine, was converted into the title compound (408 mg, 69%) which was obtained as a light yellow solid. MS (ESI): 183.0 ([M+H]⁺).

b) 2-methyl-6-((5-methyl-3-(6-methylpyridin-3-yl)isoxazol-4-yl)methoxy)-1H-pyrrolo[3,4-c]pyridin-3(2H)-one In analogy to experiment of example 9b, (5-methyl-3-(6-methylpyridin-3-yl)isoxazol-4-yl)methanol, using 6-chloro-2-methyl-1H-pyrrolo[3,4-c]pyridin-3-one instead of 6-chloro-2-isobutyl-1H-pyrrolo[3,4-c]pyridin-3-one, was converted into the title compound (89 mg, 78%) which was obtained as a white foam. MS (ESI): 351.2 ([M+H]⁺).

Example 11

N-isobutyl-6-((5-methyl-3-(6-methylpyridin-3-yl)isoxazol-4-yl)methoxy)nicotinamide

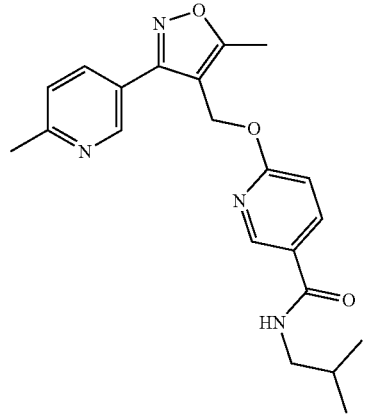 [SMILES: Cc1ccc(-c2noc(C)c2COc2ccc(C(=O)NCC(C)C)cn2)cn1]

In analogy to experiment of example 4b, 6-((5-methyl-3-(6-methyl-3-pyridyl)isoxazol-4-yl)methoxy)pyridine-3-carboxylic acid, using isobutylamine instead of (S)-2-aminopentan-1-ol, was converted into the title compound (67 mg, 74%) which was obtained as a white solid. MS (ESI): 381.2 ([M+H]$^+$).

Example 12

2-(2-hydroxyethyl)-6-((5-methyl-3-(6-methylpyridin-3-yl)isoxazol-4-yl)methoxy)-1H-pyrrolo[3,4-c]pyridin-3(2H)-one

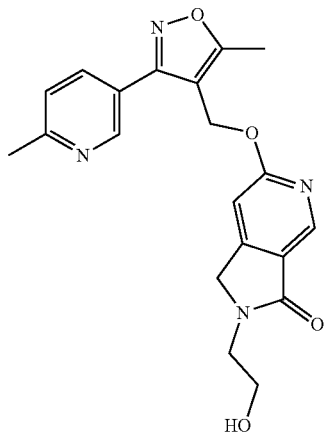 [SMILES: Cc1ccc(-c2noc(C)c2COc2cc3c(cn2)C(=O)N(CCO)C3)cn1]

a) 6-chloro-2-(2-hydroxyethyl)-1H-pyrrolo[3,4-c]pyridin-3-one

In analogy to experiment of example 9a, 6-chloro-4-formylnicotinic acid, using 2-aminoethanol instead of isobutylamine, was converted into the title compound (466 mg, 81%) which was obtained as a white solid. MS (ESI): 213.1 ([M+H]$^+$).

b) 2-(6-chloro-3-oxo-1H-pyrrolo[3,4-c]pyridin-2-yl)ethyl Acetate

To a stirred solution of 6-chloro-2-(2-hydroxyethyl)-1H-pyrrolo[3,4-c]pyridin-3-one (270 mg, 1.28 mmol) in THF (5 mL) at room temperature was added acetic anhydride (0.360 mL, 3.81 mmol). The reaction mixture was heated to 60° C. for 2 hours before being concentrated in vacuo to afford the title compound (369 mg, 100%, purity 87%) as a white solid. MS (ESI): 255.0 ([M+H]$^+$).

c) 2-(2-hydroxyethyl)-6-((5-methyl-3-(6-methylpyridin-3-yl)isoxazol-4-yl)methoxy)-1H-pyrrolo[3,4-c]pyridin-3(2H)-one In analogy to experiment of example 9b, (5-methyl-3-(6-methylpyridin-3-yl)isoxazol-4-yl)methanol (building block A), using 2-(6-chloro-3-oxo-1H-pyrrolo[3,4-c]pyridin-2-yl)ethyl acetate instead of 6-chloro-2-isobutyl-1H-pyrrolo[3,4-c]pyridin-3-one, was converted into the title compound (12 mg, 12%) which was obtained as a white solid. MS (ESI): 381.2 ([M+H]$^+$).

Example 13

(S)-2-(1-hydroxypentan-2-yl)-6-((5-methyl-3-(6-methylpyridin-3-yl)isoxazol-4-yl)methoxy)-1H-pyrrolo[3,4-c]pyridin-3(2H)-one

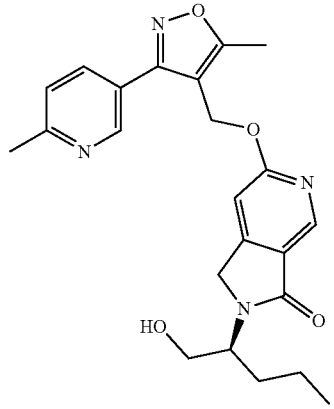 [SMILES: CCC[C@@H](CO)N1Cc2cc(OCc3c(-c4ccc(C)nc4)noc3C)ncc2C1=O]

a) 6-chloro-2-((1S)-1-(hydroxymethyl)butyl)-1H-pyrrolo[3,4-c]pyridin-3-one

In analogy to experiment of example 9a, 6-chloro-4-formylnicotinic acid, using (S)-2-aminopentan-1-ol instead of isobutylamine, was converted into the title compound (693 mg, 100%, purity 50%) which was obtained as a light brown foam. MS (ESI): 253.1 ([M+H]$^+$).

b) ((2S)-2-(6-chloro-3-oxo-1H-pyrrolo[3,4-c]pyridin-2-yl)pentyl) Acetate

In analogy to experiment of example 12b, 6-chloro-2-((1S)-1-(hydroxymethyl)butyl)-1H-pyrrolo[3,4-c]pyridin-3-one instead of 6-chloro-2-(2-hydroxyethyl)-1H-pyrrolo[3,4-c]pyridin-3-one was converted into the title compound (560 mg, 70%) which was obtained as a white solid. MS (ESI): 297.1 ([M+H]$^+$).

c) (S)-2-(1-hydroxypentan-2-yl)-6-((5-methyl-3-(6-methylpyridin-3-yl)isoxazol-4-yl)methoxy)-1H-pyrrolo[3,4-c]pyridin-3(2H)-one In analogy to experiment of example 9b, (5-methyl-3-(6-methylpyridin-3-yl)isoxazol-4-yl)methanol (building block A), using ((2S)-2-(6-chloro-3-oxo-1H-pyrrolo[3,4-c]pyridin-2-yl)pentyl) acetate instead of 6-chloro-2-isobutyl-1H-pyrrolo[3,4-c]pyridin-3-one, was converted into the title compound (140 mg, 73%) which was obtained as a white foam. MS (ESI): 423.2 ([M+H]$^+$).

Example 14

N-((1S)-1-(hydroxymethyl)butyl)-5-((5-methyl-3-(6-methyl-3-pyridyl)isoxazol-4-yl)methoxy)pyrazine-2-carboxamide

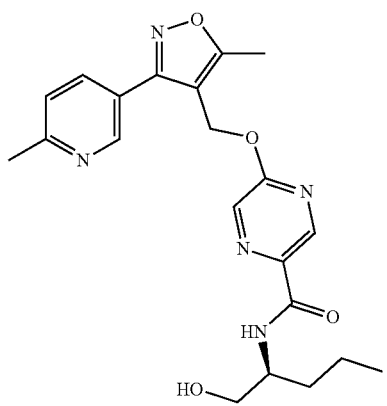 [SMILES: CCC[C@@H](CO)NC(=O)c1cnc(OCc2c(-c3ccc(C)nc3)noc2C)cn1]

a) Methyl 5-((5-methyl-3-(6-methyl-3-pyridyl)isoxazol-4-yl)methoxy)pyrazine-2-carboxylate To a stirred solution of (5-methyl-3-(6-methylpyridin-3-yl)isoxazol-4-yl)methanol (building block A, 154 mg, 0.754 mmol) in acetonitrile (3 mL) was added Cs$_2$CO$_3$ (491 mg, 1.51 mmol) followed by methyl 5-chloropyrazine-2-carboxylate (195 mg, 1.13 mmol). The reaction mixture was stirred at room temperature overnight before being diluted with EtOAc (15 mL) and washed with aqueous Na$_2$CO$_3$ (1.0 m, 15 mL), water (15 mL) and brine (15 mL). The aqueous layers were extracted with EtOAc 15 mL). The combined organic extracts were dried (MgSO$_4$) and concentrated in vacuo. Purification by flash chromatography (silica gel, 30% to 100% EtOAc in heptane) afforded the title compound (199 mg, 78%) as a white solid MS (ESI): 341.2 ([M+H]$^+$)

b) 5-((5-methyl-3-(6-methyl-3-pyridyl)isoxazol-4-yl)methoxy]pyrazine-2-carboxylic Acid To a stirred solution of methyl 5-((5-methyl-3-(6-methyl-3-pyridyl)isoxazol-4-yl)methoxy)pyrazine-2-carboxylate (2.09 g, 6.14 mmol) in a mixture of THF (17 mL), MeOH (17 mL) and water (17 mL) at 0° C. was added LiOH monohydrate (773 mg, 18.4 mmol). The reaction was allowed to warm to room temperature and stirred for 30 min before being quenched by the addition of aqueous citric acid (5 wt. %, 20 mL). The mixture was diluted with water (20 mL) and stirred at 0° C. for 1 hour. The resulting suspension was filtered on a sintered funnel and the collected solid was rinsed with ice cold water (2×10 mL) and dried under high vacuum to afford the title compound (1.47 g, 74%) as a white solid. MS (ESI): 327.1 ([M+H]$^+$).

c) N-((1S)-1-(hydroxymethyl)butyl)-5-((5-methyl-3-(6-methyl-3-pyridyl)isoxazol-4-yl)methoxy)pyrazine-2-carboxamide To a stirred solution of 5-((5-methyl-3-(6-methyl-3-pyridyl)isoxazol-4-yl)methoxy)pyrazine-2-carboxylic acid (51 mg, 0.16 mmol) and (S)-2-aminopentan-1-ol (24 mg, 0.23 mmol) in DMF (1 mL) was added N,N-diisopropylethylamine (136 µL, 0.78 mmol) followed by TBTU (60 mg, 0.19 mmol). The resulting light yellow solution was stirred overnight at room temperature then poured into water (20 mL) and extracted with EtOAc (2×20 mL). The combined organic extracts were washed with brine (20 mL), dried (MgSO$_4$) and concentrated in vacuo. The crude residue was purified by flash chromatography (silica, gradient: 80% to 100% EtOAc in heptane then 5% MeOH in EtOAc) to afford the title compound (60 mg, 93%) as a white solid. MS (ESI): 412.2 ([M+H]$^+$).

Example 15

5-((5-methyl-3-(6-methylpyridin-3-yl)isoxazol-4-yl)methoxy)-N-(tetrahydropyran-4-yl)pyrazine-2-carboxamide

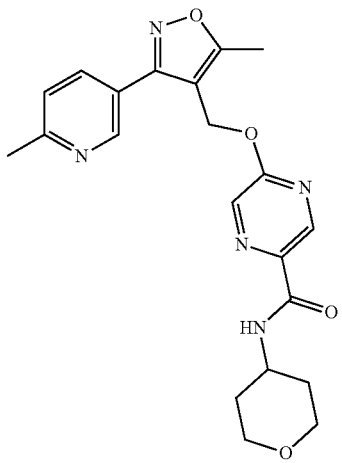 [SMILES: Cc1ccc(-c2noc(C)c2COc2cnc(C(=O)NC3CCOCC3)cn2)cn1]

In analogy to experiment of example 30, 5-((5-methyl-3-(6-methyl-3-pyridyl)isoxazol-4-yl)methoxy)pyrazine-2-carboxylic acid, using tetrahydropyran-4-amine instead of (1,1-dioxidotetrahydro-2H-thiopyran-4-yl)amine hydrochloride, was converted into the title compound (52 mg, 92%) which was obtained as a white solid. MS (ESI): 410.3 ([M+H]$^+$).

Example 16

N-(1,1-dioxothiolan-3-yl)-6-((5-methyl-3-(6-methyl-3-pyridyl)isoxazol-4-yl)methoxy)pyridine-3-carboxamide

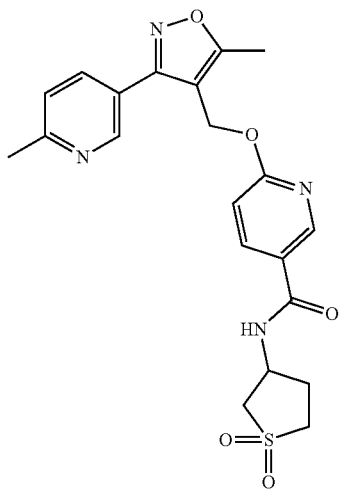 [SMILES: Cc1ccc(-c2noc(C)c2COc2ccc(C(=O)NC3CCS(=O)(=O)C3)cn2)cn1]

In analogy to experiment of example 4b, 6-((5-methyl-3-(6-methyl-3-pyridyl)isoxazol-4-yl)methoxy)pyridine-3-carboxylic acid, using 1,1-dioxothiolan-3-amine instead of (S)-2-aminopentan-1-ol, was converted into the title compound (66 mg, 80%) which was obtained as a white solid. MS (ESI): 443.2 ([M+H]$^+$).

Example 17

6-((5-methyl-3-(6-methylpyridin-3-yl)isoxazol-4-yl)methoxy)nicotinamide

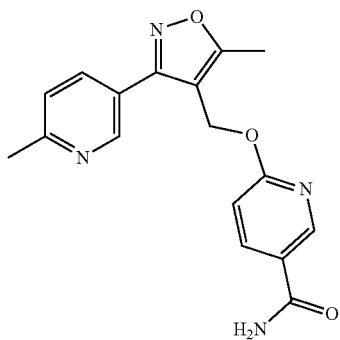 [SMILES: Cc1ccc(-c2noc(C)c2COc2ccc(C(N)=O)cn2)cn1]

To a stirred solution of 6-((5-methyl-3-(6-methyl-3-pyridyl)isoxazol-4-yl)methoxy)pyridine-3-carboxylic acid (86.8 mg, 0.267 mmol) in anhydrous DMF (2 mL) at room temperature was added 1,1'-carbonyldiimidazole (56.2 mg, 0.347 mmol). The reaction mixture was heated to 60° C. for 1 hour before being re-cooled to room temperature. After 15 min, ammonium hydroxide (25 wt. %, 0.416 mL, 2.67 mmol) was added and the reaction was stirred at room temperature. After 1 hour, Isolute® was added and the resulting solid-suspension was dried in vacuo then purified directly by flash chromatography (silica, gradient: 0% to 10% MeOH) to afford the title compound (70 mg, 81%) as a white solid. MS (ESI): 325.1 ([M+H]$^+$).

Example 18

6-((5-methyl-3-(6-methylpyridin-3-yl)isoxazol-4-yl)methoxy)pyridazine-3-carboxamide

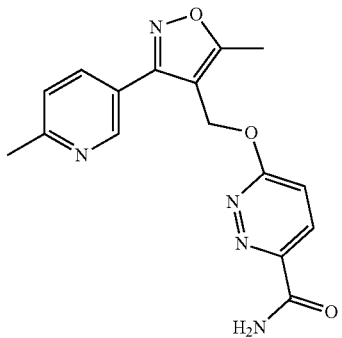 [SMILES: Cc1ccc(-c2noc(C)c2COc2ccc(C(N)=O)nn2)cn1]

To a suspension of (5-methyl-3-(6-methylpyridin-3-yl)isoxazol-4-yl)methanol (building block A, 54 mg, 0.226 mmol) and 6-chloropyridazine-3-carbonitrile (44.3 mg, 0.317 mmol) in THF (2 mL) was added under nitrogen at room temperature NaH (60% in mineral oil, 12.7 mg, 0.317 mmol). After 1 hour, DMF (1 mL) was added and the reaction mixture was stirred for further 2 hours. Aqueous NaOH (1.0 m, 0.529 mL, 0.529 mmol) was added and the reaction mixture was heated to 50° C. for 18 hours. The reaction was quenched by addition of aqueous citric acid (5 wt. %, 2 mL) followed by addition of 1.0 m aqueous NaHCO$_3$ to adjust the pH to 7. The aqueous layer was extracted with EtOAc (2×30 mL) and the combined organic extracts were washed with brine, dried (MgSO$_4$) and concentrated in vacuo. Purification by flash chromatography (silica, gradient: 0% to 5% MeOH in EtOAc) afforded the title compound (17 mg, 20%) as an off-white solid. MS (ESI): 326.1 ([M+H]$^+$).

Example 19

N-((3S)-1,1-dioxothiolan-3-yl)-6-((5-methyl-3-(6-methylpyridin-3-yl)-1,2-oxazol-4-yl)methoxy)pyridine-3-carboxamide

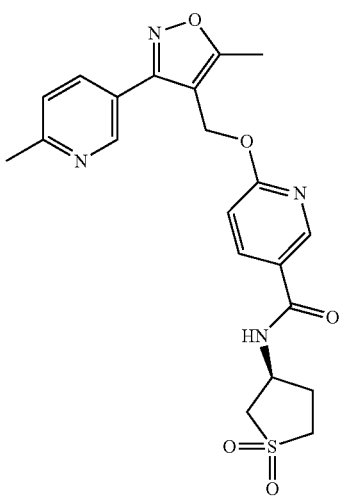 [SMILES: Cc1ccc(-c2noc(C)c2COc2ccc(C(=O)N[C@H]3CCS(=O)(=O)C3)cn2)cn1]

In analogy to experiment of example 4b, 6-((5-methyl-3-(6-methyl-3-pyridyl)isoxazol-4-yl)methoxy)pyridine-3-carboxylic acid, using 1,1-dioxothiolan-3-amine instead of (S)-2-aminopentan-1-ol, was converted into the racemic title compound (66 mg, 80%) which was obtained as a white solid. MS (ESI): 443.2 ([M+H]$^+$). Separation of the enantiomers by chiral HPLC (column: Chiralcel OD) afforded the (+)-title compound (16 mg) which was obtained as a white solid. MS (ESI): 443.2 ([M+H]$^+$).

Example 20

N-((3R)-1,1-dioxothiolan-3-yl)-6-((5-methyl-3-(6-methylpyridin-3-yl)-1,2-oxazol-4-yl)methoxy)pyridine-3-carboxamide

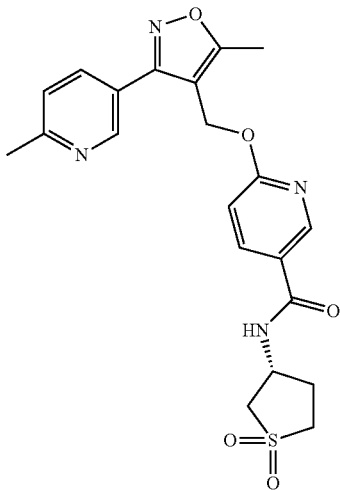 [SMILES: Cc1ccc(-c2noc(C)c2COc2ccc(C(=O)N[C@@H]3CCS(=O)(=O)C3)cn2)cn1]

In analogy to experiment of example 19, separation of the enantiomers by chiral HPLC (column: Chiralcel OD) afforded the (−)-title compound (16 mg) which was obtained as a white solid. MS (ESI): 443.2 ([M+H]$^+$).

Example 21

N-(1,1-dioxothian-4-yl)-6-((5-methyl-3-(6-methylpyridin-3-yl)-1,2-oxazol-4-yl)methoxy)pyridine-3-carboxamide

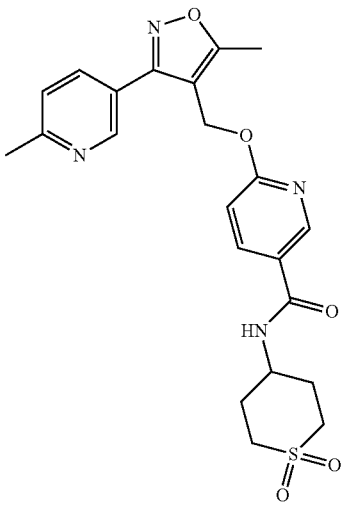 [SMILES: Cc1ccc(-c2noc(C)c2COc2ccc(C(=O)NC3CCS(=O)(=O)CC3)cn2)cn1]

a) 6-((5-methyl-3-(6-methyl-3-pyridyl)isoxazol-4-yl)methoxy)-N-tetrahydrothiopyran-4-yl-pyridine-3-carboxamide In analogy to experiment of example 4b, 6-((5-methyl-3-(6-methyl-3-pyridyl)isoxazol-4-yl)methoxy)pyridine-3-carboxylic acid, using tetrahydrothiopyran-4-amine instead of (S)-2-aminopentan-1-ol, was converted into the title compound (136 mg, 91%) which was obtained as an off-white solid. MS (ESI): 425.2 ([M+H]$^+$).

b) N-(1,1-dioxothian-4-yl)-6-((5-methyl-3-(6-methylpyridin-3-yl)-1,2-oxazol-4-yl)methoxy)pyridine-3-carboxamide To a stirred suspension of 6-((5-methyl-3-(6-methyl-3-pyridyl)isoxazol-4-yl)methoxy)-N-tetrahydrothiopyran-4-yl-pyridine-3-carboxamide (122 mg, 0.287 mmol) in a mixture of MeOH (3 mL) and water (3 mL) at room temperature was added Ozone® (353 mg, 0.575 mmol). After 3 hours, the suspension was basified by addition of aqueous Na$_2$CO$_3$ (0.5 m, 4 mL) and the mixture was stirred at room temperature for 1 hour. The suspension was filtered through a sintered funnel and the collected solid was washed with water (5 mL) and TBME (2 mL) then dried at high vacuum to afford the title compound (118 mg, 90%) as a white solid. MS (ESI): 457.2 ([M+H]$^+$).

Example 22

6-((5-methyl-3-(6-methylpyridin-3-yl)isoxazol-4-yl)methoxy)-2-(tetrahydro-2H-pyran-4-yl)-1H-pyrrolo[3,4-c]pyridin-3(2H)-one

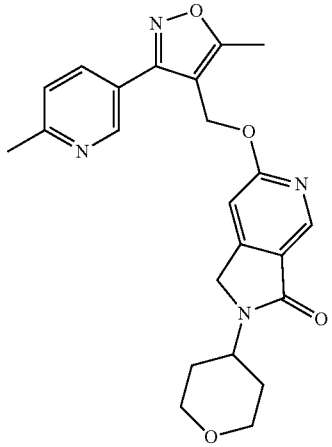 [SMILES: Cc1ccc(-c2noc(C)c2COc2cc3c(cn2)C(=O)N(C2CCOCC2)C3)cn1]

a) 6-chloro-2-tetrahydropyran-4-yl-1H-pyrrolo[3,4-c]pyridin-3-one

In analogy to experiment of example 9a, 6-chloro-4-formylnicotinic acid, using tetrahydropyran-4-amine instead of isobutylamine, was converted into the title compound (544 mg, 75%) which was obtained as a white solid. MS (ESI): 253.1 ([M+H]$^+$).

b) 6-((5-methyl-3-(6-methylpyridin-3-yl)isoxazol-4-yl)methoxy)-2-(tetrahydro-2H-pyran-4-yl)-1H-pyrrolo[3,4-c]pyridin-3(2H)-one In analogy to experiment of example 9b, (5-methyl-3-(6-methylpyridin-3-yl)isoxazol-4-yl)methanol (building block A), using 6-chloro-2-tetrahydropyran-4-yl-1H-pyrrolo[3,4-c]pyridin-3-one instead of 6-chloro-2-isobutyl-1H-pyrrolo[3,4-c]pyridin-3-one, was converted into the title compound (99 mg, 83%) which was obtained as a white solid. MS (ESI): 421.2 ([M+H]$^+$).

Example 23

N-((1S,2R)-2-hydroxycyclohexyl)-6-((5-methyl-3-(6-methylpyridin-3-yl)isoxazol-4-yl)methoxy)pyridazine-3-carboxamide

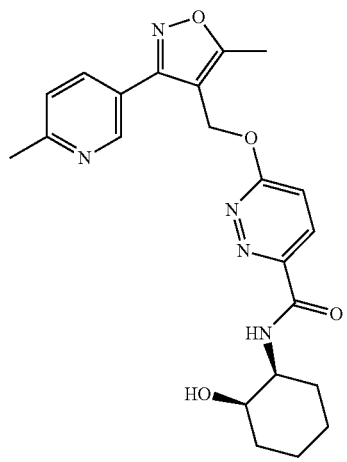 [SMILES: Cc1ccc(-c2noc(C)c2COc2ccc(C(=O)N[C@H]3CCCC[C@H]3O)nn2)cn1]

a) 4-((6-chloropyridazin-3-yloxy)methyl)-5-methyl-3-(6-methylpyridin-3-yl)isoxazole To a solution of (5-methyl-3-(6-methylpyridin-3-yl)isoxazol-4-yl)methanol (building block A, 15.9 g, 77.8 mmol) in anhydrous THF (500 mL) at 0° C. was added NaH (60% dispersion in mineral oil, 4.05 g, 101 mmol). The resulting solution was warmed to room temperature and stirred for 30 min before being cooled to 0° C. 3,6-dichloropyridazine (13.9 g, 93.4 mmol) was added over a period of 5 min and the reaction mixture was stirred for 3 hours. The reaction mixture was poured into water and ice and extracted with EtOAc (2×100 mL). The combined organic extracts were washed with brine, dried (Na$_2$SO$_4$) and concentrated in vacuo. Purification by flash chromatography (silica, gradient: 10% to 20% EtOAc in heptane) afforded the title compound (18.7 g, 76% yield) as a yellow solid. MS (ESI): 317.1 ([M+H]$^+$).

b) ethyl 6-((5-methyl-3-(6-methylpyridin-3-yl)isoxazol-4-yl)methoxy)pyridazine-3-carboxylate To a solution of 4-((6-chloropyridazin-3-yloxy)methyl)-5-methyl-3-(6-methylpyridin-3-yl)isoxazole (18.7 g, 56.0 mmol) in EtOH (280 mL) was added Na$_2$CO$_3$ (6.25 g, 59.0 mmol), 1,1'-bis(diphenylphosphino)ferrocene (3.27 g, 5.9 mmol) and Pd(OAc)$_2$ (1.33 g, 5.94 mmol). The resulting black suspension was purged by evacuation and then back filled with a stream of CO$_{(g)}$ (balloon, 1.3 L) for three time before being heated to 50° C. overnight under a CO$_{(g)}$ atmosphere. The reaction mixture was filtered directly through a plug of dicalite and the filter cake was rinsed with with EtOH (200 mL) then EtOAc (200 mL). The filtrate was concentrated in vacuo and the residue purified by flash chromatography (silica, gradient: 0% to 20% EtOAc in heptane) to afford the title compound (14.8 g, 75%) as a light yellow solid. MS (ESI): 355.2 ([M+H]$^+$).

c) 6-((5-methyl-3-(6-methylpyridin-3-yl)isoxazol-4-yl)methoxy)pyridazine-3-carboxylic Acid To a stirred solution of ethyl 6-((5-methyl-3-(6-methylpyridin-3-yl)isoxazol-4-yl)methoxy)pyridazine-3-carboxylate (2.20 g, 6.21 mmol) in a mixture of THF (7 mL) and MeOH (7 mL) and water (7 mL) was added LiOH.H$_2$O (782 mg, 18.6 mmol). The reaction mixture was stirred at room temperature overnight. The pH was adjusted to ~5 by addition of aqueous citric acid (5 wt. %) then the aqueous layer was extracted with EtOAc (2×100 mL). The combined organic extracts were washed with water (~20 mL) and brine (~20 mL) and the resulting solid precipitated during the work-up was collected through filtration on a sintered funnel. The solid was combined with the organic layers and concentrated in vacuo. The residue was triturated with EtOAc then filtered and dried under high vacuum to afford the title compound (1.51 g, 75%) as an off-white solid. MS (ESI): 327.1 ([M+H]$^+$).

d) N-((1S,2R)-2-hydroxycyclohexyl)-6-((5-methyl-3-(6-methylpyridin-3-yl)isoxazol-4-yl)methoxy)pyridazine-3-carboxamide To a stirred suspension of 6-((5-methyl-3-(6-methylpyridin-3-yl)isoxazol-4-yl)methoxy)pyridazine-3-carboxylic acid (35 mg, 0.107 mmol) and (1R,2S)-2-aminocyclohexanol hydrochloride (30 mg, 0.198 mmol) in DMF (0.6 mL) was added N,N-diisopropylethylamine (95 µL, 0.544 mmol) followed by TBTU (38 mg, 0.118 mmol). The resulting light yellow solution was stirred overnight at room temperature then poured into water (3 mL) and extracted with TBME (3×10 mL). The combined organic extracts were washed with water (3×3 mL), brine (~3 mL), dried (Na$_2$SO$_4$) and concentrated in vacuo. The resulting precipitate was triturated with TBME and EtOAc then filtered and dried under high vacuum to afford the title compound (39 mg, 86%) as an off-white solid. MS (ESI): 424.3 ([M+H]$^+$).

Example 24

N-((1S,2S)-2-hydroxycyclohexyl)-6-((5-methyl-3-(6-methylpyridin-3-yl)isoxazol-4-yl)methoxy)pyridazine-3-carboxamide

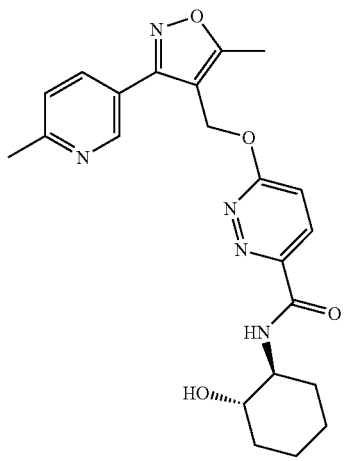 [SMILES: Cc1ccc(-c2noc(C)c2COc2ccc(C(=O)N[C@H]3CCCC[C@@H]3O)nn2)cn1]

In analogy to experiment of example 23d, 6-((5-methyl-3-(6-methylpyridin-3-yl)isoxazol-4-yl)methoxy)pyridazine-3-carboxylic acid, using (1S,2S)-2-aminocyclohexanol hydrochloride instead of (1R,2S)-2-aminocyclohexanol hydrochloride, was converted into the title compound (29 mg, 64%) which was obtained as an off-white solid. MS (ESI): 424.2 ([M+H]+).

Example 25

N-((1R,2R)-2-hydroxycyclohexyl)-6-((5-methyl-3-(6-methylpyridin-3-yl)isoxazol-4-yl)methoxy)pyridazine-3-carboxamide

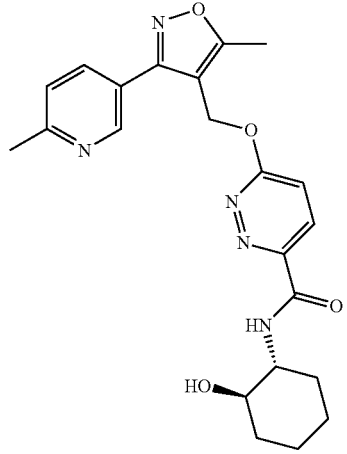 [SMILES: Cc1ccc(-c2noc(C)c2COc2ccc(C(=O)N[C@@H]3CCCC[C@H]3O)nn2)cn1]

In analogy to experiment of example 23d, 6-((5-methyl-3-(6-methylpyridin-3-yl)isoxazol-4-yl)methoxy)pyridazine-3-carboxylic acid, using (1R,2R)-2-aminocyclohexanol hydrochloride instead of (1R,2S)-2-aminocyclohexanol hydrochloride, was converted into the title compound (37 mg, 82%) which was obtained as an off-white solid. MS (ESI): 424.3 ([M+H]+).

Example 26

N-cyclopropyl-6-((5-methyl-3-(6-methylpyridin-3-yl)isoxazol-4-yl)methoxy)pyridazine-3-carboxamide

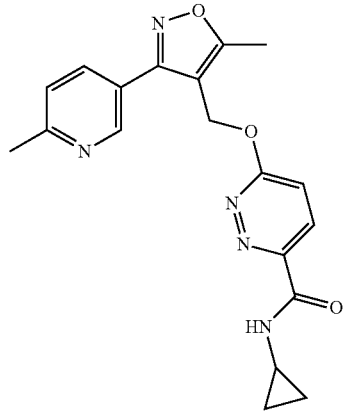 [SMILES: Cc1ccc(-c2noc(C)c2COc2ccc(C(=O)NC3CC3)nn2)cn1]

In analogy to experiment of example 23d, 6-((5-methyl-3-(6-methylpyridin-3-yl)isoxazol-4-yl)methoxy)pyridazine-3-carboxylic acid, using cyclopropylamine instead of (1R,2S)-2-aminocyclohexanol hydrochloride was converted into the title compound (51 mg, 80%) which was obtained as a white solid. MS (ESI): 366.2 ([M+H]+).

Example 27

N-((1R,2S)-2-hydroxycyclohexyl)-6-((5-methyl-3-(6-methylpyridin-3-yl)isoxazol-4-yl)methoxy)pyridazine-3-carboxamide

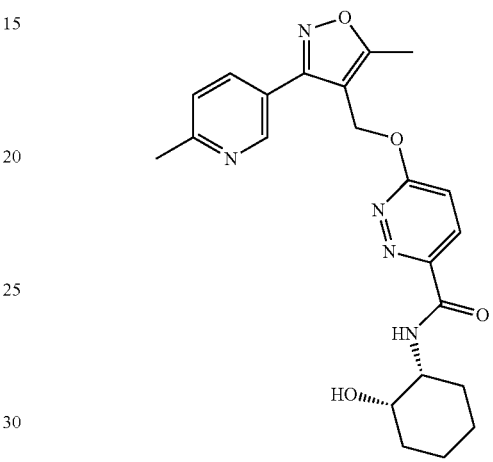

In analogy to experiment of example 23d, 6-((5-methyl-3-(6-methylpyridin-3-yl)isoxazol-4-yl)methoxy)pyridazine-3-carboxylic acid, using (1S,2R)-2-aminocyclohexanol hydrochloride instead of (1R,2S)-2-aminocyclohexanol hydrochloride, was converted into the title compound (31 mg, 68%) which was obtained as a light-brown solid. MS (ESI): 424.3 ([M+H]+).

Example 28

N-((3S,4R)-3-hydroxytetrahydropyran-4-yl)-6-((5-methyl-3-(6-methylpyridin-3-yl)isoxazol-4-yl)methoxy)pyridazine-3-carboxamide

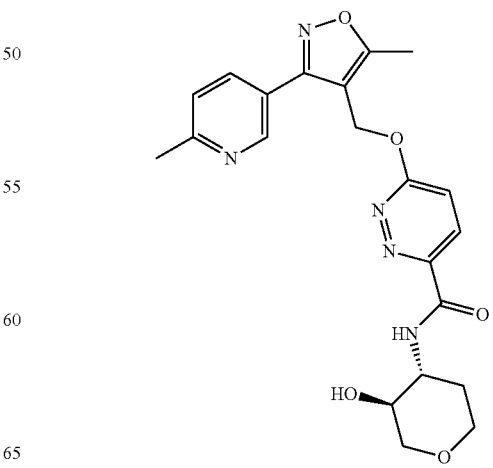

In analogy to experiment of example 23d, 6-((5-methyl-3-(6-methylpyridin-3-yl)isoxazol-4-yl)methoxy)pyridazine-3-carboxylic acid, using (3S,4R)-4-aminotetrahydro-2H-pyran-3-ol hydrochloride instead of (1R,2S)-2-aminocyclohexanol hydrochloride, was converted into the title compound (19 mg, 42%) which was obtained as an off-white foam. MS (ESI): 426.2 ([M+H]$^+$).

Example 29

N-(2-hydroxyethyl)-6-((5-methyl-3-(6-methylpyridin-3-yl)isoxazol-4-yl)methoxy)pyridazine-3-carboxamide

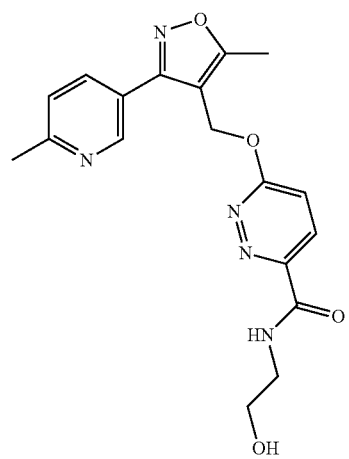

To a stirred suspension of 6-((5-methyl-3-(6-methylpyridin-3-yl)isoxazol-4-yl)methoxy)pyridazine-3-carboxylic acid (35 mg, 0.107 mmol) in DMF (0.75 mL) was added 1,1'-carbonyldiimidazole (23 mg, 0.142 mmol) and the reaction mixture was heated to 60° C. for 1 hour. After cooling to room temperature, ethanolamine (65 μL, 0.107 mmol) was added and the mixture was stirred for further 2 hours. The reaction mixture was poured into water (~3 mL) and extracted with TBME (2×10 mL). The combined organic extracts were washed with water (3×3 mL), brine (3×3 mL), dried (Na$_2$SO$_4$) and concentrated in vacuo. The aqueous layers were extracted with CH$_2$Cl$_2$ (2×20 mL) and the combined organic extracts were dried (Na$_2$SO$_4$) and concentrated in vacuo. Purification of the combined residues by flash chromatography (silica, gradient: 0% to 10% MeOH in CH$_2$Cl$_2$) afforded the title compound (25 mg, 63%) as a white solid. MS (ESI): 370.2 ([M+H]$^+$).

Example 30

N-(1,1-dioxothian-4-yl)-6-((5-methyl-3-(6-methylpyridin-3-yl)-1,2-oxazol-4-yl)methoxy)pyridazine-3-carboxamide

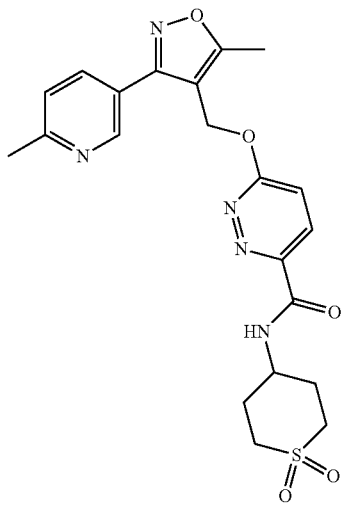 [SMILES: Cc1ccc(-c2noc(C)c2COc2ccc(C(=O)NC3CCS(=O)(=O)CC3)nn2)cn1]

To a stirred suspension of 6-((5-methyl-3-(6-methylpyridin-3-yl)isoxazol-4-yl)methoxy)pyridazine-3-carboxylic acid (40 mg, 0.123 mmol) and (1,1-dioxidotetrahydro-2H-thiopyran-4-yl)amine hydrochloride (37 mg, 0.199 mmol) in EtOAc (2.2 mL) was added triethylamine (100 μL, 0.717 mmol) followed by a solution of 1-propylphosphonic acid cyclic anhydride in EtOAc (50 wt. %, 160 mg, 150 μL, 0.252 mmol). The reaction mixture was heated to 50° C. overnight before being cooled to room temperature, diluted with EtOAc (~50 mL) and washed with saturated aqueous NaHCO$_3$ (2×10 mL). The aqueous layers were extracted with EtOAc (~50 mL). The combined organic extracts were washed with water (~5 mL) and brine (~5 mL), dried (Na$_2$SO$_4$) and concentrated in vacuo. Purification by flash chromatography (silica, gradient: 0% to 10% MeOH in CH$_2$Cl$_2$) afforded the title compound (40 mg, 68%) as an off-white solid. MS (ESI): 458.2 ([M+H]$^+$).

Example 31

N-(cyclopropylmethyl)-6-((5-methyl-3-(6-methylpyridin-3-yl)isoxazol-4-yl)methoxy)pyridazine-3-carboxamide

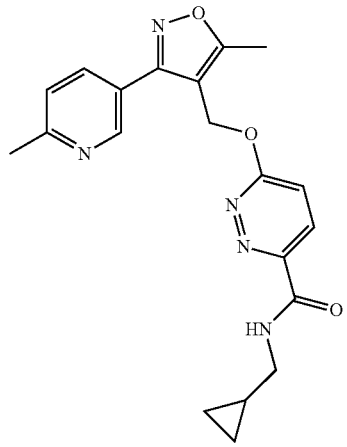 [SMILES: Cc1ccc(-c2noc(C)c2COc2ccc(C(=O)NCC3CC3)nn2)cn1]

In analogy to experiment of example 29, 6-((5-methyl-3-(6-methylpyridin-3-yl)isoxazol-4-yl)methoxy)pyridazine-3-carboxylic acid, using (aminomethyl)-cyclopropane instead of ethanolamine, was converted into the title compound (39 mg, 80%) which was obtained as an off-white solid. MS (ESI): 380.2 ([M+H]$^+$).

Example 32

N-(cyclopropylmethyl)-6-((5-methyl-3-(6-methylpyridin-3-yl)isoxazol-4-yl)methoxy)pyridazine-3-carboxamide

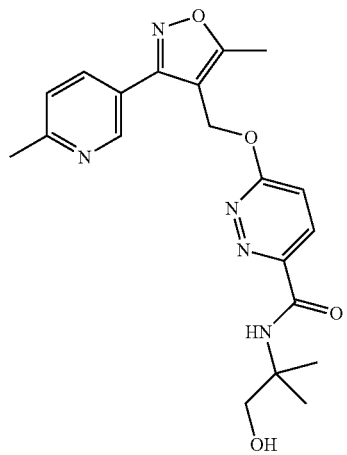 [SMILES: Cc1ccc(-c2noc(C)c2COc2ccc(C(=O)NC(C)(C)CO)nn2)cn1]

In analogy to experiment of example 29, 6-((5-methyl-3-(6-methylpyridin-3-yl)isoxazol-4-yl)methoxy)pyridazine-3-carboxylic acid, using 2-amino-2-methylpropan-1-ol instead of ethanolamine, was converted into the title compound (35 mg, 82%) which was obtained as a white foam. MS (ESI): 398.2 ([M+H]$^+$).

Example 33

N-(2-cyanoethyl)-6-((5-methyl-3-(6-methylpyridin-3-yl)isoxazol-4-yl)methoxy)pyridazine-3-carboxamide

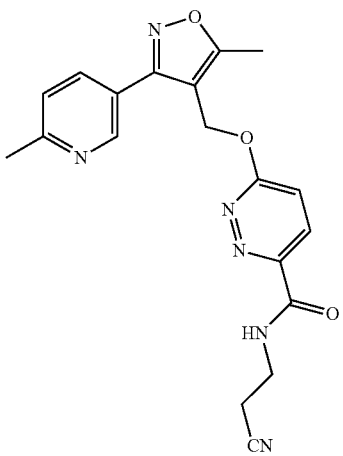 [SMILES: Cc1ccc(-c2noc(C)c2COc2ccc(C(=O)NCCC#N)nn2)cn1]

In analogy to experiment of example 29, 6-((5-methyl-3-(6-methylpyridin-3-yl)isoxazol-4-yl)methoxy)pyridazine-3-carboxylic acid, using 3-aminopropionitrile instead of ethanolamine, was converted into the title compound (34 mg, 84%) which was obtained as an off-white solid. MS (ESI): 379.2 ([M+H]$^+$).

Example 34

(RS)-6-((5-methyl-3-(6-methylpyridin-3-yl)isoxazol-4-yl)methoxy)-N-(1,1,1-trifluoropropan-2-yl)pyridazine-3-carboxamide

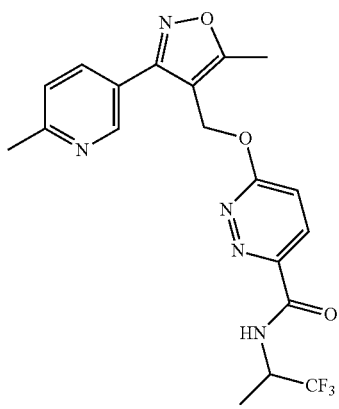 [SMILES: Cc1ccc(-c2noc(C)c2COc2ccc(C(=O)NC(C)C(F)(F)F)nn2)cn1]

In analogy to experiment of example 23d, 6-((5-methyl-3-(6-methylpyridin-3-yl)isoxazol-4-yl)methoxy)pyridazine-3-carboxylic acid, using (RS)-1,1,1-trifluoropropan-2-amine hydrochloride instead of (1R,2S)-2-aminocyclohexanol hydrochloride, was converted into the title compound (19 mg, 42%) which was obtained as an off-white solid. MS (ESI): 422.2 ([M+H]$^+$).

Example 35

6-((5-methyl-3-(6-methylpyridin-3-yl)isoxazol-4-yl)methoxy)-N-(oxetan-3-yl)pyridazine-3-carboxamide

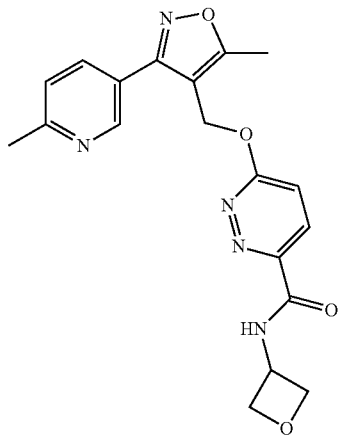 [SMILES: Cc1ccc(-c2noc(C)c2COc2ccc(C(=O)NC3COC3)nn2)cn1]

In analogy to experiment of example 23d, 6-((5-methyl-3-(6-methylpyridin-3-yl)isoxazol-4-yl)methoxy)pyridazine-3-carboxylic acid, using oxetan-3-amine hydrochloride instead of (1R,2S)-2-aminocyclohexanol hydrochloride, was converted into the title compound (36 mg, 57%) which was obtained as an off-white solid. MS (ESI): 382.2 ([M+H]$^+$).

Example 36

(RS)—N-(1,1-dioxothiolan-3-yl)-6-((5-methyl-3-(6-methylpyridin-3-yl)-1,2-oxazol-4-yl)methoxy)pyridazine-3-carboxamide

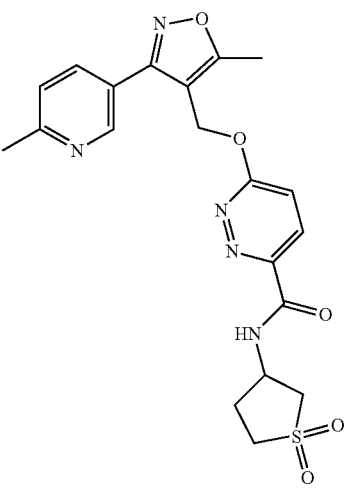 [SMILES: Cc1ccc(-c2noc(C)c2COc2ccc(C(=O)NC3CCS(=O)(=O)C3)nn2)cn1]

In analogy to experiment of example 30, 6-((5-methyl-3-(6-methylpyridin-3-yl)isoxazol-4-yl)methoxy)pyridazine-3-carboxylic acid, using (RS)-1,1-dioxothiolan-3-amine instead of (1,1-dioxidotetrahydro-2H-thiopyran-4-yl)amine hydrochloride, was converted into the title compound (89 mg, 82%) which was obtained as an off-white solid. MS (ESI): 444.2 ([M+H]$^+$).

Example 37

N-ethyl-6-((5-methyl-3-(6-methylpyridin-3-yl)isoxazol-4-yl)methoxy)pyridazine-3-carboxamide

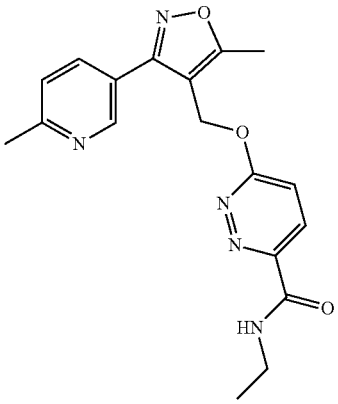 [SMILES: CCNC(=O)c1ccc(OCc2c(-c3ccc(C)nc3)noc2C)nn1]

In analogy to experiment of example 29, 6-((5-methyl-3-(6-methylpyridin-3-yl)isoxazol-4-yl)methoxy)pyridazine-3-carboxylic acid, using ethylamine (2.0 m in THF) instead of ethanolamine, was converted into the title compound (42 mg, 86%) which was obtained as an off-white solid. MS (ESI): 354.2 ([M+H]$^+$).

Example 38

N-isopropyl-6-((5-methyl-3-(6-methylpyridin-3-yl)isoxazol-4-yl)methoxy)pyridazine-3-carboxamide

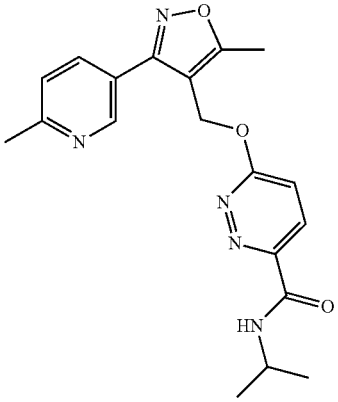 [SMILES: Cc1ccc(-c2noc(C)c2COc2ccc(C(=O)NC(C)C)nn2)cn1]

In analogy to experiment of example 29, 6-((5-methyl-3-(6-methylpyridin-3-yl)isoxazol-4-yl)methoxy)pyridazine-3-carboxylic acid, using isopropylamine instead of ethanolamine, was converted into the title compound (44 mg, 87%) which was obtained as an off-white solid. MS (ESI): 368.2 ([M+H]$^+$).

Example 39

N-isobutyl-6-((5-methyl-3-(6-methylpyridin-3-yl)isoxazol-4-yl)methoxy)pyridazine-3-carboxamide

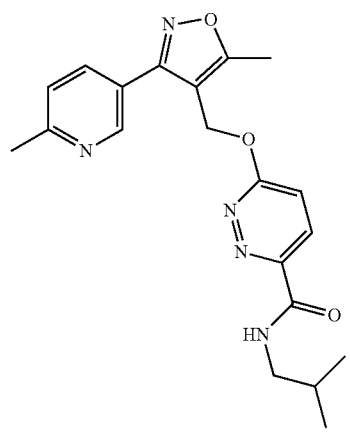 [SMILES: Cc1ccc(-c2noc(C)c2COc2ccc(C(=O)NCC(C)C)nn2)cn1]

In analogy to experiment of example 29, 6-((5-methyl-3-(6-methylpyridin-3-yl)isoxazol-4-yl)methoxy)pyridazine-3-carboxylic acid, using isobutylamine instead of ethanolamine, was converted into the title compound (46 mg, 83%) which was obtained as an off-white solid. MS (ESI): 382.2 ([M+H]$^+$).

Example 40

6-((5-methyl-3-(6-methylpyridin-3-yl)isoxazol-4-yl)methoxy)-N-(2,2,2-trifluoroethyl)pyridazine-3-carboxamide

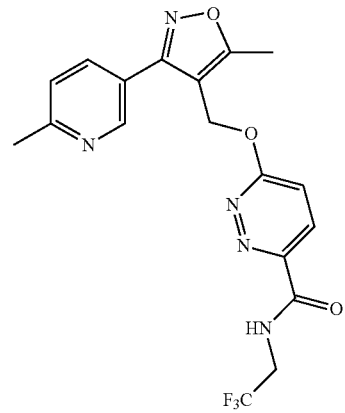 [SMILES: Cc1ccc(-c2noc(C)c2COc2ccc(C(=O)NCC(F)(F)F)nn2)cn1]

In analogy to experiment of example 23d, 6-((5-methyl-3-(6-methylpyridin-3-yl)isoxazol-4-yl)methoxy)pyridazine-3-carboxylic acid, using 2,2,2-trifluoroethanamine hydrochloride instead of (1R,2S)-2-aminocyclohexanol hydrochloride, was converted into the title compound (34 mg, 61%) which was obtained as an off-white solid. MS (ESI): 408.2 ([M+H]$^+$).

Example 41

N-tert-butyl-6-((5-methyl-3-(6-methylpyridin-3-yl)isoxazol-4-yl)methoxy)pyridazine-3-carboxamide

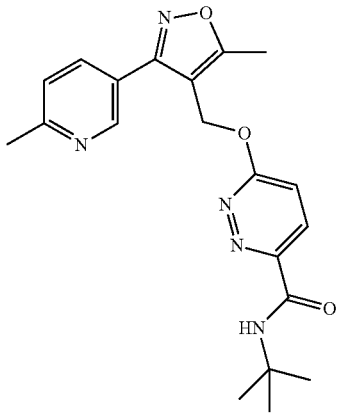 [SMILES: Cc1ccc(-c2noc(C)c2COc2ccc(C(=O)NC(C)(C)C)nn2)cn1]

In analogy to experiment of example 29, 6-((5-methyl-3-(6-methylpyridin-3-yl)isoxazol-4-yl)methoxy)pyridazine-3-carboxylic acid, using tert-butylamine instead of ethanolamine, was converted into the title compound (46 mg, 83%) which was obtained as an off-white solid. MS (ESI): 382.2 ([M+H]$^+$).

Example 42

N-(3,3-difluorocyclobutyl)-6-((5-methyl-3-(6-methylpyridin-3-yl)isoxazol-4-yl)methoxy)pyridazine-3-carboxamide

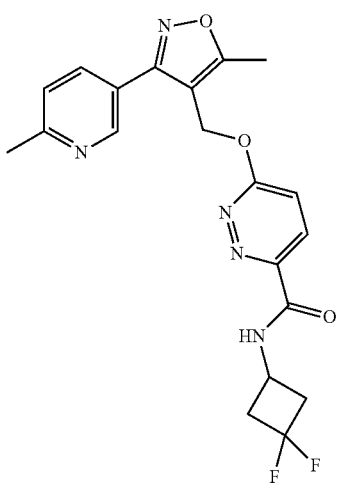 [SMILES: Cc1ccc(-c2noc(C)c2COc2ccc(C(=O)NC3CC(F)(F)C3)nn2)cn1]

In analogy to experiment of example 23d, 6-((5-methyl-3-(6-methylpyridin-3-yl)isoxazol-4-yl)methoxy)pyridazine-3-carboxylic acid, using 3,3-difluorocyclobutanamine hydrochloride instead of (1R,2S)-2-aminocyclohexanol hydrochloride, was converted into the title compound (36 mg, 63%) which was obtained as an off-white solid. MS (ESI): 416.2 ([M+H]$^+$).

Example 43

N-(4,4-difluorocyclohexyl)-6-((5-methyl-3-(6-methylpyridin-3-yl)isoxazol-4-yl)methoxy)pyridazine-3-carboxamide

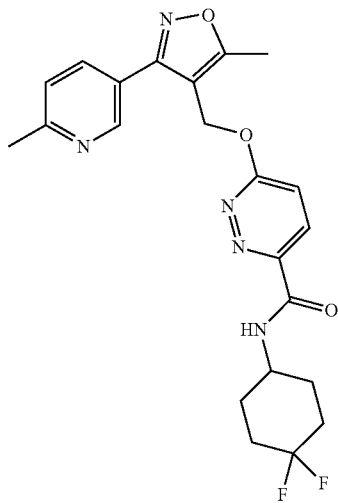 [SMILES: Cc1ccc(-c2noc(C)c2COc2ccc(C(=O)NC3CCC(F)(F)CC3)nn2)cn1]

In analogy to experiment of example 23d, 6-((5-methyl-3-(6-methylpyridin-3-yl)isoxazol-4-yl)methoxy)pyridazine-3-carboxylic acid, using 4,4-difluorocyclohexanamine hydrochloride instead of (1R,2S)-2-aminocyclohexanol hydrochloride, was converted into the title compound (51 mg, 79%) which was obtained as an off-white solid. MS (ESI): 444.2 ([M+H]$^+$).

Example 44

6-((3-(6-methyl-3-pyridyl)isoxazol-4-yl)methoxy)-N-tetrahydropyran-4-yl-pyridine-3-carboxamide

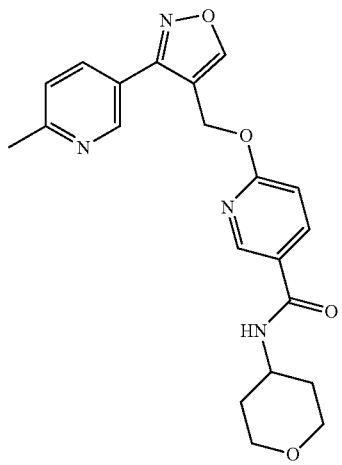 [SMILES: Cc1ccc(-c2nocc2COc2ccc(C(=O)NC3CCOCC3)cn2)cn1]

a) Methyl 6-((3-(6-methyl-3-pyridyl)isoxazol-4-yl)methoxy)pyridine-3-carboxylate In analogy to experiment of example 1a, (3-(6-methyl-3-pyridyl)isoxazol-4-yl)methanol (building block H) instead of (5-methyl-3-(6-methylpyridin-3-yl)isoxazol-4-yl)methanol (building block A) was converted into the title compound (821 mg, 48%) which was obtained as a white solid. MS (ESI): 326.1 ([M+H]$^+$).

b) 6-((3-(6-methyl-3-pyridyl)isoxazol-4-yl)methoxy)pyridine-3-carboxylic Acid

In analogy to experiment of example 4a, methyl 6-((3-(6-methyl-3-pyridyl)isoxazol-4-yl)methoxy)pyridine-3-carboxylate instead of methyl 6-((5-methyl-3-(6-methyl-3-pyridyl)isoxazol-4-yl)methoxy)pyridine-3-carboxylate was converted into the title compound (837 mg, 88%) which was obtained as a white solid. MS (ESI): 312.1 ([M+H]$^+$).

c) 6-((3-(6-methyl-3-pyridyl)isoxazol-4-yl)methoxy)-N-tetrahydropyran-4-yl-pyridine-3-carboxamide In analogy to experiment of example 4b, 6-((3-(6-methyl-3-pyridyl)isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid, using tetrahydropyran-4-amine instead of (S)-2-aminopentan-1-ol, was converted into the title compound (65 mg, 80%) which was obtained as a white solid. MS (ESI): 395.2 ([M+H]$^+$).

Example 45

(RS)-6-((5-methyl-3-(6-methylpyridin-3-yl)isoxazol-4-yl)methoxy)-N-(tetrahydrofuran-3-yl)pyridazine-3-carboxamide

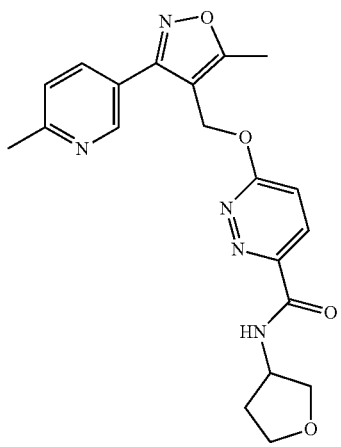 [SMILES: Cc1ccc(-c2noc(C)c2COc2ccc(C(=O)NC3CCOC3)nn2)cn1]

In analogy to experiment of example 23d, 6-((5-methyl-3-(6-methylpyridin-3-yl)isoxazol-4-yl)methoxy)pyridazine-3-carboxylic acid, using (RS)-tetrahydrofuran-3-amine hydrochloride instead of (1R,2S)-2-aminocyclohexanol hydrochloride, was converted into the title compound (33 mg, 58%) which was obtained as an off-white solid. MS (ESI): 396.3 ([M+H]$^+$).

Example 46

N-methyl-6-((5-methyl-3-(6-methylpyridin-3-yl)isoxazol-4-yl)methoxy)pyridazine-3-carboxamide

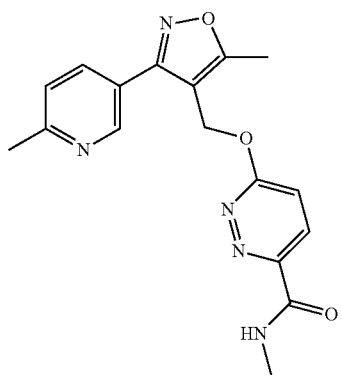 [SMILES: CNC(=O)c1ccc(OCc2c(-c3ccc(C)nc3)noc2C)nn1]

In analogy to experiment of example 29, 6-((5-methyl-3-(6-methylpyridin-3-yl)isoxazol-4-yl)methoxy)pyridazine-3-carboxylic acid, using methylamine (2.0 m solution in THF) instead of ethanolamine, was converted into the title compound (38 mg, 73%) which was obtained as an off-white solid. MS (ESI): 340.2 ([M+H]$^+$).

Example 47

(3,3-difluoroazetidin-1-yl)(6-((5-methyl-3-(6-methylpyridin-3-yl)isoxazol-4-yl)methoxy)pyridazin-3-yl)methanone

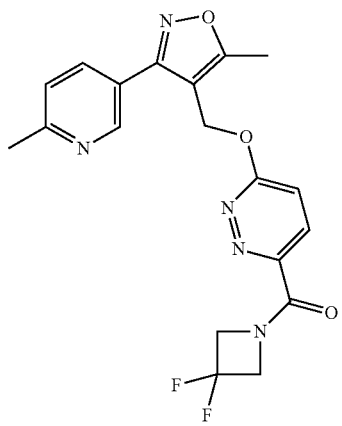 [SMILES: Cc1ccc(-c2noc(C)c2COc2ccc(C(=O)N3CC(F)(F)C3)nn2)cn1]

In analogy to experiment of example 30, 6-((5-methyl-3-(6-methylpyridin-3-yl)isoxazol-4-yl)methoxy)pyridazine-3-carboxylic acid, using 3,3-difluoroazetidine hydrochloride instead of (1,1-dioxidotetrahydro-2H-thiopyran-4-yl)amine hydrochloride, was converted into the title compound (53 mg, 82%) which was obtained as an off-white solid. MS (ESI): 402.2 ([M+H]$^+$).

Example 48

(3,3-difluoropyrrolidin-1-yl)(6-((5-methyl-3-(6-methylpyridin-3-yl)isoxazol-4-yl)methoxy)pyridazin-3-yl)methanone

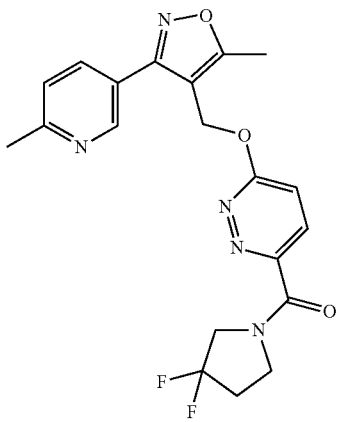 [SMILES: Cc1ccc(-c2noc(C)c2COc2ccc(C(=O)N3CCC(F)(F)C3)nn2)cn1]

In analogy to experiment of example 30, 6-((5-methyl-3-(6-methylpyridin-3-yl)isoxazol-4-yl)methoxy)pyridazine-3-carboxylic acid, using 3,3-difluoropyrrolidine hydrochloride instead of (1,1-dioxidotetrahydro-2H-thiopyran-4-yl)amine hydrochloride, was converted into the title compound (46 mg, 80%) which was obtained as an off-white solid. MS (ESI): 416.2 ([M+H]$^+$).

Example 49

6-((5-methyl-3-(6-methylpyridin-3-yl)isoxazol-4-yl)methoxy)-N-((3-methyloxetan-3-yl)methyl)pyridazine-3-carboxamide

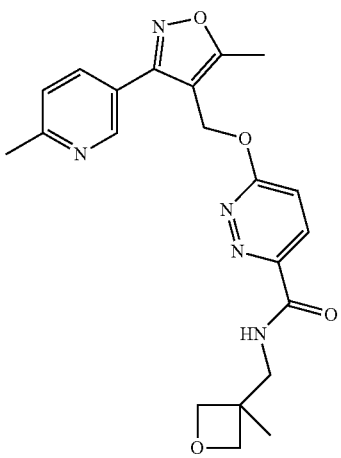 [SMILES: Cc1ccc(-c2noc(C)c2COc2ccc(C(=O)NCC3(C)COC3)nn2)cn1]

In analogy to experiment of example 30, 6-((5-methyl-3-(6-methylpyridin-3-yl)isoxazol-4-yl)methoxy)pyridazine-3-carboxylic acid, using (3-methyloxetan-3-yl)methanamine instead of (1,1-dioxidotetrahydro-2H-thiopyran-4-yl)amine hydrochloride, was converted into the title compound (40 mg, 71%) which was obtained as an off-white solid. MS (ESI): 410.2 ([M+H]$^+$).

Example 50

6-((5-methyl-3-(6-methyl-3-pyridyl)isoxazol-4-yl)methoxy)-N-(oxetan-3-ylmethyl)pyridazine-3-carboxamide

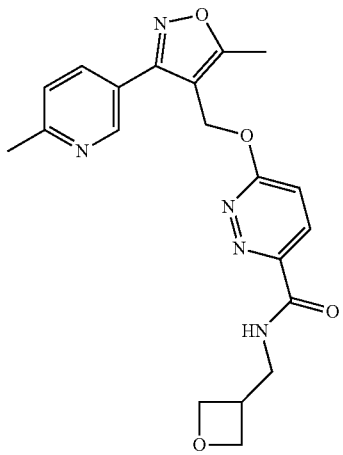 [SMILES: Cc1ccc(-c2noc(C)c2COc2ccc(C(=O)NCC3COC3)nn2)cn1]

In analogy to experiment of example 30, 6-((5-methyl-3-(6-methylpyridin-3-yl)isoxazol-4-yl)methoxy)pyridazine-3-carboxylic acid, using 3-aminomethyloxetane instead of (1,1-dioxidotetrahydro-2H-thiopyran-4-yl)amine hydrochloride, was converted into the title compound (33 mg, 58%) which was obtained as an off-white solid. MS (ESI): 396.2 ([M+H]$^+$).

Example 51

N-((3-hydroxyoxetan-3-yl)methyl)-6-((5-methyl-3-(6-methylpyridin-3-yl)isoxazol-4-yl)methoxy)pyridazine-3-carboxamide

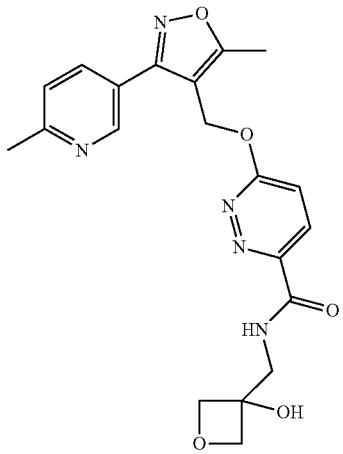 [SMILES: Cc1ccc(-c2noc(C)c2COc2ccc(C(=O)NCC3(O)COC3)nn2)cn1]

In analogy to experiment of example 30, 6-((5-methyl-3-(6-methylpyridin-3-yl)isoxazol-4-yl)methoxy)pyridazine-3-carboxylic acid, using 3-(aminomethyl)oxetan-3-ol instead of (1,1-dioxidotetrahydro-2H-thiopyran-4-yl)amine hydrochloride, was converted into the title compound (44 mg, 74%) which was obtained as an off-white foam. MS (ESI): 412.2 ([M+H]$^+$).

Example 52

6-((5-methyl-3-(6-methylpyridin-3-yl)isoxazol-4-yl)methoxy)-N-((3R,4R)-3-methyltetrahydropyran-4-yl)pyridazine-3-carboxamide

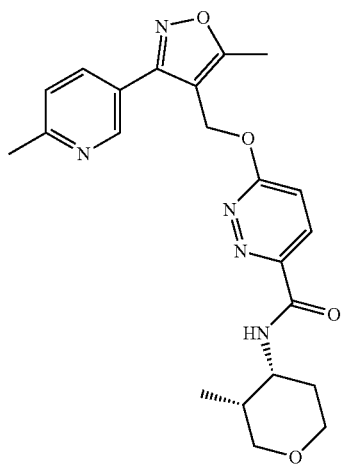 [SMILES: Cc1ccc(-c2noc(C)c2COc2ccc(C(=O)N[C@@H]3CCOC[C@@H]3C)nn2)cn1]

In analogy to experiment of example 23d, 6-((5-methyl-3-(6-methylpyridin-3-yl)isoxazol-4-yl)methoxy)pyridazine-3-carboxylic acid, using (3R,4R)-3-methyltetrahydro-2H-pyran-4-amine hydrochloride instead of (1R,2S)-2-aminocyclohexanol hydrochloride, was converted into the title compound (44 mg, 75%) which was obtained as an off-white foam. MS (ESI): 424.3 ([M+H]$^+$).

Example 53

(4,4-difluoropiperidin-1-yl)(6-((5-methyl-3-(6-methylpyridin-3-yl)isoxazol-4-yl)methoxy)pyridazin-3-yl)methanone

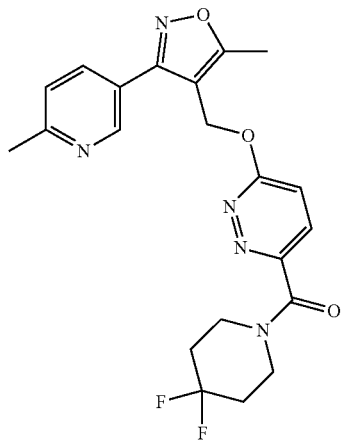 [SMILES: Cc1ccc(-c2noc(C)c2COc2ccc(C(=O)N3CCC(F)(F)CC3)nn2)cn1]

In analogy to experiment of example 30, 6-((5-methyl-3-(6-methylpyridin-3-yl)isoxazol-4-yl)methoxy)pyridazine-3- carboxylic acid, using 4,4-difluoropiperidine hydrochloride instead of (1,1-dioxidotetrahydro-2H-thiopyran-4-yl)amine hydrochloride, was converted into the title compound (41 mg, 59%) which was obtained as a white solid. MS (ESI): 430.2 ([M+H]$^+$).

Example 54

N-(1-(methoxymethyl)cyclopropyl)-6-((5-methyl-3-(6-methylpyridin-3-yl)isoxazol-4-yl)methoxy)pyridazine-3-carboxamide

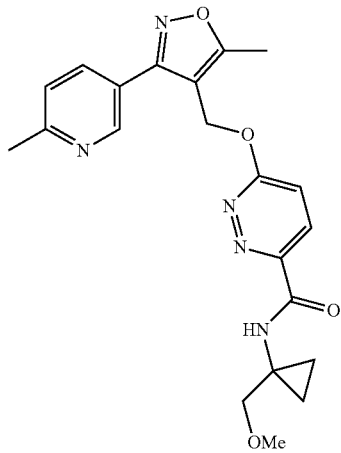 [SMILES: COCC1(NC(=O)c2ccc(OCc3c(-c4ccc(C)nc4)noc3C)nn2)CC1]

In analogy to experiment of example 30, 6-((5-methyl-3-(6-methylpyridin-3-yl)isoxazol-4-yl)methoxy)pyridazine-3-carboxylic acid, using 1-(methoxymethyl)cyclopropanamine hydrochloride instead of (1,1-dioxidotetrahydro-2H-thiopyran-4-yl)amine hydrochloride, was converted into the title compound (41 mg, 59%) which was obtained as an off-white solid. MS (ESI): 410.3 ([M+H]$^+$).

Example 55

(3-methoxyazetidin-1-yl)(6-((5-methyl-3-(6-methylpyridin-3-yl)isoxazol-4-yl)methoxy)pyridazin-3-yl)methanone

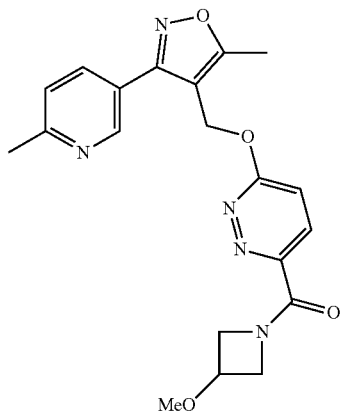 [SMILES: COC1CN(C(=O)c2ccc(OCc3c(-c4ccc(C)nc4)noc3C)nn2)C1]

In analogy to experiment of example 30, 6-((5-methyl-3-(6-methylpyridin-3-yl)isoxazol-4-yl)methoxy)pyridazine-3-carboxylic acid, using 3-methoxyazetidine hydrochloride instead of (1,1-dioxidotetrahydro-2H-thiopyran-4-yl)amine hydrochloride, was converted into the title compound (45 mg, 74%) which was obtained as an off-white solid. MS (ESI): 396.2 ([M+H]$^+$).

Example 56

(3-hydroxy-3-methylazetidin-1-yl)(6-((5-methyl-3-(6-methylpyridin-3-yl)isoxazol-4-yl)methoxy)pyridazin-3-yl)methanone

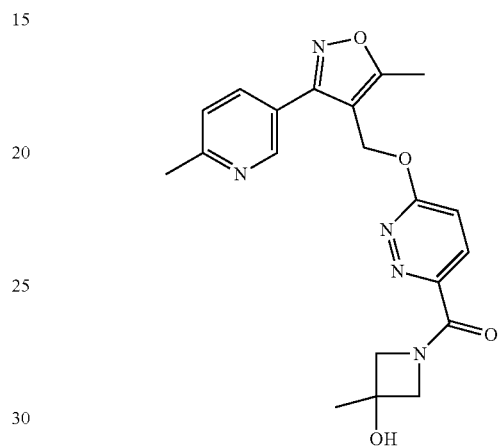

In analogy to experiment of example 30, 6-((5-methyl-3-(6-methylpyridin-3-yl)isoxazol-4-yl)methoxy)pyridazine-3-carboxylic acid, using 3-methylazetidin-3-ol hydrochloride instead of (1,1-dioxidotetrahydro-2H-thiopyran-4-yl)amine hydrochloride, was converted into the title compound (27 mg, 45%) which was obtained as an off-white foam. MS (ESI): 396.2 ([M+H]$^+$).

Example 57 azetidin-1-yl(6-((5-methyl-3-(6-methylpyridin-3-yl)isoxazol-4-yl)methoxy)pyridazin-3-yl)methanone

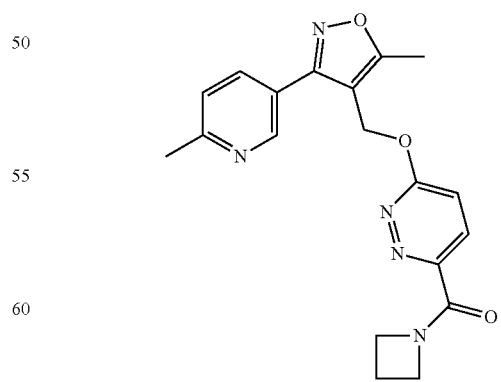

In analogy to experiment of example 29, 6-((5-methyl-3-(6-methylpyridin-3-yl)isoxazol-4-yl)methoxy)pyridazine-3-carboxylic acid, using azetidine instead of ethanolamine, was converted into the title compound (26 mg, 44%) which was obtained as an off-white solid. MS (ESI): 366.2 ([M+H]$^+$).

Example 58

(RS)—N-(2,2-dimethyltetrahydropyran-4-yl)-6-((5-methyl-3-(6-methylpyridin-3-yl)isoxazol-4-yl)methoxy)pyridazine-3-carboxamide

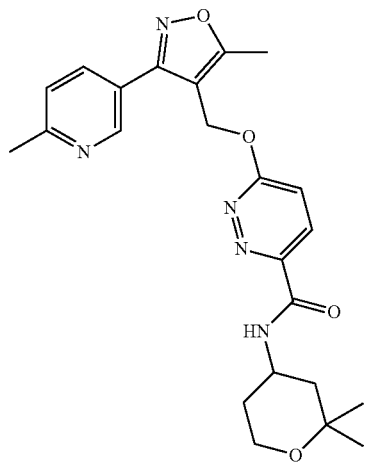

In analogy to experiment of example 30, 6-((5-methyl-3-(6-methylpyridin-3-yl)isoxazol-4-yl)methoxy)pyridazine-3-carboxylic acid, using (RS)-2,2-dimethyltetrahydropyran-4-amine instead of (1,1-dioxidotetrahydro-2H-thiopyran-4-yl)amine hydrochloride, was converted into the title compound (52 mg, 78%) which was obtained as a white foam. MS (ESI): 438.3 ([M+H]$^+$).

Example 59

6-((5-methyl-3-(6-methylpyridin-3-yl)isoxazol-4-yl)methoxy)-N-(1-(trifluoromethyl)cyclopropyl)pyridazine-3-carboxamide

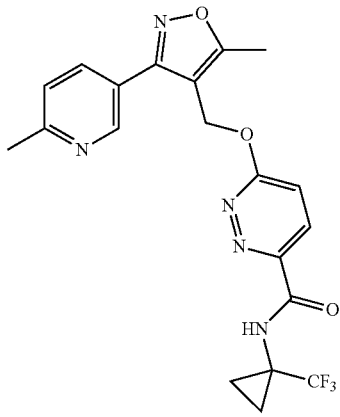 [SMILES: Cc1ccc(-c2noc(C)c2COc2ccc(C(=O)NC3(C(F)(F)F)CC3)nn2)cn1]

In analogy to experiment of example 23d, 6-((5-methyl-3-(6-methylpyridin-3-yl)isoxazol-4-yl)methoxy)pyridazine-3-carboxylic acid, using 1-(trifluoromethyl)cyclopropan-amine hydrochloride instead of (1R,2S)-2-aminocyclohexanol hydrochloride, was converted into the title compound (46 mg, 69%) which was obtained as an off-white solid. MS (ESI): 434.2 ([M+H]$^+$).

Example 60

(6-((5-methyl-3-(6-methylpyridin-3-yl)isoxazol-4-yl)methoxy)pyridazin-3-yl)(morpholino)methanone

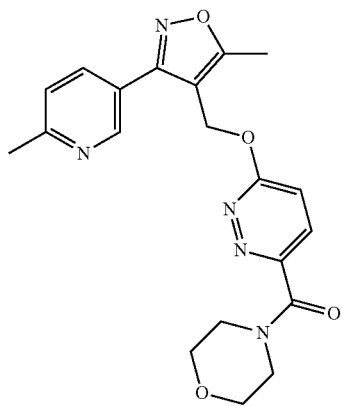 [SMILES: Cc1ccc(-c2noc(C)c2COc2ccc(C(=O)N3CCOCC3)nn2)cn1]

In analogy to experiment of example 29, 6-((5-methyl-3-(6-methylpyridin-3-yl)isoxazol-4-yl)methoxy)pyridazine-3-carboxylic acid, using morpholine instead of ethanolamine was converted into the title compound (41 mg, 68%) which was obtained as an off-white solid. MS (ESI): 396.3 ([M+H]$^+$).

Example 61

(6-((5-methyl-3-(6-methylpyridin-3-yl)isoxazol-4-yl)methoxy)pyridazin-3-yl)(2-oxa-6-azaspiro[3.3]heptan-6-yl)methanone

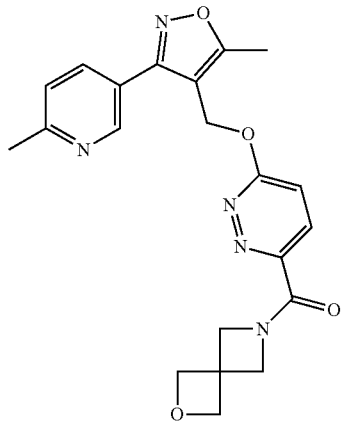 [SMILES: Cc1ccc(-c2noc(C)c2COc2ccc(C(=O)N3CC4(COC4)C3)nn2)cn1]

In analogy to experiment of example 30, 6-((5-methyl-3-(6-methylpyridin-3-yl)isoxazol-4-yl)methoxy)pyridazine-3-carboxylic acid, using 2-oxa-6-azaspiro[3.3]heptane hydrochloride instead of (1,1-dioxidotetrahydro-2H-thiopyran-4-yl)amine hydrochloride, was converted into the title compound (20 mg, 30%) which was obtained as a white foam. MS (ESI): 408.2 ([M+H]$^+$).

Example 62

4-methyl-6-((5-methyl-3-(6-methylpyridin-3-yl)isoxazol-4-yl)methoxy)-N-(tetrahydropyran-4-yl)pyridazine-3-carboxamide

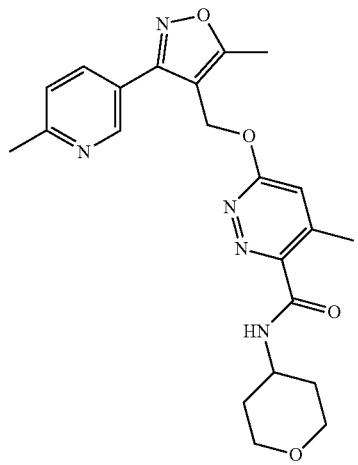

a) 4-((6-chloro-5-methyl-pyridazin-3-yl)oxymethyl)-5-methyl-3-(6-methyl-3-pyridyl)isoxazole In analogy to experiment of example 23a, (5-methyl-3-(6-methylpyridin-3-yl)isoxazol-4-yl)methanol (building block A), using 3,6-dichloro-4-methylpyridazine instead of 3,6-dichloropyridazine, was converted into a 1:1 mixture of the title compound and the isomeric 4-((6-chloro-4-methyl-pyridazin-3-yl)oxymethyl)-5-methyl-3-(6-methyl-3-pyridyl)isoxazole (1.45 g, 89%) which was obtained as a light brown oil. MS (ESI): 331.1 ([M+H]$^+$).

b) ethyl 4-methyl-6-((5-methyl-3-(6-methyl-3-pyridyl)isoxazol-4-yl)methoxy)pyridazine-3-carboxylate In analogy to experiment of example 23b, 4-((6-chloro-4-methyl-pyridazin-3-yl)oxymethyl)-5-methyl-3-(6-methyl-3-pyridyl)isoxazole and 4-((6-chloro-5-methyl-pyridazin-3-yl)oxymethyl)-5-methyl-3-(6-methyl-3-pyridyl)isoxazole instead of 4-((6-chloropyridazin-3-yloxy)methyl)-5-methyl-3-(6-methylpyridin-3-yl)isoxazole was converted into the title compound (310 mg, 21%) as a light yellow oil, following separation of regioisomers by flash chromatography (silica, gradient: 0% to 80% EtOAc in heptane). MS (ESI): 369.2 ([M+H]$^+$).

c) 4-methyl-6-((5-methyl-3-(6-methyl-3-pyridyl)isoxazol-4-yl)methoxy)pyridazine-3-carboxylic Acid In analogy to experiment of example 23c, ethyl 4-methyl-6-((5-methyl-3-(6-methyl-3-pyridyl)isoxazol-4-yl)methoxy)pyridazine-3-carboxylate instead of ethyl 6-((5-methyl-3-(6-methylpyridin-3-yl)isoxazol-4-yl)methoxy)pyridazine-3-carboxylate was converted into the title compound (213 mg, 72%) which was obtained as a white solid. MS (ESI): 341.1 ([M+H]$^+$).

d) 4-methyl-6-((5-methyl-3-(6-methylpyridin-3-yl)isoxazol-4-yl)methoxy)-N-(tetrahydropyran-4-yl)pyridazine-3-carboxamide In analogy to experiment of example 23d, 4-methyl-6-((5-methyl-3-(6-methyl-3-pyridyl)isoxazol-4-yl)methoxy)pyridazine-3-carboxylic acid instead of 6-((5-methyl-3-(6-methylpyridin-3-yl)isoxazol-4-yl)methoxy)pyridazine-3-carboxylic acid, using tetrahydropyran-4-amine instead of (1R,2S)-2-aminocyclohexanol hydrochloride, was converted into the title compound (49 mg, 89%) which was obtained as a white solid. MS (ESI): 424.2 ([M+H]$^+$).

Example 63

(6-((5-methyl-3-(6-methylpyridin-3-yl)isoxazol-4-yl)methoxy)pyridazin-3-yl)(6-oxa-1-azaspiro[3.3]heptan-1-yl)methanone

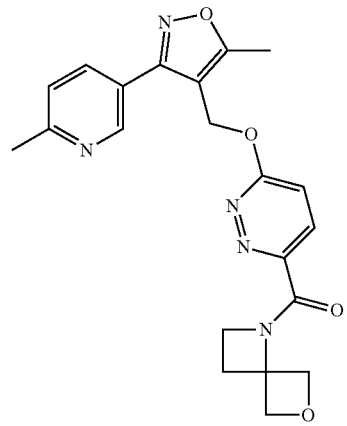 [SMILES: Cc1ccc(-c2noc(C)c2COc2ccc(C(=O)N3CCC34COC4)nn2)cn1]

In analogy to experiment of example 30, 6-((5-methyl-3-(6-methylpyridin-3-yl)isoxazol-4-yl)methoxy)pyridazine-3-carboxylic acid, using 6-oxa-1-azaspiro[3.3]heptane oxalate instead of (1,1-dioxidotetrahydro-2H-thiopyran-4-yl)amine hydrochloride, was converted into the title compound (43 mg, 62%) which was obtained as an off-white foam. MS (ESI): 408.2 ([M+H]$^+$).

Example 64

6-((5-methyl-3-(6-methylpyridin-3-yl)isoxazol-4-yl)methoxy)-N-(1,1,1-trifluoro-2-methylpropan-2-yl)pyridazine-3-carboxamide

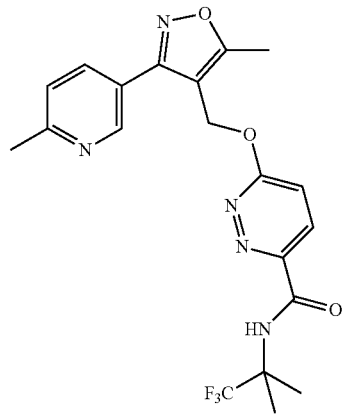 [SMILES: Cc1ccc(-c2noc(C)c2COc2ccc(C(=O)NC(C)(C)C(F)(F)F)nn2)cn1]

In analogy to experiment of example 30, 6-((5-methyl-3-(6-methylpyridin-3-yl)isoxazol-4-yl)methoxy)pyridazine-3-carboxylic acid, using 1,1,1-trifluoro-2-methylpropan-2-amine instead of (1,1-dioxidotetrahydro-2H-thiopyran-4-yl)amine hydrochloride, was converted into the title compound (41 mg, 62%) which was obtained as an off-white solid. MS (ESI): 436.2 ([M+H]$^+$).

Example 65

(3-fluoroazetidin-1-yl)(6-((5-methyl-3-(6-methylpyridin-3-yl)isoxazol-4-yl)methoxy)pyridazin-3-yl)methanone

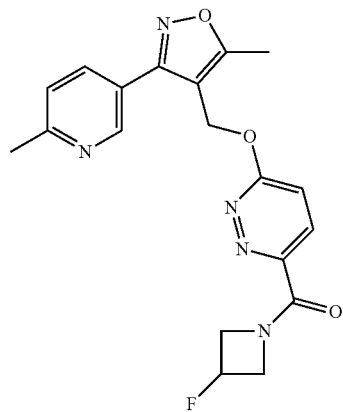 [SMILES: Cc1ccc(-c2noc(C)c2COc2ccc(C(=O)N3CC(F)C3)nn2)cn1]

In analogy to experiment of example 30, 6-((5-methyl-3-(6-methylpyridin-3-yl)isoxazol-4-yl)methoxy)pyridazine-3-carboxylic acid, using 3-fluoroazetidine hydrochloride instead of (1,1-dioxidotetrahydro-2H-thiopyran-4-yl)amine hydrochloride, was converted into the title compound (52 mg, 89%) which was obtained as an off-white solid. MS (ESI): 384.2 ([M+H]$^+$).

Example 66

(3-hydroxyazetidin-1-yl)(6-((5-methyl-3-(6-methylpyridin-3-yl)isoxazol-4-yl)methoxy)pyridazin-3-yl)methanone

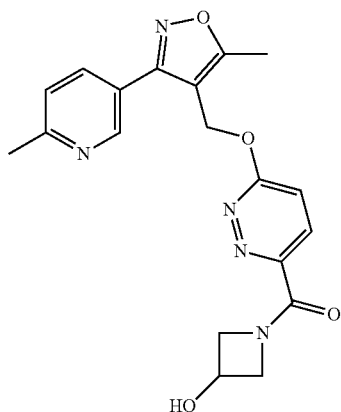 [SMILES: Cc1ccc(-c2noc(C)c2COc2ccc(C(=O)N3CC(O)C3)nn2)cn1]

In analogy to experiment of example 30, 6-((5-methyl-3-(6-methylpyridin-3-yl)isoxazol-4-yl)methoxy)pyridazine-3-carboxylic acid, using 3-hydroxyazetidine hydrochloride instead of (1,1-dioxidotetrahydro-2H-thiopyran-4-yl)amine hydrochloride, was converted into the title compound (19 mg, 31%) which was obtained as an off-white solid. MS (ESI): 382.2 ([M+H]$^+$).

Example 67

(3-fluoro-3-methylazetidin-1-yl)(6-((5-methyl-3-(6-methylpyridin-3-yl)isoxazol-4-yl)methoxy)pyridazin-3-yl)methanone

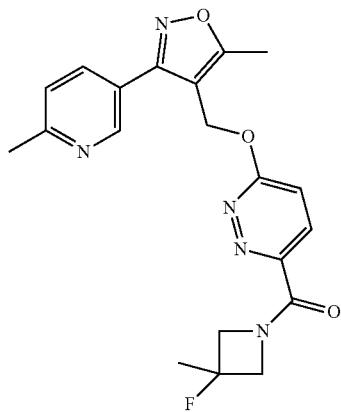 [SMILES: Cc1ccc(-c2noc(C)c2COc2ccc(C(=O)N3CC(C)(F)C3)nn2)cn1]

In analogy to experiment of example 30, 6-((5-methyl-3-(6-methylpyridin-3-yl)isoxazol-4-yl)methoxy)pyridazine-3-carboxylic acid, using 3-fluoro-3-methylazetidine hydrochloride instead of (1,1-dioxidotetrahydro-2H-thiopyran-4-yl)amine hydrochloride, was converted into the title compound (51 mg, 84%) which was obtained as an off-white solid. MS (ESI): 398.2 ([M+H]$^+$).

Example 68 ethyl 1-(6-((5-methyl-3-(6-methylpyridin-3-yl)isoxazol-4-yl)methoxy)pyridazine-3-carboxamido)cyclopropanecarboxylate

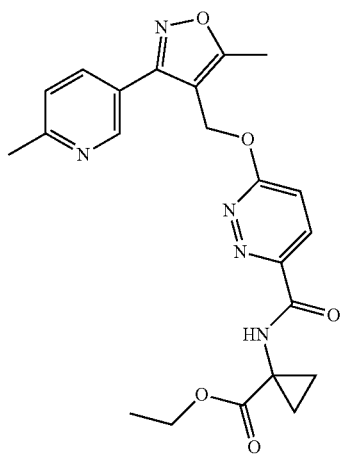 [SMILES: CCOC(=O)C1(NC(=O)c2ccc(OCc3c(-c4ccc(C)nc4)noc3C)nn2)CC1]

In analogy to experiment of example 30, 6-((5-methyl-3-(6-methylpyridin-3-yl)isoxazol-4-yl)methoxy)pyridazine-3-carboxylic acid, using ethyl 1-aminocyclopropanecarboxylate hydrochloride instead of (1,1-dioxidotetrahydro-2H-thiopyran-4-yl)amine hydrochloride, was converted into the title compound (99 mg, 92%) which was obtained as an off-white solid. MS (ESI): 438.3 ([M+H]$^+$).

Example 69

N-(1-cyanocyclopropyl)-6-((5-methyl-3-(6-methylpyridin-3-yl)isoxazol-4-yl)methoxy)pyridazine-3-carboxamide

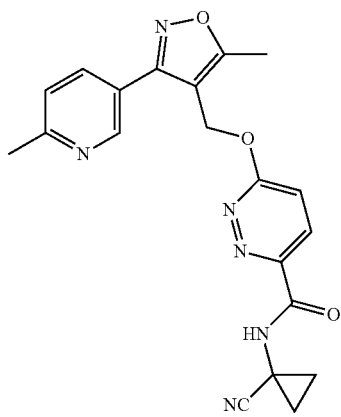 [SMILES: Cc1ccc(-c2noc(C)c2COc2ccc(C(=O)NC3(C#N)CC3)nn2)cn1]

In analogy to experiment of example 30, 6-((5-methyl-3-(6-methylpyridin-3-yl)isoxazol-4-yl)methoxy)pyridazine-3-carboxylic acid, using 1-aminocyclopropanecarbonitrile hydrochloride instead of (1,1-dioxidotetrahydro-2H-thiopyran-4-yl)amine hydrochloride, was converted into the title compound (44 mg, 74%) which was obtained as a white solid. MS (ESI): 391.2 ([M+H]$^+$).

Example 70

5-methyl-6-((5-methyl-3-(6-methylpyridin-3-yl)isoxazol-4-yl)methoxy)pyridazine-3-carboxamide

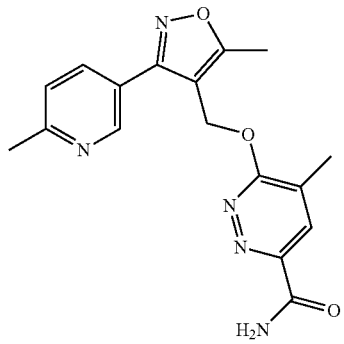 [SMILES: Cc1ccc(-c2noc(C)c2COc2nnc(C(N)=O)cc2C)cn1]

a) 4-((6-chloro-4-methyl-pyridazin-3-yl)oxymethyl)-5-methyl-3-(6-methyl-3-pyridyl)isoxazole In analogy to experiment of example 23a, (5-methyl-3-(6-methylpyridin-3-yl)isoxazol-4-yl)methanol (building block A), using 3,6-dichloro-4-methylpyridazine instead of 3,6-dichloropyridazine, was converted into a 1:1 mixture of the title compound and the isomeric 4-((6-chloro-5-methyl-pyridazin-3-yl)oxymethyl)-5-methyl-3-(6-methyl-3-pyridyl)isoxazole (1.45 g, 89%) which was obtained as a light brown oil. MS (ESI): 331.1 ([M+H]$^+$).

b) ethyl 5-methyl-6-((5-methyl-3-(6-methyl-3-pyridyl)isoxazol-4-yl)methoxy)pyridazine-3-carboxylate In analogy to experiment of example 23b, 4-((6-chloro-4-methyl-pyridazin-3-yl)oxymethyl)-5-methyl-3-(6-methyl-3-pyridyl)isoxazole and 4-((6-chloro-5-methyl-pyridazin-3-yl)oxymethyl)-5-methyl-3-(6-methyl-3-pyridyl)isoxazole instead of 4-((6-chloropyridazin-3-yloxy)methyl)-5-methyl-3-(6-methylpyridin-3-yl)isoxazole was converted into the title compound (271 mg, 18%) as a white solid, following separation of regioisomers by flash chromatography (silica, gradient: 0% to 80% EtOAc in heptane). MS (ESI): 369.2 ([M+H]$^+$).

c) 5-methyl-6-((5-methyl-3-(6-methyl-3-pyridyl)isoxazol-4-yl)methoxy)pyridazine-3-carboxylic Acid In analogy to experiment of example 23c, ethyl 5-methyl-6-((5-methyl-3-(6-methyl-3-pyridyl)isoxazol-4-yl)methoxy)pyridazine-3-carboxylate instead of ethyl 6-((5-methyl-3-(6-methylpyridin-3-yl)isoxazol-4-yl)methoxy)pyridazine-3-carboxylate was converted into the title compound (372 mg, 72%) which was obtained as a white solid. MS (ESI): 341.2 ([M+H]$^+$).

d) 5-methyl-6-((5-methyl-3-(6-methylpyridin-3-yl)isoxazol-4-yl)methoxy)pyridazine-3-carboxamide In analogy to experiment of example 29, 5-methyl-6-((5-methyl-3-(6-methyl-3-pyridyl)isoxazol-4-yl)methoxy)pyridazine-3-carboxylic acid instead of 6-((5-methyl-3-(6-methylpyridin-3-yl)isoxazol-4-yl)methoxy)pyridazine-3-carboxylic acid, using ammonium hydroxide solution (~25 wt. %) instead of ethanolamine, was converted into the title compound (15 mg, 31%) which was obtained as a white solid. MS (ESI): 340.1 ([M+H]+).

Example 71

5-methyl-6-((5-methyl-3-(6-methylpyridin-3-yl)isoxazol-4-yl)methoxy)-N-(tetrahydropyran-4-yl)pyridazine-3-carboxamide

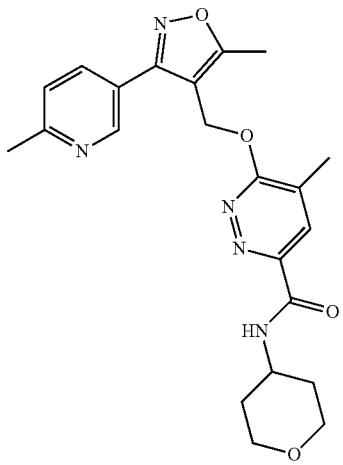 [SMILES: Cc1ccc(-c2noc(C)c2COc2nnc(C(=O)NC3CCOCC3)cc2C)cn1]

In analogy to experiment of example 23d, 5-methyl-6-((5-methyl-3-(6-methyl-3-pyridyl)isoxazol-4-yl)methoxy)pyridazine-3-carboxylic acid instead of 6-((5-methyl-3-(6-methylpyridin-3-yl)isoxazol-4-yl)methoxy)pyridazine-3-carboxylic acid, using tetrahydropyran-4-amine instead of (1R,2S)-2-aminocyclohexanol hydrochloride, was converted into the title compound (43 mg, 86%) which was obtained as a light-brown oil. MS (ESI): 424.3 ([M+H]+).

Example 72

N-(1,1-dioxothian-4-yl)-5-((5-methyl-3-(6-methyl-3-pyridyl)isoxazol-4-yl)methoxy)pyrazine-2-carboxamide

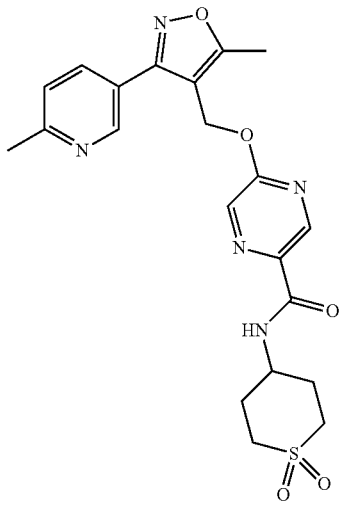 [SMILES: Cc1ccc(-c2noc(C)c2COc2cnc(C(=O)NC3CCS(=O)(=O)CC3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid was converted into the title compound (45 mg, 64%) which was obtained as a white solid. MS (ESI): 458.2 ([M+H]+).

Example 73

N-(2-hydroxy-1,1-dimethyl-ethyl)-5-((5-methyl-3-(6-methyl-3-pyridyl)isoxazol-4-yl)methoxy)pyrazine-2-carboxamide

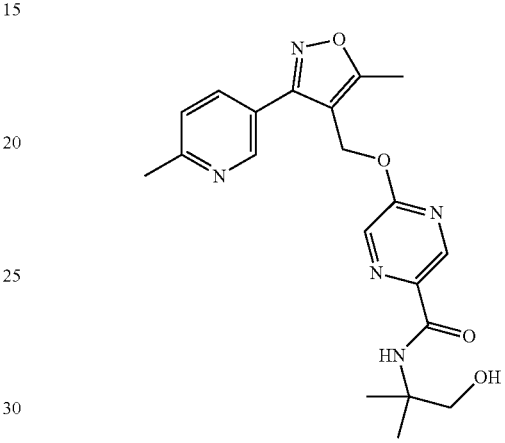

In analogy to experiment of example 29, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using 2-amino-2-methylpropan-1-ol instead of ethanolamine, was converted into the title compound (51 mg, 84%) which was obtained as a white foam. MS (ESI): 398.3 ([M+H]+).

Example 74

N-cyclopropyl-5-((5-methyl-3-(6-methyl-3-pyridyl)isoxazol-4-yl)methoxy)pyrazine-2-carboxamide

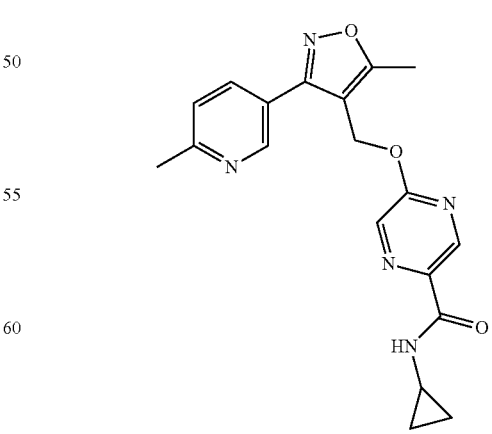

In analogy to experiment of example 30, methyl 6-((5-methyl-3-(6-methylpyridin-3-yl)isoxazol-4-yl)methoxy)

pyridazine-3-carboxylate instead of 6-((5-methyl-3-(6-methylpyridin-3-yl)isoxazol-4-yl)methoxy)pyridazine-3-carboxylic acid, using cyclopropanamine instead of (1,1-dioxidotetrahydro-2H-thiopyran-4-yl)amine hydrochloride, was converted into the title compound (53 mg, 95%) which was obtained as a white solid. MS (ESI): 366.2 ([M+H]$^+$).

Example 75

(RS)-6-((5-methyl-3-(6-methylpyridin-3-yl)isoxazol-4-yl)methoxy)-N-(3-methyltetrahydrofuran-3-yl)pyridazine-3-carboxamide

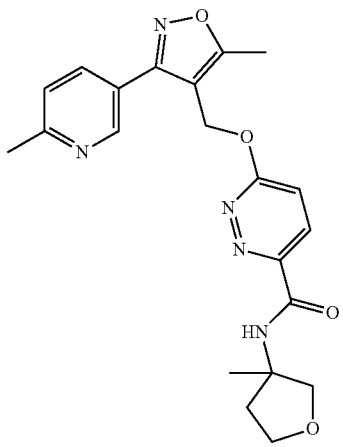 [SMILES: Cc1ccc(-c2noc(C)c2COc2ccc(C(=O)NC3(C)CCOC3)nn2)cn1]

In analogy to experiment of example 30, 6-((5-methyl-3-(6-methylpyridin-3-yl)isoxazol-4-yl)methoxy)pyridazine-3-carboxylic acid, using (RS)-3-amino-3-methyloxolane instead of (1,1-dioxidotetrahydro-2H-thiopyran-4-yl)amine hydrochloride was converted into the title compound (50 mg, 76%) which was obtained as an off-white foam. MS (ESI): 410.3 ([M+H]$^+$).

Example 76

6-((5-methyl-3-(6-methylpyridin-3-yl)isoxazol-4-yl)methoxy)-N-(1-methylcyclopropyl)pyridazine-3-carboxamide

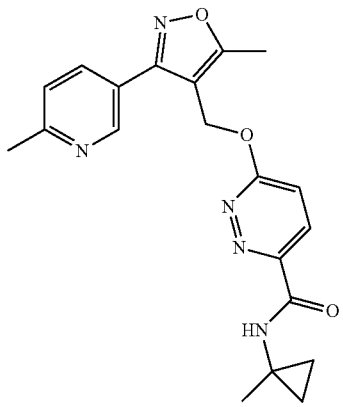 [SMILES: Cc1ccc(-c2noc(C)c2COc2ccc(C(=O)NC3(C)CC3)nn2)cn1]

In analogy to experiment of example 30, 6-((5-methyl-3-(6-methylpyridin-3-yl)isoxazol-4-yl)methoxy)pyridazine-3- carboxylic acid, using 1-methylcyclopropanamine hydrochloride instead of (1,1-dioxidotetrahydro-2H-thiopyran-4-yl)amine hydrochloride was converted into the title compound (54 mg, 93%) which was obtained as an off-white solid. MS (ESI): 380.2 ([M+H]$^+$).

Example 77

5-((5-methyl-3-(6-methyl-3-pyridyl)isoxazol-4-yl)methoxy)-N-(oxetan-3-yl)pyrazine-2-carboxamide

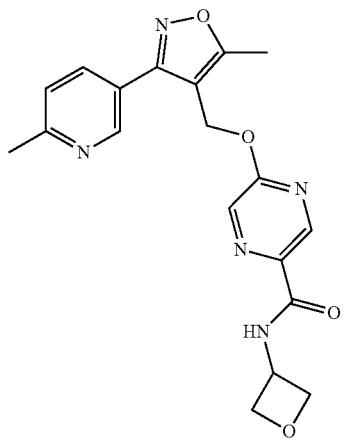 [SMILES: Cc1ccc(-c2noc(C)c2COc2cnc(C(=O)NC3COC3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using oxetan-3-amine hydrochloride instead of (1,1-dioxidotetrahydro-2H-thiopyran-4-yl)amine hydrochloride, was converted into the title compound (50 mg, 86%) which was obtained as a white solid. MS (ESI): 382.2 ([M+H]$^+$).

Example 78

5-((5-methyl-3-(6-methyl-3-pyridyl)isoxazol-4-yl)methoxy)-N-(2,2,2-trifluoroethyl)pyrazine-2-carboxamide

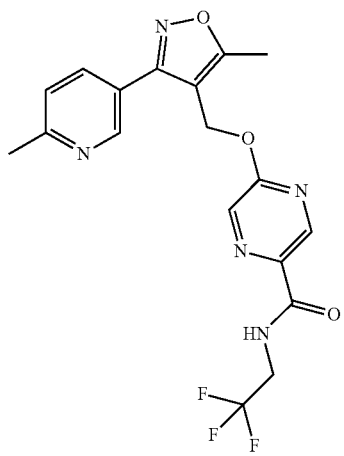 [SMILES: Cc1ccc(-c2noc(C)c2COc2cnc(C(=O)NCC(F)(F)F)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using 2,2,2-trifluoroethanamine hydrochloride instead of (1,1-dioxidotetrahydro-2H-thiopyran-4-yl)amine hydrochloride, was converted into the title compound (54 mg, 87%) which was obtained as a white solid. MS (ESI): 408.2 ([M+H]$^+$).

Example 79

N-(4-hydroxy-2-methylbutan-2-yl)-6-((5-methyl-3-(6-methylpyridin-3-yl)isoxazol-4-yl)methoxy)pyridazine-3-carboxamide

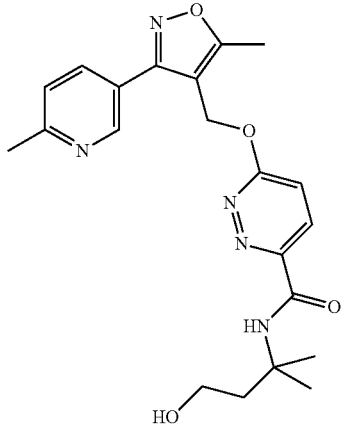 [SMILES: Cc1ccc(-c2noc(C)c2COc2ccc(C(=O)NC(C)(C)CCO)nn2)cn1]

In analogy to experiment of example 29, 6-((5-methyl-3-(6-methylpyridin-3-yl)isoxazol-4-yl)methoxy)pyridazine-3-carboxylic acid, using 3-amino-3-methylbutan-1-ol instead of ethanolamine, was converted into the title compound (45 mg, 71%) which was obtained as an off-white solid. MS (ESI): 412.2 ([M+H]$^+$).

Example 80

6-((5-methyl-3-(6-methylpyridin-3-yl)isoxazol-4-yl)methoxy)-N-(2-methyl-4-(methylsulfonyl)butan-2-yl)pyridazine-3-carboxamide

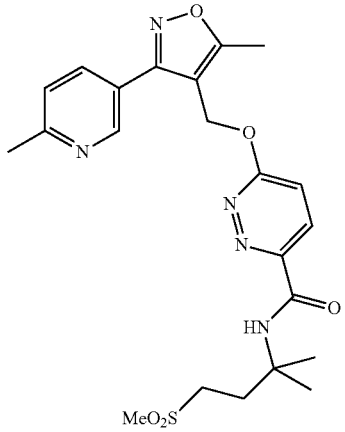 [SMILES: Cc1ccc(-c2noc(C)c2COc2ccc(C(=O)NC(C)(C)CCS(C)(=O)=O)nn2)cn1]

In analogy to experiment of example 29, 6-((5-methyl-3-(6-methylpyridin-3-yl)isoxazol-4-yl)methoxy)pyridazine-3-carboxylic acid, using 2-methyl-4-methylsulfonyl-butan-2-amine instead of ethanolamine, was converted into the title compound (36 mg, 47%) which was obtained as an off-white foam. MS (ESI): 474.2 ([M+H]$^+$).

Example 81

(S)-6-((5-methyl-3-(6-methylpyridin-3-yl)isoxazol-4-yl)methoxy)-N-(3-methyltetrahydrofuran-3-yl)pyridazine-3-carboxamide or Enantiomer

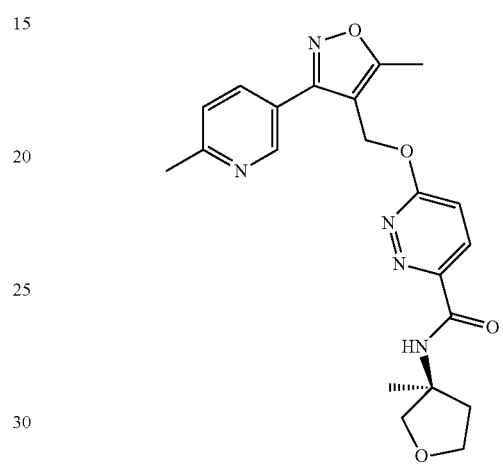

Separation of the enantiomers of (RS)-6-((5-methyl-3-(6-methylpyridin-3-yl)isoxazol-4-yl)methoxy)-N-(3-methyltetrahydrofuran-3-yl)pyridazine-3-carboxamide (example 75) by chiral HPLC (column: Chiralpak AD, 35 mL/min, i-PrOH/heptane: 40/60; 18 bar; 220 nm) afforded the (+)-title compound (22 mg) which was obtained as an off-white solid. MS (ESI): 410.2 ([M+H]$^+$).

Example 82

(R)-6-((5-methyl-3-(6-methylpyridin-3-yl)isoxazol-4-yl)methoxy)-N-(3-methyltetrahydrofuran-3-yl)pyridazine-3-carboxamide or Enantiomer

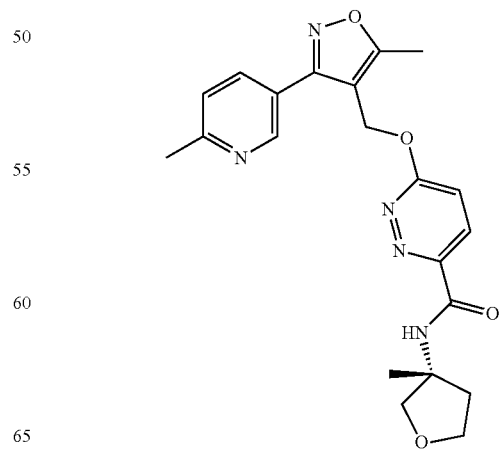

Separation of the enantiomers of (RS)-6-((5-methyl-3-(6-methylpyridin-3-yl)isoxazol-4-yl)methoxy)-N-(3-methyl-tetrahydrofuran-3-yl)pyridazine-3-carboxamide (example 75) by chiral HPLC (column: Chiralpak AD, 35 mL/min, i-PrOH/heptane: 40/60; 18 bar; 220 nm) afforded the (−)-title compound (20 mg) which was obtained as an off-white foam. MS (ESI): 410.2 ([M+H]$^+$).

Example 83

6-((5-methyl-3-(6-methylpyridin-3-yl) isoxazol-4-yl)methoxy)-N-(3-methyloxetan-3-yl)pyridazine-3-carboxamide

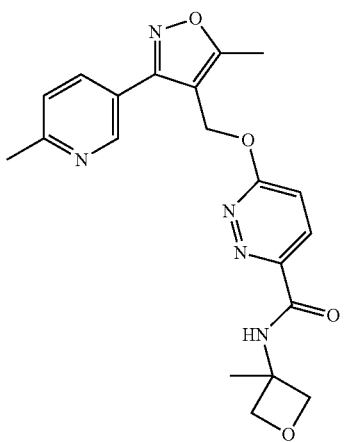 [SMILES: Cc1ccc(-c2noc(C)c2COc2ccc(C(=O)NC3(C)COC3)nn2)cn1]

In analogy to experiment of example 23d, 6-((5-methyl-3-(6-methylpyridin-3-yl)isoxazol-4-yl)methoxy)pyridazine-3-carboxylic acid, using 3-methyloxetan-3-amine hydrochloride instead of (1R,2S)-2-aminocyclohexanol hydrochloride, was converted into the title compound (61 mg, 84%) which was obtained as an off-white solid. MS (ESI): 396.2 ([M+H]$^+$).

Example 84

1-(6-((5-methyl-3-(6-methylpyridin-3-yl)isoxazol-4-yl)methoxy)pyridazine-3-carbonyl)azetidine-3-carbonitrile

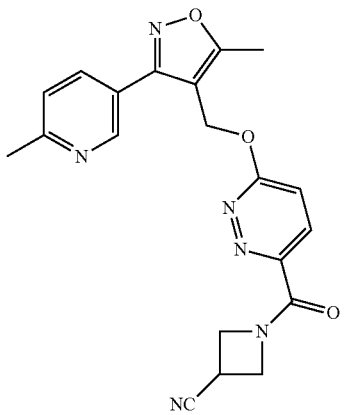 [SMILES: Cc1ccc(-c2noc(C)c2COc2ccc(C(=O)N3CC(C#N)C3)nn2)cn1]

In analogy to experiment of example 30, 6-((5-methyl-3-(6-methylpyridin-3-yl)isoxazol-4-yl)methoxy)pyridazine-3-carboxylic acid, using azetidine-3-carbonitrile hydrochloride instead of (1,1-dioxidotetrahydro-2H-thiopyran-4-yl)amine hydrochloride, was converted into the title compound (42 mg, 70%) which was obtained as an off-white solid. MS (ESI): 391.2 ([M+H]$^+$).

Example 85

N-(1-(hydroxymethyl)cyclopropyl)-6-((5-methyl-3-(6-methylpyridin-3-yl)isoxazol-4-yl)methoxy)pyridazine-3-carboxamide

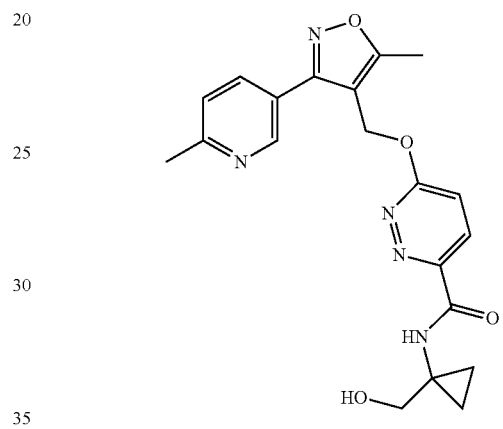

To a stirred suspension of 6-((5-methyl-3-(6-methylpyridin-3-yl)isoxazol-4-yl)methoxy)pyridazine-3-carboxylic acid (78 mg, 0.191 mmol) in anhydrous THF (1.5 mL) was added triethylamine (30 μL, 0.215 mmol). The resulting solution was cooled to −16° C. (NaCl/ice bath) before a solution of ethyl chloroformate (22.6 mg, 20 μL, 0.208 mmol) in THF (0.2 mL) was added dropwise. After 30 min, the resulting white precipitate was filtered through a sintered funnel and the collected solid rinsed with a minimal amount of anhydrous THF. The filtrate was re-cooled to −16° C. (NaCl/ice bath) and a solution of NaBH$_4$ (18 mg, 0.476 mmol) in water (0.8 mL) was added dropwise. Upon addition, the reaction was allowed to warm to 0° C. for 2 hours then to room temperature for 1 hour. The reaction was quenched by the addition of saturated aqueous NaHCO$_3$ (5 mL), then diluted with water (5 mL) and extracted with EtOAc (2×15 mL). The combined organic extracts were washed with brine, dried (Na$_2$SO$_4$) and concentrated in vacuo. Purification by flash chromatography (silica, gradient: 0% to 5% MeOH in CH$_2$Cl$_2$) afforded the title compound (21 mg, 27%) as an off-white solid. MS (ESI): 396.2 ([M+H]$^+$).

Example 86

N-(4,4-difluorocyclohexyl)-5-((5-methyl-3-(6-methyl-3-pyridyl)isoxazol-4-yl)methoxy)pyrazine-2-carboxamide

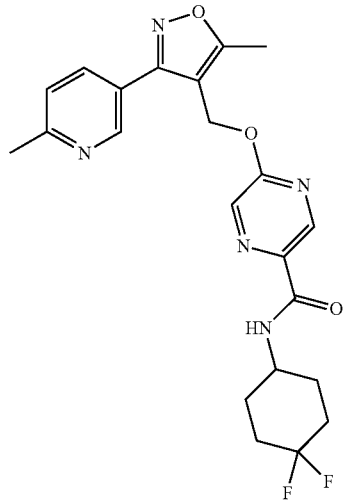 [SMILES: Cc1ccc(-c2noc(C)c2COc2cnc(C(=O)NC3CCC(F)(F)CC3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using 4,4-difluorocyclohexanamine hydrochloride instead of (1,1-dioxidotetrahydro-2H-thiopyran-4-yl)amine hydrochloride, was converted into the title compound (41 mg, 88%) which was obtained as an off-white solid. MS (ESI): 444.3 ([M+H]$^+$).

Example 87

(S)-6-((5-methyl-3-(6-methylpyridin-3-yl)isoxazol-4-yl)methoxy)-N-(tetrahydrofuran-3-yl)pyridazine-3-carboxamide

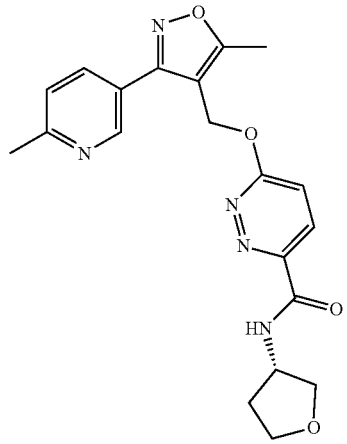 [SMILES: Cc1ccc(-c2noc(C)c2COc2ccc(C(=O)N[C@H]3CCOC3)nn2)cn1]

In analogy to experiment of example 23d, 6-((5-methyl-3-(6-methylpyridin-3-yl)isoxazol-4-yl)methoxy)pyridazine-3-carboxylic acid, using (S)-tetrahydrofuran-3-amine hydrochloride instead of (1R,2S)-2-aminocyclohexanol hydrochloride, was converted into the title compound (52 mg, 82%) which was obtained as a white foam. MS (ESI): 396.2 ([M+H]$^+$).

Example 88

(S)—N-(1-cyanobutan-2-yl)-6-((5-methyl-3-(6-methylpyridin-3-yl)isoxazol-4-yl)methoxy) pyridazine-3-carboxamide

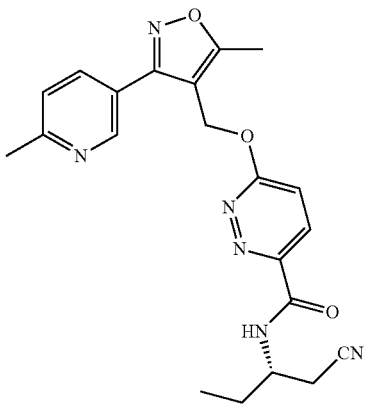 [SMILES: CC[C@@H](CC#N)NC(=O)c1ccc(OCc2c(-c3ccc(C)nc3)noc2C)nn1]

In analogy to experiment of example 29, 6-((5-methyl-3-(6-methylpyridin-3-yl)isoxazol-4-yl)methoxy)pyridazine-3-carboxylic acid, using (S)-3-aminopentanenitrile instead of ethanolamine, was converted into the title compound (61 mg, 93%) which was obtained as an off-white foam. MS (ESI): 407.2 ([M+H]$^+$).

Example 89

(R)-5-((5-Methyl-3-(6-methylpyridin-3-yl)isoxazol-4-yl)methoxy)-N-(tetrahydrofuran-3-yl)pyrazine-2-carboxamide

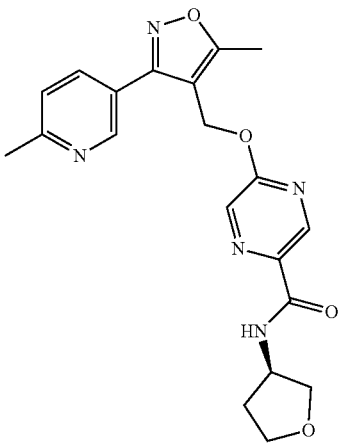 [SMILES: Cc1ccc(-c2noc(C)c2COc2cnc(C(=O)N[C@@H]3CCOC3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using (R)-tetrahydrofuran-3-amine hydrochloride instead of (1,1-dioxidotetrahydro-2H-thiopyran-4-yl)amine hydrochloride, was converted into the title compound (40 mg, 73%) which was obtained as an off-white solid. MS (ESI): 396.2 ([M+H]+).

Example 90

N-(2-Hydroxyethyl)-5-((5-methyl-3-(6-methylpyridin-3-yl)isoxazol-4-yl)methoxy)pyrazine-2-carboxamide

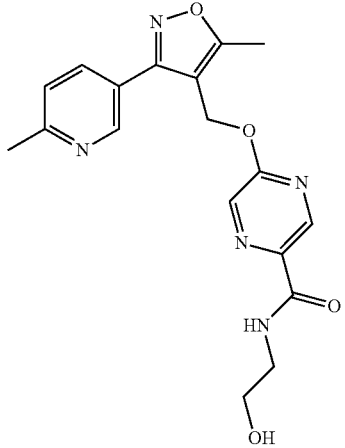 [SMILES: Cc1ccc(-c2noc(C)c2COc2cnc(C(=O)NCCO)cn2)cn1]

In analogy to experiment of example 14c, 5-((5-methyl-3-(6-methyl-3-pyridyl)isoxazol-4-yl)methoxy)pyrazine-2-carboxylic acid, using ethanolamine instead of (S)-2-aminopentan-1-ol, was converted into the title compound (39 mg, 77%) which was obtained as a white solid. MS (ESI): 370.2 ([M+H]+).

Example 91

2-(1,1-dioxothian-4-yl)-6-((5-methyl-3-(6-methylpyridin-3-yl)-1,2-oxazol-4-yl)methoxy)-1H-pyrrolo[3,4-c]pyridin-3-one

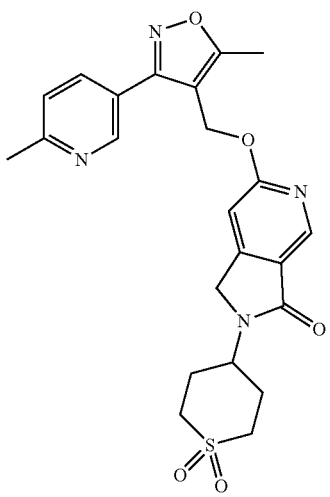 [SMILES: Cc1ccc(-c2noc(C)c2COc2cc3c(cn2)C(=O)N(C2CCS(=O)(=O)CC2)C3)cn1]

a) 6-chloro-2-(1,1-dioxothian-4-yl)-1H-pyrrolo[3,4-c]pyridin-3-one

In analogy to experiment of example 9a, 6-chloro-4-formylnicotinic acid, using (1,1-dioxidotetrahydro-2H-thiopyran-4-yl)amine hydrochloride instead of isobutylamine, was converted into the title compound (137 mg, 42%) which was obtained as a light yellow solid. MS (ESI): 301.0 ([M+H]+).

b) 2-(1,1-dioxothian-4-yl)-6-((5-methyl-3-(6-methylpyridin-3-yl)-1,2-oxazol-4-yl)methoxy)-1H-pyrrolo[3,4-c]pyridin-3-one In analogy to experiment of example 9b, (5-methyl-3-(6-methylpyridin-3-yl)isoxazol-4-yl)methanol (building block A), using 6-chloro-2-(1,1-dioxothian-4-yl)-1H-pyrrolo[3,4-c]pyridin-3-one instead of 6-chloro-2-isobutyl-1H-pyrrolo[3,4-c]pyridin-3-one, was converted into the title compound (15 mg, 12%) which was obtained as a yellow solid. MS (ESI): 469.2 ([M+H]+).

Example 92

(S)-5-((5-Methyl-3-(6-methylpyridin-3-yl)isoxazol-4-yl)methoxy)-N-(tetrahydrofuran-3-yl)pyrazine-2-carboxamide

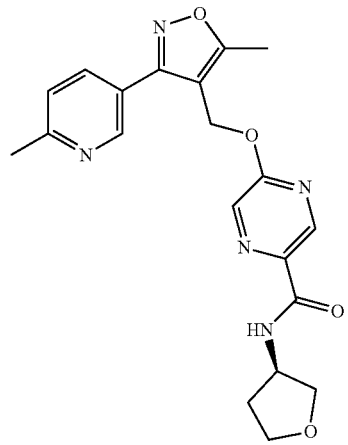 [SMILES: Cc1ccc(-c2noc(C)c2COc2cnc(C(=O)N[C@@H]3CCOC3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using (S)-tetrahydrofuran-3-amine hydrochloride instead of (1,1-dioxidotetrahydro-2H-thiopyran-4-yl)amine hydrochloride, was converted into the title compound (37 mg, 76%) which was obtained as a white solid. MS (ESI): 396.2 ([M+H]+).

Example 93

2-((5-methyl-3-(6-methyl-3-pyridyl)isoxazol-4-yl)methoxy]-6-tetrahydropyran-4-yl-7H-pyrrolo[3,4-b]pyridin-5-one

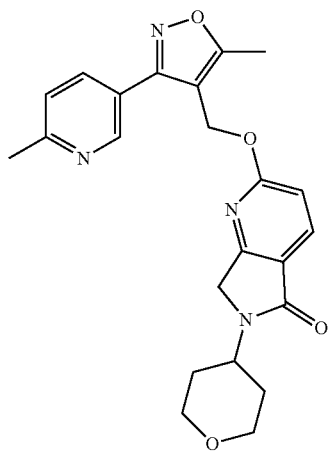 [SMILES: Cc1ccc(-c2noc(C)c2COc2ccc3c(n2)CN(C2CCOCC2)C3=O)cn1]

a) ethyl 2-(bromomethyl)-6-chloro-pyridine-3-carboxylate

To a stirred solution of ethyl 6-chloro-2-methylnicotinate (0.810 g, 4.06 mmol) in $CCl_4$ (8 mL) at room temperature was added N-bromosuccinimide (1.00 g, 5.62 mmol) followed by AIBN (33 mg, 0.201 mmol). The reaction mixture was heated at reflux overnight before all the volatiles were removed by rotary evaporation under reduced pressure. The resulting crude residue was purified by flash chromatography (silica, gradient: 0% to 15% EtOAc in heptane) to afford the title compound (1.04 g, 55%, purity ca. 60%) as a light yellow oil. MS (ESI): 278.1 ([M+H]$^+$).

b) 2-chloro-6-tetrahydropyran-4-yl-7H-pyrrolo[3,4-b]pyridin-5-one

To a stirred solution of ethyl 2-(bromomethyl)-6-chloropyridine-3-carboxylate (0.380 g, 0.819 mmol, purity ca. 60%) in anhydrous THF (3.4 mL) at room temperature was added tetrahydropyran-4-amine (0.34 mL, 3.28 mmol). The reaction mixture was heated to 50° C. overnight before being re-cooled to room temperature. The mixture was diluted with EtOAc (40 mL) and the organic layer washed with a mixture of water (5 mL) and brine (5 mL). The aqueous layer was extracted with EtOAc (40 mL) and the combined organic extracts were dried ($Na_2SO_4$) and concentrated in vacuo. Purification by flash chromatography (silica, gradient: 0% to 10% MeOH in $CH_2Cl_2$) afforded the title compound (192 mg, 93%) as a white solid. MS (ESI): 253.1 ([M+H]$^+$).

c) 2-((5-methyl-3-(6-methyl-3-pyridyl)isoxazol-4-yl)methoxy)-6-tetrahydropyran-4-yl-7H-pyrrolo[3,4-b]pyridin-5-one In analogy to experiment of example 9b, (5-methyl-3-(6-methylpyridin-3-yl)isoxazol-4-yl)methanol (building block A), using 2-chloro-6-tetrahydropyran-4-yl-7H-pyrrolo[3,4-b]pyridin-5-one instead of 6-chloro-2-isobutyl-1H-pyrrolo[3,4-c]pyridin-3-one, was converted into the title compound (77 mg, 75%) which was obtained as a light yellow solid. MS (ESI): 421.3 ([M+H]$^+$).

Example 94

N-(1,1-dioxothiolan-3-yl)-5-((5-methyl-3-(6-methylpyridin-3-yl)-1,2-oxazol-4-yl)methoxy)pyrazine-2-carboxamide

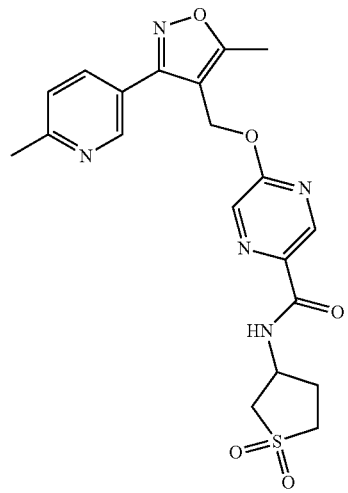 [SMILES: Cc1ccc(-c2noc(C)c2COc2cnc(C(=O)NC3CCS(=O)(=O)C3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using 3-aminotetrahydrothiophene 1,1-dioxide instead of (1,1-dioxidotetrahydro-2H-thiopyran-4-yl)amine hydrochloride, was converted into the title compound (40 mg, 65%) which was obtained as a white solid. MS (ESI): 444.4 ([M+H]$^+$).

Example 95

N-(cyclopropylmethyl)-5-((5-methyl-3-(6-methylpyridin-3-yl)isoxazol-4-yl)methoxy)pyrazine-2-carboxamide

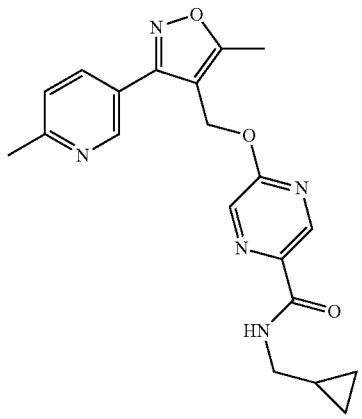 [SMILES: Cc1ccc(-c2noc(C)c2COc2cnc(C(=O)NCC3CC3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using cyclopropylmethanamine instead of (1,1-dioxidotetrahydro-2H-thiopyran-4-yl)amine hydrochloride, was converted into the title compound (50 mg, 86%) which was obtained as a white solid. MS (ESI): 380.2 ([M+H]$^+$).

Example 96

2-(4,4-difluorocyclohexyl)-6-((5-methyl-3-(6-methylpyridin-3-yl)isoxazol-4-yl)methoxy)-1H-pyrrolo[3,4-c]pyridin-3(2H)-one

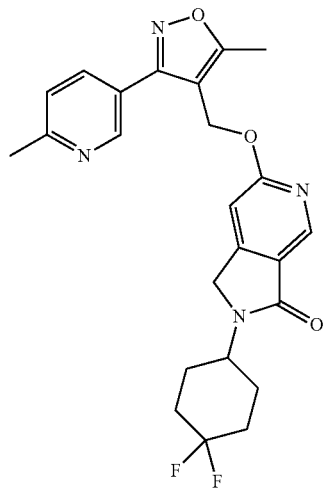 [SMILES: Cc1ccc(-c2noc(C)c2COc2cc3c(cn2)C(=O)N(C2CCC(F)(F)CC2)C3)cn1]

a) 6-chloro-2-(4,4-difluorocyclohexyl)-1H-pyrrolo[3,4-c]pyridin-3-one

In analogy to experiment of example 9a, 6-chloro-4-formylnicotinic acid, using 4,4-difluorocyclohexanamine hydrochloride instead of isobutylamine, was converted into the title compound (211 mg, 45%) which was obtained as an off-white solid. MS (ESI): 287.1 ([M+H]$^+$).

b) 2-(4,4-difluorocyclohexyl)-6-((5-methyl-3-(6-methylpyridin-3-yl)isoxazol-4-yl)methoxy)-1H-pyrrolo[3,4-c]pyridin-3(2H)-one In analogy to experiment of example 9b, (5-methyl-3-(6-methylpyridin-3-yl)isoxazol-4-yl)methanol (building block A), using 6-chloro-2-(4,4-difluorocyclohexyl)-1H-pyrrolo[3,4-c]pyridin-3-one instead of 6-chloro-2-isobutyl-1H-pyrrolo[3,4-c]pyridin-3-one, was converted into the title compound (90 mg, 81%) which was obtained as a light brown solid. MS (ESI): 455.3 ([M+H]$^+$).

Example 97

6-((5-methyl-3-(6-methylpyridin-3-yl)isoxazol-4-yl)methoxy)-N-(4-methyltetrahydropyran-4-yl)pyridazine-3-carboxamide

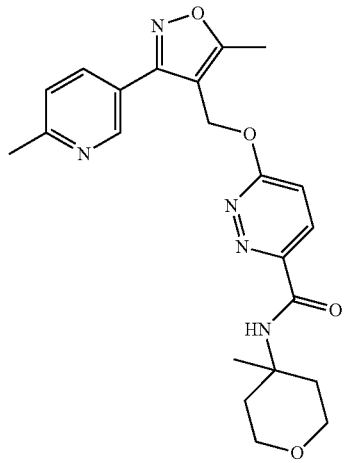

In analogy to experiment of example 30, 6-((5-methyl-3-(6-methylpyridin-3-yl)isoxazol-4-yl)methoxy)pyridazine-3-carboxylic acid, using 4-methyltetrahydropyran-4-amine hydrochloride instead of (1,1-dioxidotetrahydro-2H-thiopyran-4-yl)amine hydrochloride, was converted into the title compound (54 mg, 79%) which was obtained as an off-white foam. MS (ESI): 424.3 ([M+H]$^+$).

Example 98

(R)-5-((5-methyl-3-(6-methylpyridin-3-yl)isoxazol-4-yl)methoxy)-N-(tetrahydropyran-3-yl)pyrazine-2-carboxamide

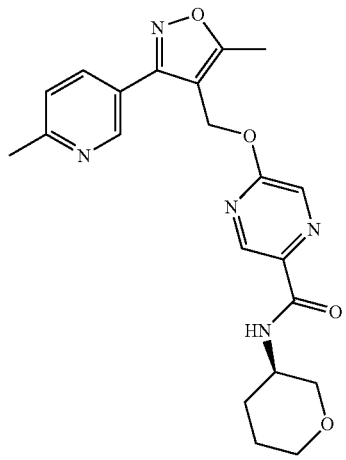 [SMILES: Cc1ccc(-c2noc(C)c2COc2cnc(C(=O)N[C@@H]3CCCOC3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using (R)-tetrahydropyran-3-amine hydrochloride instead of (1,1-dioxidotetrahydro-2H-thiopyran-4-yl)amine hydro-

Example 99

(R)-6-((5-methyl-3-(6-methylpyridin-3-yl)isoxazol-4-yl)methoxy)-N-(tetrahydropyran-3-yl)pyridazine-3-carboxamide

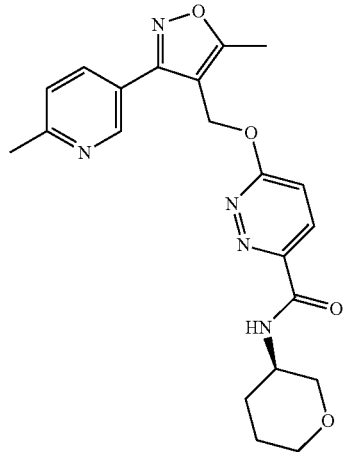 [SMILES: Cc1ccc(-c2noc(C)c2COc2ccc(C(=O)N[C@@H]3CCCOC3)nn2)cn1]

In analogy to experiment of example 30, 6-((5-methyl-3-(6-methylpyridin-3-yl)isoxazol-4-yl)methoxy)pyridazine-3-carboxylic acid, using (R)-tetrahydropyran-3-amine hydrochloride instead of (1,1-dioxidotetrahydro-2H-thiopyran-4-yl)amine hydrochloride, was converted into the title compound (51 mg, 90%) which was obtained as a white solid. MS (ESI): 410.3 ([M+H]$^+$).

Example 100

6-((5-methyl-3-(6-methylpyridin-3-yl)isoxazol-4-yl)methoxy)-N-(2-oxaspiro[3.3]heptan-6-yl)pyridazine-3-carboxamide

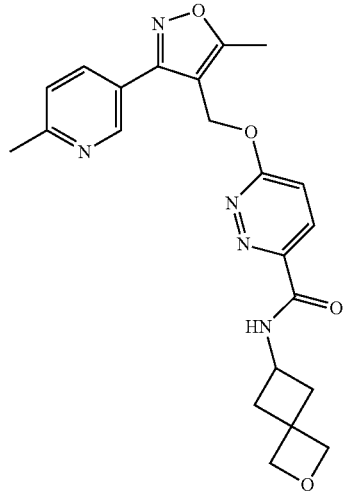 [SMILES: Cc1ccc(-c2noc(C)c2COc2ccc(C(=O)NC3CC4(COC4)C3)nn2)cn1]

In analogy to experiment of example 30, 6-((5-methyl-3-(6-methylpyridin-3-yl)isoxazol-4-yl)methoxy)pyridazine-3-carboxylic acid, using 2-oxaspiro[3.3]heptan-6-amine hydrochloride instead of (1,1-dioxidotetrahydro-2H-thiopyran-4-yl)amine hydrochloride, was converted into the title compound (388 mg, 70%) which was obtained as an off-white solid. MS (ESI): 422.2 ([M+H]$^+$).

Example 101

5-((5-methyl-3-(6-methylpyridin-3-yl)isoxazol-4-yl)methoxy)-N-(2-oxaspiro[3.3]heptan-6-yl)pyrazine-2-carboxamide

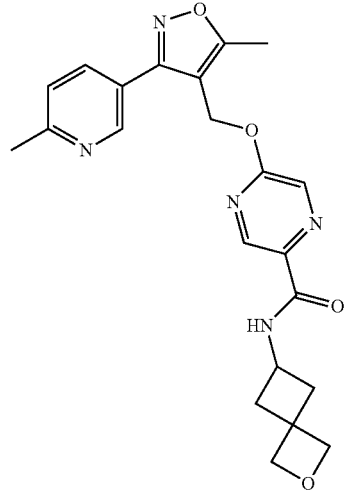 [SMILES: Cc1ccc(-c2noc(C)c2COc2cnc(C(=O)NC3CC4(COC4)C3)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using 2-oxaspiro[3.3]heptan-6-amine hydrochloride instead of (1,1-dioxidotetrahydro-2H-thiopyran-4-yl)amine hydrochloride, was converted into the title compound (355 mg, 72%) which was obtained as a white solid. MS (ESI): 422.3 ([M+H]$^+$).

Example 102

5-((5-methyl-3-(6-methylpyridin-3-yl)isoxazol-4-yl)methoxy)-N-(cis-4-(ttifluoromethyl)cyclohexyl)pyrazine-2-carboxamide

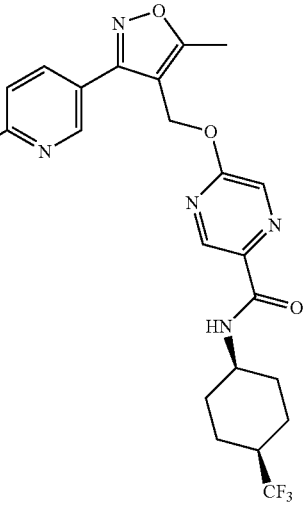

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using 4-(trifluoromethyl)cyclohexanamine hydrochloride instead of (1,1-dioxidotetrahydro-2H-thiopyran-4-yl)amine hydrochloride, was converted into the title compound (45 mg, 34%) which was obtained as an off-white foam. MS (ESI): 476.2 ([M+H]+).

Example 103

(S)-6-((5-methyl-3-(6-methylpyridin-3-yl)isoxazol-4-yl)methoxy)-N-(tetrahydropyran-3-yl)pyridazine-3-carboxamide

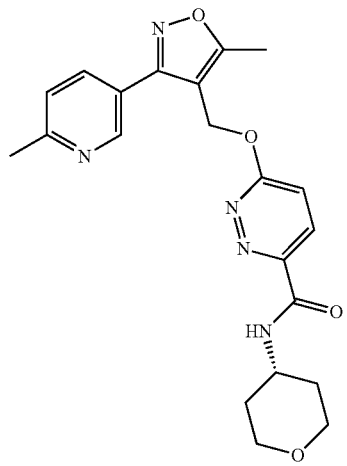

In analogy to experiment of example 30, 6-((5-methyl-3-(6-methylpyridin-3-yl)isoxazol-4-yl)methoxy)pyridazine-3-carboxylic acid, using (S)-tetrahydropyran-3-amine hydrochloride instead of (1,1-dioxidotetrahydro-2H-thiopyran-4-yl)amine hydrochloride, was converted into the title compound (43 mg, 76%) which was obtained as a white foam. MS (ESI): 410.3 ([M+H]+).

Example 104

N-(cis-4-hydroxy-4-methylcyclohexyl)-5-((5-methyl-3-(6-methylpyridin-3-yl)isoxazol-4-yl)methoxy)pyrazine-2-carboxamide

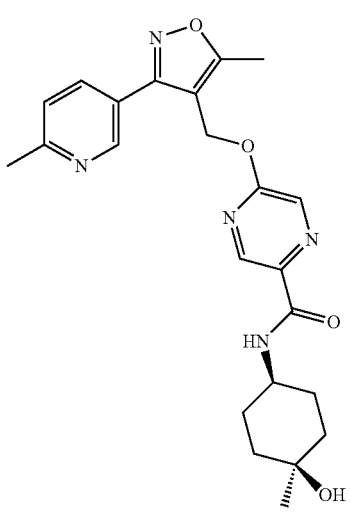 [SMILES: Cc1ccc(-c2noc(C)c2COc2cnc(C(=O)N[C@H]3CC[C@@](C)(O)CC3)cn2)cn1]

In analogy to experiment of example 14c, 5-((5-methyl-3-(6-methyl-3-pyridyl)isoxazol-4-yl)methoxy)pyrazine-2-carboxylic acid, using cis-4-amino-1-methylcyclohexanol 2,2,2-trifluoroacetate instead of (S)-2-aminopentan-1-ol, was converted into the title compound (18 mg, 13%) which was obtained as an off-white solid. MS (ESI): 438.2 ([M+H]+).

Example 105

N-(trans-4-hydroxy-4-methylcyclohexyl)-5-((5-methyl-3-(6-methylpyridin-3-yl)isoxazol-4-yl)methoxy)pyrazine-2-carboxamide

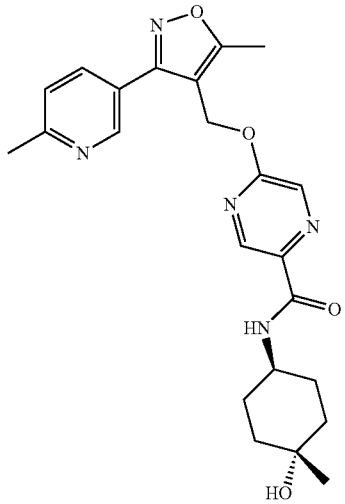 [SMILES: Cc1ccc(-c2noc(C)c2COc2cnc(C(=O)N[C@H]3CC[C@](C)(O)CC3)cn2)cn1]

In analogy to experiment of example 14c, 5-((5-methyl-3-(6-methyl-3-pyridyl)isoxazol-4-yl)methoxy)pyrazine-2-carboxylic acid, using trans-4-amino-1-methylcyclohexanol 2,2,2-trifluoroacetate instead of (S)-2-aminopentan-1-ol, was converted into the title compound (50 mg, 37%) which was obtained as an off-white solid. MS (ESI): 438.2 ([M+H]+).

Example 106

6-((5-methyl-3-(6-methylpyridin-3-yl)isoxazol-4-yl)methoxy)-N-(4-methyltetrahydropyran-4-yl)nicotinamide

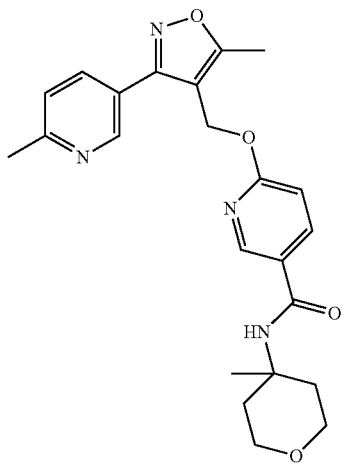 [SMILES: Cc1ccc(-c2noc(C)c2COc2ccc(C(=O)NC3(C)CCOCC3)cn2)cn1]

125

In analogy to experiment of example 30, 6-((5-methyl-3-(6-methyl-3-pyridyl)isoxazol-4-yl)methoxy)pyridine-3-carboxylic acid instead of 6-((5-(5-methyl-3-(6-methylpyridin-3-yl)isoxazol-4-yl)methoxy)pyridazine-3-carboxylic acid, using 4-methyltetrahydropyran-4-amine hydrochloride instead of (1,1-dioxidotetrahydro-2H-thiopyran-4-yl)amine hydrochloride, was converted into the title compound (48 mg, 75%) which was obtained as a colorless oil. MS (ESI): 423.3 ([M+H]$^+$).

Example 107

6-((5-methyl-3-(6-methylpyridin-3-yl)isoxazol-4-yl)methoxy)-2-(tetrahydro-2H-thiopyran-4-yl)-1H-pyrrolo[3,4-c]pyridin-3(2H)-one

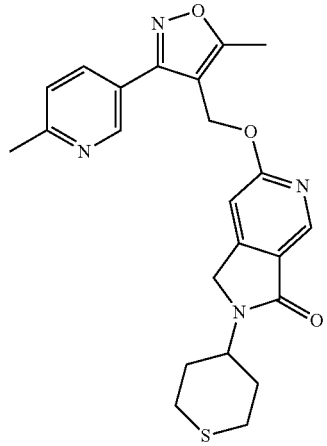 [SMILES: Cc1ccc(-c2noc(C)c2COc2cc3c(cn2)C(=O)N(C2CCSCC2)C3)cn1]

a) 6-chloro-2-tetrahydrothiopyran-4-yl-1H-pyrrolo[3,4-c]pyridin-3-one

In analogy to experiment of example 9a, 6-chloro-4-formylnicotinic acid, using tetrahydrothiopyran-4-amine instead of isobutylamine, was converted into the title compound (585 mg, 45%) which was obtained as a light brown solid. MS (ESI): 269.1 ([M+H]$^+$).

b) 6-((5-methyl-3-(6-methylpyridin-3-yl)isoxazol-4-yl)methoxy)-2-(tetrahydro-2H-thiopyran-4-yl)-1H-pyrrolo[3,4-c]pyridin-3(2H)-one In analogy to experiment of example 9b, (5-methyl-3-(6-methylpyridin-3-yl)isoxazol-4-yl)methanol (building block A), using 6-chloro-2-tetrahydrothiopyran-4-yl-1H-pyrrolo[3,4-c]pyridin-3-one instead of 6-chloro-2-isobutyl-1H-pyrrolo[3,4-c]pyridin-3-one, was converted into the title compound (379 mg, 59%) which was obtained as a yellow solid. MS (ESI): 437.3 ([M+H]$^+$).

126

Example 108

6-((5-methyl-3-(6-methylpyridazin-3-yl)isoxazol-4-yl)methoxy)-N-tetrahydropyran-4-yl-pyridine-3-carboxamide

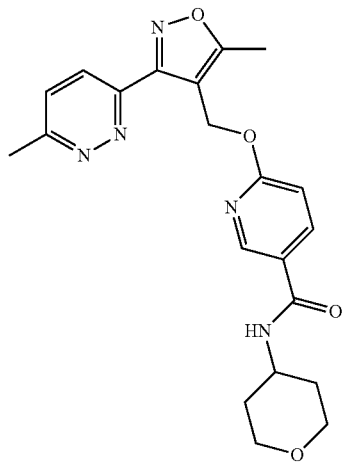 [SMILES: Cc1ccc(-c2noc(C)c2COc2ccc(C(=O)NC3CCOCC3)cn2)nn1]

Methyl 6-((5-methyl-3-(6-methylpyridazin-3-yl)isoxazol-4-yl)methoxy)pyridine-3-carboxylate In analogy to experiment of example 1a, (5-methyl-3-(6-methylpyridazin-3-yl)isoxazol-4-yl)methanol (building block I) instead of (5-methyl-3-(6-methylpyridin-3-yl)isoxazol-4-yl)methanol (building block A) was converted into the title compound (751 mg, 60%) which was obtained as a light yellow oil. MS (ESI): 341.1 ([M+H]$^+$).

6-((5-methyl-3-(6-methylpyridazin-3-yl)isoxazol-4-yl)methoxy)pyridine-3-carboxylic Acid In analogy to experiment of example 4a, methyl 6-((5-methyl-3-(6-methylpyridazin-3-yl)isoxazol-4-yl)methoxy)pyridine-3-carboxylate instead of methyl 6-((5-methyl-3-(6-methyl-3-pyridyl)isoxazol-4-yl)methoxy)pyridine-3-carboxylate was converted into the title compound (400 mg, 83%) which was obtained as a white solid. MS (ESI): 327.0 ([M+H]$^+$).

6-((5-methyl-3-(6-methylpyridazin-3-yl)isoxazol-4-yl)methoxy)-N-tetrahydropyran-4-yl-pyridine-3-carboxamide In analogy to experiment of example 4b, 6-((5-methyl-3-(6-methylpyridazin-3-yl)isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid, using tetrahydropyran-4-amine instead of (S)-2-aminopentan-1-ol, was converted into the title compound (85 mg, 67%) which was obtained as a white solid. MS (ESI): 410.1 ([M+H]$^+$).

Example 109

N-((1S)-1-(hydroxymethyl)butyl)-6-((5-methyl-3-(6-methylpyridazin-3-yl)isoxazol-4-yl)methoxy)pyridine-3-carboxamide

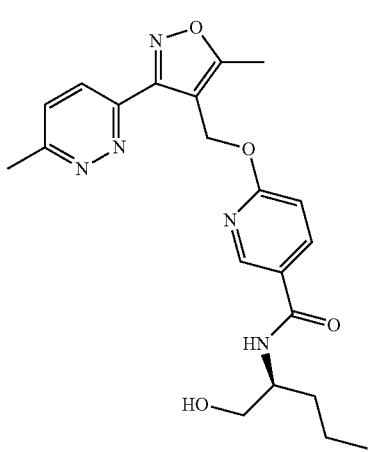 [SMILES: CCC[C@@H](CO)NC(=O)c1ccc(OCc2c(-c3ccc(C)nn3)noc2C)nc1]

In analogy to experiment of example 4b, 6-((5-methyl-3-(6-methylpyridazin-3-yl)isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid was converted into the title compound (151 mg, 79%) which was obtained as a white solid. MS (ESI): 412.1 ([M+H]⁺).

Example 110

6-((5-methyl-3-(6-methylpyridin-3-yl)isoxazol-4-yl)methoxy)-N-(4-methyltetrahydrothiopyran-4-yl)pyridazine-3-carboxamide

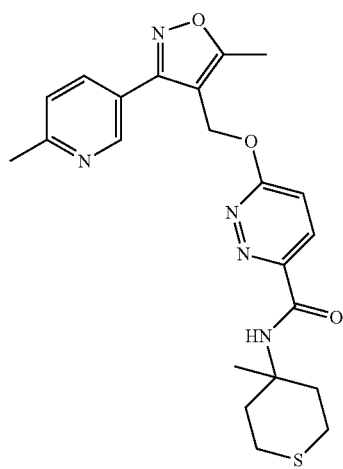 [SMILES: Cc1ccc(-c2noc(C)c2COc2ccc(C(=O)NC3(C)CCSCC3)nn2)cn1]

In analogy to experiment of example 30, 6-((5-methyl-3-(6-methylpyridin-3-yl)isoxazol-4-yl)methoxy)pyridazine-3-carboxylic acid, using 4-methyltetrahydrothiopyran-4-amine hydrochloride instead of (1,1-dioxidotetrahydro-2H-thiopyran-4-yl)amine hydrochloride, was converted into the title compound (94 mg, 83%) which was obtained as an off-white foam. MS (ESI): 440.3 ([M+H]⁺).

Example 111

N-(4-methyl-1,1-dioxidotetrahydro-2H-thiopyran-4-yl)-6-((5-methyl-3-(6-methylpyridin-3-yl)isoxazol-4-yl)methoxy)pyridazine-3-carboxamide

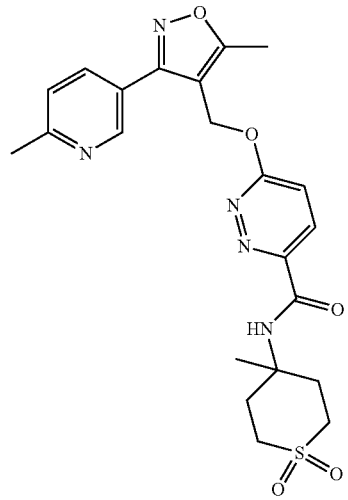 [SMILES: Cc1ccc(-c2noc(C)c2COc2ccc(C(=O)NC3(C)CCS(=O)(=O)CC3)nn2)cn1]

To a stirred suspension of 6-((5-methyl-3-(6-methylpyridin-3-yl)isoxazol-4-yl)methoxy)-N-(4-methyltetrahydro-2H-thiopyran-4-yl)pyridazine-3-carboxamide (example 68, 60 mg, 0.130 mmol) in a mixture of MeOH (1.4 mL) and water (0.14 mL) was added Ozone® (159 mg, 0.259 mmol) and the reaction mixture was stirred at room temperature for 2 hours. The suspension was basified by addition of aqueous Na₂CO₃ (0.5 m, 3 mL) and stirred for further 2 hours. The reaction mixture was poured into water (5 mL) and extracted with CH₂Cl₂ (2×15 mL). The combined organic extracts were dried (Na₂SO₄), filtered and concentrated in vacuo. Purification by flash chromatography (silica, gradient: 20% to 100% EtOAc in heptane) afforded the title compound (41 mg, 64%) as an off-white foam. MS (ESI): 472.3 ([M+H]⁺).

Example 112

(2,2-dioxido-2-thia-6-azaspiro[3.3]heptan-6-yl)(6-((5-methyl-3-(6-methylpyridin-3-yl)isoxazol-4-yl)methoxy)pyridazin-3-yl)methanone

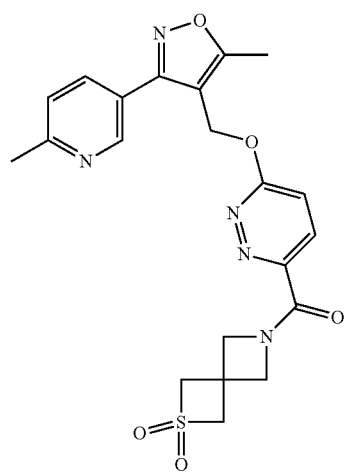 [SMILES: Cc1ccc(-c2noc(C)c2COc2ccc(C(=O)N3CC4(C3)CS(=O)(=O)C4)nn2)cn1]

In analogy to experiment of example 30, 6-((5-methyl-3-(6-methylpyridin-3-yl)isoxazol-4-yl)methoxy)pyridazine-3-carboxylic acid, using 2-thia-6-azaspiro[3.3]heptane 2,2-dioxide 2,2,2-trifluoroacetate instead of (1,1-dioxidotetrahydro-2H-thiopyran-4-yl)amine hydrochloride, was converted into the title compound (53 mg, 90%) which was obtained as an off-white solid. MS (ESI): 456.3 ([M+H]⁺).

Example 113

(2,2-dioxido-2-thia-6-azaspiro[3.3]heptan-6-yl)(5-((5-methyl-3-(6-methylpyridin-3-yl)isoxazol-4-yl)methoxy)pyrazin-2-yl)methanone

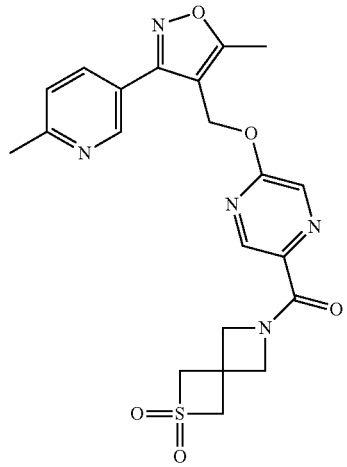 [SMILES: Cc1ccc(-c2noc(C)c2COc2cnc(C(=O)N3CC4(C3)CS(=O)(=O)C4)cn2)cn1]

In analogy to experiment of example 30, 5-((5-methyl-3-(6-methyl-3-pyridyl)isoxazol-4-yl)methoxy)pyrazine-2-carboxylic acid instead of 6-((5-methyl-3-(6-methylpyridin-3-yl)isoxazol-4-yl)methoxy)pyridazine-3-carboxylic acid, using 2-thia-6-azaspiro[3.3]heptane 2,2-dioxide 2,2,2-trifluoroacetate instead of (1,1-dioxidotetrahydro-2H-thiopyran-4-yl)amine hydrochloride, was converted into the title compound (45 mg, 80%) which was obtained as an off-white solid. MS (ESI): 456.3 ([M+H]⁺).

Example 114

6-((5-methyl-3-(6-methylpyridin-3-yl)isoxazol-4-yl)methoxy)-N-(1-methylcyclopentyl)pyridazine-3-carboxamide

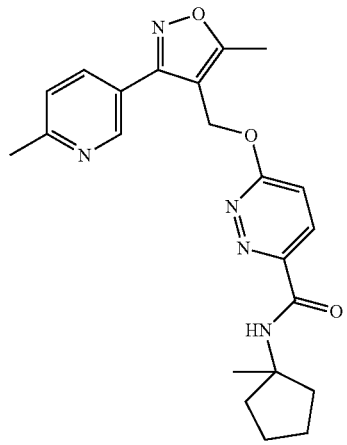 [SMILES: Cc1ccc(-c2noc(C)c2COc2ccc(C(=O)NC3(C)CCCC3)nn2)cn1]

In analogy to experiment of example 30, 6-((5-methyl-3-(6-methylpyridin-3-yl)isoxazol-4-yl)methoxy)pyridazine-3-carboxylic acid, using 1-methylcyclopentanamine hydrochloride instead of (1,1-dioxidotetrahydro-2H-thiopyran-4-yl)amine hydrochloride, was converted into the title compound (46 mg, 88%) which was obtained as an off-white foam. MS (ESI): 408.3 ([M+H]⁺).

Example 115

5-((5-methyl-3-(6-methylpyridin-3-yl)isoxazol-4-yl)methoxy)-N-(4,4,4-trifluorobutyl)pyrazine-2-carboxamide

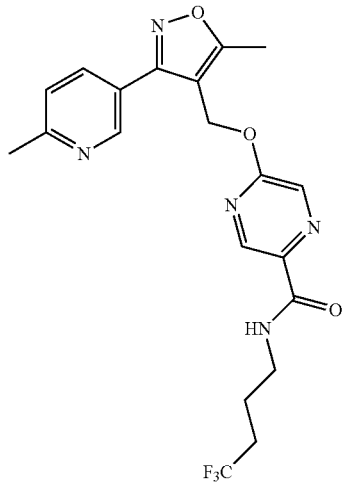 [SMILES: Cc1ccc(-c2noc(C)c2COc2cnc(C(=O)NCCCC(F)(F)F)cn2)cn1]

In analogy to experiment of example 14c, 5-((5-methyl-3-(6-methyl-3-pyridyl)isoxazol-4-yl)methoxy)pyrazine-2-carboxylic acid, using 4,4,4-trifluorobutan-1-amine instead of (S)-2-aminopentan-1-ol, was converted into the title compound (50 mg, 94%) which was obtained as an off-white solid. MS (ESI): 436.2 ([M+H]⁺).

Example 116

N-(1-isopropylazetidin-3-yl)-6-((5-methyl-3-(6-methylpyridin-3-yl)isoxazol-4-yl)methoxy)pyridazine-3-carboxamide

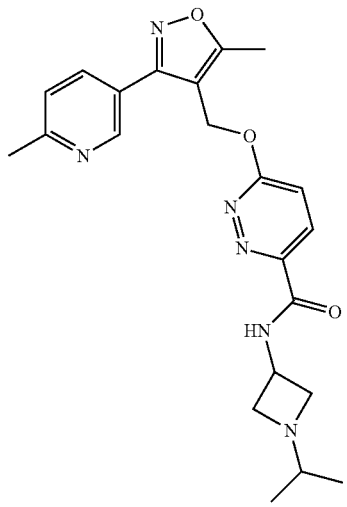 [SMILES: Cc1ccc(-c2noc(C)c2COc2ccc(C(=O)NC3CN(C(C)C)C3)nn2)cn1]

In analogy to experiment of example 30, 6-((5-methyl-3-(6-methylpyridin-3-yl)isoxazol-4-yl)methoxy)pyridazine-3-carboxylic acid, using 1-isopropylazetidin-3-amine hydrochloride instead of (1,1-dioxidotetrahydro-2H-thiopyran-4-yl)amine hydrochloride, was converted into the title compound (25 mg, 41%) which was obtained as a white foam. MS (ESI): 423.3 ([M+H]$^+$).

Example 117

6-((5-methyl-3-(6-methylpyridin-3-yl)isoxazol-4-yl)methoxy)-2-(2-oxaspiro[3.3]heptan-6-yl)-1H-pyrrolo[3,4-c]pyridin-3(2H)-one

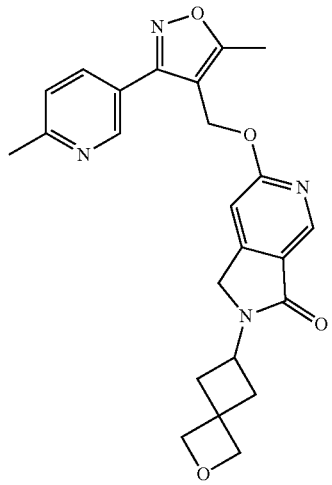 [SMILES: Cc1ccc(-c2noc(C)c2COc2cc3c(cn2)C(=O)N(C2CC4(COC4)C2)C3)cn1]

a) 6-chloro-2-(2-oxaspiro[3.3]heptan-6-yl)-1H-pyrrolo[3,4-c]pyridin-3(2H)-one

In analogy to experiment of example 9a, 6-chloro-4-formylnicotinic acid, using 2-oxaspiro[3.3]heptan-6-amine hydrochloride instead of isobutylamine, was converted into the title compound (96 mg, 37%) which was obtained as a light yellow solid. MS (ESI): 265.2 ([M+H]$^+$).

b) 6-((5-methyl-3-(6-methylpyridin-3-yl)isoxazol-4-yl)methoxy)-2-(2-oxaspiro[3.3]heptan-6-yl)-1H-pyrrolo[3,4-c]pyridin-3(2H)-one In analogy to experiment of example 9b, (5-methyl-3-(6-methylpyridin-3-yl)isoxazol-4-yl)methanol, using 6-chloro-2-(2-oxaspiro[3.3]heptan-6-yl)-1H-pyrrolo[3,4-c]pyridin-3(2H)-one instead of 6-chloro-2-isobutyl-1H-pyrrolo[3,4-c]pyridin-3-one, was converted into the title compound (59 mg, 51%) which was obtained as a light yellow solid. MS (ESI): 433.3 ([M+H]$^+$).

Example 118

6-((5-methyl-3-(6-methylpyridin-3-yl)isoxazol-4-yl)methoxy)-N-(1-methylcyclobutyl)pyridazine-3-carboxamide

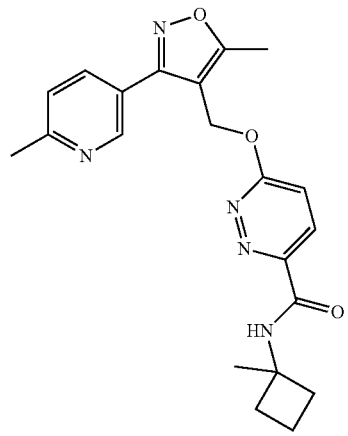 [SMILES: Cc1ccc(-c2noc(C)c2COc2ccc(C(=O)NC3(C)CCC3)nn2)cn1]

In analogy to experiment of example 30, 6-((5-methyl-3-(6-methylpyridin-3-yl)isoxazol-4-yl)methoxy)pyridazine-3-carboxylic acid, using 1-methylcyclobutanamine hydrochloride instead of (1,1-dioxidotetrahydro-2H-thiopyran-4-yl)amine hydrochloride, was converted into the title compound (23 mg, 48%) which was obtained as a white foam. MS (ESI): 394.3 ([M+H]$^+$).

Example 119

6-((5-ethyl-3-(6-methylpyridin-3-yl)isoxazol-4-yl)methoxy)-N-tetrahydropyran-4-yl-pyridine-3-carboxamide

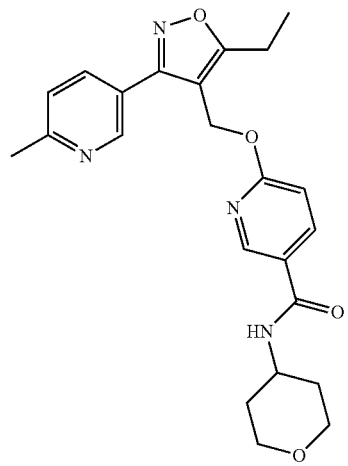 [SMILES: CCc1onc(-c2ccc(C)nc2)c1COc1ccc(C(=O)NC2CCOCC2)cn1]

a) Methyl 6-((5-ethyl-3-(6-methyl-3-pyridyl)isoxazol-4-yl)methoxy)pyridine-3-carboxylate In analogy to experiment of example 1a, (5-ethyl-3-(6-methyl-3-pyridyl)isoxazol-4-yl)methanol (building block B)

instead of (5-methyl-3-(6-methylpyridin-3-yl)isoxazol-4-yl) methanol (building block A) was converted into the title compound (743 mg, 77%) which was obtained as a light yellow oil. MS (ESI): 354.3 ([M+H]$^+$).

b) 6-((5-ethyl-3-(6-methyl-3-pyridyl)isoxazol-4-yl) methoxy)pyridine-3-carboxylic Acid In analogy to experiment of example 4a, methyl 6-((5-ethyl-3-(6-methyl-3-pyridyl)isoxazol-4-yl)methoxy)pyridine-3-carboxylate instead of methyl 6-((5-methyl-3-(6-methyl-3-pyridyl)isoxazol-4-yl)methoxy)pyridine-3-carboxylate was converted into the title compound (591 mg, 87%) which was obtained as an off-white solid. MS (ESI): 340.2 ([M+H]$^+$).

c) 6-((5-ethyl-3-(6-methylpyridin-3-yl)isoxazol-4-yl) methoxy)-N-tetrahydropyran-4-yl-pyridine-3-carboxamide In analogy to experiment of example 30, 6-((5-ethyl-3-(6-methyl-3-pyridyl)isoxazol-4-yl)methoxy)pyridine-3-carboxylic acid instead of 6-((5-methyl-3-(6-methylpyridin-3-yl)isoxazol-4-yl)methoxy)pyridazine-3-carboxylic acid, using tetrahydropyran-4-amine instead of (1,1-dioxidotetrahydro-2H-thiopyran-4-yl)amine hydrochloride, was converted into the title compound (56 mg, 90%) which was obtained as an off-white solid. MS (ESI): 423.3 ([M+H]$^+$).

Example 120

N-(1,1-dioxidotetrahydro-2H-thiopyran-4-yl)-6-((5-ethyl-3-(6-methylpyridin-3-yl)isoxazol-4-yl) methoxy)pyridine-3-carboxamide

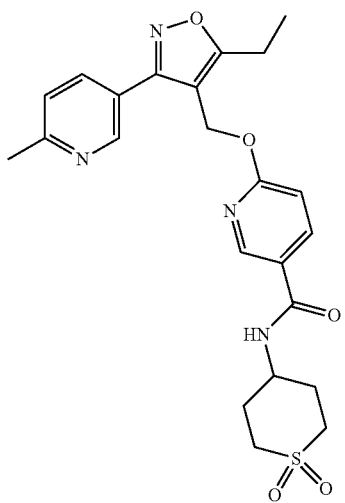 [SMILES: CCc1onc(-c2ccc(C)nc2)c1COc1ccc(C(=O)NC2CCS(=O)(=O)CC2)cn1]

In analogy to experiment of example 30, 6-((5-ethyl-3-(6-methyl-3-pyridyl)isoxazol-4-yl)methoxy)pyridine-3-carboxylic acid instead of 6-((5-methyl-3-(6-methylpyridin-3-yl)isoxazol-4-yl)methoxy)pyridazine-3-carboxylic acid was converted into the title compound (44 mg, 64%) which was obtained as an off-white solid. MS (ESI): 471.3 ([M+H]).

Example 121

6-((5-ethyl-3-(6-methylpyridin-3-yl)isoxazol-4-yl) methoxy)-N-(tetrahydropyran-4-yl)pyridazine-3-carboxamide

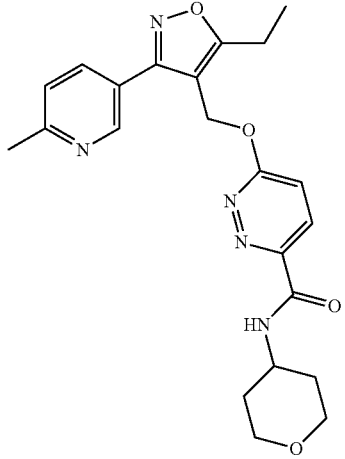 [SMILES: CCc1onc(-c2ccc(C)nc2)c1COc1ccc(C(=O)NC2CCOCC2)nn1]

a) 4-((6-chloropyridazin-3-yl)oxymethyl)-5-ethyl-3-(6-methyl-3-pyridyl)isoxazole In analogy to experiment of example 23a, (5-ethyl-3-(6-methyl-3-pyridyl)isoxazol-4-yl)methanol (building block B) instead of (5-methyl-3-(6-methylpyridin-3-yl)isoxazol-4-yl) methanol (building block A) was converted into the title compound (1.2 g, 91%) which was obtained as a yellow oil. MS (ESI): 331.2 ([M+H]$^+$).

b) ethyl 6-((5-ethyl-3-(6-methyl-3-pyridyl)isoxazol-4-yl)methoxy)pyridazine-3-carboxylate In analogy to experiment of example 23b, 4-((6-chloropyridazin-3-yl)oxymethyl)-5-ethyl-3-(6-methyl-3-pyridyl)isoxazole instead of 4-((6-chloropyridazin-3-yl)oxymethyl)-5-methyl-3-(6-methyl-3-pyridyl)isoxazole was converted into the title compound (272 mg, 21%) which was obtained as a light-brown oil. MS (ESI): 369.2 ([M+H]$^+$).

c) 6-((5-ethyl-3-(6-methyl-3-pyridyl)isoxazol-4-yl) methoxy)pyridazine-3-carboxylic Acid In analogy to experiment of example 23c, ethyl 6-((5-ethyl-3-(6-methyl-3-pyridyl)isoxazol-4-yl)methoxy) pyridazine-3-carboxylate instead of ethyl 6-((5-methyl-3-(6-methyl-3-pyridyl)isoxazol-4-yl)methoxy)pyridazine-3-carboxylate was converted into the title compound (192 mg, 91%) which was obtained as an off-white solid. MS (ESI): 341.2 ([M+H]$^+$).

d) 6-((5-ethyl-3-(6-methylpyridin-3-yl)isoxazol-4-yl)methoxy)-N-(tetrahydropyran-4-yl)pyridazine-3-carboxamide In analogy to experiment of example 23d, 6-((5-ethyl-3-(6-methyl-3-pyridyl)isoxazol-4-yl)methoxy)pyridazine-3-carboxylic acid instead of 6-((5-methyl-3-(6-methyl-3-pyridyl)isoxazol-4-yl)methoxy)pyridazine-3-carboxylic acid, using tetrahydropyran-4-amine in place of (1R,2S)-2-aminocyclohexanol hydrochloride, was converted into the title compound (38 mg, 87%) which was obtained as an off-white solid. MS (ESI): 424.3 ([M+H]$^+$).

Example 122

6-((5-ethyl-3-(6-methylpyridin-3-yl)isoxazol-4-yl)methoxy)-N-(3-methyloxetan-3-yl)pyridazine-3-carboxamide

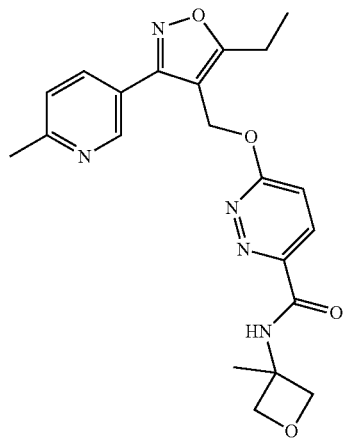 [SMILES: CCc1onc(-c2ccc(C)nc2)c1COc1ccc(C(=O)NC2(C)COC2)nn1]

In analogy to experiment of example 23d, 6-((5-ethyl-3-(6-methyl-3-pyridyl)isoxazol-4-yl)methoxy)pyridazine-3-carboxylic acid instead of 6-((5-methyl-3-(6-methyl-3-pyridyl)isoxazol-4-yl)methoxy)pyridazine-3-carboxylic acid, using 3-methyloxetan-3-amine hydrochloride in place of (1R,2S)-2-aminocyclohexanol hydrochloride, was converted into the title compound (46 mg, 96%) which was obtained as an off-white solid. MS (ESI): 410.3 ([M+H]$^+$).

Example 123

N-cyclopropyl-6-((5-ethyl-3-(6-methylpyridin-3-yl)isoxazol-4-yl)methoxy)pyridazine-3-carboxamide

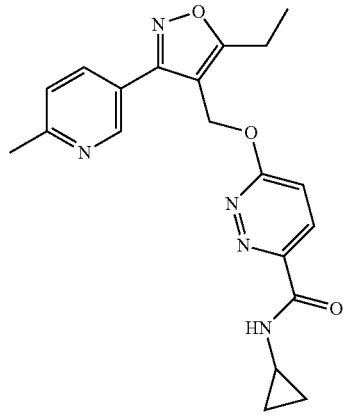 [SMILES: CCc1onc(-c2ccc(C)nc2)c1COc1ccc(C(=O)NC2CC2)nn1]

In analogy to experiment of example 23d, 6-((5-ethyl-3-(6-methyl-3-pyridyl)isoxazol-4-yl)methoxy)pyridazine-3-carboxylic acid instead of 6-((5-methyl-3-(6-methyl-3-pyridyl)isoxazol-4-yl)methoxy)pyridazine-3-carboxylic acid, using cyclopropanamine in place of (1R,2S)-2-aminocyclohexanol hydrochloride, was converted into the title compound (37 mg, 95%) which was obtained as an off-white solid. MS (ESI): 380.2 ([M+H]$^+$).

Example 124

(R)—N-(1-hydroxypentan-2-yl)-6-((5-methyl-3-(6-methylpyridin-3-yl)isoxazol-4-yl)methoxy)pyridine-3-carboxamide

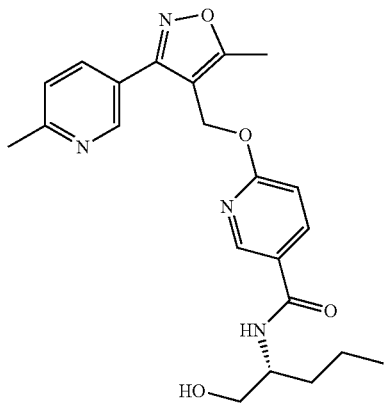 [SMILES: CCC[C@H](CO)NC(=O)c1ccc(OCc2c(-c3ccc(C)nc3)noc2C)nc1]

In analogy to experiment of example 4b, 6-((5-methyl-3-(6-methyl-3-pyridyl)isoxazol-4-yl)methoxy)pyridine-3-carboxylic acid, using (R)-2-aminopentan-1-ol instead of (S)-2-aminopentan-1-ol, was converted into the title compound (156 mg, 82%) which was obtained as a white solid. MS (ESI): 411.3 ([M+H]$^+$).

Example 125

6-((5-(difluoromethyl)-3-(6-methyl-3-pyridyl)isoxazol-4-yl)methoxy)-N-((1S)-1-(hydroxymethyl)butyl)pyridine-3-carboxamide

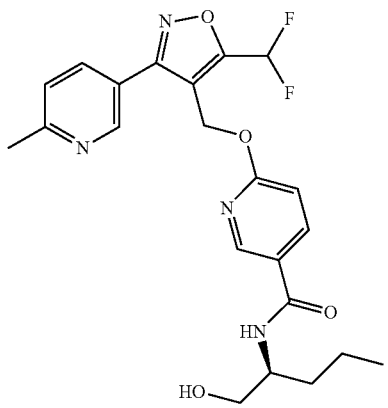 [SMILES: CCC[C@@H](CO)NC(=O)c1ccc(OCc2c(-c3ccc(C)nc3)noc2C(F)F)nc1]

a) Methyl 6-((5-(difluoromethyl)-3-(6-methyl-3-pyridyl)isoxazol-4-yl)methoxy)pyridine-3-carboxylate In analogy to experiment of example 1a, (5-(difluoromethyl)-3-(6-methyl-3-pyridyl)isoxazol-4-yl)methanol (building block J) instead of (5-methyl-3-(6-methylpyridin-3-yl)isoxazol-4-yl)methanol (building block A) was converted into the title compound (146 mg, 58%) which was obtained as a colorless oil. MS (ESI): 376.2 ([M+H]+).

b) 6-((5-(difluoromethyl)-3-(6-methyl-3-pyridyl)isoxazol-4-yl)methoxy)pyridine-3-carboxylic Acid In analogy to experiment of example 4a, methyl 6-((5-(difluoromethyl)-3-(6-methyl-3-pyridyl)isoxazol-4-yl)methoxy)pyridine-3-carboxylate instead of methyl 6-((5-methyl-3-(6-methyl-3-pyridyl)isoxazol-4-yl)methoxy)pyridine-3-carboxylate was converted into the title compound (23 mg, 97%) which was obtained as an off-white solid. MS (ESI): 362.2 ([M+H]+).

c) 6-((5-(difluoromethyl)-3-(6-methyl-3-pyridyl)isoxazol-4-yl)methoxy)-N-((1S)-1-(hydroxymethyl)butyl)pyridine-3-carboxamide In analogy to experiment of example 4b, 6-((5-(difluoromethyl)-3-(6-methyl-3-pyridyl)isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid was converted into the title compound (13 mg, 50%) which was obtained as an off-white foam. MS (ESI): 447.3 ([M+H]+).

Example 126

6-((5-(difluoromethyl)-3-(6-methyl-3-pyridyl)isoxazol-4-yl)methoxy)-N-tetrahydropyran-4-yl-pyridine-3-carboxamide

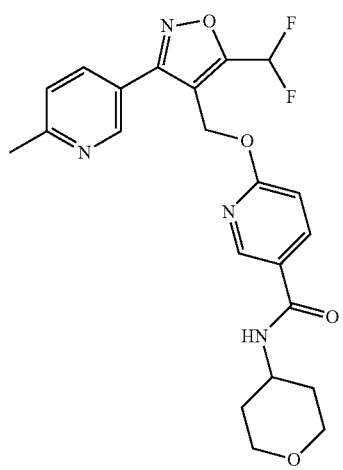 [SMILES: Cc1ccc(-c2noc(C(F)F)c2COc2ccc(C(=O)NC3CCOCC3)cn2)cn1]

In analogy to experiment of example 4b, 6-((5-(difluoromethyl)-3-(6-methyl-3-pyridyl)isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid, using tetrahydropyran-4-amine instead of (S)-2-aminopentan-1-ol, was converted into the title compound (17 mg, 29%) which was obtained as an off-white solid. MS (ESI): 445.3 ([M+H]+).

Example 127

N-((3R,4S)-3-hydroxytetrahydropyran-4-yl)-6-((5-methyl-3-(6-methyl-3-pyridyl)isoxazol-4-yl)methoxy)pyridine-3-carboxamide

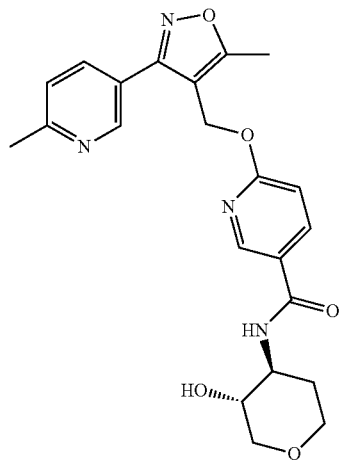 [SMILES: Cc1ccc(-c2noc(C)c2COc2ccc(C(=O)N[C@H]3CCOC[C@@H]3O)cn2)cn1]

To a stirred solution of 6-((5-methyl-3-(6-methyl-3-pyridyl)isoxazol-4-yl)methoxy)pyridine-3-carboxylic acid (50 mg, 0.154 mmol) in anhydrous DMF (2 mL) were added at room temperature under an argon atmosphere (3R,4S)-4-aminotetrahydro-2H-pyran-3-ol hydrochloride (28 mg, 0.184 mmol), HATU (70 mg, 0.184 mmol) and N-ethyldiisopropylamine (131 µL, 0.768 mmol). The reaction mixture was stirred for 17 hours at room temperature. The resulting clear yellow solution was was poured into water (10 mL) then extracted with EtOAc (2×20 mL). The combined organic extracts were dried (MgSO4), filtered and concentrated in vacuo. Purification by flash chromatography (silica, gradient: 0% to 10% MeOH in CH2Cl2) afforded the title compound (59 mg, 90%) as a white solid. MS (ESI): 425.3 ([M+H]+).

Example 128

6-((3-(6-cyclopropyl-3-pyridyl)-5-methyl-isoxazol-4-yl)methoxy)-N-tetrahydropyran-4-yl-pyridine-3-carboxamide

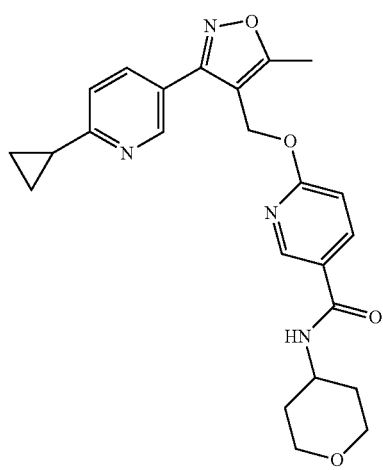 [SMILES: Cc1onc(-c2ccc(C3CC3)nc2)c1COc1ccc(C(=O)NC2CCOCC2)cn1]

a) Methyl 6-((3-(6-cyclopropyl-3-pyridyl)-5-methyl-isoxazol-4-yl)methoxy)pyridine-3-carboxylate In analogy to experiment of example 1a, (3-(6-cyclopropyl-3-pyridyl)-5-methyl-isoxazol-4-yl)methanol (building block K) instead of (5-methyl-3-(6-methylpyridin-3-yl)isoxazol-4-yl)methanol (building block A), using methyl 6-fluoropyridine-3-carboxylate instead of methyl 6-chloronicotinate, was converted into the title compound (920 mg, 25%) which was obtained as colorless oil. MS (ESI): 365.8 ([M+H]$^+$).

b) 6-((3-(6-cyclopropyl-3-pyridyl)-5-methyl-isoxazol-4-yl)methoxy)pyridine-3-carboxylic Acid In analogy to experiment of example 4a, methyl 6-((3-(6-cyclopropyl-3-pyridyl)-5-methyl-isoxazol-4-yl)methoxy)pyridine-3-carboxylate instead of methyl 6-((5-methyl-3-(6-methyl-3-pyridyl)isoxazol-4-yl)methoxy)pyridine-3-carboxylate was converted into the title compound (740 mg, 83%) which was obtained as a white solid. MS (ESI): 352.0 ([M+H]$^+$).

c) 6-((3-(6-cyclopropyl-3-pyridyl)-5-methyl-isoxazol-4-yl)methoxy)-N-tetrahydropyran-4-yl-pyridine-3-carboxamide In analogy to experiment of example 4b, 6-((3-(6-cyclopropyl-3-pyridyl)-5-methyl-isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid, using tetrahydropyran-4-amine instead of (S)-2-aminopentan-1-ol, was converted into the title compound (120 mg, 74%) which was obtained as a white solid. MS (ESI): 435.1 ([M+H]$^+$).

Example 129

6-((3-(6-cyclopropyl-3-pyridyl)-5-methyl-isoxazol-4-yl)methoxy)-N-((1S)-1-(hydroxymethyl)butyl)pyridine-3-carboxamide

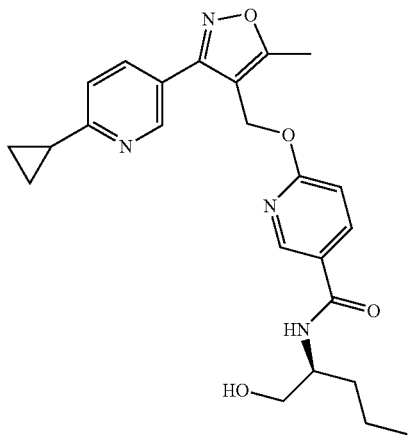 [SMILES: CCC[C@@H](CO)NC(=O)c1ccc(OCc2c(-c3ccc(C4CC4)nc3)noc2C)nc1]

In analogy to experiment of example 4b, 6-((3-(6-cyclopropyl-3-pyridyl)-5-methyl-isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid was converted into the title compound (140 mg, 59%) which was obtained as yellow oil. MS (ESI): 437.1 ([M+H]$^+$).

Example 130

6-((3-(6-cyclopropyl-3-pyridyl)-5-methyl-isoxazol-4-yl)methoxy)-N-(1,1-dioxothian-4-yl)pyridine-3-carboxamide

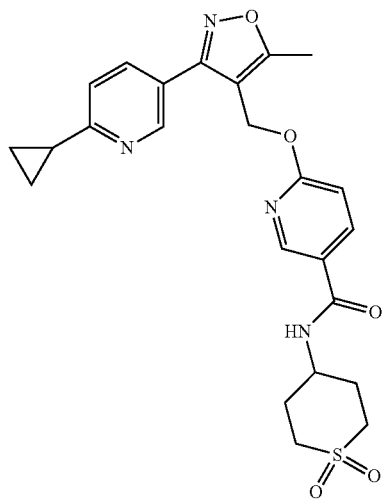 [SMILES: Cc1onc(-c2ccc(C3CC3)nc2)c1COc1ccc(C(=O)NC2CCS(=O)(=O)CC2)cn1]

In analogy to experiment of example 4b, 6-((3-(6-cyclopropyl-3-pyridyl)-5-methyl-isoxazol-4-yl)methoxy)pyridine-3-carboxylic acid instead of 6-((5-methyl-3-(6-methyl-3-pyridyl)isoxazol-4-yl)methoxy)pyridine-3-carboxylic acid, using (1,1-dioxidotetrahydro-2H-thiopyran-4-yl)amine hydrochloride instead of (S)-2-aminopentan-1-ol, was converted into the title compound (110 mg, 87%) which was obtained as a white solid. MS (ESI): 483.1 ([M+H]$^+$).

Example 131

N-((1R,2S)-3,3-difluoro-2-hydroxycyclohexyl)-6-((5-methyl-3-(6-methylpyridin-3-yl)isoxazol-4-yl)methoxy)pyridine-3-carboxamide

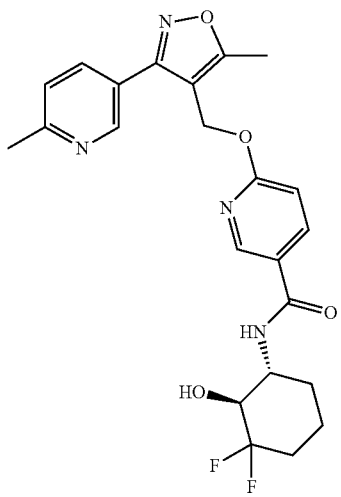 [SMILES: Cc1ccc(-c2noc(C)c2COc2ccc(C(=O)N[C@@H]3CCCC(F)(F)[C@H]3O)cn2)cn1]

In analogy to experiment of example 127, 6-((5-methyl-3-(6-methyl-3-pyridyl)isoxazol-4-yl)methoxy)pyridine-3-carboxylic acid, using (1S,6R)-6-amino-2,2-difluorocyclohexanol instead of (3R,4S)-4-aminotetrahydro-2H-pyran-3-ol hydrochloride, was converted into the title compound (50 mg, 70%) which was obtained as a white solid. MS (ESI): 459.5 ([M+H]$^+$).

Example 132

N-((1R,2R)-2-hydroxycyclohexyl)-6-((5-methyl-3-(6-methylpyridin-3-yl)isoxazol-4-yl)methoxy)pyridine-3-carboxamide

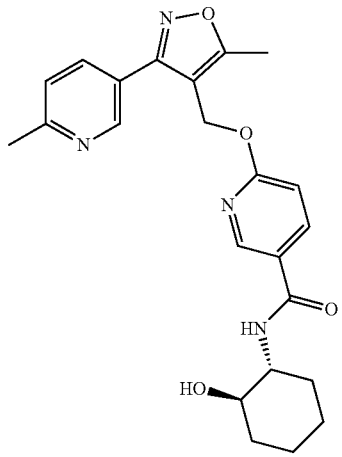 [SMILES: Cc1ccc(-c2noc(C)c2COc2ccc(C(=O)N[C@@H]3CCCC[C@H]3O)cn2)cn1]

In analogy to experiment of example 127, 6-((5-methyl-3-(6-methyl-3-pyridyl)isoxazol-4-yl)methoxy)pyridine-3-carboxylic acid, using (1R,2R)-2-aminocyclohexanol hydrochloride instead of (3R,4S)-4-aminotetrahydro-2H-pyran-3-ol hydrochloride, was converted into the title compound (39 mg, 60%) which was obtained as a white solid. MS (ESI): 423.4 ([M+H]$^+$).

Example 133

N-((1S,2R)-3,3-difluoro-2-hydroxycyclohexyl)-6-((5-methyl-3-(6-methylpyridin-3-yl)isoxazol-4-yl)methoxy)pyridine-3-carboxamide

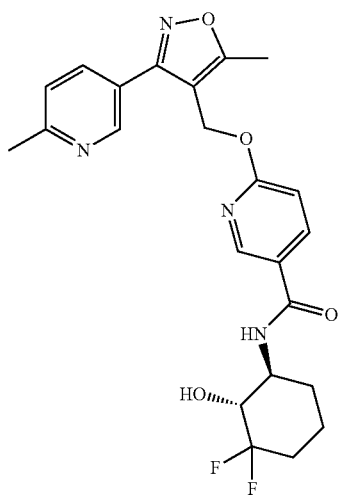 [SMILES: Cc1ccc(-c2noc(C)c2COc2ccc(C(=O)N[C@H]3CCCC(F)(F)[C@@H]3O)cn2)cn1]

In analogy to experiment of example 127, 6-((5-methyl-3-(6-methyl-3-pyridyl)isoxazol-4-yl)methoxy)pyridine-3-carboxylic acid, using (1R,6S)-6-amino-2,2-difluorocyclohexanol instead of (3R,4S)-4-aminotetrahydro-2H-pyran-3-ol hydrochloride, was converted into the title compound (66 mg, 94%) which was obtained as a white solid. MS (ESI): 459.4 ([M+H]$^+$).

Example 134

N-((3S,4R)-3-hydroxytetrahydro-2H-pyran-4-yl)-6-((5-methyl-3-(6-methylpyridin-3-yl)isoxazol-4-yl)methoxy)pyridine-3-carboxamide

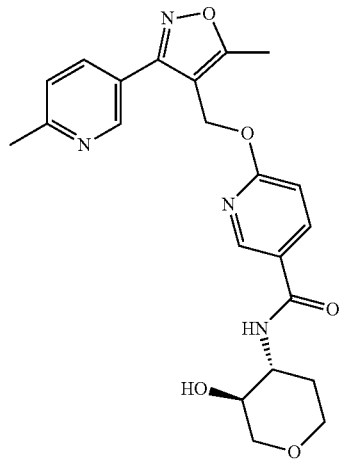 [SMILES: Cc1ccc(-c2noc(C)c2COc2ccc(C(=O)N[C@@H]3CCOC[C@H]3O)cn2)cn1]

In analogy to experiment of example 127, 6-((5-methyl-3-(6-methyl-3-pyridyl)isoxazol-4-yl)methoxy)pyridine-3-carboxylic acid, using (3S,4R)-4-aminotetrahydro-2H-pyran-3-ol hydrochloride instead of (3R,4S)-4-aminotetrahydro-2H-pyran-3-ol hydrochloride, was converted into the title compound (51 mg, 78%) which was obtained as a white solid. MS (ESI): 425.3 ([M+H]$^+$).

Example 135

N-((1S,2S)-2-hydroxycyclohexyl)-6-((5-methyl-3-(6-methylpyridin-3-yl)isoxazol-4-yl)methoxy)pyridine-3-carboxamide

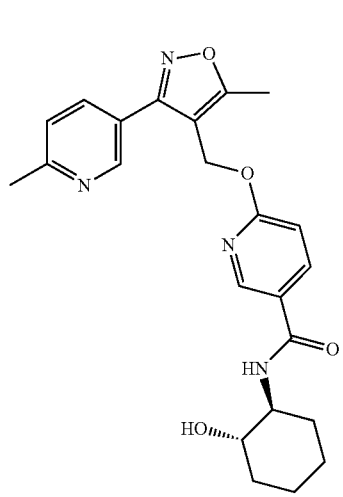 [SMILES: Cc1ccc(-c2noc(C)c2COc2ccc(C(=O)N[C@H]3CCCC[C@@H]3O)cn2)cn1]

In analogy to experiment of example 127, 6-((5-methyl-3-(6-methyl-3-pyridyl)isoxazol-4-yl)methoxy)pyridine-3-carboxylic acid, using (1S,2S)-2-aminocyclohexanol hydrochloride instead of (3R,4S)-4-aminotetrahydro-2H-pyran-3-ol hydrochloride, was converted into the title compound (30 mg, 46%) which was obtained as a white solid. MS (ESI): 423.4 ([M+H]⁺).

Example 136

2-fluoro-N-methyl-6-((5-methyl-3-(6-methylpyridin-3-yl)isoxazol-4-yl)methoxy)pyridine-3-carboxamide

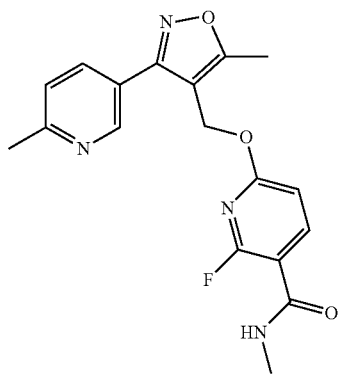 [SMILES: CNC(=O)c1ccc(OCc2c(-c3ccc(C)nc3)noc2C)nc1F]

a) Methyl 2-fluoro-6-((5-methyl-3-(6-methyl-3-pyridyl)isoxazol-4-yl)methoxy)-pyridine-3-carboxylate To a stirred solution of (5-methyl-3-(6-methylpyridin-3-yl)isoxazol-4-yl)methanol (0.5 g, 2.45 mmol) in THF (12 ml) at 0° C. was added under argon methyl 2,6-difluoropyridine-3-carboxylate (551 mg, 3.18 mmol) followed by NaH (55% dispersion in mineral oil, 139 mg, 3.18 mmol). The mixture was stirred at room temperature for 3 hours before a second portion of NaH (55% dispersion in mineral oil, 139 mg, 3.18 mmol) was added. The reaction mixture was stirred at room temperature for 3 hours before being poured into water (30 mL) then extracted with EtOAc (2×30 mL). The combined organic extracts were washed with brine, dried (MgSO₄) and concentrated in vacuo. Purification by flash chromatography (silica, gradient: 0% to 40% EtOAc in heptane) afforded the title compound (323 mg, 37%, white solid) as a 2:5 mixture with its regioisomer methyl 6-fluoro-2-((5-methyl-3-(6-methyl-3-pyridyl)isoxazol-4-yl)methoxy)pyridine-3-carboxylate. MS (ESI): 358.2 ([M+H]⁺).

b) 2-fluoro-6-((5-methyl-3-(6-methyl-3-pyridyl)isoxazol-4-yl)methoxy)pyridine-3-carboxylic Acid To a stirred solution of methyl 2-fluoro-6-((5-methyl-3-(6-methyl-3-pyridyl)isoxazol-4-yl)methoxy)-pyridine-3-carboxylate and methyl 6-fluoro-2-((5-methyl-3-(6-methyl-3-pyridyl)isoxazol-4-yl)methoxy)pyridine-3-carboxylate (418 mg, 1.17 mmol) in a mixture of MeOH (3 mL) and THF (3 mL) at room temperature were added water (0.9 mL) followed by aqueous NaOH (1.0 m, 1.64 mmol, 1.64 mL). The reaction mixture was stirred at room temperature for 1 hour, before being quenched by addition of aqueous HCl (1.0 m, 1.64 mL). The mixture was evaporated to dryness by rotary evaporation under reduced pressure to provide the title compound (546 mg, quantitative, white solid) as a 2:5 mixture with its regioisomer 6-fluoro-2-((5-methyl-3-(6-methyl-3-pyridyl)isoxazol-4-yl)methoxy)-pyridine-3-carboxylic acid. MS (ESI): 344.1 ([M+H]⁺).

c) 2-fluoro-N-methyl-6-((5-methyl-3-(6-methyl-3-pyridyl)isoxazol-4-yl)methoxy)pyridine-3-carboxamide In analogy to experiment of example 127, 6-((5-methyl-3-(6-methyl-3-pyridyl)isoxazol-4-yl)methoxy)pyridine-3-carboxylic acid, using methylamine hydrochloride instead of (3R,4S)-4-aminotetrahydro-2H-pyran-3-ol hydrochloride, was converted into the title compound (35 mg, 7%) which was obtained as a white solid after preparative HPLC removal of the undesired regioisomer. MS (ESI): 357.1 ([M+H]⁺).

Example 137

6-((3-(6-methoxypyridin-3-yl)-5-methylisoxazol-4-yl)methoxy)-N-tetrahydropyran-4-yl-pyridine-3-carboxamide

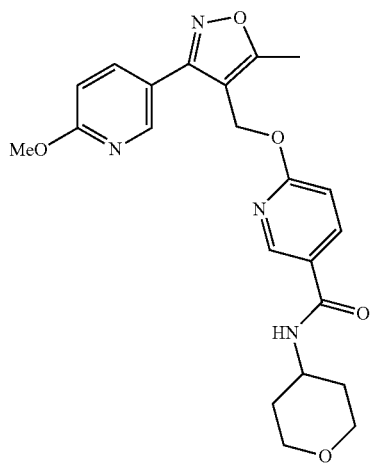 [SMILES: COc1ccc(-c2noc(C)c2COc2ccc(C(=O)NC3CCOCC3)cn2)cn1]

a) Methyl 6-((3-(6-methoxy-3-pyridyl)-5-methyl-isoxazol-4-yl)methoxy)pyridine-3-carboxylate To a stirred solution of (3-(6-methoxypyridin-3-yl)-5-methylisoxazol-4-yl)methanol (building block M, 1.44 g, 6.54 mmol) in anhydrous THF (30 mL) at 0° C. were added under argon methyl 6-chloropyridine-3-carboxylate (1.18 g, 6.87 mmol) followed by NaH (55% dispersion in mineral oil, 300 mg, 6.87 mmol). The reaction mixture was stirred at room temperature for 18 hours before being poured into water (50 mL) then extracted with EtOAc (2×50 mL). The combined organic extracts were washed with water, dried (MgSO₄) and concentrated in vacuo. Purification by flash chromatography (silica, gradient: 0% to 30% EtOAc in heptane) afforded the title compound (1.51 g, 65%) as a white solid. MS (ESI): 356.1 ([M+H]⁺).

b) 6-((3-(6-methoxy-3-pyridyl)-5-methyl-isoxazol-4-yl)methoxy)pyridine-3-carboxylic Acid To a stirred solution of methyl 6-((3-(6-methoxypyridin-3-yl)-5-methylisoxazol-4-yl)methoxy)pyridine-3-carboxylate (1.51 g, 4.25 mmol) in a mixture of MeOH (11 mL) and THF (11 mL) at room temperature were added water (3 mL) followed by aqueous NaOH (1.0 m, 8.5 ml, 8.5 mmol). The reaction mixture was stirred at room temperature for 1 hour then heated to 50° C. for 1.5 hours until a solution was formed. The mixture was cooled to room temperature then quenched by addition of aqueous HCl (1.0 m, 8.5 mL). The resulting suspension was diluted with water (10 mL) and filtered on a sintered funnel. The collected solid was rinsed with water (40 mL) and heptane (20 mL) then dried under high vacuum to provide the title compound (1.39 g, 96%) as white solid. MS (ESI): 342.1 ([M+H]$^+$).

c) 6-((3-(6-methoxypyridin-3-yl)-5-methylisoxazol-4-yl)methoxy)-N-tetrahydropyran-4-yl-pyridine-3-carboxamide To a stirred solution of 6-((3-(6-methoxy-3-pyridyl)-5-methyl-isoxazol-4-yl)methoxy)pyridine-3-carboxylic acid (200 mg, 586 µmop in anhydrous DMF (3 mL) was added at room temperature under an argon atmosphere tetrahydropyran-4-amine (72.8 µL, 0.703 mmol), N-ethyldiisopropylamine (512 µL, 2.93 mmol) and HATU (267 mg, 0.703 mmol). The resulting yellow solution was stirred at room temperature overnight before being poured into water (20 mL) then extracted with EtOAc (2×30 mL). The combined organic extracts were washed with water and brine, dried (MgSO$_4$) and concentrated in vacuo. Purification by flash chromatography (silica, gradient: 0% to 5% MeOH in CH$_2$Cl$_2$) afforded the title compound (230 mg, 92%) as white solid. MS (ESI): 425.2 ([M+H]$^+$).

Example 138

N-isopropyl-6-((3-(6-methoxypyridin-3-yl)-5-methylisoxazol-4-yl)methoxy)pyridine-3-carboxamide

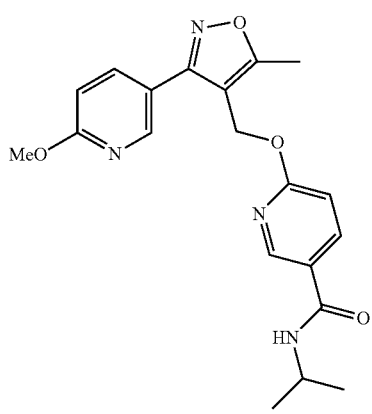 [SMILES: COc1ccc(-c2noc(C)c2COc2ccc(C(=O)NC(C)C)cn2)cn1]

In analogy to experiment of example 137, 6-((3-(6-methoxy-3-pyridyl)-5-methyl-isoxazol-4-yl)methoxy)pyridine-3-carboxylic acid, using isopropylamine instead of tetrahydropyran-4-amine, was converted into the title compound (218 mg, 97%) which was obtained as a white solid. MS (ESI): 383.2 ([M+H]$^+$).

Example 139

(S)—N-(1-hydroxypentan-2-yl)-6-((3-(6-methoxypyridin-3-yl)-5-methylisoxazol-4-yl)methoxy)pyridine-3-carboxamide

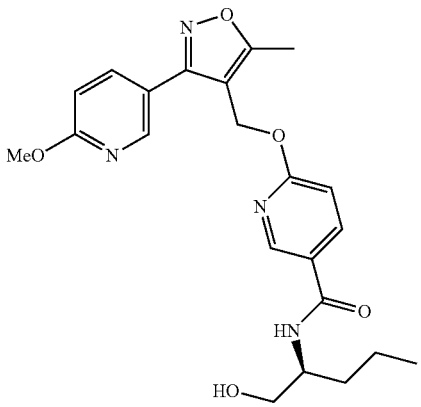 [SMILES: CCC[C@@H](CO)NC(=O)c1ccc(OCc2c(-c3ccc(OC)nc3)noc2C)nc1]

In analogy to experiment of example 137, 6-((3-(6-methoxy-3-pyridyl)-5-methyl-isoxazol-4-yl)methoxy)pyridine-3-carboxylic acid, using (S)-2-aminopentan-1-ol instead of tetrahydropyran-4-amine, was converted into the title compound (131 mg, 52%) which was obtained as a white solid. MS (ESI): 427.3 ([M+H]$^+$).

Example 140

(1,1-dioxidothiomorpholino)(6-((3-(6-methoxypyridin-3-yl)-5-methylisoxazol-4-yl)methoxy)pyridin-3-yl)methanone

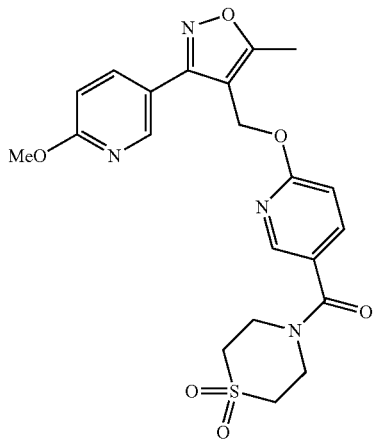 [SMILES: COc1ccc(-c2noc(C)c2COc2ccc(C(=O)N3CCS(=O)(=O)CC3)cn2)cn1]

In analogy to experiment of example 137, 6-((3-(6-methoxy-3-pyridyl)-5-methyl-isoxazol-4-yl)methoxy)pyridine-3-carboxylic acid, using thiomorpholine 1,1-dioxide instead of tetrahydropyran-4-amine, was converted into the title compound (244 mg, 91%) which was obtained as a white solid. MS (ESI): 459.2 ([M+H]$^+$).

Example 141

(S)-6-((3-(6-(dimethylamino)pyridin-3-yl)-5-methyl-isoxazol-4-yl)methoxy)-N-(1-hydroxypentan-2-yl) nicotinamide

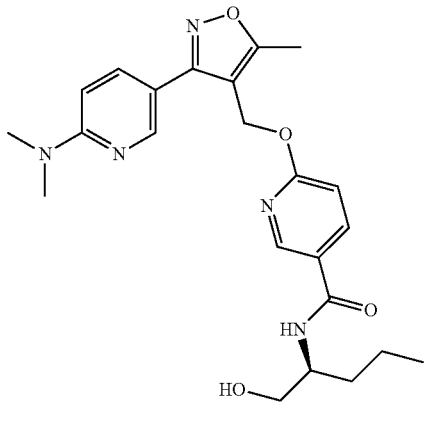 [SMILES: CCC[C@@H](CO)NC(=O)c1ccc(OCc2c(-c3ccc(N(C)C)nc3)noc2C)nc1]

a) Methyl 6-((3-(6-(dimethylamino)-3-pyridyl)-5-methyl-isoxazol-4-yl)methoxy)pyridine-3-carboxylate In analogy to experiment of example 137a, (3-(6-(dimethylamino)pyridin-3-yl)-5-methylisoxazol-4-yl)methanol (building block N) instead of (3-(6-methoxypyridin-3-yl)-5-methylisoxazol-4-yl)methanol (building block M) was converted into the title compound (843 mg, 70%) which was obtained as a light yellow solid. MS (ESI): 369.2 ([M+H]$^+$).

b) 6-((3-(6-(dimethylamino)-3-pyridyl)-5-methyl-isoxazol-4-yl)methoxy)pyridine-3-carboxylic Acid In analogy to experiment of example 137b, methyl 6-((3-(6-(dimethylamino)-3-pyridyl)-5-methyl-isoxazol-4-yl)methoxy)pyridine-3-carboxylate instead of methyl 6-((3-(6-methoxypyridin-3-yl)-5-methylisoxazol-4-yl)methoxy)pyridine-3-carboxylate was converted into the title compound (563 mg, 74%) which was obtained as a white solid. MS (ESI): 355.0 ([M+H]$^+$).

c) (S)-6-((3-(6-(dimethylamino)pyridin-3-yl)-5-methylisoxazol-4-yl)methoxy)-N-(1-hydroxypentan-2-yl)nicotinamide In analogy to experiment of example 137c, 6-((3-(6-(dimethylamino)-3-pyridyl)-5-methyl-isoxazol-4-yl)methoxy)pyridine-3-carboxylic acid instead of 6-((3-(6-methoxy-3-pyridyl)-5-methyl-isoxazol-4-yl)methoxy)pyridine-3-carboxylic acid, using (S)-2-aminopentan-1-ol instead of tetrahydropyran-4-amine, was converted into the title compound (93 mg, 67%) which was obtained as a white solid. MS (ESI): 440.3 ([M+H]$^+$).

Example 142

4-methoxy-6-((5-methyl-3-(6-methylpyridin-3-yl) isoxazol-4-yl)methoxy)-N-(tetrahydropyran-4-yl) nicotinamide

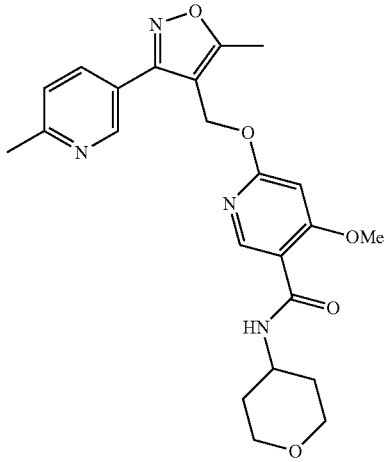 [SMILES: COc1cc(OCc2c(-c3ccc(C)nc3)noc2C)ncc1C(=O)NC1CCOCC1]

a) Methyl 4-methoxy-6-((5-methyl-3-(6-methyl-3-pyridyl)isoxazol-4-yl)methoxy)pyridine-3-carboxylate In analogy to experiment of example 137a, (5-methyl-3-(6-methylpyridin-3-yl)isoxazol-4-yl)methanol (building block A) instead of (3-(6-methoxypyridin-3-yl)-5-methylisoxazol-4-yl)methanol (building block M), using methyl 6-chloro-4-methoxy-pyridine-3-carboxylate instead of methyl 6-chloropyridine-3-carboxylate, was converted into the title compound (67 mg, 27%) which was obtained as a light yellow solid. MS (ESI): 370.1 ([M+H]$^+$).

b) 4-methoxy-6-((5-methyl-3-(6-methyl-3-pyridyl) isoxazol-4-yl)methoxy)pyridine-3-carboxylic Acid In analogy to experiment of example 137b, methyl 4-methoxy-6-((5-methyl-3-(6-methyl-3-pyridyl)isoxazol-4-yl)methoxy)pyridine-3-carboxylate instead of methyl 6-((3-(6-methoxypyridin-3-yl)-5-methylisoxazol-4-yl)methoxy) pyridine-3-carboxylate was converted into the title compound (70 mg, 99%) which was obtained as a light yellow solid. MS (ESI): 356.2 ([M+H]$^+$).

c) (S)-6-((3-(6-(dimethylamino)pyridin-3-yl)-5-methylisoxazol-4-yl)methoxy)-N-(1-hydroxypentan-2-yl)nicotinamide In analogy to experiment of example 137c, 4-methoxy-6-((5-methyl-3-(6-methyl-3-pyridyl)isoxazol-4-yl) methoxy)pyridine-3-carboxylic acid instead of 6-((3-(6-methoxy-3-pyridyl)-5-methyl-isoxazol-4-yl)methoxy) pyridine-3-carboxylic acid was converted into the title compound (29 mg, 46%) which was obtained as a white solid. MS (ESI): 439.2 ([M+H]$^+$).

Example 143

6-((3-(5-fluoro-6-methyl-3-pyridyl)-5-methyl-isoxazol-4-yl)methoxy)-N-tetrahydropyran-4-yl-pyridine-3-carboxamide

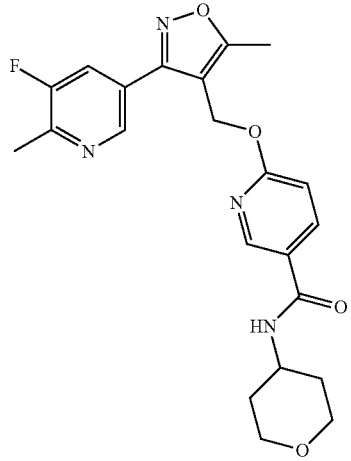 [SMILES: Cc1ncc(-c2noc(C)c2COc2ccc(C(=O)NC3CCOCC3)cn2)cc1F]

a) Methyl 6-((3-(5-fluoro-6-methyl-3-pyridyl)-5-methyl-isoxazol-4-yl)methoxy)pyridine-3-carboxylate In analogy to experiment of example 137a, (3-(5-fluoro-6-methylpyridin-3-yl)-5-methyl-1,2-oxazol-4-yl)methanol (building block O) instead of (3-(6-methoxypyridin-3-yl)-5-methylisoxazol-4-yl)methanol (building block M), using methyl 6-fluoropyridine-3-carboxylate instead of methyl 6-chloropyridine-3-carboxylate, was converted into the title compound (118 mg, 62%) which was obtained as a light yellow solid. MS (ESI): 358.2 ([M+H]$^+$).

b) 6-((3-(5-fluoro-6-methyl-3-pyridyl)-5-methyl-isoxazol-4-yl)methoxy)pyridine-3-carboxylic Acid In analogy to experiment of example 137b, methyl 6-((3-(5-fluoro-6-methyl-3-pyridyl)-5-methyl-isoxazol-4-yl)methoxy)pyridine-3-carboxylate instead of methyl 6-((3-(6-methoxypyridin-3-yl)-5-methylisoxazol-4-yl)methoxy)pyridine-3-carboxylate was converted into the title compound (120 mg, 99%) which was obtained as a light yellow solid. MS (ESI): 344.1 ([M+H]$^+$).

c) 6-((3-(5-fluoro-6-methyl-3-pyridyl)-5-methyl-isoxazol-4-yl)methoxy)-N-tetrahydropyran-4-yl-pyridine-3-carboxamide In analogy to experiment of example 137c, 6-((3-(5-fluoro-6-methyl-3-pyridyl)-5-methyl-isoxazol-4-yl)methoxy)pyridine-3-carboxylic acid instead of 6-((3-(6-methoxy-3-pyridyl)-5-methyl-isoxazol-4-yl)methoxy)pyridine-3-carboxylic acid was converted into the title compound (28 mg, 38%) which was obtained as a white solid. MS (ESI): 427.3 ([M+H]$^+$).

Example 144

6((3-(5-fluoro-6-methyl-3-pyridyl)-5-methyl-isoxazol-4-yl)methoxy)-N-isopropyl-pyridine-3-carboxamide

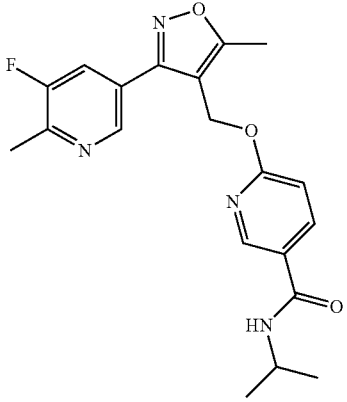 [SMILES: Cc1ncc(-c2noc(C)c2COc2ccc(C(=O)NC(C)C)cn2)cc1F]

In analogy to experiment of example 137c, 6-((3-(5-fluoro-6-methyl-3-pyridyl)-5-methyl-isoxazol-4-yl)methoxy)pyridine-3-carboxylic acid instead of 6-((3-(6-methoxy-3-pyridyl)-5-methyl-isoxazol-4-yl)methoxy)pyridine-3-carboxylic acid, using isopropylamine instead of tetrahydropyran-4-amine, was converted into the title compound (20 mg, 59%) which was obtained as a yellow solid. MS (ESI): 385.2 ([M+H]$^+$).

Example 145

6-((3-(5-fluoro-6-methyl-3-pyridyl)-5-methyl-isoxazol-4-yl)methoxy)-N-((1S)-1-(hydroxymethyl)butyl)pyridine-3-carboxamide

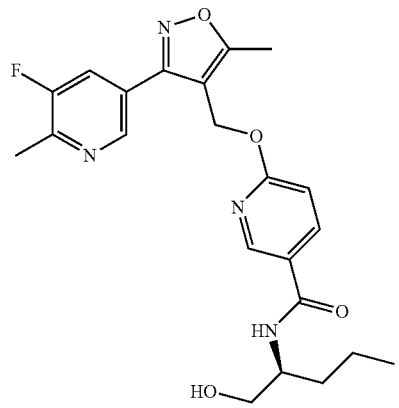 [SMILES: CCC[C@@H](CO)NC(=O)c1ccc(OCc2c(-c3cnc(C)c(F)c3)noc2C)nc1]

In analogy to experiment of example 137c, 6-((3-(5-fluoro-6-methyl-3-pyridyl)-5-methyl-isoxazol-4-yl)methoxy)pyridine-3-carboxylic acid instead of 6-((3-(6-methoxy-3-pyridyl)-5-methyl-isoxazol-4-yl)methoxy)pyridine-3-carboxylic acid, using (S)-2-aminopentan-1-ol instead of tetrahydropyran-4-amine, was converted into the title compound (27 mg, 54%) which was obtained as an off-white solid. MS (ESI): 429.2 ([M+H]$^+$).

Example 146

N-((1r,4r)-4-hydroxy-4-methylcyclohexyl)-6-((5-methyl-3-(6-methylpyridin-3-yl)isoxazol-4-yl)methoxy)pyridazine-3-carboxamide

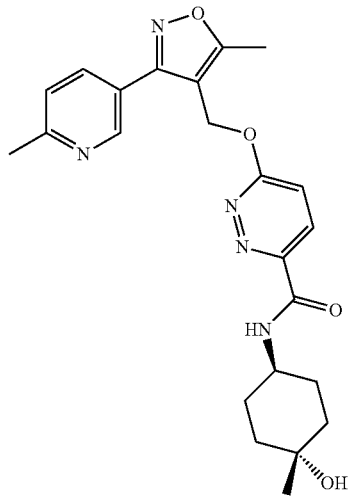 [SMILES: Cc1ccc(-c2noc(C)c2COc2ccc(C(=O)N[C@H]3CC[C@](C)(O)CC3)nn2)cn1]

In analogy to experiment of example 23d, 6-((5-methyl-3-(6-methylpyridin-3-yl)isoxazol-4-yl)methoxy)pyridazine-3-carboxylic acid, using trans-4-amino-1-methylcyclohexanol instead of (1R,2S)-2-aminocyclohexanol hydrochloride, was converted into the title compound (107 mg, 91%) which was obtained as an off-white foam. MS (ESI): 438.3 ([M+H]$^+$).

Example 147

N-(1,3-dihydroxy-2-methylpropan-2-yl)-6-((5-methyl-3-(6-methylpyridin-3-yl)isoxazol-4-yl)methoxy)pyridazine-3-carboxamide

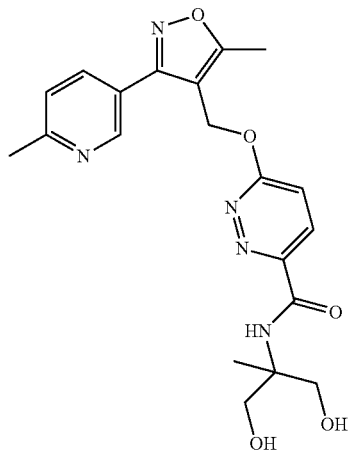 [SMILES: Cc1ccc(-c2noc(C)c2COc2ccc(C(=O)NC(C)(CO)CO)nn2)cn1]

To a stirred suspension of 6-((5-methyl-3-(6-methylpyridin-3-yl)isoxazol-4-yl)methoxy)-N-(3-methyloxetan-3-yl)pyridazine-3-carboxamide (example 83, 32.5 mg, 82.2 μmop in water (100 mL) at room temperature was added aqueous HCl (1.0 m, 82.2 μL, 82.2 μmol). After 2 hours, a second portion of aqueous HCl (1.0 m, 411 μL, 411 μmol) was added and the mixture was stirred for another 2 hours. Finally, a third portion of aqueous HCl (1.0 m, 3.29 mL, 3.29 mmol) was added and the resulting solution was stirred at room temperature for 20 hours. The reaction was quenched by the addition of aqueous NaHCO$_3$ (1.0 m, 9 mL), then diluted with EtOAc (10 mL). The layers were separated and the aqueous phase was subsequently extracted with EtOAc (2×10 mL). The combined organic extracts were dried (MgSO$_4$) and concentrated in vacuo. Purification by flash chromatography (silica, gradient: 50% EtOAc in heptane to 10% MeOH in EtOAc) afforded the title compound (9 mg, 27%) as a light-brown oil. MS (ESI): 414.3 ([M+H]$^+$).

Example 148

N-((1s,4s)-4-hydroxy-4-methylcyclohexyl)-6-((5-methyl-3-(6-methylpyridin-3-yl)isoxazol-4-yl)methoxy)pyridazine-3-carboxamide

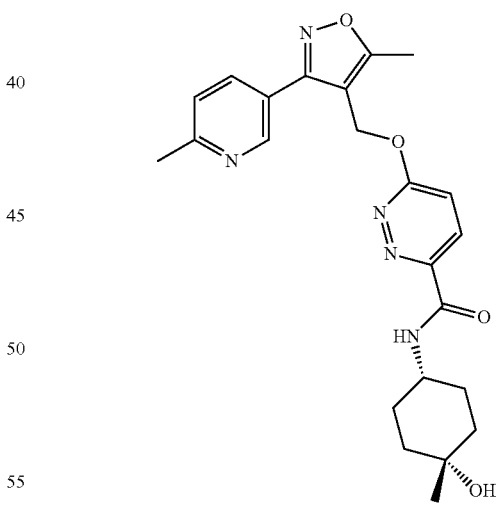

In analogy to experiment of example 23d, 6-((5-methyl-3-(6-methylpyridin-3-yl)isoxazol-4-yl)methoxy)pyridazine-3-carboxylic acid, using cis-4-amino-1-methylcyclohexanol 2,2,2-trifluoroacetate instead of (1R,2S)-2-aminocyclohexanol hydrochloride, was converted into the title compound (64 mg, 64%) which was obtained as a white solid. MS (ESI): 438.3 ([M+H]$^+$).

Example 149

N-((1R,3S)-3-hydroxy-3-(trifluoromethyl)cyclopentyl)-6-((5-methyl-3-(6-methylpyridin-3-yl)isoxazol-4-yl)methoxy)pyridazine-3-carboxamide or Enantiomer

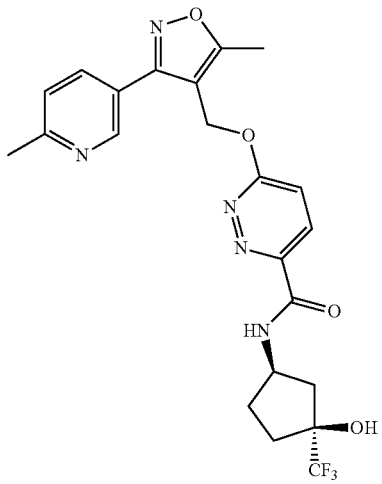 [SMILES: Cc1ccc(-c2noc(C)c2COc2ccc(C(=O)N[C@@H]3CC[C@@](O)(C(F)(F)F)C3)nn2)cn1]

In analogy to experiment of example 30, 6-((5-methyl-3-(6-methylpyridin-3-yl)isoxazol-4-yl)methoxy)pyridazine-3-carboxylic acid using, cis-3-amino-1-(trifluoromethyl)cyclopentanol hydrochloride instead of (1,1-dioxidotetrahydro-2H-thiopyran-4-yl)amine hydrochloride, was converted into the racemic title compound (161 mg, 47%) which was obtained as a white solid. MS (ESI): 478.2 ([M+H]$^+$).

Separation of the enantiomers by chiral HPLC (column: Chiralpak AD) afforded the title compound (65 mg) which was obtained as a white solid. MS (ESI): 478.4 ([M+H]$^+$).

Example 150

N-((1S,3R)-3-hydroxy-3-(trifluoromethyl)cyclopentyl)-6-((5-methyl-3-(6-methylpyridin-3-yl)isoxazol-4-yl)methoxy)pyridazine-3-carboxamide or Enantiomer

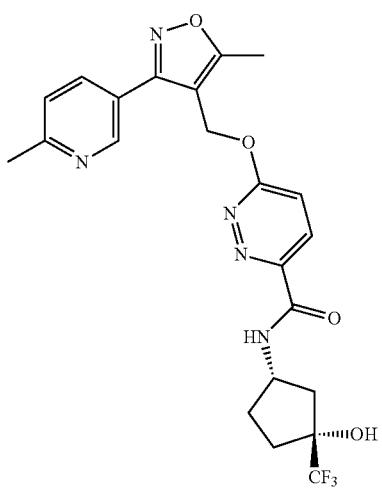 [SMILES: Cc1ccc(-c2noc(C)c2COc2ccc(C(=O)N[C@H]3CC[C@](O)(C(F)(F)F)C3)nn2)cn1]

In analogy to experiment of example 30, 6-((5-methyl-3-(6-methylpyridin-3-yl)isoxazol-4-yl)methoxy)pyridazine-3-carboxylic acid, using cis-3-amino-1-(trifluoromethyl)cyclopentanol hydrochloride instead of (1,1-dioxidotetrahydro-2H-thiopyran-4-yl)amine hydrochloride, was converted into the racemic title compound (161 mg, 47%) which was obtained as a white solid. MS (ESI): 478.2 ([M+H]$^+$).

Separation of the enantiomers by chiral HPLC (column: Chiralpak AD) afforded the title compound (82 mg) which was obtained as a white solid. MS (ESI): 478.4 ([M+H]$^+$).

Example 151

(1S,4S)-2-oxa-5-azabicyclo[2.2.1]heptan-5-yl(6-((5-methyl-3-(6-methylpyridin-3-yl)isoxazol-4-yl)methoxy)pyridazin-3-yl)methanone

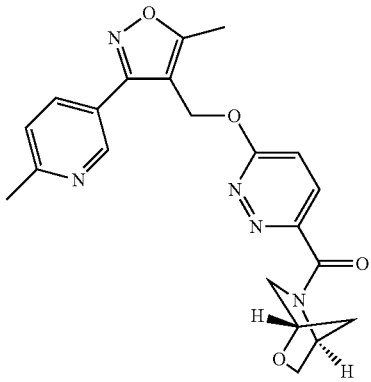 [SMILES: Cc1ccc(-c2noc(C)c2COc2ccc(C(=O)N3C[C@@H]4C[C@H]3CO4)nn2)cn1]

In analogy to experiment of example 23d, 6-((5-methyl-3-(6-methylpyridin-3-yl)isoxazol-4-yl)methoxy)pyridazine-3-carboxylic acid, using (1S,4S)-2-oxa-5-azabicyclo[2.2.1]heptane hydrochloride instead of (1R,2S)-2-aminocyclohexanol hydrochloride, was converted into the title compound (26 mg, 69%) which was obtained as a light brown foam. MS (ESI): 408.2 ([M+H]$^+$).

Example 152

N-((1RS,3RS)-3-hydroxycyclopentyl)-6-((5-methyl-3-(6-methylpyridin-3-yl)isoxazol-4-yl)methoxy)pyridazine-3-carboxamide

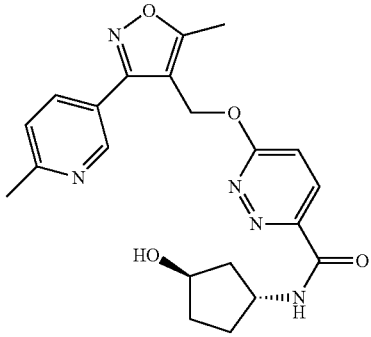 [SMILES: Cc1ccc(-c2noc(C)c2COc2ccc(C(=O)N[C@@H]3CC[C@@H](O)C3)nn2)cn1]

In analogy to experiment of example 23d, 6-((5-methyl-3-(6-methylpyridin-3-yl)isoxazol-4-yl)methoxy)pyridazine-3-carboxylic acid, using racemic trans-(1RS,3RS)-3-aminocyclopentanol hydrochloride instead of (1R,2S)-2-aminocyclohexanol hydrochloride, was converted into the title compound (21 mg, 56%) which was obtained as a light brown foam. MS (ESI): 410.2 ([M+H]+).

Example 153 trans-N-(4-hydroxycyclohexyl)-6-((5-methyl-3-(6-methylpyridin-3-yl)isoxazol-4-yl)methoxy)pyridazine-3-carboxamide

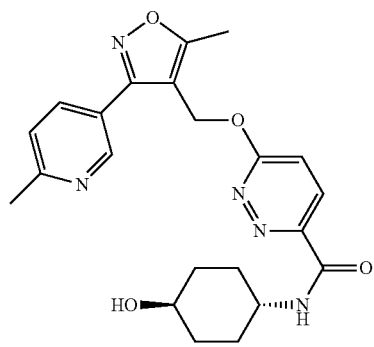 [SMILES: Cc1ccc(-c2noc(C)c2COc2ccc(C(=O)N[C@H]3CC[C@H](O)CC3)nn2)cn1]

In analogy to experiment of example 23d, 6-((5-methyl-3-(6-methylpyridin-3-yl)isoxazol-4-yl)methoxy)pyridazine-3-carboxylic acid, using trans-4-aminocyclohexanol instead of (1R,2S)-2-aminocyclohexanol hydrochloride, was converted into the title compound (23 mg, 59%) which was obtained as a light brown solid. MS (ESI): 424.2 ([M+H]+).

Example 154 trans-N-(4-methoxycyclohexyl)-6-((5-methyl-3-(6-methylpyridin-3-yl)isoxazol-4-yl)methoxy)pyridazine-3-carboxamide

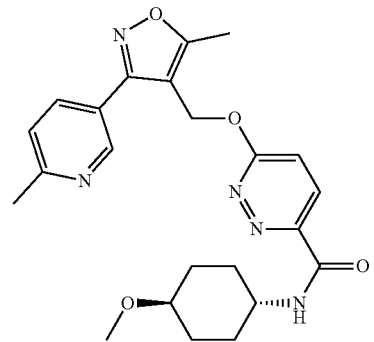 [SMILES: CO[C@H]1CC[C@H](NC(=O)c2ccc(OCc3c(-c4ccc(C)nc4)noc3C)nn2)CC1]

In analogy to experiment of example 23d, 6-((5-methyl-3-(6-methylpyridin-3-yl)isoxazol-4-yl)methoxy)pyridazine-3-carboxylic acid, using trans-4-methoxycyclohexanamine hydrochloride instead of (1R,2S)-2-aminocyclohexanol hydrochloride, was converted into the title compound (22 mg, 55%) which was obtained as a light brown foam. MS (ESI): 438.3 ([M+H]+).

Example 155

(6,6-difluoro-2-azaspiro[3.3]heptan-2-yl)(6-((5-methyl-3-(6-methylpyridin-3-yl)isoxazol-4-yl)methoxy)pyridazin-3-yl)methanone

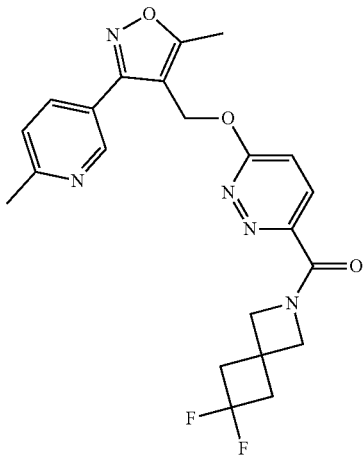 [SMILES: Cc1ccc(-c2noc(C)c2COc2ccc(C(=O)N3CC4(C3)CC(F)(F)C4)nn2)cn1]

In analogy to experiment of example 23d, 6-((5-methyl-3-(6-methylpyridin-3-yl)isoxazol-4-yl)methoxy)pyridazine-3-carboxylic acid, using 6,6-difluoro-2-azaspiro[3.3]heptane 2,2,2-trifluoroacetate instead of (1R,2S)-2-aminocyclohexanol hydrochloride, was converted into the title compound (12 mg, 30%) which was obtained as a white foam. MS (ESI): 442.2 ([M+H]+).

Example 156

N-(3-hydroxycyclohexyl)-6-((5-methyl-3-(6-methylpyridin-3-yl)isoxazol-4-yl)methoxy)pyridazine-3-carboxamide

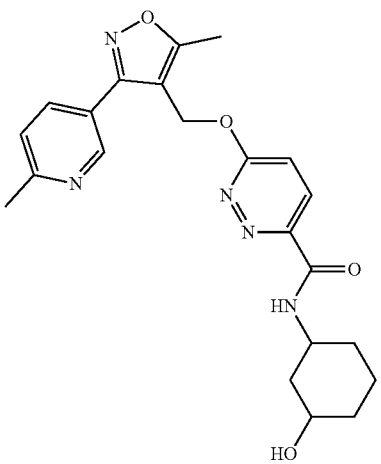 [SMILES: Cc1ccc(-c2noc(C)c2COc2ccc(C(=O)NC3CCCC(O)C3)nn2)cn1]

In analogy to experiment of example 23d, 6-((5-methyl-3-(6-methylpyridin-3-yl)isoxazol-4-yl)methoxy)pyridazine-3-carboxylic acid, using 3-aminocyclohexanol instead of (1R,2S)-2-aminocyclohexanol hydrochloride, was converted into the title compound (16 mg, 41%) which was obtained as an off-white foam. MS (ESI): 424.2 ([M+H]+).

Example 157

3-oxa-6-azabicyclo[3.1.1]heptan-6-yl(6-((5-methyl-3-(6-methylpyridin-3-yl)isoxazol-4-yl)methoxy)pyridazin-3-yl)methanone

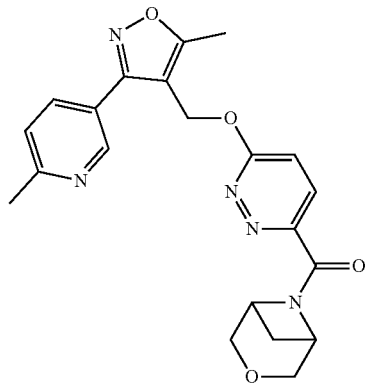 [SMILES: Cc1ccc(-c2noc(C)c2COc2ccc(C(=O)N3C4COCC3C4)nn2)cn1]

In analogy to experiment of example 23d, 6-((5-methyl-3-(6-methylpyridin-3-yl)isoxazol-4-yl)methoxy)pyridazine-3-carboxylic acid, using 3-oxa-6-azabicyclo[3.1.1]heptane 2,2,2-trifluoroacetate instead of (1R,2S)-2-aminocyclohexanol hydrochloride, was converted into the title compound (21 mg, 56%) which was obtained as a off-white foam. MS (ESI): 408.2 ([M+H]$^+$).

Example 158 cis-N-(4-methoxycyclohexyl)-6-((5-methyl-3-(6-methylpyridin-3-yl)isoxazol-4-yl)methoxy)pyridazine-3-carboxamide

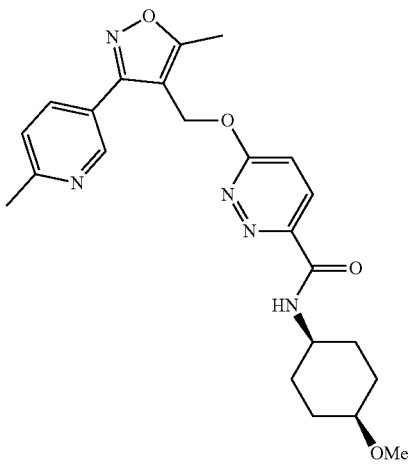 [SMILES: CO[C@H]1CC[C@@H](NC(=O)c2ccc(OCc3c(-c4ccc(C)nc4)noc3C)nn2)CC1]

In analogy to experiment of example 23d, 6-((5-methyl-3-(6-methylpyridin-3-yl)isoxazol-4-yl)methoxy)pyridazine-3-carboxylic acid, using cis-4-methoxycyclohexanamine instead of (1R,2S)-2-aminocyclohexanol hydrochloride, was converted into the title compound (18 mg, 45%) which was obtained as a off-white foam. MS (ESI): 438.3 ([M+H]$^+$).

Example 159

6-((3-(6-chloropyridin-3-yl)-5-methylisoxazol-4-yl)methoxy)-N-(tetrahydropyran-4-yl)pyridazine-3-carboxamide

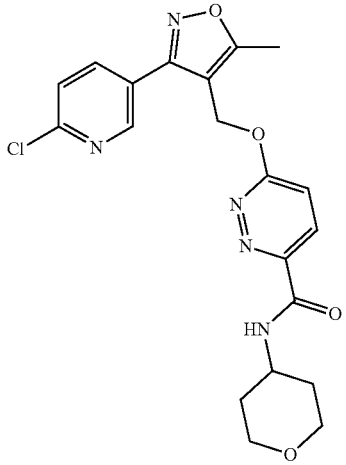 [SMILES: Cc1onc(-c2ccc(Cl)nc2)c1COc1ccc(C(=O)NC2CCOCC2)nn1]

In analogy to experiment of example 183, (3-(6-chloro-3-pyridyl)-5-methyl-isoxazol-4-yl)methanol (building block F) instead of (5-cyclopropyl-3-(6-methyl-3-pyridyl)isoxazol-4-yl)methanol (building block D) was converted into the title compound (32 mg, 33%) which was obtained as a white solid. MS (ESI): 430.2 ([M+H]$^+$).

Example 160

(S)-6-((3-(6-chloropyridin-3-yl)-5-methylisoxazol-4-yl)methoxy)-N-(tetrahydrofuran-3-yl)pyridazine-3-carboxamide

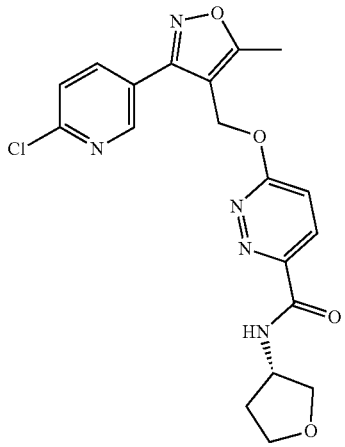 [SMILES: Cc1onc(-c2ccc(Cl)nc2)c1COc1ccc(C(=O)N[C@H]2CCOC2)nn1]

In analogy to experiment of example 183, (3-(6-chloro-3-pyridyl)-5-methyl-isoxazol-4-yl)methanol (building block F) instead of (5-cyclopropyl-3-(6-methyl-3-pyridyl)isoxazol-4-yl)methanol (building block D), using (S)-6-chloro-N-(tetrahydrofuran-3-yl)pyridazine-3-carboxamide instead of 6-chloro-N-(tetrahydropyran-4-yl)pyridazine-3-carboxamide, was converted into the title compound (18 mg, 32%) which was obtained as a white solid. MS (ESI): 438.1 ([M+H]$^+$).

Example 161

6-((3-(6-chloropyridin-3-yl)-5-methylisoxazol-4-yl)methoxy)-N-(3-methyloxetan-3-yl)pyridazine-3-carboxamide

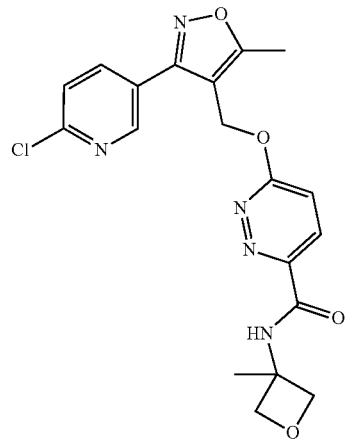 [SMILES: Cc1onc(-c2ccc(Cl)nc2)c1COc1ccc(C(=O)NC2(C)COC2)nn1]

In analogy to experiment of example 183, (3-(6-chloro-3-pyridyl)-5-methyl-isoxazol-4-yl)methanol (building block F) instead of (5-cyclopropyl-3-(6-methyl-3-pyridyl)isoxazol-4-yl)methanol (building block D), using 6-chloro-N-(3-methyloxetan-3-yl)pyridazine-3-carboxamide instead of 6-chloro-N-(tetrahydropyran-4-yl)pyridazine-3-carboxamide, was converted into the title compound (18 mg, 32%) which was obtained as a white solid. MS (ESI): 416.2 ([M+H]$^+$).

Example 162

6-((3-(6-chloropyridin-3-yl)-5-methylisoxazol-4-yl)methoxy)-N-(2-oxaspiro[3.3]heptan-6-yl)pyridazine-3-carboxamide

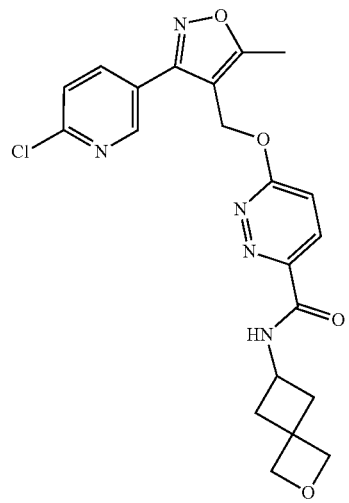 [SMILES: Cc1onc(-c2ccc(Cl)nc2)c1COc1ccc(C(=O)NC2CC3(COC3)C2)nn1]

In analogy to experiment of example 183, (3-(6-chloro-3-pyridyl)-5-methyl-isoxazol-4-yl)methanol (building block F) instead of (5-cyclopropyl-3-(6-methyl-3-pyridyl)isoxazol-4-yl)methanol (building block D), using 6-chloro-N-(2-oxaspiro[3.3]heptan-6-yl)pyridazine-3-carboxamide instead of 6-chloro-N-(tetrahydropyran-4-yl)pyridazine-3-carboxamide, was converted into the title compound (17 mg, 29%) which was obtained as a white solid. MS (ESI): 442.2 ([M+H]$^+$).

Example 163 trans-N-(3-methoxycyclobutyl)-6-((5-methyl-3-(6-methyl-3-pyridyl)isoxazol-4-yl)methoxy)pyridazine-3-carboxamide

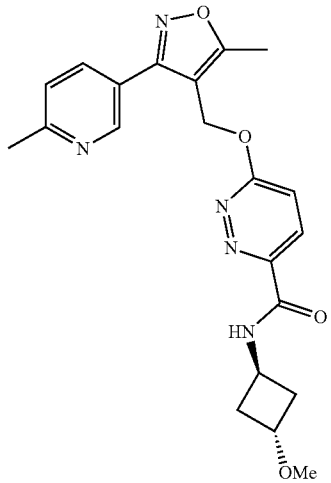 [SMILES: CO[C@H]1C[C@H](NC(=O)c2ccc(OCc3c(-c4ccc(C)nc4)noc3C)nn2)C1]

a) trans-tert-butyl N-(3-methoxycyclobutyl)carbamate

To a stirred solution of trans-tert-butyl N-(3-hydroxycyclobutyl)carbamate (100 mg, 0.534 mmol) in anhydrous THF (2.0 mL) at 0° C. was added NaH (60% in mineral oil, 32 mg, 0.801 mmol). After 30 min, iodomethane (43.4 µL, 0.694 mmol) wad added and the reaction mixture was allowed to warm to room temperature for 2.5 hours. LC-MS analysis showed no starting material left but only mono-methylated and di-methylated products. The reaction was quenched by addition of saturated aqueous NaHCO$_3$ (1 mL), diluted with water (15 mL) and extracted with EtOAc (2×15 mL). The combined organic extracts were washed with brine, dried (MgSO$_4$) and concentrated in vacuo. Purification by flash chromatography (silica, gradient: 0% to 15% EtOAc in heptane) afforded the title compound (32 mg, 30%) as white crystals. MS (ESI): 146.1 ([M–C$_4$H$_8$+H]$^+$).

b) trans-3-methoxycyclobutanamine 2,2,2-trifluoroacetate

To a stirred solution of trans-tert-butyl N-(3-methoxycyclobutyl)carbamate (42 mg, 0.209 mmol) in CH$_2$Cl$_2$ (2 mL) at 0° C. was added TFA (130 µl, 1.69 mmol) and the resulting yellow solution was allowed to warm to room temperature. After 2 hours, all volatiles were removed by rotary evaporation under reduced pressure to afford the title compound (60 mg, quantitative) as a light yellow oil. MS (ESI): 102.2 ([M+H]⁺).

c) trans-N-(3-methoxycyclobutyl)-6-((5-methyl-3-(6-methyl-3-pyridyl)isoxazol-4-yl)methoxy)pyridazine-3-carboxamide To a stirred solution of trans-3-methoxycyclobutanamine 2,2,2-trifluoroacetate (45 mg, 0.209 mmol) in anhydrous DMF (0.8 mL) under argon was added 6-((5-methyl-3-(6-methylpyridin-3-yl)isoxazol-4-yl)methoxy)pyridazine-3-carboxylic acid (45 mg, 0.138 mmol), N,N-diisopropylethylamine (200 µL, 1.15 mmol) and TBTU (66.4 mg, 0.207 mmol). The resulting yellow solution was stirred overnight at room temperature then purified directly by preparative HPLC (column: C-18, eluent: H₂O and CH₃CN with 0.05% HCO₂H) to afford the title compound (18.2 mg, 32.3%) as an orange powder. MS (ESI): 410.2 ([M+H]⁺).

Example 164 cis-N-(3-methoxycyclobutyl)-6-((5-methyl-3-(6-methyl-3-pyridyl)isoxazol-4-yl)methoxy)pyridazine-3-carboxamide

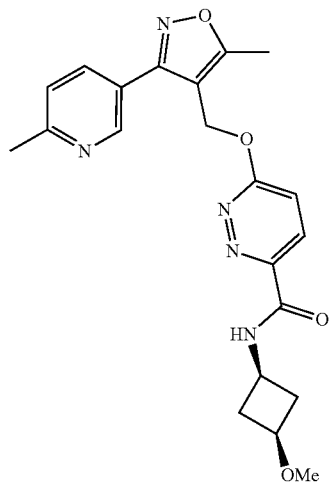 [SMILES: CO[C@H]1C[C@@H](NC(=O)c2ccc(OCc3c(-c4ccc(C)nc4)noc3C)nn2)C1]

a) cis-tert-butyl N-(3-methoxycyclobutyl)carbamate

In analogy to experiment of example 163a, cis-tert-butyl N-(3-hydroxycyclobutyl) carbamate instead of trans-tert-butyl N-(3-hydroxycyclobutyl)carbamate was converted into the title compound (59 mg, 55%) which was obtained as white crystals. MS (ESI): 146.1 ([M−C₄H₈+H]⁺).

b) cis-3-methoxycyclobutanamine 2,2,2-trifluoroacetate

In analogy to experiment of example 163b, cis-tert-butyl N-(3-methoxycyclobutyl) carbamate instead of trans-tert-butyl N-(3-methoxycyclobutyl)carbamate was converted into the title compound (62 mg, quantitative) which was obtained as a light yellow oil. MS (ESI): 102.2 ([M+H]⁺).

c) cis-N-(3-methoxycyclobutyl)-6-((5-methyl-3-(6-methyl-3-pyridyl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using cis-3-methoxycyclobutanamine 2,2,2-trifluoroacetate instead of trans-3-methoxycyclobutanamine 2,2,2-trifluoroacetate, was converted into the title compound (10.7 mg, 17%) which was obtained as an orange powder. MS (ESI): 410.3 ([M+H]⁺).

Example 165

6-((5-cyclopropyl-3-(6-methylpyridazin-3-yl)isoxazol-4-yl)methoxy)-N-(tetrahydropyran-4-yl)pyridazine-3-carboxamide

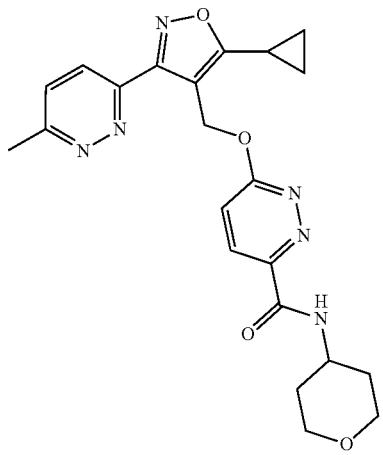

In analogy to experiment of example 183, (5-cyclopropyl-3-(6-methylpyridazin-3-yl)isoxazol-4-yl)methanol (building block L) instead of (5-cyclopropyl-3-(6-methyl-3-pyridyl)isoxazol-4-yl)methanol (building block D) was converted into the title compound (10 mg, 19%) which was obtained as an off-white solid. MS (ESI): 437.3 ([M+H]⁺).

Example 166 trans-N-((1RS,3RS)-3-methoxycyclopentyl)-6-((5-methyl-3-(6-methylpyridin-3-yl)isoxazol-4-yl)methoxy)pyridazine-3-carboxamide

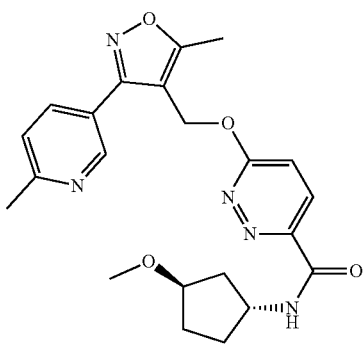 [SMILES: CO[C@@H]1CC[C@@H](NC(=O)c2ccc(OCc3c(-c4ccc(C)nc4)noc3C)nn2)C1]

In analogy to experiment of example 23d, 6-((5-methyl-3-(6-methylpyridin-3-yl)isoxazol-4-yl)methoxy)pyridazine-3-carboxylic acid, using racemic trans-(1RS,3RS)-3-methoxycyclopentanamine bis-2,2,2-trifluoroacetate instead of (1R,2S)-2-aminocyclohexanol hydrochloride, was converted into the title compound (33 mg, 51%) which was obtained as a white solid. MS (ESI): 424.2 ([M+H]$^+$).

Example 167

N-(6,6-difluorospiro[3.3]heptan-2-yl)-6-((5-methyl-3-(6-methylpyridin-3-yl)isoxazol-4-yl)methoxy)pyridazine-3-carboxamide

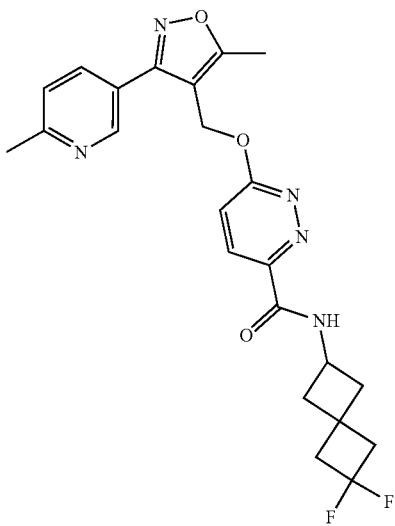 [SMILES: Cc1ccc(-c2noc(C)c2COc2ccc(C(=O)NC3CC4(C3)CC(F)(F)C4)nn2)cn1]

In analogy to experiment of example 23d, 6-((5-methyl-3-(6-methylpyridin-3-yl)isoxazol-4-yl)methoxy)pyridazine-3-carboxylic acid, using 6,6-difluorospiro[3.3]heptan-2-amine in place of (1R,2S)-2-aminocyclohexanol hydrochloride, was converted into the title compound (20 mg, 47%) which was obtained as a light brown amorphous. MS (ESI): 456.5 ([M+H]$^+$).

Example 168

6-((5-(fluoromethyl)-3-(6-methylpyridin-3-yl)isoxazol-4-yl)methoxy)-N-(tetrahydropyran-4-yl)pyridazine-3-carboxamide

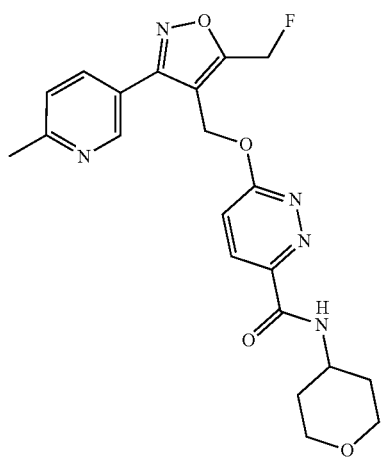

a) ethyl 6-((5-(fluoromethyl)-3-(6-methyl-3-pyridyl)isoxazol-4-yl)methoxy)pyridazine-3-carboxylate In analogy to experiment of example 7a, (5-(fluoromethyl)-3-(6-methylpyridin-3-yl)isoxazol-4-yl)methanol (building block C) instead of (5-methyl-3-(6-methylpyridin-3-yl)isoxazol-4-yl)methanol (building block A) was converted into the title compound (120 mg, 19%) which was obtained as an orange oil. MS (ESI): 359.2 ([M+H]$^+$).

b) 6-((5-(fluoromethyl)-3-(6-methyl-3-pyridyl)isoxazol-4-yl)methoxy)pyridazine-3-carboxylic Acid In analogy to experiment of example 23c, ethyl 6-((5-(fluoromethyl)-3-(6-methyl-3-pyridyl)isoxazol-4-yl)methoxy)pyridazine-3-carboxylate instead of ethyl 6-((5-methyl-3-(6-methylpyridin-3-yl)isoxazol-4-yl)methoxy)pyridazine-3-carboxylate was converted into the title compound (65 mg, 94%) which was obtained as an off-white solid. MS (ESI): 345.2 ([M+H]$^+$).

c) 6-((5-(fluoromethyl)-3-(6-methylpyridin-3-yl)isoxazol-4-yl)methoxy)-N-(tetrahydropyran-4-yl)pyridazine-3-carboxamide In analogy to experiment of example 30, 6-((5-(fluoromethyl)-3-(6-methyl-3-pyridyl)isoxazol-4-yl)methoxy)pyridazine-3-carboxylic acid instead of 6-((5-methyl-3-(6-methyl-3-pyridyl)isoxazol-4-yl)methoxy)pyridazine-3-carboxylic acid, using tetrahydropyran-4-amine instead of (1,1-dioxidotetrahydro-2H-thiopyran-4-yl)amine hydrochloride, was converted into the title compound (81 mg, 50%) which was obtained as an off-white solid. MS (ESI): 428.3 ([M+H]$^+$).

Example 169 cis-N-3-((2,2-difluoroethoxy)cyclobutyl)-6-((5-methyl-3-(6-methylpyridin-3-yl)isoxazol-4-yl)methoxy)pyridazine-3-carboxamide

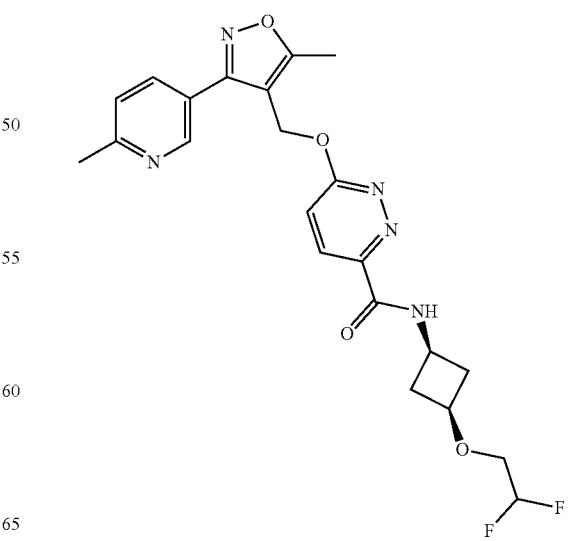

a) cis-tert-butyl N-(3-(2,2-difluoroethoxy)cyclobutyl)carbamate

In analogy to experiment of example 163a, cis-tert-butyl N-(3-hydroxycyclobutyl) carbamate instead of trans-tert-butyl N-(3-hydroxycyclobutyl)carbamate, using 2,2-difluoroethyl trifluoromethanesulfonate instead of iodomethane, was converted into the title compound (109 mg, 81%) which was obtained as white crystals. MS (ESI): 196.1 ([M−C$_4$H$_8$+H]$^+$).

b) cis-3-(2,2-difluoroethoxy)cyclobutanamine 2,2,2-trifluoroacetate

In analogy to experiment of example 163b, cis-tert-butyl N-(3-(2,2-difluoroethoxy)cyclobutyl)carbamate instead of trans-tert-butyl N-(3-methoxycyclobutyl)carbamate was converted into the title compound (81 mg, quantitative) which was obtained as a light yellow oil. MS (ESI): 152.2 ([M+H]$^+$).

c) cis-N-3-((2,2-difluoroethoxy)cyclobutyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using cis-3-(2,2-difluoroethoxy)cyclobutanamine 2,2,2-trifluoroacetate instead of trans-3-methoxycyclobutanamine 2,2,2-trifluoroacetate, was converted into the title compound (25 mg, 45%) which was obtained as a colorless amorphous. MS (ESI): 460.3 ([M+H]$^+$).

Example 170 trans-N-3-((2,2-difluoroethoxy)cyclobutyl)-6-((5-methyl-3-(6-methylpyridin-3-yl)isoxazol-4-yl)methoxy)pyridazine-3-carboxamide

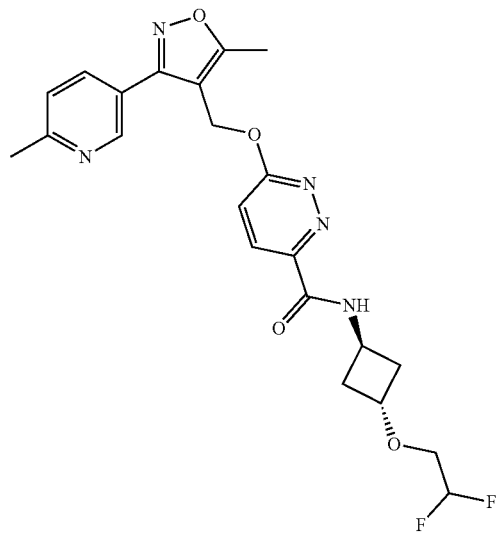 [SMILES: Cc1ccc(-c2noc(C)c2COc2ccc(C(=O)N[C@H]3C[C@H](OCC(F)F)C3)nn2)cn1]

a) trans-tert-butyl N-(3-(2,2-difluoroethoxy)cyclobutyl)carbamate

In analogy to experiment of example 163a, trans-tert-butyl N-(3-hydroxycyclobutyl) carbamate, using 2,2-difluoroethyl trifluoromethanesulfonate instead of iodomethane, was converted into the title compound (95 mg, 71%) which was obtained as white crystals. MS (ESI): 196.1 ([M−C$_4$H$_8$+H]$^+$).

b) trans-3-(2,2-difluoroethoxy)cyclobutanamine 2,2,2-trifluoroacetate

In analogy to experiment of example 163b, trans-tert-butyl N-(3-(2,2-difluoroethoxy)cyclobutyl)carbamate instead of trans-tert-butyl N-(3-methoxycyclobutyl)carbamate was converted into the title compound (70 mg, quantitative) which was obtained as a light yellow oil. MS (ESI): 152.2 ([M+H]$^+$).

c) trans-N-3-((2,2-difluoroethoxy)cyclobutyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using trans-3-(2,2-difluoroethoxy)cyclobutanamine 2,2,2-trifluoroacetate instead of trans-3-methoxycyclobutanamine 2,2,2-trifluoroacetate, was converted into the title compound (34 mg, 60%) which was obtained as a white foam. MS (ESI): 460.2 ([M+H]$^+$).

Example 171 cis-N-(3-ethoxycyclobutyl)-6-((5-methyl-3-(6-methylpyridin-3-yl)isoxazol-4-yl)methoxy)pyridazine-3-carboxamide

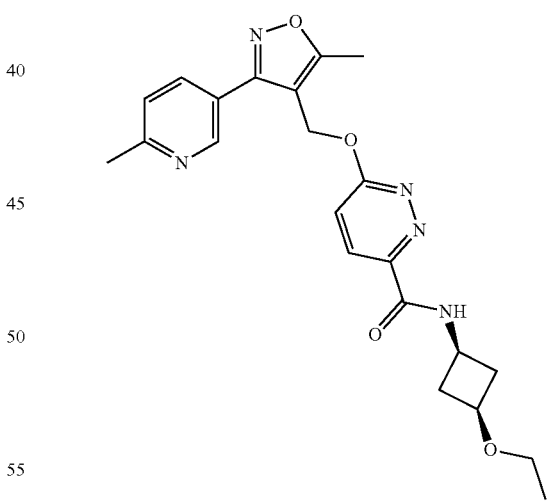

a) cis-tert-butyl N-(3-ethoxycyclobutyl)carbamate

In analogy to experiment of example 163a, cis-tert-butyl N-(3-hydroxycyclobutyl) carbamate instead of trans-tert-butyl N-(3-hydroxycyclobutyl)carbamate, using iodoethane instead of iodomethane, was converted into the title compound (83 mg, 73%) which was obtained as a white solid. MS (ESI): 216.1 ([M+H]$^+$), 160.1 ([M−C$_4$H$_8$+H]$^+$).

b) cis-3-ethoxycyclobutanamine 2,2,2-trifluoroacetate

In analogy to experiment of example 163b, cis-tert-butyl N-(3-ethoxycyclobutyl)carbamate instead of trans-tert-butyl N-(3-methoxycyclobutyl)carbamate was converted into the title compound (90 mg, quantitative) which was obtained as a light yellow oil. MS (ESI): 116.1 ([M+H]$^+$).

c) cis-N-(3-ethoxycyclobutyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using cis-3-ethoxycyclobutanamine 2,2,2-trifluoroacetate instead of trans-3-methoxycyclobutanamine 2,2,2-trifluoroacetate, was converted into the title compound (54 mg, 61%) which was obtained as a white foam. MS (ESI): 424.3 ([M+H]$^+$).

Example 172 trans-N-(3-ethoxycyclobutyl)-6-((5-methyl-3-(6-methylpyridin-3-yl)isoxazol-4-yl)methoxy)pyridazine-3-carboxamide

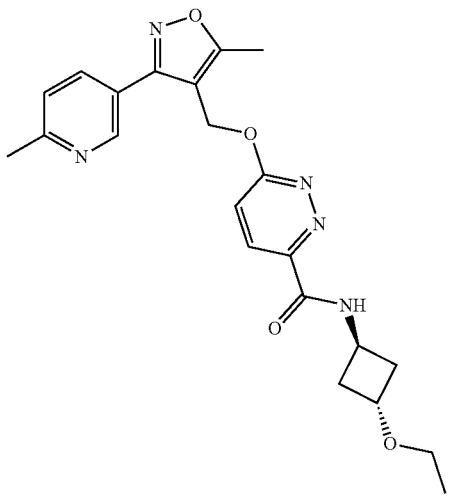 [SMILES: CCO[C@H]1C[C@H](NC(=O)c2ccc(OCc3c(-c4ccc(C)nc4)noc3C)nn2)C1]

a) trans-tert-butyl N-(3-ethoxycyclobutyl)carbamate

In analogy to experiment of example 163a, trans-tert-butyl N-(3-hydroxycyclobutyl) carbamate, using iodoethane instead of iodomethane, was converted into the title compound (72 mg, 63%) which was obtained as white solid. MS (ESI): 160.1 ([M−C$_4$H$_8$+H]$^+$).

b) trans-3-ethoxycyclobutanamine 2,2,2-trifluoroacetate

In analogy to experiment of example 163b, trans-tert-butyl N-(3-ethoxycyclobutyl)carbamate instead of trans-tert-butyl N-(3-methoxycyclobutyl)carbamate was converted into the title compound (88 mg, quantitative) which was obtained as a light yellow oil. MS (ESI): 116.1 ([M+H]$^+$).

c) trans-N-(3-ethoxycyclobutyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using trans-3-ethoxycyclobutanamine 2,2,2-trifluoroacetate instead of trans-3-methoxycyclobutanamine 2,2,2-trifluoroacetate, was converted into the title compound (70 mg, 77%) which was obtained as a white foam. MS (ESI): 424.3 ([M+H]$^+$).

Example 173 cis-N-(3-(difluoromethoxy)cyclobutyl)-6-((5-methyl-3-(6-methylpyridin-3-yl)isoxazol-4-yl)methoxy)pyridazine-3-carboxamide

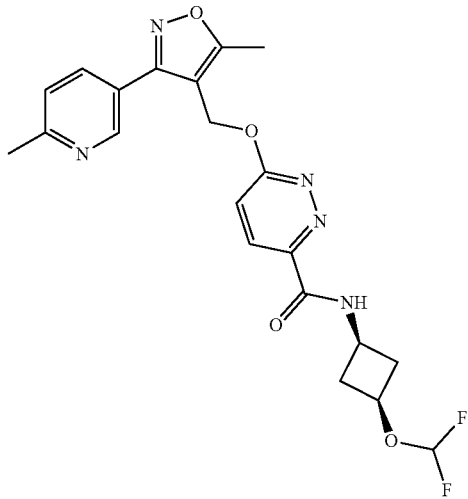 [SMILES: Cc1ccc(-c2noc(C)c2COc2ccc(C(=O)N[C@H]3C[C@@H](OC(F)F)C3)nn2)cn1]

a) cis-tert-butyl N-(3-(difluoromethoxy)cyclobutyl)carbamate

To a stirred solution of cis-tert-butyl N-(3-hydroxycyclobutyl)carbamate (100 mg, 0.534 mmol) in acetonitrile (2 mL) under argon was added CuI (20.3 mg, 0.107 mmol). The reaction mixture was stirred vigorously and heated to 45° C. for 30 min, before a solution of 2,2-difluoro-2-(fluorosulfonyl)acetic acid (190 mg, 110 µL, 1.07 mmol) in acetonitrile (2.0 mL) was added dropwise over a period of 40 min. The reaction mixture was stirred at 45° C. for 3 hours then cooled to room temperature, adsorbed on silica and concentrated in vacuo. Purification by flash chromatography (silica, gradient: 0% to 10% EtOAc in heptane) afforded the title compound (82.5 mg, 65.1%) as a white solid. MS (ESI): 182.1 ([M−C$_4$H$_8$+H]$^+$).

b) cis-3-(difluoromethoxy)cyclobutanamine 2,2,2-trifluoroacetate

In analogy to experiment of example 163b, cis-tert-butyl N-(3-(difluoromethoxy)cyclobutyl)carbamate instead of trans-tert-butyl N-(3-methoxycyclobutyl)carbamate was converted into the title compound (43 mg, quantitative) which was obtained as a light yellow oil. MS (ESI): 138.1 ([M+H]$^+$).

c) cis-N-(3-(difluoromethoxy)cyclobutyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using cis-3-(difluoromethoxy)cyclobutanamine 2,2,2-trifluoroacetate instead of trans-3-methoxycyclobutanamine 2,2,2-trifluoroacetate, was converted into the title compound (41 mg, 66%) which was obtained as a colorless amorphous. MS (ESI): 446.3 ([M+H]$^+$).

Example 174 trans-N-(3-(difluoromethoxy)cyclobutyl)-6-((5-methyl-3-(6-methylpyridin-3-yl)isoxazol-4-yl)methoxy)pyridazine-3-carboxamide

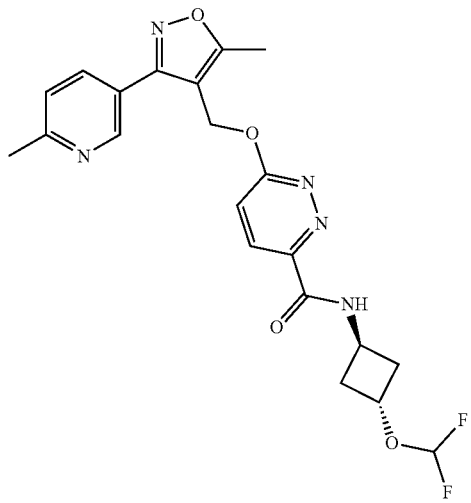 [SMILES: Cc1ccc(-c2noc(C)c2COc2ccc(C(=O)N[C@H]3C[C@H](OC(F)F)C3)nn2)cn1]

a) trans-tert-butyl N-(3-(difluoromethoxy)cyclobutyl)carbamate

In analogy to experiment of example 173a, trans-tert-butyl N-(3-hydroxycyclobutyl)carbamate instead of cis-tert-butyl N-(3-hydroxycyclobutyl)carbamate was converted into the title compound (97 mg, 77%) which was obtained as a white solid. MS (ESI): 182.0 ([M−C$_4$H$_8$+H]$^+$).

b) trans-3-(difluoromethoxy)cyclobutanamine 2,2,2-trifluoroacetate

In analogy to experiment of example 163b, trans-tert-butyl N-(3-(difluoromethoxy)cyclobutyl)carbamate instead of trans-tert-butyl N-(3-methoxycyclobutyl)carbamate was converted into the title compound (42 mg, quantitative) which was obtained as a light yellow oil. MS (ESI): 138.1 ([M+H]$^+$).

c) trans-N-(3-(difluoromethoxy)cyclobutyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using trans-3-(difluoromethoxy)cyclobutanamine 2,2,2-trifluoroacetate instead of trans-3-methoxycyclobutanamine 2,2,2-trifluoroacetate, was converted into the title compound (37 mg, 60%) which was obtained as a white solid. MS (ESI): 446.3 ([M+H]$^+$).

Example 175 trans-N-(3-cyclopropoxycyclobutyl)-6-((5-methyl-3-(6-methylpyridin-3-yl)isoxazol-4-yl)methoxy)pyridazine-3-carboxamide

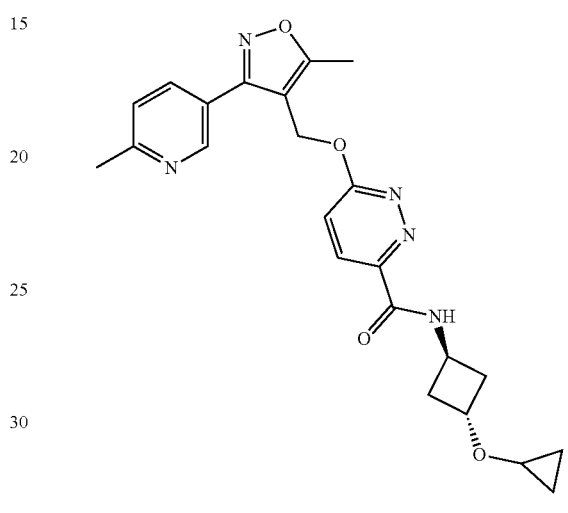

a) trans-tert-butyl N-(3-(vinyloxy)cyclobutyl)carbamate

A round-bottomed flask was charged with trans-tert-butyl N-(3-hydroxycyclobutyl)carbamate (150 mg, 0.801 mmol), 4,7-diphenyl-1,10-phenanthroline (2.70 mg, 8.12 μmop, Pd(OAc)$_2$ (3 mg, 13.4 μmop, triethylamine (112 μL, 0.801 mmol) and 1-(vinyloxy)butane (2.0 mL). The resulting mixture was degassed for 5 min by bubbling argon through the reaction medium. The reaction was heated to 80° C. and stirred overnight before being cooled to room temperature then filtered directly through a pad of dicalite. The filter cake was rinsed with Et$_2$O and the filtrate concentrated in vacuo. The resulting crude residue was purified by flash chromatography (silica, gradient: 0% to 7% EtOAc in heptane) to afford the title compound (113 mg, 66%) as a yellow crystalline solid. MS (ESI): 158.1 ([M−C$_4$H$_8$+H]$^+$).

b) trans-tert-butyl N-(3-cyclopropoxycyclobutyl)carbamate

To a stirred solution of diethylzinc (1.0 m solution in heptane, 1.04 mL, 1.04 mmol) in anhydrous CH$_2$Cl$_2$ (1 mL) under argon at 0° C. was added a solution of TFA (80 μL, 1.04 mmol) in anhydrous CH$_2$Cl$_2$ (1 mL) over a period of 20 min. The resulting white suspension was stirred for 20 min at 0° C., then a solution of diiodomethane (279 mg, 84 μL, 1.04 mmol) in anhydrous CH$_2$Cl$_2$ (1 mL) was added dropwise to form a colorless solution which was stirred for further 20 min. Finally, a solution of trans-tert-butyl N-(3-(vinyloxy)cyclobutyl)carbamate (110.5 mg, 0.518 mmol) in anhydrous CH$_2$Cl$_2$ (1.50 mL) was added dropwise and the resulting light red solution was stirred at 0° C. for 1 hours then allowed to warm to room temperature and stirred overnight. The reaction was re-cooled to 0° C. then quenched by the addition of saturated aqueous Na₂CO₃ (0.6 mL). After 5 min, triethylamine (144 μL, 1.04 mmol) was added followed by di-tert-butyl dicarbonate (226 mg, 1.04 mmol) and the reaction mixture was stirred at room temperature for 1 hour. The reaction mixture was diluted with water (5 mL) and extracted with EtOAc (3×20 mL). The combined organic extracts were washed with brine, dried (Na₂SO₄) and concentrated in vacuo. Purification by flash chromatography (silica, gradient: 0% to 9% EtOAc in heptane) afforded the title compound (91 mg, 77%) as a white needles. MS (ESI): 172.1 ([M−C₄H₈+H]⁺).

c) trans-3-cyclopropoxycyclobutanamine 2,2,2-trifluoroacetate

In analogy to experiment of example 163b, trans-tert-butyl N-(3-cyclopropoxycyclobutyl)carbamate instead of trans-tert-butyl N-(3-methoxycyclobutyl)carbamate was converted into the title compound (43 mg, quantitative) which was obtained as an off-white. MS (ESI): 128.1 ([M+H]⁺).

d) trans-N-(3-cyclopropoxycyclobutyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using trans-3-cyclopropoxycyclobutanamine 2,2,2-trifluoroacetate instead of trans-3-methoxycyclobutanamine 2,2,2-trifluoroacetate, was converted into the title compound (42 mg, 70%) which was obtained as a colorless amorphous. MS (ESI): 436.3 ([M+H]⁺).

Example 176 cis-N-(3-cyclopropoxycyclobutyl)-6-((5-methyl-3-(6-methylpyridin-3-yl)isoxazol-4-yl)methoxy)pyridazine-3-carboxamide a) cis-tert-butyl N-(3-(vinyloxy)cyclobutyl)carbamate In analogy to experiment of example 175a, cis-tert-butyl N-(3-hydroxycyclobutyl)carbamate instead of trans-tert-butyl N-(3-hydroxycyclobutyl)carbamate was converted into the title compound (107 mg, 63%) which was obtained as a yellow crystalline solid. MS (ESI): 158.1 ([M−C₄H₈+H]⁺).

b) cis-tert-butyl N-(3-cyclopropoxycyclobutyl)carbamate

In analogy to experiment of example 175b, cis-tert-butyl N-(3-(vinyloxy)cyclobutyl)carbamate instead of trans-tert-butyl N-(3-(vinyloxy)cyclobutyl)carbamate was converted into the title compound (91 mg, 81%) which was obtained as a white needles. MS (ESI): 172.1 ([M−C₄H₈+H]⁺).

c) cis-3-cyclopropoxycyclobutanamine 2,2,2-trifluoroacetate

In analogy to experiment of example 163b, cis-tert-butyl N-(3-cyclopropoxycyclobutyl)carbamate instead of trans-tert-butyl N-(3-methoxycyclobutyl)carbamate was converted into the title compound (44 mg, quantitative) which was obtained as an off-white amorphous. MS (ESI): 128.1 ([M+H]⁺).

d) cis-N-(3-cyclopropoxycyclobutyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using cis-3-cyclopropoxycyclobutanamine 2,2,2-trifluoroacetate instead of trans-3-methoxycyclobutanamine 2,2,2-trifluoroacetate, was converted into the title compound (43 mg, 71%) which was obtained as a white foam. MS (ESI): 436.3 ([M+H]⁺).

Example 177

6-((3-(6-chloropyridin-3-yl)-5-cyclopropylisoxazol-4-yl)methoxy)-N-(3-methyloxetan-3-yl)pyridazine-3-carboxamide

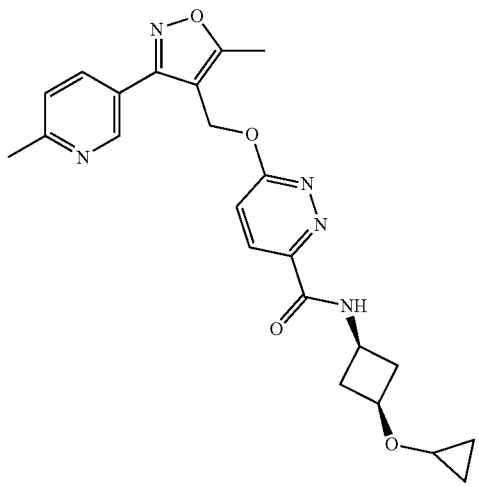 [SMILES: Cc1ccc(-c2noc(C)c2COc2ccc(C(=O)N[C@H]3C[C@@H](OC4CC4)C3)nn2)cn1]

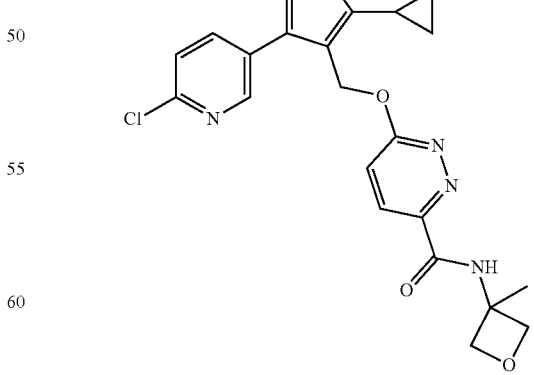

In analogy to experiment of example 183, (3-(6-chloro-3-pyridyl)-5-cyclopropyl-isoxazol-4-yl)methanol (building block G) instead of (5-cyclopropyl-3-(6-methyl-3-pyridyl)isoxazol-4-yl)methanol (building block D), using 6-chloro- N-(3-methyloxetan-3-yl)pyridazine-3-carboxamide instead of 6-chloro-N-(tetrahydropyran-4-yl)pyridazine-3-carboxamide, was converted into the title compound (8.5 mg, 16%) which was obtained as a white solid. MS (ESI): 442.2 ([M+H]+).

Example 178

6-((3-(6-chloropyridin-3-yl)-5-cyclopropylisoxazol-4-yl)methoxy)-N-(2-oxaspiro[3.3]heptan-6-yl)pyridazine-3-carboxamide

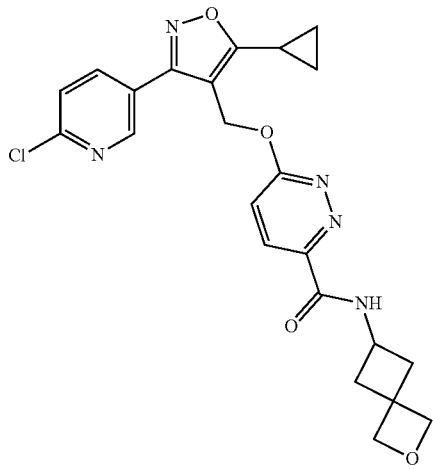 [SMILES: O=C(NC1CC2(COC2)C1)c1ccc(OCc2c(-c3ccc(Cl)nc3)noc2C2CC2)nn1]

In analogy to experiment of example 183, (3-(6-chloro-3-pyridyl)-5-cyclopropyl-isoxazol-4-yl)methanol (building block G) instead of (5-cyclopropyl-3-(6-methyl-3-pyridyl)isoxazol-4-yl)methanol (building block D), using 6-chloro-N-(2-oxaspiro[3.3]heptan-6-yl)pyridazine-3-carboxamide instead of 6-chloro-N-(tetrahydropyran-4-yl)pyridazine-3-carboxamide, was converted into the title compound (13 mg, 23%) which was obtained as a pink solid. MS (ESI): 468.3 ([M+H]+).

Example 179

(S)-6-((3-(6-chloropyridin-3-yl)-5-cyclopropylisoxazol-4-yl)methoxy)-N-(tetrahydrofuran-3-yl)pyridazine-3-carboxamide

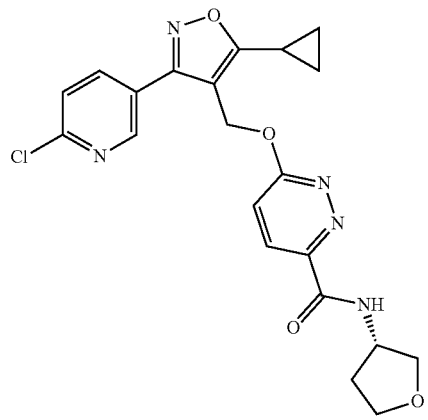 [SMILES: O=C(N[C@H]1CCOC1)c1ccc(OCc2c(-c3ccc(Cl)nc3)noc2C2CC2)nn1]

In analogy to experiment of example 183, (3-(6-chloro-3-pyridyl)-5-cyclopropyl-isoxazol-4-yl)methanol (building block G) instead of (5-cyclopropyl-3-(6-methyl-3-pyridyl)isoxazol-4-yl)methanol (building block D), using (S)-6-chloro-N-(tetrahydrofuran-3-yl)pyridazine-3-carboxamide instead of 6-chloro-N-(tetrahydropyran-4-yl)pyridazine-3-carboxamide, was converted into the title compound (14 mg, 27%) which was obtained as a white solid. MS (ESI): 442.2 ([M+H]+).

Example 180

6-((5-cyclopropyl-3-(6-methylpyridin-3-yl)isoxazol-4-yl)methoxy)-N-(3-methyloxetan-3-yl)pyridazine-3-carboxamide

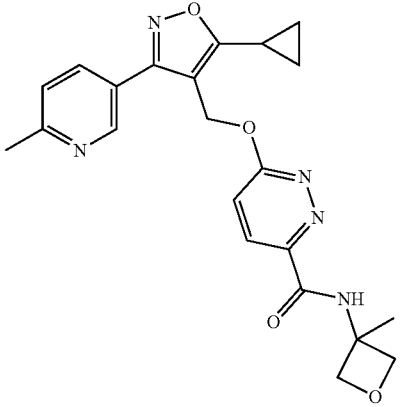 [SMILES: Cc1ccc(-c2noc(C3CC3)c2COc2ccc(C(=O)NC3(C)COC3)nn2)cn1]

In analogy to experiment of example 183, (5-cyclopropyl-3-(6-methyl-3-pyridyl)isoxazol-4-yl)methanol (building block D), using 6-chloro-N-(3-methyloxetan-3-yl)pyridazine-3-carboxamide instead of 6-chloro-N-(tetrahydropyran-4-yl)pyridazine-3-carboxamide, was converted into the title compound (27 mg, 49%) which was obtained as a white solid. MS (ESI): 422.3 ([M+H]+).

Example 181

6-((5-cyclopropyl-3-(6-methylpyridin-3-yl)isoxazol-4-yl)methoxy)-N-(2-oxaspiro[3.3]heptan-6-yl)pyridazine-3-carboxamide

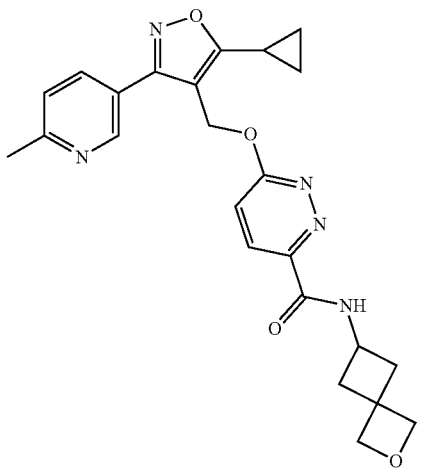 [SMILES: Cc1ccc(-c2noc(C3CC3)c2COc2ccc(C(=O)NC3CC4(COC4)C3)nn2)cn1]

In analogy to experiment of example 183, (5-cyclopropyl-3-(6-methyl-3-pyridyl)isoxazol-4-yl)methanol (building block D), using 6-chloro-N-(2-oxaspiro[3.3]heptan-6-yl)pyridazine-3-carboxamide instead of 6-chloro-N-(tetrahydropyran-4-yl)pyridazine-3-carboxamide, was converted into the title compound (6.5 mg, 11%) which was obtained as a white solid. MS (ESI): 448.3 ([M+H]$^+$).

Example 182

(S)-6-((5-cyclopropyl-3-(6-methylpyridin-3-yl)isoxazol-4-yl)methoxy)-N-(tetrahydrofuran-3-yl)pyridazine-3-carboxamide

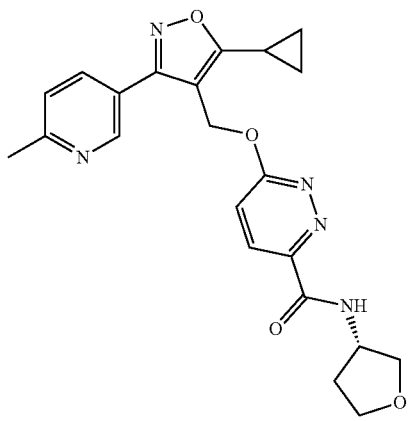 [SMILES: Cc1ccc(-c2noc(C3CC3)c2COc2ccc(C(=O)N[C@H]3CCOC3)nn2)cn1]

In analogy to experiment of example 183, (5-cyclopropyl-3-(6-methyl-3-pyridyl)isoxazol-4-yl)methanol (building block D), using 6-chloro-N-((3S)-tetrahydrofuran-3-yl)pyridazine-3-carboxamide instead of 6-chloro-N-(tetrahydropyran-4-yl)pyridazine-3-carboxamide, was converted into the title compound (10 mg, 21%) which was obtained as a white solid. MS (ESI): 422.3 ([M+H]$^+$).

Example 183

6-((5-cyclopropyl-3-(6-methylpyridin-3-yl)isoxazol-4-yl)methoxy)-N-(tetrahydropyran-4-yl)pyridazine-3-carboxamide

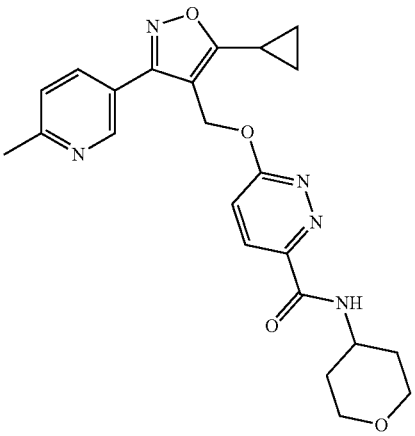 [SMILES: Cc1ccc(-c2noc(C3CC3)c2COc2ccc(C(=O)NC3CCOCC3)nn2)cn1]

To a stirred solution of (5-cyclopropyl-3-(6-methyl-3-pyridyl)isoxazol-4-yl)methanol (building block D, 30 mg, 0.130 mmol) and 6-chloro-N-(tetrahydropyran-4-yl)pyridazine-3-carboxamide (35 mg, 0.130 mmol) in anhydrous N,N-dimethylacetamide (0.60 mL) was added Cs$_2$CO$_3$ (46.7 mg, 0.143 mmol). The reaction mixture was stirred at room temperature for 15 hours then filtered and purified directly by preparative HPLC (column: C-18, eluent: H$_2$O and CH$_3$CN with 0.05% HCO$_2$H) to afford the title compound as a white solid (23 mg, 40%). MS (ESI): 436.3 ([M+H]$^+$).

Example 184

6-((5-(fluoromethyl)-3-(6-methylpyridin-3-yl)isoxazol-4-yl)methoxy)-N-(1-(trifluoromethyl)cyclopropyl)pyridazine-3-carboxamide

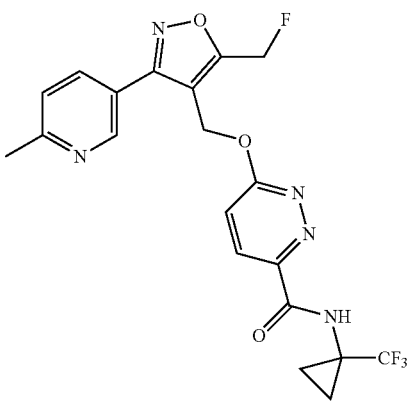 [SMILES: Cc1ccc(-c2noc(CF)c2COc2ccc(C(=O)NC3(C(F)(F)F)CC3)nn2)cn1]

In analogy to experiment of example 163c, 6-((5-(fluoromethyl)-3-(6-methyl-3-pyridyl)isoxazol-4-yl)methoxy)pyridazine-3-carboxylic acid instead of 6-((5-methyl-3-(6-methylpyridin-3-yl)isoxazol-4-yl)methoxy)pyridazine-3-carboxylic acid, using 1-(trifluoromethyl)cyclopropanamine instead of trans-3-methoxycyclobutanamine 2,2,2-trifluoroacetate, was converted into the title compound (10 mg, 51%) which was obtained as a colorless amorphous. MS (ESI): 452.3 ([M+H]$^+$).

Example 185

6-((5-methyl-3-(6-(trifluoromethyl)pyridin-3-yl)isoxazol-4-yl)methoxy)-N-(tetrahydropyran-4-yl)pyridazine-3-carboxamide

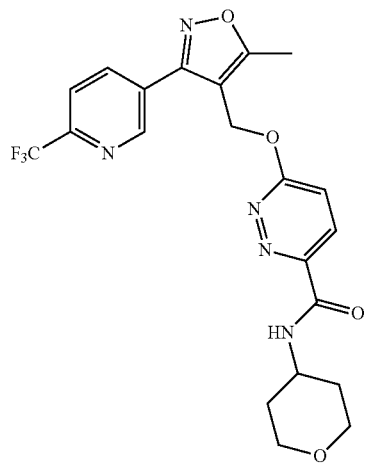 [SMILES: Cc1onc(-c2ccc(C(F)(F)F)nc2)c1COc1ccc(C(=O)NC2CCOCC2)nn1]

To a stirred solution of (5-methyl-3-(6-(trifluoromethyl)pyridin-3-yl)isoxazol-4-yl)methanol (building block E, 56 mg, 0.217 mmol) and 6-chloro-N-(tetrahydropyran-4-yl)pyridazine-3-carboxamide (62.9 mg, 260 μmop in anhydrous N,N-dimethylacetamide (0.60 mL) at room temperature was added $Cs_2CO_3$ (141 mg, 0.434 mmol). After 17 hours, the reaction mixture was diluted with EtOAc (15 mL) and the organic layer was washed with aqueous $Na_2CO_3$ (1.0 m, 10 mL), half saturated brine (15 mL) and brine (15 mL). The aqueous layers were extracted with EtOAc (15 mL). The combined organic extracts were dried ($MgSO_4$) and concentrated in vacuo. Purification by flash chromatography (silica, gradient: 15% to 100% EtOAc in heptane) afforded the title compound (32 mg, 32%) as an off-white solid. MS (ESI): 464.2 ($[M+H]^+$).

Example 186

N-((2S)-7-oxabicyclo[2.2.1]heptan-2-yl)-6-((5-methyl-3-(6-methylpyridin-3-yl)isoxazol-4-yl)methoxy)pyridazine-3-carboxamide

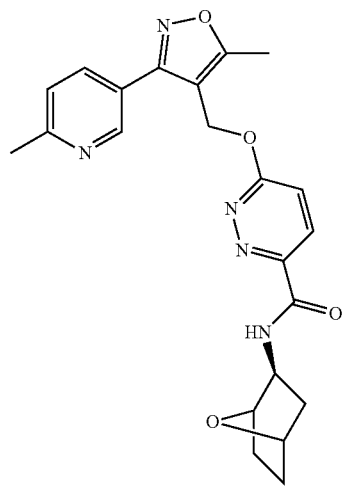 [SMILES: Cc1ccc(-c2noc(C)c2COc2ccc(C(=O)N[C@H]3CC4CCC3O4)nn2)cn1]

In analogy to experiment of example 30, 6-((5-methyl-3-(6-methylpyridin-3-yl)isoxazol-4-yl)methoxy)pyridazine-3-carboxylic acid, using (1R,2S,4S)-7-oxabicyclo[2.2.1]heptan-2-amine instead of (1,1-dioxidotetrahydro-2H-thiopyran-4-yl)amine hydrochloride, was converted into the racemic title compound (48 mg, 80%) which was obtained as a white foam. MS (ESI): 422.2 ($[M+H]^+$).

Example 187

(RS)-6-((5-methyl-3-(6-methylpyridin-3-yl)isoxazol-4-yl)methoxy)-N-(oxepan-4-yl)pyridazine-3-carboxamide

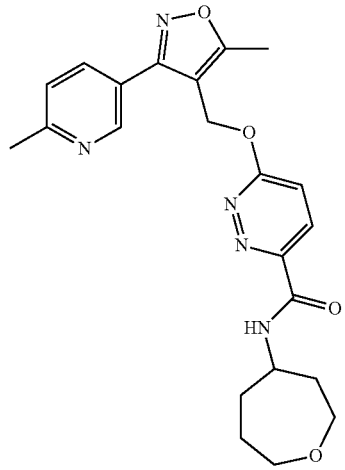 [SMILES: Cc1ccc(-c2noc(C)c2COc2ccc(C(=O)NC3CCCOCC3)nn2)cn1]

In analogy to experiment of example 30, 6-((5-methyl-3-(6-methylpyridin-3-yl)isoxazol-4-yl)methoxy)pyridazine-3-carboxylic acid, using racemic (RS)-oxepan-4-amine instead of (1,1-dioxidotetrahydro-2H-thiopyran-4-yl)amine hydrochloride, was converted into the racemic title compound (48 mg, 72%) which was obtained as a white foam. MS (ESI): 424.2 ($[M+H]^+$).

Example 188

6-((5-methyl-3-(6-methyl-3-pyridyl)isoxazol-4-yl)methoxy)-N-((1R,3S,4R)-7-oxabicyclo[2.2.1]heptan-3-yl)pyridazine-3-carboxamide or Enantiomer

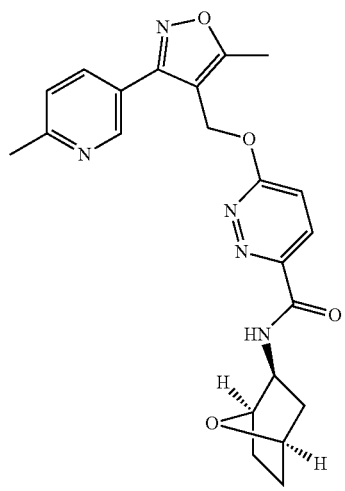 [SMILES: Cc1ccc(-c2noc(C)c2COc2ccc(C(=O)N[C@H]3C[C@H]4CC[C@H]3O4)nn2)cn1]

In analogy to experiment of example 30, 6-((5-methyl-3-(6-methylpyridin-3-yl)isoxazol-4-yl)methoxy)pyridazine-3-carboxylic acid using racemic (1R*,3S*,4R*)-7-oxabicyclo[2.2.1]heptan-2-amine instead of (1,1-dioxidotetrahydro-2H-thiopyran-4-yl)amine hydrochloride was converted into the racemic title compound (48 mg, 80%) which was obtained as a white solid. MS (ESI): 422.2 ([M+H]$^+$). Separation of the enantiomers by chiral HPLC (column: Reprosil Chiral-NR) afforded the enantiopure (+)-title compound (17 mg) which was obtained as a light-brown gum. MS (ESI): 422.2 ([M+H]$^+$).

Example 189

6-((5-methyl-3-(6-methyl-3-pyridyl)isoxazol-4-yl)methoxy)-N-((1S,3R,4S)-7-oxabicyclo[2.2.1]heptan-3-yl)pyridazine-3-carboxamide or Enantiomer

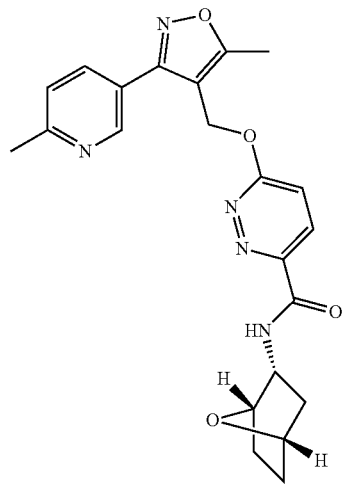 [SMILES: Cc1ccc(-c2noc(C)c2COc2ccc(C(=O)N[C@@H]3C[C@@H]4CC[C@@H]3O4)nn2)cn1]

In analogy to experiment of example 30, 6-((5-methyl-3-(6-methylpyridin-3-yl)isoxazol-4-yl)methoxy)pyridazine-3-carboxylic acid using racemic (1S*,3R*,4S*)-7-oxabicyclo[2.2.1]heptan-2-amine instead of (1,1-dioxidotetrahydro-2H-thiopyran-4-yl)amine hydrochloride was converted into the racemic title compound (48 mg, 80%) which was obtained as a white solid. MS (ESI): 422.2 ([M+H]$^+$). Separation of the enantiomers by chiral HPLC (column: Reprosil Chiral-NR) afforded the enantiopure (−)-title compound (16 mg) which was obtained as a light-brown gum. MS (ESI): 422.2 ([M+H]$^+$).

Example 190

N-((1R,3R)-3-ethoxycyclopentyl)-6-((5-methyl-3-(6-methylpyridin-3-yl)isoxazol-4-yl)methoxy)pyridazine-3-carboxamide

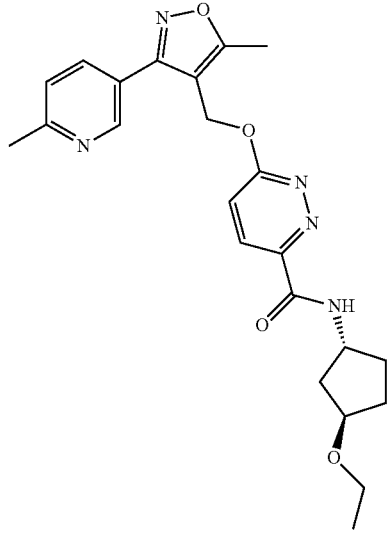 [SMILES: CCO[C@@H]1CC[C@@H](NC(=O)c2ccc(OCc3c(-c4ccc(C)nc4)noc3C)nn2)C1]

a) tert-butyl ((1R,3R)-3-ethoxycyclopentyl)carbamate

In analogy to experiment of example 163a, tert-butyl ((1R,3R)-3-hydroxycyclopentyl)carbamate, using iodoethane instead of iodomethane, was converted into the title compound (35 mg, 31%) which was obtained as colorless oil. MS (ESI): 174.1 ([M−C$_4$H$_8$+H]$^+$).

b) (1R,3R)-3-ethoxycyclopentanamine 2,2,2-trifluoroacetate

In analogy to experiment of example 163b, tert-butyl ((1R,3R)-3-ethoxycyclopentyl)carbamate instead of trans-tert-butyl N-(3-methoxycyclobutyl)carbamate was converted into the title compound (33 mg, quantitative) which was obtained as a light yellow oil. MS (ESI): 130.1 ([M+H]$^+$).

c) N-((1R,3R)-3-ethoxycyclopentyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using (1R,3R)-3-ethoxycyclopentanamine 2,2,2-trifluoroacetate instead of trans-3-methoxycyclobutanamine 2,2,2-trifluoroacetate, was converted into the title compound (39 mg, 83%) which was obtained as a colorless amorphous. MS (ESI): 438.3 ([M+H]$^+$).

Example 191

N-((1R,3R)-3-(2,2-difluoroethoxy)cyclopentyl)-6-((5-methyl-3-(6-methylpyridin-3-yl)isoxazol-4-yl)methoxy)pyridazine-3-carboxamide

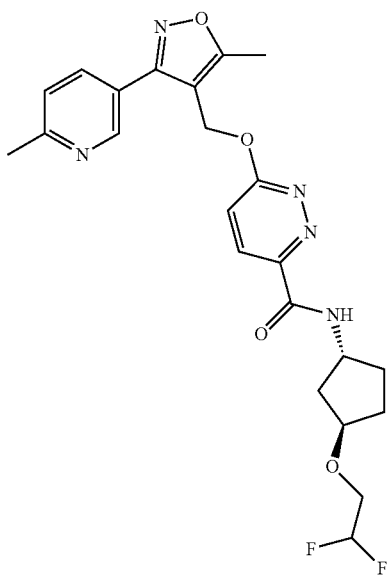 [SMILES: Cc1ccc(-c2noc(C)c2COc2ccc(C(=O)N[C@@H]3CC[C@@H](OCC(F)F)C3)nn2)cn1]

a) tert-butyl ((1R,3R)-3-(2,2-difluoroethoxy)cyclopentyl)carbamate

In analogy to experiment of example 163a, tert-butyl ((1R,3R)-3-hydroxycyclopentyl)carbamate, using 2,2-difluoroethyl trifluoromethanesulfonate instead of iodomethane, was converted into the title compound (88 mg, 67%) which was obtained as white crystals. MS (ESI): 210.1 ([M−$C_4H_8$+H]$^+$).

b) (1R,3R)-3-(2,2-difluoroethoxy)cyclopentanamine 2,2,2-trifluoroacetate

In analogy to experiment of example 163b, tert-butyl ((1R,3R)-3-(2,2-difluoroethoxy)cyclopentyl)carbamate instead of trans-tert-butyl N-(3-methoxycyclobutyl)carbamate was converted into the title compound (38 mg, quantitative) which was obtained as a light yellow oil. MS (ESI): 166.2 ([M+H]$^+$).

c) N-((1R,3R)-3-(2,2-difluoroethoxy)cyclopentyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using (1R,3R)-3-(2,2-difluoroethoxy)cyclopentanamine 2,2,2-trifluoroacetate instead of trans-3-methoxycyclobutanamine 2,2,2-trifluoroacetate, was converted into the title compound (37 mg, 73%) which was obtained as a colorless amorphous: 474.3 ([M+H]$^+$).

Example 192

6-((5-(fluoromethyl)-3-(6-methylpyridazin-3-yl)isoxazol-4-yl)methoxy)-N-(tetrahydropyran-4-yl)pyridazine-3-carboxamide

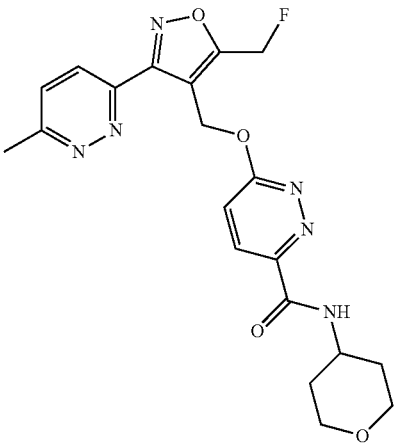 [SMILES: Cc1ccc(-c2noc(CF)c2COc2ccc(C(=O)NC3CCOCC3)nn2)nn1]

In analogy to experiment of example 183, (5-(fluoromethyl)-3-(6-methylpyridazin-3-yl)isoxazol-4-yl)methanol (building block P) instead of (5-cyclopropyl-3-(6-methyl-3-pyridyl)isoxazol-4-yl)methanol (building block D) was converted into the title compound (15 mg, 31%) which was obtained as a white powder. MS (ESI): 429.2 ([M+H]$^+$).

Example 193

6-((5-methyl-3-(6-methylpyridazin-3-yl)isoxazol-4-yl)methoxy)-N-(tetrahydropyran-4-yl)pyridazine-3-carboxamide

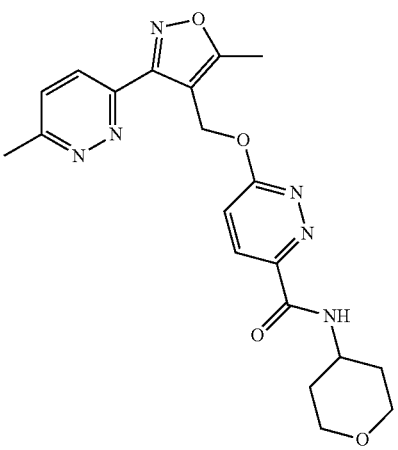 [SMILES: Cc1ccc(-c2noc(C)c2COc2ccc(C(=O)NC3CCOCC3)nn2)nn1]

In analogy to experiment of example 183, (5-methyl-3-(6-methylpyridazin-3-yl)isoxazol-4-yl)methanol (building block I) instead of (5-cyclopropyl-3-(6-methyl-3-pyridyl)isoxazol-4-yl)methanol (building block D) was converted into the title compound (8.8 mg, 15%) which was obtained as a light yellow powder. MS (ESI): 411.2 ([M+H]$^+$).

Example 194 trans-N-(4-(2,2-difluoroethoxy)cyclohexyl)-6-((5-methyl-3-(6-methylpyridin-3-yl)-1,2-oxazol-4-yl)methoxy)pyridazine-3-carboxamide

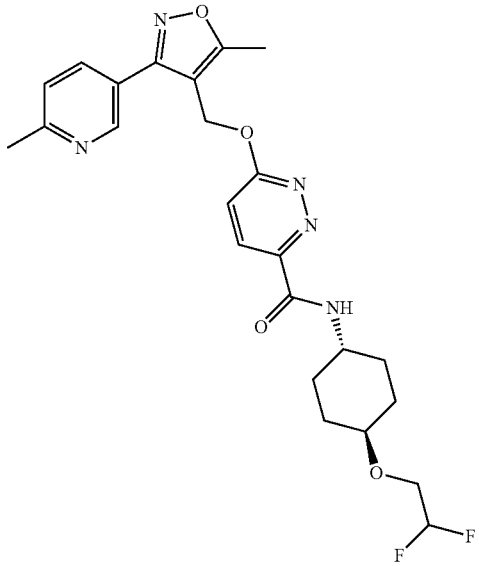 [SMILES: Cc1ccc(-c2noc(C)c2COc2ccc(C(=O)N[C@H]3CC[C@H](OCC(F)F)CC3)nn2)cn1]

a) trans-tert-butyl N-(4-(2,2-difluoroethoxy)cyclohexyl)carbamate

In analogy to experiment of example 163a, trans-tert-butyl N-(4-hydroxycyclohexyl) carbamate, using 2,2-difluoroethyl trifluoromethanesulfonate instead of iodomethane, was converted into the title compound (69 mg, 53%) which was obtained as white crystals. MS (ESI): 224.1 ([M−C$_4$H$_8$+H]$^+$).

b) trans-4-(2,2-difluoroethoxy)cyclohexanamine 2,2,2-trifluoroacetate

In analogy to experiment of example 163b, trans-tert-butyl N-(4-(2,2-difluoroethoxy)cyclohexyl)carbamate instead of trans-tert-butyl N-(3-methoxycyclobutyl)carbamate was converted into the title compound (72 mg, quantitative) which was obtained as a light yellow oil. MS (ESI): 180.1 ([M+H]$^+$).

c) trans-N-4-((2,2-difluoroethoxy)cyclohexyl)-6-((5-methyl-3-(6-methylpyridin-3-yl)isoxazol-4-yl)methoxy)pyridazine-3-carboxamide In analogy to experiment of example 163c, 6-((5-methyl-3-(6-methylpyridin-3-yl)isoxazol-4-yl)methoxy)pyridazine-3-carboxylic acid, using trans-4-(2,2-difluoroethoxy)cyclohexanamine 2,2,2-trifluoroacetate instead of trans-3-methoxycyclobutanamine 2,2,2-trifluoroacetate, was converted into the title compound (15 mg, 17%) which was obtained as a white powder. MS (ESI): 488.2 ([M+H]$^+$).

Example 195

N-(4-ethoxycyclohexyl)-6-((5-methyl-3-(6-methylpyridin-3-yl)-1,2-oxazol-4-yl)methoxy)pyridazine-3-carboxamide

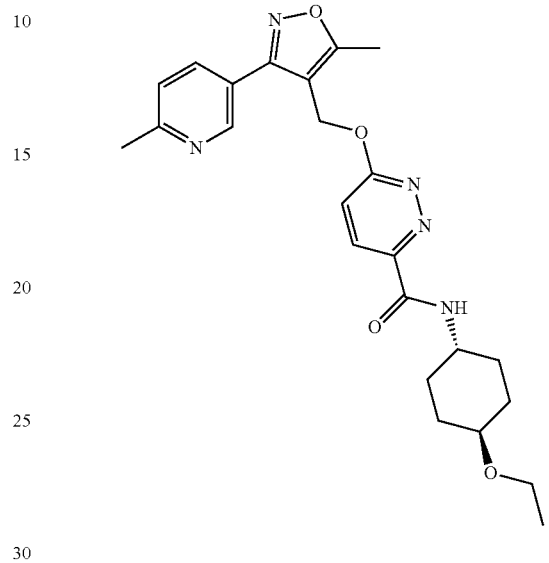

a) trans-tert-butyl N-(4-ethoxycyclohexyl)carbamate

In analogy to experiment of example 163a, trans-tert-butyl N-(4-hydroxycyclohexyl) carbamate, using iodoethane instead of iodomethane, was converted into the title compound (20 mg, 18%) which was obtained as white solid. MS (ESI): 188.1 ([M−C$_4$H$_8$+H]$^+$).

b) trans-4-ethoxycyclohexanamine 2,2,2-trifluoroacetate

In analogy to experiment of example 163b, trans-tert-butyl N-(4-ethoxycyclohexyl)carbamate instead of trans-tert-butyl N-(3-methoxycyclobutyl)carbamate was converted into the title compound (21 mg, quantitative) which was obtained as a light yellow oil. MS (ESI): 144.1 ([M+H]$^+$).

c) trans-N-(4-ethoxycyclohexyl)-6-((5-methyl-3-(6-methylpyridin-3-yl)isoxazol-4-yl)methoxy) pyridazine-3-carboxamide In analogy to experiment of example 163c, 6-((5-methyl-3-(6-methylpyridin-3-yl)isoxazol-4-yl)methoxy)pyridazine-3-carboxylic acid, using trans-4-ethoxycyclohexanamine 2,2,2-trifluoroacetate instead of trans-3-methoxycyclobutanamine 2,2,2-trifluoroacetate, was converted into the title compound (15 mg, 55%) which was obtained as a white powder. MS (ESI): 452.2 ([M+H]$^+$).

Reference Example A 6-((5-methyl-3-(3-pyridyl)isoxazol-4-yl)methoxy)-N-tetrahydropyran-4-yl-pyridazine-3-carboxamide

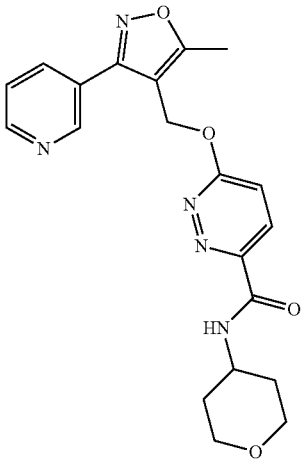 [SMILES: Cc1onc(-c2cccnc2)c1COc1ccc(C(=O)NC2CCOCC2)nn1]

a) (3Z)—N-hydroxypyridine-3-carboximidoyl Chloride

To a stirred solution of (3E)-pyridine-3-carbaldehyde oxime (25.0 g, 205 mmol) in DMF (205 mL) at room temperature was added in small portion (caution: reaction exotermic) N-chlorosuccinimide (27.34 g, 205 mmol). The reaction mixture was stirred at room temperature for 20 hours then poured into water and ice (200 mL). The resulting light brown precipitate was collected through filtration on a sintered funnel then washed with water (50 mL) and dried at high vacuum to afford the title compound (16.53 g, 52%) as a light brown solid. MS (ESI): 157.0 ([M+H]$^+$).

b) ethyl 5-methyl-3-(3-pyridyl)isoxazole-4-carboxylate

To a stirred suspension of (3Z)—N-hydroxypyridine-3-carboximidoyl chloride (18.6 g, 119 mmol) in Et$_2$O (202 mL) at 0° C. was added ethyl but-2-ynoate (13.9 mL, 119 mmol) followed by Et$_3$N (19.9 mL, 143 mmol). After 30 min, the mixture was allowed to warm to room temperature and the resulting suspension was stirred overnight. The reaction mixture was poured into a 1:1 mixture of brine and water (150 mL) and extracted with EtOAc (2×100 mL). The organic phase was filtered off through a sintered funnel to remove an insoluble brown precipitate then the filtrate was washed with brine, dried (Na$_2$SO$_4$) and concentrated in vacuo. Purification by flash chromatography (silica, gradient: 20% to 80% EtOAc in heptane) afforded the title compound (8.11 g, 29%) as an off-white solid. MS (ESI): 233.1 ([M+H]$^+$).

c) (5-methyl-3-(3-pyridyl)isoxazol-4-yl)methanol

In analogy to experiment of building block M c, ethyl 5-methyl-3-(3-pyridyl)isoxazole-4-carboxylate instead of ethyl 3-(6-methoxy-3-pyridyl)-5-methyl-isoxazole-4-carboxylate was converted into the title compound (4.32 mg, 66%) which was obtained as a light yellow solid. MS (ESI): 191.2 ([M+H]$^+$).

d) 4-((6-chloropyridazin-3-yl)oxymethyl)-5-methyl-3-(3-pyridyl)isoxazole

In analogy to experiment of example 23a, (5-methyl-3-(3-pyridyl)isoxazol-4-yl)methanol instead of (5-methyl-3-(6-methylpyridin-3-yl)isoxazol-4-yl)methanol (building block A) was converted into the title compound (2.53 g, 81%) which was obtained as a light yellow solid. MS (ESI): 303.1 ([M+H]$^+$).

e) Ethyl 6-((5-methyl-3-(3-pyridyl)isoxazol-4-yl)methoxy)pyridazine-3-carboxylate In analogy to experiment of example 23b, 4-((6-chloropyridazin-3-yl)oxymethyl)-5-methyl-3-(3-pyridyl)isoxazole instead of 4-((6-chloropyridazin-3-yloxy)methyl)-5-methyl-3-(6-methylpyridin-3-yl)isoxazole was converted into the title compound (1.91 g, 69%) which was obtained as a light yellow solid. MS (ESI): 341.2 ([M+H]$^+$).

f) 6-((5-methyl-3-(3-pyridyl)isoxazol-4-yl)methoxy)-N-tetrahydropyran-4-yl-pyridazine-3-carboxamide In analogy to experiment of example 1b, ethyl 6-((5-methyl-3-(3-pyridyl)isoxazol-4-yl)methoxy)pyridazine-3-carboxylate instead of methyl 6-((5-methyl-3-(6-methyl-3-pyridyl)isoxazol-4-yl)methoxy)pyridine-3-carboxylate was converted into the title compound (122 mg, 77%) which was obtained as an off-white solid. MS (ESI): 396.2 ([M+H]$^+$).

Reference Example RE-B 6-((3-(5-chloro-2-pyridyl)-5-methyl-isoxazol-4-yl)methoxy)-N-tetrahydropyran-4-yl-pyridazine-3-carboxamide

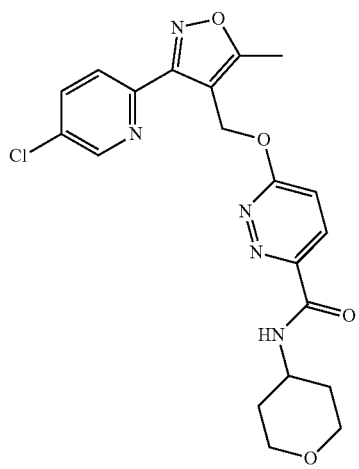 [SMILES: Cc1onc(-c2ccc(Cl)cn2)c1COc1ccc(C(=O)NC2CCOCC2)nn1]

a) (2E)-5-chloropyridine-2-carbaldehyde Oxime

In analogy to experiment of building block I a, 5-chloropyridine-2-carbaldehyde was converted into the title compound (6.74 g, 89%) which was obtained as a light brown solid. MS (ESI): 157.0 ([M+H]$^+$).

b) ethyl 3-(5-chloro-2-pyridyl)-5-methyl-isoxazole-4-carboxylate

To a stirred suspension of (2E)-5-chloropyridine-2-carbaldehyde oxime (1.00 g, 6.40 mmol) in CHCl$_3$ (20 mL) at room temperature was added a solution of N-chlorosuccinimide (853 mg, 6.40 mmol) in CHCl$_3$ (20 mL) followed by a catalytic amount of pyridine (51 mL, 0.64 mmol). After 30 min, the mixture was heated to 50° C. for 3 hours. The resulting brown suspension was allowed to warm to room temperature before the addition of a solution of (E)-ethyl 3-(pyrrolidin-1-yl)but-2-enoate (1.170 g, 6.40 mmol) in CHCl$_3$ (0.8 mL). The reaction mixture was heated to 50° C. followed by the addition of a solution of Et$_3$N (0.890 mL, 6.4 mmol) in CHCl$_3$ (0.8 mL). The reaction was stirred at 50° C. for 30 min before being poured into ice and water (50 mL) and extracted with CH$_2$Cl$_2$ (2×50 mL). The combined organic extracts were washed with brine (50 mL), dried (Na$_2$SO$_4$) and concentrated in vacuo. Purification by flash chromatography (silica, gradient: 0% to 50% EtOAc in heptane) afforded the title compound (1.35 g, 79%) as a light yellow oil. MS (ESI): 267.1 ([M+H]$^+$).

c) (3-(5-chloro-2-pyridyl)-5-methyl-isoxazol-4-yl)methanol

In analogy to experiment of building block M c, ethyl 3-(5-chloro-2-pyridyl)-5-methyl-isoxazole-4-carboxylate instead of ethyl 3-(6-methoxy-3-pyridyl)-5-methyl-isoxazole-4-carboxylate was converted into the title compound (773 mg, 73%) which was obtained as an off-white solid. MS (ESI): 225.0 ([M+H]$^+$).

d) 4-((6-chloropyridazin-3-yl)oxymethyl)-3-(5-chloro-2-pyridyl)-5-methyl-isoxazole In analogy to experiment of example 23a, (3-(5-chloro-2-pyridyl)-5-methyl-isoxazol-4-yl)methanol instead of (5-methyl-3-(6-methylpyridin-3-yl)isoxazol-4-yl)methanol (building block A) was converted into the title compound (2.47 g, 83%) which was obtained as a light brown solid. MS (ESI): 337.0 ([M+H]$^+$).

e) Ethyl 6-((3-(5-chloro-2-pyridyl)-5-methyl-isoxazol-4-yl)methoxy)pyridazine-3-carboxylate In analogy to experiment of example 23b, 4-((6-chloropyridazin-3-yl)oxymethyl)-3-(5-chloro-2-pyridyl)-5-methyl-isoxazole instead of 4-((6-chloropyridazin-3-yloxy)methyl)-5-methyl-3-(6-methylpyridin-3-yl)isoxazole was converted into the title compound (1.89 g, 72%) which was obtained as a white solid. MS (ESI): 375.1 ([M+H]$^+$).

f) 6-((3-(5-chloro-2-pyridyl)-5-methyl-isoxazol-4-yl)methoxy)pyridazine-3-carboxylic Acid In analogy to experiment of example 23c, ethyl 6-((3-(5-chloro-2-pyridyl)-5-methyl-isoxazol-4-yl)methoxy)pyridazine-3-carboxylate instead of ethyl 6-((5-methyl-3-(6-methylpyridin-3-yl)isoxazol-4-yl)methoxy)pyridazine-3-carboxylate was converted into the title compound (1.57 g, 93%) which was obtained as a white solid. MS (ESI): 347.1 ([M+H]$^+$).

g) 6-((3-(5-chloro-2-pyridyl)-5-methyl-isoxazol-4-yl)methoxy)-N-tetrahydropyran-4-yl-pyridazine-3-carboxamide In analogy to experiment of example 23d, 6-((3-(5-chloro-2-pyridyl)-5-methyl-isoxazol-4-yl)methoxy) pyridazine-3-carboxylic acid instead of 6-((5-methyl-3-(6-methylpyridin-3-yl)isoxazol-4-yl)methoxy)pyridazine-3-carboxylic acid was converted into the title compound (69 mg, 64%) which was obtained as a white solid. MS (ESI): 430.1 ([M+H]$^+$).

The invention claimed is:

1. A compound selected from
6-((5-methyl-3-(6-methyl-3-pyridyl)isoxazol-4-yl)methoxy)-N-tetrahydropyran-4-yl-pyridine-3-carboxamide;
N-(cyclopropylmethyl)-6-((5-methyl-3-(6-methyl-3-pyridyl)isoxazol-4-yl)methoxy)pyridine-3-carboxamide;
N-ethyl-6-((5-methyl-3-(6-methyl-3-pyridyl)isoxazol-4-yl)methoxy)pyridine-3-carboxamide;
N-((1S)-1-(hydroxymethyl)butyl)-6-((5-methyl-3-(6-methyl-3-pyridyl)isoxazol-4-yl)methoxy)pyridine-3-carboxamide;
6-((5-cyclopropyl-3-(6-methyl-3-pyridyl)isoxazol-4-yl)methoxy)-N-((1S)-1-(hydroxymethyl)butyl)pyridine-3-carboxamide;
6-((5-cyclopropyl-3-(6-methyl-3-pyridyl)isoxazol-4-yl)methoxy)-N-tetrahydropyran-4-yl-pyridine-3-carboxamide;
(S)—N-(1-hydroxypentan-2-yl)-6-((5-methyl-3-(6-methylpyridin-3-yl)isoxazol-4-yl)methoxy)pyridazine-3-carboxamide;
6-((5-methyl-3-(6-methylpyridin-3-yl)isoxazol-4-yl)methoxy)-N-(tetrahydro-2H-pyran-4-yl)pyridazine-3-carboxamide;
2-isobutyl-6-((5-methyl-3-(6-methylpyridin-3-yl)isoxazol-4-yl)methoxy)-1H-pyrrolo[3,4-c]pyridin-3(2H)-one;
2-methyl-6-((5-methyl-3-(6-methylpyridin-3-yl)isoxazol-4-yl)methoxy)-1H-pyrrolo[3,4-c]pyridin-3(2H)-one;
N-isobutyl-6-((5-methyl-3-(6-methylpyridin-3-yl)isoxazol-4-yl)methoxy)nicotinamide;
2-(2-hydroxyethyl)-6-((5-methyl-3-(6-methylpyridin-3-yl)isoxazol-4-yl)methoxy)-1H-pyrrolo[3,4-c]pyridin-3(2H)-one;
(S)-2-(1-hydroxypentan-2-yl)-6-((5-methyl-3-(6-methylpyridin-3-yl)isoxazol-4-yl)methoxy)-1H-pyrrolo[3,4-c]pyridin-3(2H)-one;
(S)—N-(1-hydroxypentan-2-yl)-5-((5-methyl-3-(6-methylpyridin-3-yl)isoxazol-4-yl)methoxy)pyrazine-2-carboxamide;
5-((5-methyl-3-(6-methylpyridin-3-yl)isoxazol-4-yl)methoxy)-N-(tetrahydro-2H-pyran-4-yl)pyrazine-2-carboxamide;
N-(1,1-dioxothiolan-3-yl)-6-((5-methyl-3-(6-methyl-3-pyridyl)isoxazol-4-yl)methoxy)pyridine-3-carboxamide;
6-((5-methyl-3-(6-methylpyridin-3-yl)isoxazol-4-yl)methoxy)nicotinamide;
6-((5-methyl-3-(6-methylpyridin-3-yl)isoxazol-4-yl)methoxy)pyridazine-3-carboxamide;
N-((3S)-1,1-dioxothiolan-3-yl)-6-((5-methyl-3-(6-methylpyridin-3-yl)-1,2-oxazol-4-yl)methoxy)pyridine-3-carboxamide;

N-((3R)-1,1-dioxothiolan-3-yl)-6-((5-methyl-3-(6-methylpyridin-3-yl)-1,2-oxazol-4-yl)methoxy)pyridine-3-carboxamide;
N-(1,1-dioxothian-4-yl)-6-((5-methyl-3-(6-methylpyridin-3-yl)-1,2-oxazol-4-yl)methoxy)pyridine-3-carboxamide;
6-((5-methyl-3-(6-methylpyridin-3-yl)isoxazol-4-yl)methoxy)-2-(tetrahydro-2H-pyran-4-yl)-1H-pyrrolo[3,4-c]pyridin-3(2H)-one;
N-((1S,2R)-2-Hydroxycyclohexyl)-6-((5-methyl-3-(6-methylpyridin-3-yl)isoxazol-4-yl)methoxy)pyridazine-3-carboxamide;
N-((1S,2S)-2-Hydroxycyclohexyl)-6-((5-methyl-3-(6-methylpyridin-3-yl)isoxazol-4-yl)methoxy)pyridazine-3-carboxamide;
N-((1R,2R)-2-Hydroxycyclohexyl)-6-((5-methyl-3-(6-methylpyridin-3-yl)isoxazol-4-yl)methoxy)pyridazine-3-carboxamide;
N-cyclopropyl-6-((5-methyl-3-(6-methylpyridin-3-yl)isoxazol-4-yl)methoxy)pyridazine-3-carboxamide;
N-((1R,2S)-2-hydroxycyclohexyl)-6-((5-methyl-3-(6-methylpyridin-3-yl)isoxazol-4-yl)methoxy)pyridazine-3-carboxamide;
N-((3S,4R)-3-hydroxytetrahydropyran-4-yl)-6-((5-methyl-3-(6-methylpyridin-3-yl)isoxazol-4-yl)methoxy)pyridazine-3-carboxamide;
N-(2-hydroxyethyl)-6-((5-methyl-3-(6-methylpyridin-3-yl)isoxazol-4-yl)methoxy)pyridazine-3-carboxamide;
N-(1,1-dioxothian-4-yl)-6-((5-methyl-3-(6-methylpyridin-3-yl)-1,2-oxazol-4-yl)methoxy)pyridazine-3-carboxamide;
N-(cyclopropylmethyl)-6-((5-methyl-3-(6-methylpyridin-3-yl)isoxazol-4-yl)methoxy)pyridazine-3-carboxamide;
N-(cyclopropylmethyl)-6-((5-methyl-3-(6-methylpyridin-3-yl)isoxazol-4-yl)methoxy)pyridazine-3-carboxamide;
N-(2-cyanoethyl)-6-((5-methyl-3-(6-methylpyridin-3-yl)isoxazol-4-yl)methoxy)pyridazine-3-carboxamide;
(RS)-6-((5-methyl-3-(6-methylpyridin-3-yl)isoxazol-4-yl)methoxy)-N-(1,1,1-trifluoropropan-2-yl)pyridazine-3-carboxamide;
6-((5-methyl-3-(6-methylpyridin-3-yl)isoxazol-4-yl)methoxy)-N-(oxetan-3-yl)pyridazine-3-carboxamide;
(RS)—N-(1,1-dioxothiolan-3-yl)-6-((5-methyl-3-(6-methylpyridin-3-yl)-1,2-oxazol-4-yl)methoxy)pyridazine-3-carboxamide;
N-ethyl-6-((5-methyl-3-(6-methylpyridin-3-yl)isoxazol-4-yl)methoxy)pyridazine-3-carboxamide;
N-isopropyl-6-((5-methyl-3-(6-methylpyridin-3-yl)isoxazol-4-yl)methoxy)pyridazine-3-carboxamide;
N-isobutyl-6-((5-methyl-3-(6-methylpyridin-3-yl)isoxazol-4-yl)methoxy)pyridazine-3-carboxamide;
6-((5-methyl-3-(6-methylpyridin-3-yl)isoxazol-4-yl)methoxy)-N-(2,2,2-trifluoroethyl)pyridazine-3-carboxamide;
N-tert-butyl-6-((5-methyl-3-(6-methylpyridin-3-yl)isoxazol-4-yl)methoxy)pyridazine-3-carboxamide;
N-(3,3-difluorocyclobutyl)-6-((5-methyl-3-(6-methylpyridin-3-yl)isoxazol-4-yl)methoxy)pyridazine-3-carboxamide;
N-(4,4-difluorocyclohexyl)-6-((5-methyl-3-(6-methylpyridin-3-yl)isoxazol-4-yl)methoxy)pyridazine-3-carboxamide;
6-((3-(6-methyl-3-pyridyl)isoxazol-4-yl)methoxy)-N-tetrahydropyran-4-yl-pyridine-3-carboxamide;
(RS)-6-((5-methyl-3-(6-methylpyridin-3-yl)isoxazol-4-yl)methoxy)-N-(tetrahydrofuran-3-yl)pyridazine-3-carboxamide;
N-methyl-6-((5-methyl-3-(6-methylpyridin-3-yl)isoxazol-4-yl)methoxy)pyridazine-3-carboxamide;
(3,3-difluoroazetidin-1-yl)(6-((5-methyl-3-(6-methylpyridin-3-yl)isoxazol-4-yl)methoxy)pyridazin-3-yl)methanone;
(3,3-difluoropyrrolidin-1-yl)(6-((5-methyl-3-(6-methylpyridin-3-yl)isoxazol-4-yl)methoxy)pyridazin-3-yl)methanone;
6-((5-methyl-3-(6-methylpyridin-3-yl)isoxazol-4-yl)methoxy)-N-((3-methyloxetan-3-yl)methyl)pyridazine-3-carboxamide;
6-((5-methyl-3-(6-methyl-3-pyridyl)isoxazol-4-yl)methoxy)-N-(oxetan-3-ylmethyl)pyridazine-3-carboxamide;
N-((3-hydroxyoxetan-3-yl)methyl)-6-((5-methyl-3-(6-methylpyridin-3-yl)isoxazol-4-yl)methoxy)pyridazine-3-carboxamide;
6-((5-methyl-3-(6-methylpyridin-3-yl)isoxazol-4-yl)methoxy)-N-((3R,4R)-3-methyltetrahydropyran-4-yl)pyridazine-3-carboxamide;
(4,4-difluoropiperidin-1-yl)(6-((5-methyl-3-(6-methylpyridin-3-yl)isoxazol-4-yl)methoxy)pyridazin-3-yl)methanone;
N-(1-(methoxymethyl)cyclopropyl)-6-((5-methyl-3-(6-methylpyridin-3-yl)isoxazol-4-yl)methoxy)pyridazine-3-carboxamide;
(3-methoxyazetidin-1-yl)(6-((5-methyl-3-(6-methylpyridin-3-yl)isoxazol-4-yl)methoxy)pyridazin-3-yl)methanone;
(3-hydroxy-3-methylazetidin-1-yl)(6-((5-methyl-3-(6-methylpyridin-3-yl)isoxazol-4-yl)methoxy)pyridazin-3-yl)methanone;
azetidin-1-yl(6-((5-methyl-3-(6-methylpyridin-3-yl)isoxazol-4-yl)methoxy)pyridazin-3-yl)methanone;
(RS)—N-(2,2-dimethyltetrahydropyran-4-yl)-6-((5-methyl-3-(6-methylpyridin-3-yl)isoxazol-4-yl)methoxy)pyridazine-3-carboxamide;
6-((5-methyl-3-(6-methylpyridin-3-yl)isoxazol-4-yl)methoxy)-N-(1-(trifluoromethyl)cyclopropyl)pyridazine-3-carboxamide;
(6-((5-methyl-3-(6-methylpyridin-3-yl)isoxazol-4-yl)methoxy)pyridazin-3-yl)(morpholino)methanone;
(6-((5-methyl-3-(6-methylpyridin-3-yl)isoxazol-4-yl)methoxy)pyridazin-3-yl)(2-oxa-6-azaspiro[3.3]heptan-6-yl)methanone;
4-methyl-6-((5-methyl-3-(6-methylpyridin-3-yl)isoxazol-4-yl)methoxy)-N-(tetrahydropyran-4-yl)pyridazine-3-carboxamide;
(6-((5-methyl-3-(6-methylpyridin-3-yl)isoxazol-4-yl)methoxy)pyridazin-3-yl)(6-oxa-1-azaspiro[3.3]heptan-1-yl)methanone;
6-((5-methyl-3-(6-methylpyridin-3-yl)isoxazol-4-yl)methoxy)-N-(1,1,1-trifluoro-2-methylpropan-2-yl)pyridazine-3-carboxamide;
(3-fluoroazetidin-1-yl)(6-((5-methyl-3-(6-methylpyridin-3-yl)isoxazol-4-yl)methoxy)pyridazin-3-yl)methanone;
(3-hydroxyazetidin-1-yl)(6-((5-methyl-3-(6-methylpyridin-3-yl)isoxazol-4-yl)methoxy)pyridazin-3-yl)methanone;
(3-fluoro-3-methylazetidin-1-yl)(6-((5-methyl-3-(6-methylpyridin-3-yl)isoxazol-4-yl)methoxy)pyridazin-3-yl)methanone;

ethyl 1-(6-((5-methyl-3-(6-methylpyridin-3-yl)isoxazol-4-yl)methoxy)pyridazine-3-carboxamido)cyclopropanecarboxylate;
N-(1-cyanocyclopropyl)-6-((5-methyl-3-(6-methylpyridin-3-yl)isoxazol-4-yl)methoxy)pyridazine-3-carboxamide;
5-methyl-6-((5-methyl-3-(6-methylpyridin-3-yl)isoxazol-4-yl)methoxy)pyridazine-3-carboxamide;
5-methyl-6-((5-methyl-3-(6-methylpyridin-3-yl)isoxazol-4-yl)methoxy)-N-(tetrahydropyran-4-yl)pyridazine-3-carboxamide;
N-(1,1-dioxothian-4-yl)-5-((5-methyl-3-(6-methyl-3-pyridyl)isoxazol-4-yl)methoxy)pyrazine-2-carboxamide;
N-(2-hydroxy-1,1-dimethyl-ethyl)-5-((5-methyl-3-(6-methyl-3-pyridyl)isoxazol-4-yl)methoxy)pyrazine-2-carboxamide;
N-cyclopropyl-5-((5-methyl-3-(6-methyl-3-pyridyl)isoxazol-4-yl)methoxy)pyrazine-2-carboxamide;
(RS)-6-((5-methyl-3-(6-methylpyridin-3-yl)isoxazol-4-yl)methoxy)-N-(3-methyltetrahydrofuran-3-yl)pyridazine-3-carboxamide;
6-((5-methyl-3-(6-methylpyridin-3-yl)isoxazol-4-yl)methoxy)-N-(1-methylcyclopropyl)pyridazine-3-carboxamide;
5-((5-methyl-3-(6-methyl-3-pyridyl)isoxazol-4-yl)methoxy)-N-(oxetan-3-yl)pyrazine-2-carboxamide;
5-((5-methyl-3-(6-methyl-3-pyridyl)isoxazol-4-yl)methoxy)-N-(2,2,2-trifluoroethyl)pyrazine-2-carboxamide;
N-(4-hydroxy-2-methylbutan-2-yl)-6-((5-methyl-3-(6-methylpyridin-3-yl)isoxazol-4-yl)methoxy)pyridazine-3-carboxamide;
6-((5-methyl-3-(6-methylpyridin-3-yl)isoxazol-4-yl)methoxy)-N-(2-methyl-4-(methylsulfonyl)butan-2-yl)pyridazine-3-carboxamide;
(S)-6-((5-methyl-3-(6-methylpyridin-3-yl)isoxazol-4-yl)methoxy)-N-(3-methyltetrahydrofuran-3-yl)pyridazine-3-carboxamide;
(R)-6-((5-methyl-3-(6-methylpyridin-3-yl)isoxazol-4-yl)methoxy)-N-(3-methyltetrahydrofuran-3-yl)pyridazine-3-carboxamide;
6-((5-methyl-3-(6-methylpyridin-3-yl)isoxazol-4-yl)methoxy)-N-(3-methyloxetan-3-yl)pyridazine-3-carboxamide;
1-(6-((5-methyl-3-(6-methylpyridin-3-yl)isoxazol-4-yl)methoxy)pyridazine-3-carbonyl)azetidine-3-carbonitrile;
N-(1-(hydroxymethyl)cyclopropyl)-6-((5-methyl-3-(6-methylpyridin-3-yl)isoxazol-4-yl)methoxy)pyridazine-3-carboxamide;
N-(4,4-difluorocyclohexyl)-5-((5-methyl-3-(6-methyl-3-pyridyl)isoxazol-4-yl)methoxy)pyrazine-2-carboxamide;
(S)-6-((5-methyl-3-(6-methylpyridin-3-yl)isoxazol-4-yl)methoxy)-N-(tetrahydrofuran-3-yl)pyridazine-3-carboxamide;
(S)—N-(1-cyanobutan-2-yl)-6-((5-methyl-3-(6-methylpyridin-3-yl)isoxazol-4-yl)methoxy)pyridazine-3-carboxamide;
(R)-5-((5-Methyl-3-(6-methylpyridin-3-yl)isoxazol-4-yl)methoxy)-N-(tetrahydrofuran-3-yl)pyrazine-2-carboxamide;
N-(2-Hydroxyethyl)-5-((5-methyl-3-(6-methylpyridin-3-yl)isoxazol-4-yl)methoxy)pyrazine-2-carboxamide;
2-(1,1-Dioxothian-4-yl)-6-[[5-methyl-3-(6-methylpyridin-3-yl)-1,2-oxazol-4-yl]methoxy]-1#H!-pyrrolo[3,4-c]pyridin-3-one;
(S)-5-((5-Methyl-3-(6-methylpyridin-3-yl)isoxazol-4-yl)methoxy)-N-(tetrahydrofuran-3-yl)pyrazine-2-carboxamide;
2-((5-methyl-3-(6-methyl-3-pyridyl)isoxazol-4-yl)methoxy]-6-tetrahydropyran-4-yl-7H-pyrrolo[3,4-b]pyridin-5-one;
N-(1,1-Dioxothiolan-3-yl)-5-((5-methyl-3-(6-methylpyridin-3-yl)-1,2-oxazol-4-yl)methoxy)pyrazine-2-carboxamide;
N-(Cyclopropylmethyl)-5-((5-methyl-3-(6-methylpyridin-3-yl)isoxazol-4-yl)methoxy)pyrazine-2-carboxamide;
2-(4,4-Difluorocyclohexyl)-6-((5-methyl-3-(6-methylpyridin-3-yl)isoxazol-4-yl)methoxy)-1H-pyrrolo[3,4-c]pyridin-3(2H)-one;
6-((5-Methyl-3-(6-methylpyridin-3-yl)isoxazol-4-yl)methoxy)-N-(4-methyltetrahydro-2H-pyran-4-yl)pyridazine-3-carboxamide;
(R)-5-((5-Methyl-3-(6-methylpyridin-3-yl)isoxazol-4-yl)methoxy)-N-(tetrahydro-2H-pyran-3-yl)pyrazine-2-carboxamide;
(R)-6-((5-methyl-3-(6-methylpyridin-3-yl)isoxazol-4-yl)methoxy)-N-(tetrahydropyran-3-yl)pyridazine-3-carboxamide;
6-((5-methyl-3-(6-methylpyridin-3-yl)isoxazol-4-yl)methoxy)-N-(2-oxaspiro[3.3]heptan-6-yl)pyridazine-3-carboxamide;
5-((5-Methyl-3-(6-methylpyridin-3-yl)isoxazol-4-yl)methoxy)-N-(2-oxaspiro[3.3]heptan-6-yl)pyrazine-2-carboxamide;
5-((5-Methyl-3-(6-methylpyridin-3-yl)isoxazol-4-yl)methoxy)-N-((cis)-4-(trifluoromethyl)cyclohexyl)pyrazine-2-carboxamide;
(S)-6-((5-methyl-3-(6-methylpyridin-3-yl)isoxazol-4-yl)methoxy)-N-(tetrahydropyran-3-yl)pyridazine-3-carboxamide;
N-((cis)-4-Hydroxy-4-methylcyclohexyl)-5-((5-methyl-3-(6-methylpyridin-3-yl)isoxazol-4-yl)methoxy)pyrazine-2-carboxamide;
N-((trans)-4-Hydroxy-4-methylcyclohexyl)-5-((5-methyl-3-(6-methylpyridin-3-yl)isoxazol-4-yl)methoxy)pyrazine-2-carboxamide;
6-((5-methyl-3-(6-methylpyridin-3-yl)isoxazol-4-yl)methoxy)-N-(4-methyltetrahydro-2H-pyran-4-yl)nicotinamide;
6-((5-Methyl-3-(6-methylpyridin-3-yl)isoxazol-4-yl)methoxy)-2-(tetrahydro-2H-thiopyran-4-yl)-1H-pyrrolo[3,4-c]pyridin-3(2H)-one;
6-((5-methyl-3-(6-methylpyridazin-3-yl)isoxazol-4-yl)methoxy)-N-tetrahydropyran-4-yl-pyridine-3-carboxamide;
N-((1S)-1-(hydroxymethyl)butyl)-6-((5-methyl-3-(6-methylpyridazin-3-yl)isoxazol-4-yl)methoxy)pyridine-3-carboxamide;
6-((5-methyl-3-(6-methylpyridin-3-yl)isoxazol-4-yl)methoxy)-N-(4-methyltetrahydrothiopyran-4-yl)pyridazine-3-carboxamide;
N-(4-methyl-1,1-dioxidotetrahydro-2H-thiopyran-4-yl)-6-((5-methyl-3-(6-methylpyridin-3-yl)isoxazol-4-yl)methoxy)pyridazine-3-carboxamide;
(2,2-dioxido-2-thia-6-azaspiro[3.3]heptan-6-yl)(6-((5-methyl-3-(6-methylpyridin-3-yl)isoxazol-4-yl)methoxy)pyridazin-3-yl)methanone;

(2,2-Dioxido-2-thia-6-azaspiro[3.3]heptan-6-yl)(5-((5-methyl-3-(6-methylpyridin-3-yl)isoxazol-4-yl)methoxy)pyrazin-2-yl)methanone;
6-((5-methyl-3-(6-methylpyridin-3-yl)isoxazol-4-yl)methoxy)-N-(1-methylcyclopentyl)pyridazine-3-carboxamide;
5-((5-Methyl-3-(6-methylpyridin-3-yl)isoxazol-4-yl)methoxy)-N-(4,4,4-trifluorobutyl)pyrazine-2-carboxamide;
N-(1-isopropylazetidin-3-yl)-6-((5-methyl-3-(6-methylpyridin-3-yl)isoxazol-4-yl)methoxy)pyridazine-3-carboxamide;
6-((5-Methyl-3-(6-methylpyridin-3-yl)isoxazol-4-yl)methoxy)-2-(2-oxaspiro[3.3]heptan-6-yl)-1H-pyrrolo[3,4-c]pyridin-3(2H)-one;
6-((5-methyl-3-(6-methylpyridin-3-yl)isoxazol-4-yl)methoxy)-N-(1-methylcyclobutyl)pyridazine-3-carboxamide;
6-((5-Ethyl-3-(6-methylpyridin-3-yl)isoxazol-4-yl)methoxy)-N-(tetrahydro-2H-pyran-4-yl)nicotinamide;
N-(1,1-Dioxidotetrahydro-2H-thiopyran-4-yl)-6-((5-ethyl-3-(6-methylpyridin-3-yl)isoxazol-4-yl)methoxy)nicotinamide;
6-((5-ethyl-3-(6-methylpyridin-3-yl)isoxazol-4-yl)methoxy)-N-(tetrahydropyran-4-yl)pyridazine-3-carboxamide;
6-((5-ethyl-3-(6-methylpyridin-3-yl)isoxazol-4-yl)methoxy)-N-(3-methyloxetan-3-yl)pyridazine-3-carboxamide;
N-cyclopropyl-6-((5-ethyl-3-(6-methylpyridin-3-yl)isoxazol-4-yl)methoxy)pyridazine-3-carboxamide;
(R)—N-(1-hydroxypentan-2-yl)-6-((5-methyl-3-(6-methylpyridin-3-yl)isoxazol-4-yl)methoxy)nicotinamide;
6-((5-(difluoromethyl)-3-(6-methyl-3-pyridyl)isoxazol-4-yl)methoxy)-N-((1S)-1-(hydroxymethyl)butyl)pyridine-3-carboxamide;
6-((5-(difluoromethyl)-3-(6-methyl-3-pyridyl)isoxazol-4-yl)methoxy)-N-tetrahydropyran-4-yl-pyridine-3-carboxamide;
N-(3R,4S)-3-hydroxytetrahydropyran-4-yl)-6-((5-methyl-3-(6-methyl-3-pyridyl)isoxazol-4-yl)methoxy)pyridine-3-carboxamide;
6-((3-(6-cyclopropyl-3-pyridyl)-5-methyl-isoxazol-4-yl)methoxy)-N-tetrahydropyran-4-yl-pyridine-3-carboxamide;
6-((3-(6-cyclopropyl-3-pyridyl)-5-methyl-isoxazol-4-yl)methoxy)-N-((1S)-1-(hydroxymethyl)butyl)pyridine-3-carboxamide;
6-((3-(6-cyclopropyl-3-pyridyl)-5-methyl-isoxazol-4-yl)methoxy)-N-(1,1-dioxothian-4-yl)pyridine-3-carboxamide;
N-((1R,2S)-3,3-difluoro-2-hydroxycyclohexyl)-6-((5-methyl-3-(6-methylpyridin-3-yl)isoxazol-4-yl)methoxy)nicotinamide;
N-((1R,2R)-2-hydroxycyclohexyl)-6-((5-methyl-3-(6-methylpyridin-3-yl)isoxazol-4-yl)methoxy)nicotinamide;
N-((1S,2R)-3,3-difluoro-2-hydroxycyclohexyl)-6-((5-methyl-3-(6-methylpyridin-3-yl)isoxazol-4-yl)methoxy)nicotinamide;
N-(3S,4R)-3-hydroxytetrahydro-2H-pyran-4-yl)-6-((5-methyl-3-(6-methylpyridin-3-yl)isoxazol-4-yl)methoxy)nicotinamide;
N-((1S,2S)-2-hydroxycyclohexyl)-6-((5-methyl-3-(6-methylpyridin-3-yl)isoxazol-4-yl)methoxy)nicotinamide;
2-fluoro-N-methyl-6-((5-methyl-3-(6-methylpyridin-3-yl)isoxazol-4-yl)methoxy)nicotinamide;
6-((3-(6-methoxypyridin-3-yl)-5-methylisoxazol-4-yl)methoxy)-N-(tetrahydro-2H-pyran-4-yl)nicotinamide;
N-isopropyl-6-((3-(6-methoxypyridin-3-yl)-5-methylisoxazol-4-yl)methoxy)nicotinamide;
(S)—N-(1-hydroxypentan-2-yl)-6-((3-(6-methoxypyridin-3-yl)-5-methylisoxazol-4-yl)methoxy)nicotinamide;
(1,1-dioxidothiomorpholino)(6-((3-(6-methoxypyridin-3-yl)-5-methylisoxazol-4-yl)methoxy)pyridin-3-yl)methanone;
(S)-6-((3-(6-(dimethylamino)pyridin-3-yl)-5-methyl-isoxazol-4-yl)methoxy)-N-(1-hydroxypentan-2-yl)nicotinamide;
4-methoxy-6-((5-methyl-3-(6-methylpyridin-3-yl)isoxazol-4-yl)methoxy)-N-(tetrahydro-2H-pyran-4-yl)nicotinamide;
6-((3-(5-fluoro-6-methyl-3-pyridyl)-5-methyl-isoxazol-4-yl)methoxy)-N-tetrahydropyran-4-yl-pyridine-3-carboxamide;
6((3-(5-fluoro-6-methyl-3-pyridyl)-5-methyl-isoxazol-4-yl)methoxy)-N-isopropyl-pyridine-3-carboxamide;
6-((3-(5-fluoro-6-methyl-3-pyridyl)-5-methyl-isoxazol-4-yl)methoxy)-N-((1S)-1-(hydroxymethyl)butyl)pyridine-3-carboxamide;
N-((1r,4r)-4-hydroxy-4-methylcyclohexyl)-6-((5-methyl-3-(6-methylpyridin-3-yl)isoxazol-4-yl)methoxy)pyridazine-3-carboxamide;
N-(1,3-dihydroxy-2-methylpropan-2-yl)-6-((5-methyl-3-(6-methylpyridin-3-yl)isoxazol-4-yl)methoxy)pyridazine-3-carboxamide;
N-((1s,4s)-4-hydroxy-4-methylcyclohexyl)-6-((5-methyl-3-(6-methylpyridin-3-yl)isoxazol-4-yl)methoxy)pyridazine-3-carboxamide;
N-((1R,3S)-3-hydroxy-3-(trifluoromethyl)cyclopentyl)-6-((5-methyl-3-(6-methylpyridin-3-yl)isoxazol-4-yl)methoxy)pyridazine-3-carboxamide;
N-((1S,3R)-3-hydroxy-3-(trifluoromethyl)cyclopentyl)-6-((5-methyl-3-(6-methylpyridin-3-yl)isoxazol-4-yl)methoxy)pyridazine-3-carboxamide;
(1S,4S)-2-oxa-5-azabicyclo[2.2.1]heptan-5-yl(6-((5-methyl-3-(6-methylpyridin-3-yl)isoxazol-4-yl)methoxy)pyridazin-3-yl)methanone;
N-((1RS,3RS)-3-hydroxycyclopentyl)-6-((5-methyl-3-(6-methylpyridin-3-yl)isoxazol-4-yl)methoxy)pyridazine-3-carboxamide;
trans-N-(4-hydroxycyclohexyl)-6-((5-methyl-3-(6-methylpyridin-3-yl)isoxazol-4-yl)methoxy)pyridazine-3-carboxamide;
trans-N-(4-methoxycyclohexyl)-6-((5-methyl-3-(6-methylpyridin-3-yl)isoxazol-4-yl)methoxy)pyridazine-3-carboxamide;
(6,6-difluoro-2-azaspiro[3.3]heptan-2-yl)(6-((5-methyl-3-(6-methylpyridin-3-yl)isoxazol-4-yl)methoxy)pyridazin-3-yl)methanone;
N-(3-hydroxycyclohexyl)-6-((5-methyl-3-(6-methylpyridin-3-yl)isoxazol-4-yl)methoxy)pyridazine-3-carboxamide;
3-oxa-6-azabicyclo[3.1.1]heptan-6-yl(6-((5-methyl-3-(6-methylpyridin-3-yl)isoxazol-4-yl)methoxy)pyridazin-3-yl)methanone;
cis-N-(4-methoxycyclohexyl)-6-((5-methyl-3-(6-methylpyridin-3-yl)isoxazol-4-yl)methoxy)pyridazine-3-carboxamide;

6-((3-(6-chloropyridin-3-yl)-5-methylisoxazol-4-yl)methoxy)-N-(tetrahydro-2H-pyran-4-yl)pyridazine-3-carboxamide;

(S)-6-((3-(6-chloropyridin-3-yl)-5-methylisoxazol-4-yl)methoxy)-N-(tetrahydrofuran-3-yl)pyridazine-3-carboxamide;

6-((3-(6-chloropyridin-3-yl)-5-methylisoxazol-4-yl)methoxy)-N-(3-methyloxetan-3-yl)pyridazine-3-carboxamide;

6-((3-(6-chloropyridin-3-yl)-5-methylisoxazol-4-yl)methoxy)-N-(2-oxaspiro[3.3]heptan-6-yl)pyridazine-3-carboxamide;

trans-N-(3-methoxycyclobutyl)-6-((5-methyl-3-(6-methyl-3-pyridyl)isoxazol-4-yl)methoxy)pyridazine-3-carboxamide;

cis-N-(3-methoxycyclobutyl)-6-((5-methyl-3-(6-methyl-3-pyridyl)isoxazol-4-yl)methoxy)pyridazine-3-carboxamide;

6-((5-cyclopropyl-3-(6-methylpyridazin-3-yl)isoxazol-4-yl)methoxy)-N-(tetrahydro-2H-pyran-4-yl)pyridazine-3-carboxamide;

trans-N-((1RS,3RS)-3-methoxycyclopentyl)-6-((5-methyl-3-(6-methylpyridin-3-yl)isoxazol-4-yl)methoxy)pyridazine-3-carboxamide;

N-(6,6-difluorospiro[3.3]heptan-2-yl)-6-((5-methyl-3-(6-methylpyridin-3-yl)isoxazol-4-yl)methoxy)pyridazine-3-carboxamide;

6-((5-(fluoromethyl)-3-(6-methylpyridin-3-yl)isoxazol-4-yl)methoxy)-N-(tetrahydropyran-4-yl)pyridazine-3-carboxamide;

cis-N-3-((2,2-difluoroethoxy)cyclobutyl)-6-((5-methyl-3-(6-methylpyridin-3-yl)isoxazol-4-yl)methoxy)pyridazine-3-carboxamide;

trans-N-3-((2,2-difluoroethoxy)cyclobutyl)-6-((5-methyl-3-(6-methylpyridin-3-yl)isoxazol-4-yl)methoxy)pyridazine-3-carboxamide;

cis-N-(3-ethoxycyclobutyl)-6-((5-methyl-3-(6-methylpyridin-3-yl)isoxazol-4-yl)methoxy)pyridazine-3-carboxamide;

trans-N-(3-ethoxycyclobutyl)-6-((5-methyl-3-(6-methylpyridin-3-yl)isoxazol-4-yl)methoxy)pyridazine-3-carboxamide;

cis-N-(3-(difluoromethoxy)cyclobutyl)-6-((5-methyl-3-(6-methylpyridin-3-yl)isoxazol-4-yl)methoxy)pyridazine-3-carboxamide;

trans-N-(3-(difluoromethoxy)cyclobutyl)-6-((5-methyl-3-(6-methylpyridin-3-yl)isoxazol-4-yl)methoxy)pyridazine-3-carboxamide;

trans-N-(3-cyclopropoxycyclobutyl)-6-((5-methyl-3-(6-methylpyridin-3-yl)isoxazol-4-yl)methoxy)pyridazine-3-carboxamide;

cis-N-(3-cyclopropoxycyclobutyl)-6-((5-methyl-3-(6-methylpyridin-3-yl)isoxazol-4-yl)methoxy)pyridazine-3-carboxamide;

6-((3-(6-chloropyridin-3-yl)-5-cyclopropylisoxazol-4-yl)methoxy)-N-(3-methyloxetan-3-yl)pyridazine-3-carboxamide;

6-((3-(6-chloropyridin-3-yl)-5-cyclopropylisoxazol-4-yl)methoxy)-N-(2-oxaspiro[3.3]heptan-6-yl)pyridazine-3-carboxamide;

(S)-6-((3-(6-chloropyridin-3-yl)-5-cyclopropylisoxazol-4-yl)methoxy)-N-(tetrahydrofuran-3-yl)pyridazine-3-carboxamide;

6-((5-cyclopropyl-3-(6-methylpyridin-3-yl)isoxazol-4-yl)methoxy)-N-(3-methyloxetan-3-yl)pyridazine-3-carboxamide;

6-((5-cyclopropyl-3-(6-methylpyridin-3-yl)isoxazol-4-yl)methoxy)-N-(2-oxaspiro[3.3]heptan-6-yl)pyridazine-3-carboxamide;

(S)-6-((5-cyclopropyl-3-(6-methylpyridin-3-yl)isoxazol-4-yl)methoxy)-N-(tetrahydrofuran-3-yl)pyridazine-3-carboxamide;

6-((5-cyclopropyl-3-(6-methylpyridin-3-yl)isoxazol-4-yl)methoxy)-N-(tetrahydropyran-4-yl)pyridazine-3-carboxamide;

6-((5-(fluoromethyl)-3-(6-methylpyridin-3-yl)isoxazol-4-yl)methoxy)-N-(1-(trifluoromethyl)cyclopropyl)pyridazine-3-carboxamide;

6-((5-methyl-3-(6-(trifluoromethyl)pyridin-3-yl)isoxazol-4-yl)methoxy)-N-(tetrahydropyran-4-yl)pyridazine-3-carboxamide;

N-((2S)-7-oxabicyclo[2.2.1]heptan-2-yl)-6-((5-methyl-3-(6-methylpyridin-3-yl)isoxazol-4-yl)methoxy)pyridazine-3-carboxamide;

(RS)-6-((5-methyl-3-(6-methylpyridin-3-yl)isoxazol-4-yl)methoxy)-N-(oxepan-4-yl)pyridazine-3-carboxamide;

6-((5-methyl-3-(6-methyl-3-pyridyl)isoxazol-4-yl)methoxy)-N-((1R,3S,4R)-7-oxabicyclo[2.2.1]heptan-3-yl)pyridazine-3-carboxamide;

N-((2R)-7-oxabicyclo[2.2.1]heptan-2-yl)-6-((5-methyl-3-(6-methylpyridin-3-yl)isoxazol-4-yl)methoxy)pyridazine-3-carboxamide;

N-((1R,3R)-3-ethoxycyclopentyl)-6-((5-methyl-3-(6-methylpyridin-3-yl)isoxazol-4-yl)methoxy)pyridazine-3-carboxamide;

N-((1R,3R)-3-(2,2-difluoroethoxy)cyclopentyl)-6-((5-methyl-3-(6-methylpyridin-3-yl)isoxazol-4-yl)methoxy)pyridazine-3-carboxamide;

6-((5-(fluoromethyl)-3-(6-methylpyridazin-3-yl)isoxazol-4-yl)methoxy)-N-(tetrahydro-2H-pyran-4-yl)pyridazine-3-carboxamide;

6-((5-methyl-3-(6-methylpyridazin-3-yl)isoxazol-4-yl)methoxy)-N-(tetrahydro-2H-pyran-4-yl)pyridazine-3-carboxamide;

N-[4-(2,2-difluoroethoxy)cyclohexyl]-6-[[5-methyl-3-(6-methylpyridin-3-yl)-1,2-oxazol-4-yl]methoxy]pyridazine-3-carboxamide;

N-(4-ethoxycyclohexyl)-6-[[5-methyl-3-(6-methylpyridin-3-yl)-1,2-oxazol-4-yl]methoxy]pyridazine-3-carboxamide;

or a stereoisomer or pharmaceutically acceptable salts thereof.

2. A compound selected from

N-((1S)-1-(hydroxymethyl)butyl)-6-((5-methyl-3-(6-methyl-3-pyridyl)isoxazol-4-yl)methoxy)pyridine-3-carboxamide;

6-((5-methyl-3-(6-methylpyridin-3-yl)isoxazol-4-yl)methoxy)-N-(tetrahydro-2H-pyran-4-yl)pyridazine-3-carboxamide;

N-cyclopropyl-6-((5-methyl-3-(6-methylpyridin-3-yl)isoxazol-4-yl)methoxy)pyridazine-3-carboxamide;

(RS)-6-((5-methyl-3-(6-methylpyridin-3-yl)isoxazol-4-yl)methoxy)-N-(1,1,1-trifluoropropan-2-yl)pyridazine-3-carboxamide;

N-isopropyl-6-((5-methyl-3-(6-methylpyridin-3-yl)isoxazol-4-yl)methoxy)pyridazine-3-carboxamide;

N-tert-butyl-6-((5-methyl-3-(6-methylpyridin-3-yl)isoxazol-4-yl)methoxy)pyridazine-3-carboxamide;

N-(1-(methoxymethyl)cyclopropyl)-6-((5-methyl-3-(6-methylpyridin-3-yl)isoxazol-4-yl)methoxy)pyridazine-3-carboxamide;

6-((5-methyl-3-(6-methylpyridin-3-yl)isoxazol-4-yl)
methoxy)-N-(1-(trifluoromethyl)cyclopropyl)
pyridazine-3-carboxamide;

5-methyl-6-((5-methyl-3-(6-methylpyridin-3-yl)isoxazol-4-yl)methoxy)-N-(tetrahydropyran-4-yl)pyridazine-3-carboxamide;

6-((5-methyl-3-(6-methylpyridin-3-yl)isoxazol-4-yl)
methoxy)-N-(1-methylcyclopropyl)pyridazine-3-carboxamide;

(S)-6-((5-methyl-3-(6-methylpyridin-3-yl)isoxazol-4-yl)
methoxy)-N-(3-methyltetrahydrofuran-3-yl)
pyridazine-3-carboxamide;

(R)-6-((5-methyl-3-(6-methylpyridin-3-yl)isoxazol-4-yl)
methoxy)-N-(3-methyltetrahydrofuran-3-yl)
pyridazine-3-carboxamide;

6-((5-methyl-3-(6-methylpyridin-3-yl)isoxazol-4-yl)
methoxy)-N-(3-methyloxetan-3-yl)pyridazine-3-carboxamide;

(S)-6-((5-methyl-3-(6-methylpyridin-3-yl)isoxazol-4-yl)
methoxy)-N-(tetrahydrofuran-3-yl)pyridazine-3-carboxamide;

6-((5-Methyl-3-(6-methylpyridin-3-yl)isoxazol-4-yl)
methoxy)-N-(4-methyltetrahydro-2H-pyran-4-yl)
pyridazine-3-carboxamide;

(R)-6-((5-methyl-3-(6-methylpyridin-3-yl)isoxazol-4-yl)
methoxy)-N-(tetrahydropyran-3-yl)pyridazine-3-carboxamide;

6-((5-methyl-3-(6-methylpyridin-3-yl)isoxazol-4-yl)
methoxy)-N-(2-oxaspiro[3.3]heptan-6-yl)pyridazine-3-carboxamide;

6-((5-methyl-3-(6-methylpyridin-3-yl)isoxazol-4-yl)
methoxy)-N-(1-methylcyclobutyl)pyridazine-3-carboxamide;

6-((3-(5-fluoro-6-methyl-3-pyridyl)-5-methyl-isoxazol-4-yl)methoxy)-N-((1S)-1-(hydroxymethyl)butyl)pyridine-3-carboxamide;

6-((5-cyclopropyl-3-(6-methylpyridazin-3-yl)isoxazol-4-yl)methoxy)-N-(tetrahydro-2H-pyran-4-yl)pyridazine-3-carboxamide;

6-((5-(fluoromethyl)-3-(6-methylpyridin-3-yl)isoxazol-4-yl)methoxy)-N-(tetrahydropyran-4-yl)pyridazine-3-carboxamide;

6-((5-cyclopropyl-3-(6-methylpyridin-3-yl)isoxazol-4-yl)
methoxy)-N-(3-methyloxetan-3-yl)pyridazine-3-carboxamide;

(RS)-6-((5-methyl-3-(6-methylpyridin-3-yl)isoxazol-4-yl)methoxy)-N-(oxepan-4-yl)pyridazine-3-carboxamide;

6-((5-(fluoromethyl)-3-(6-methylpyridazin-3-yl)isoxazol-4-yl)methoxy)-N-(tetrahydro-2H-pyran-4-yl)
pyridazine-3-carboxamide;

6-((5-methyl-3-(6-methylpyridazin-3-yl)isoxazol-4-yl)
methoxy)-N-(tetrahydro-2H-pyran-4-yl)pyridazine-3-carboxamide;

or a stereoisomer or pharmaceutically acceptable salts thereof.

3. A pharmaceutical composition comprising a compound according to claim 1 and a therapeutically inert carrier.

4. A compound selected from:

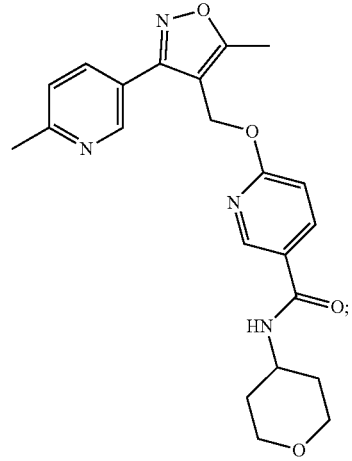

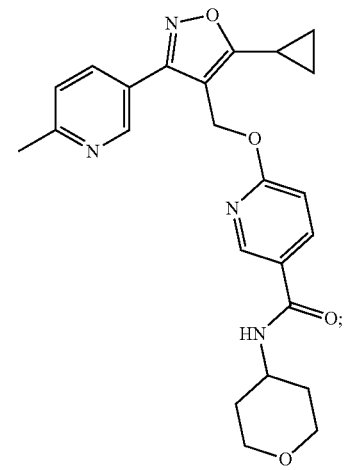

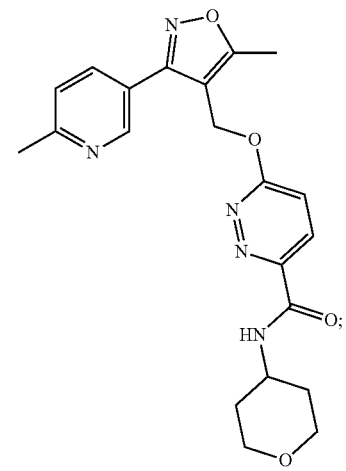

199
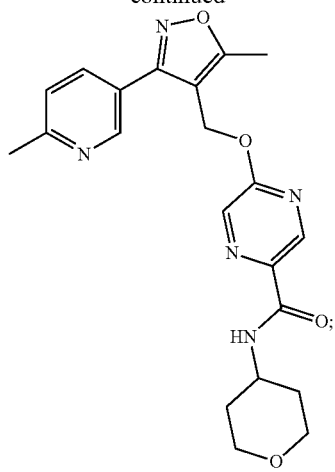
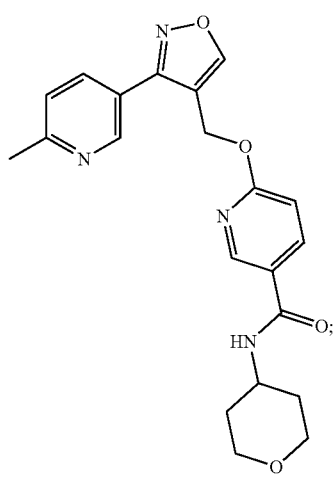
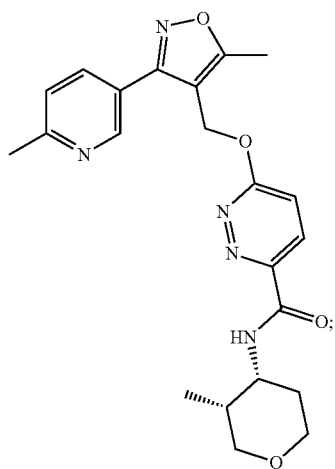
200
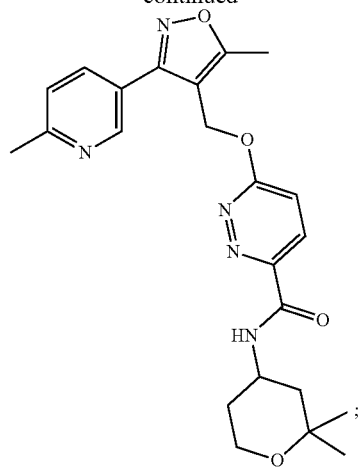
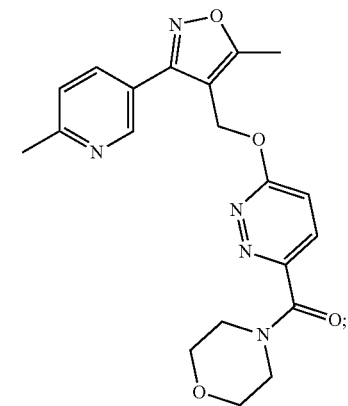
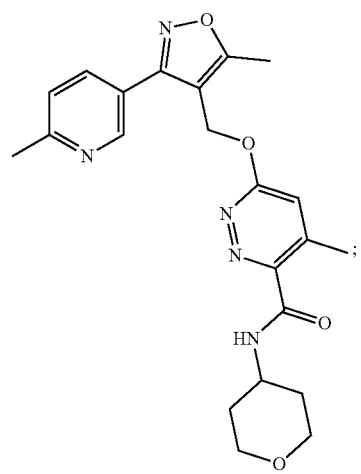

201
-continued
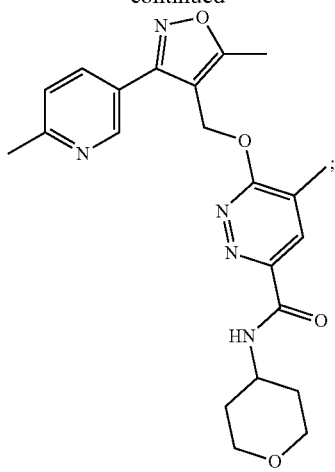
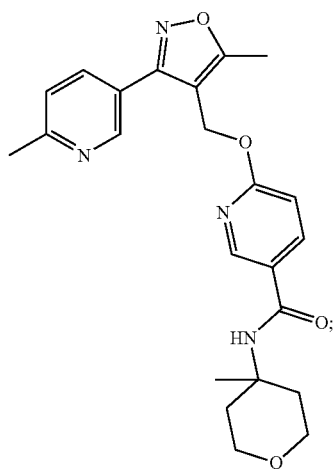
202
-continued
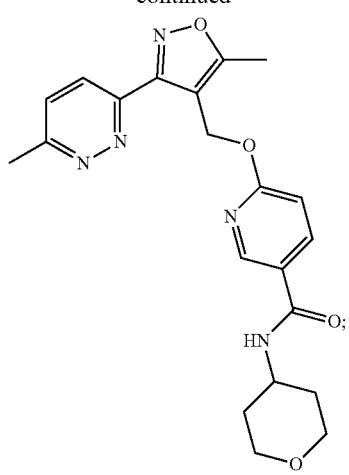

203
-continued
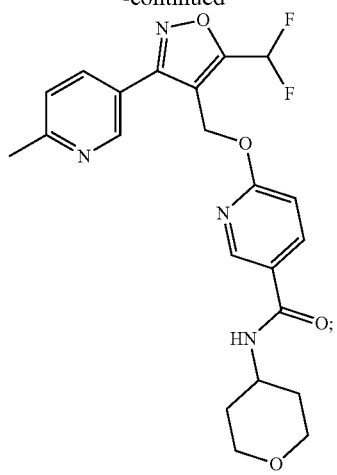
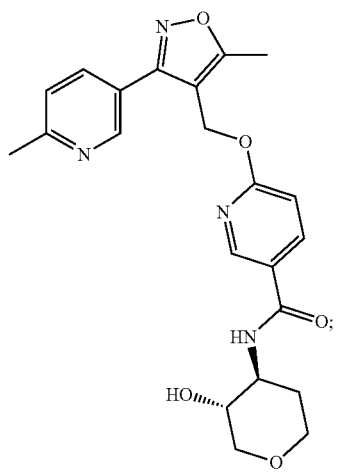
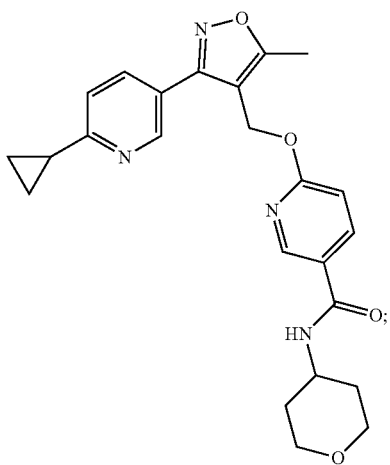
204
-continued
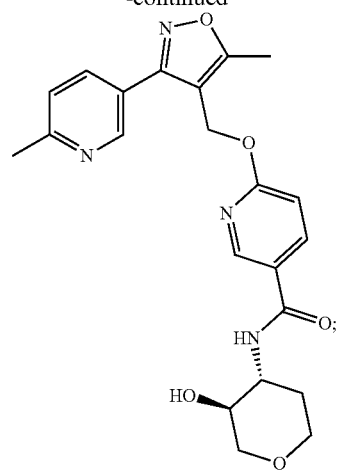
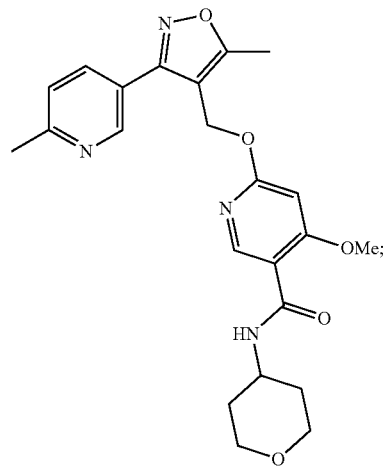
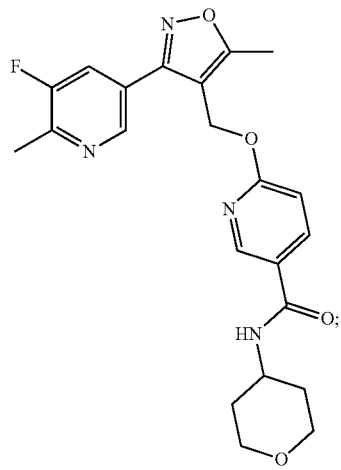

205
-continued
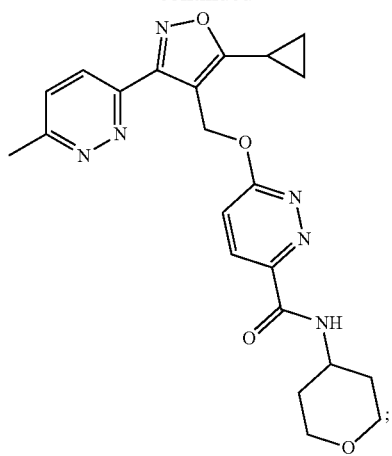
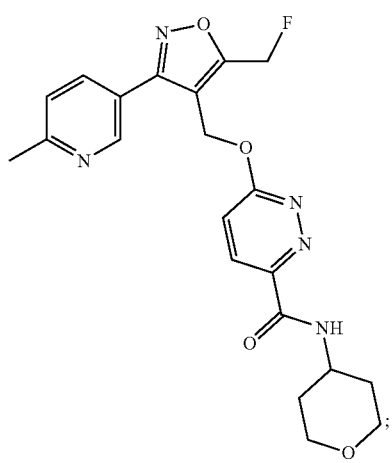
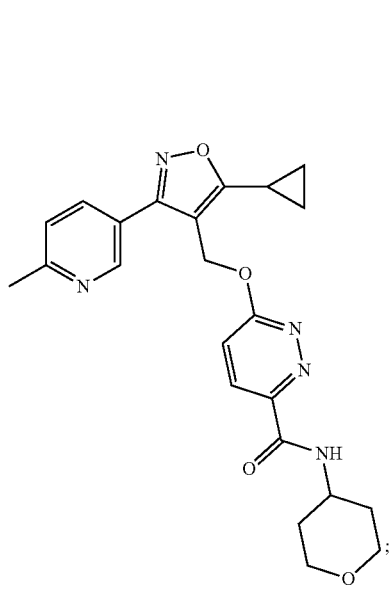
206
-continued
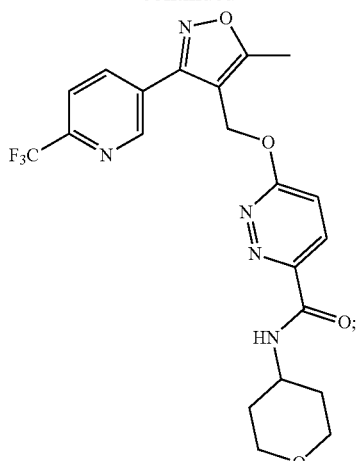
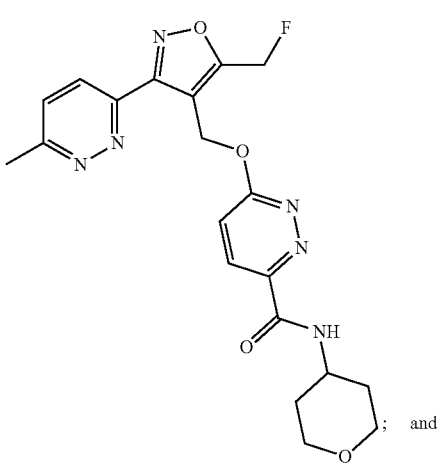; and
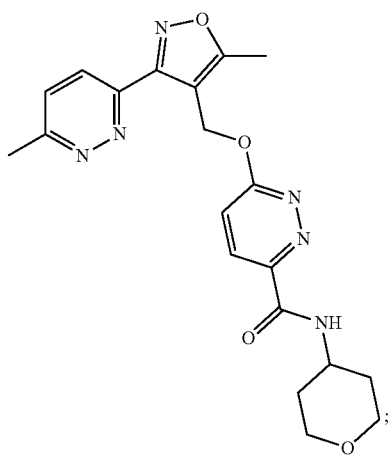;
or a stereoisomer or a pharmaceutically acceptable salt thereof.

5. The compound of claim 4, selected from:
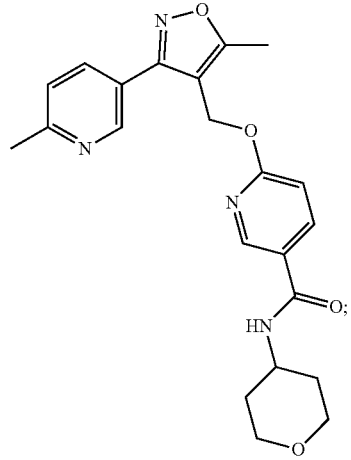
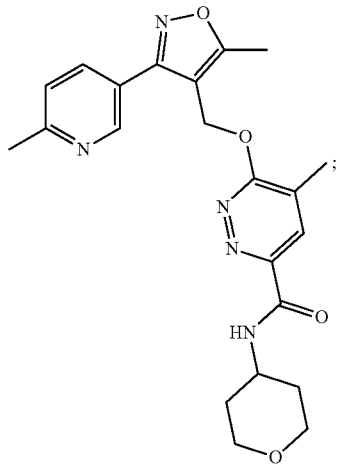
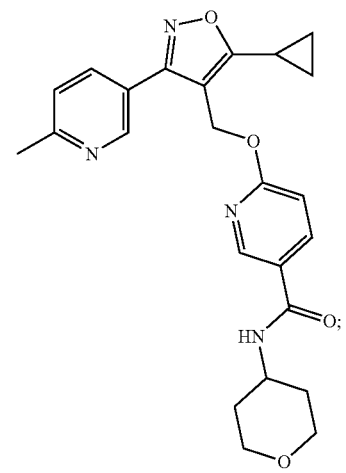
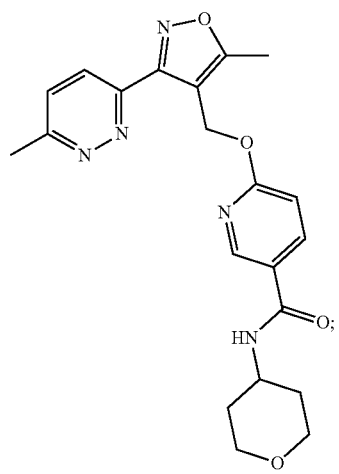
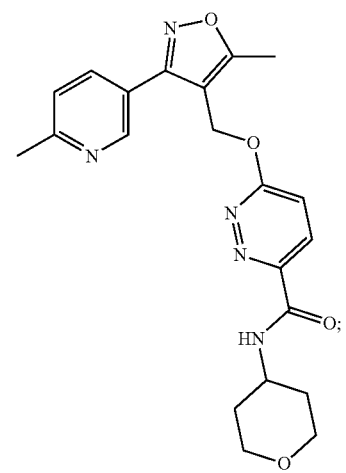
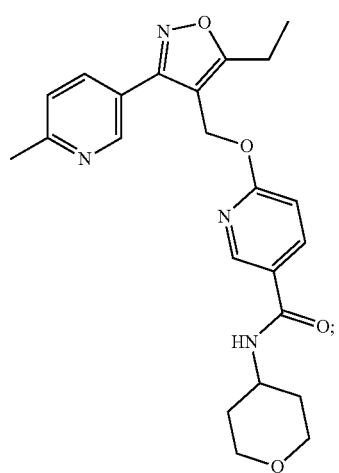

209
-continued
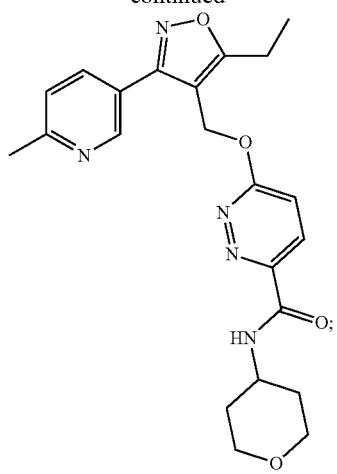
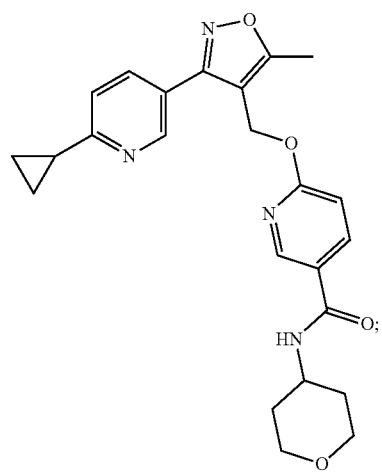
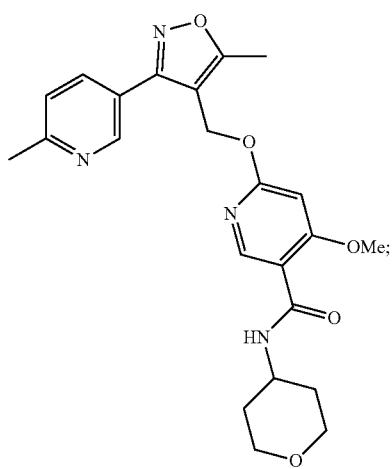
210
-continued
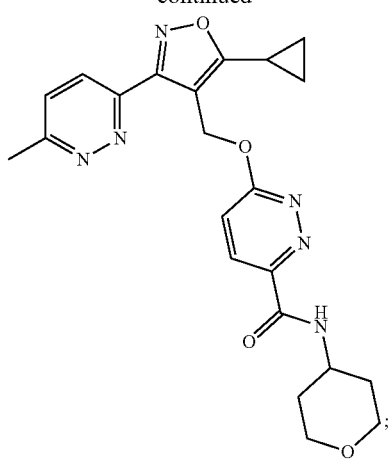
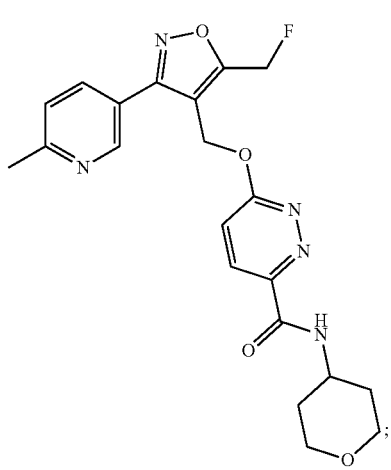
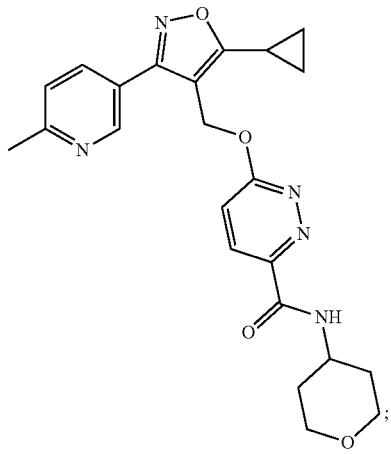

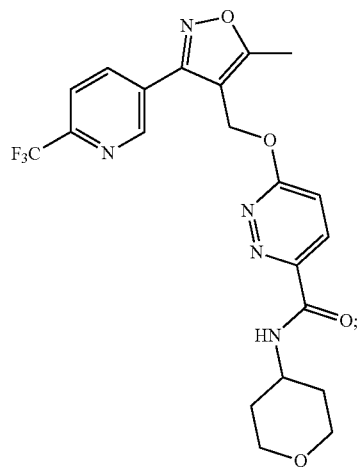
6. The compound of claim 5, selected from:
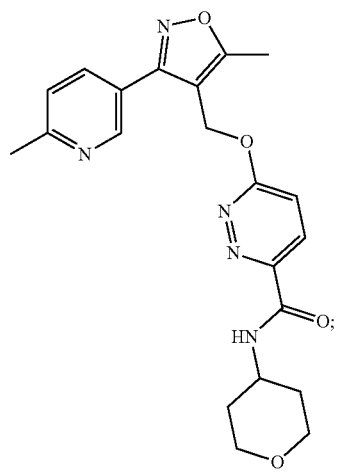
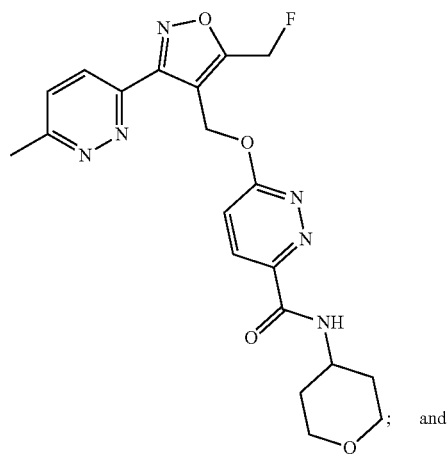
; and
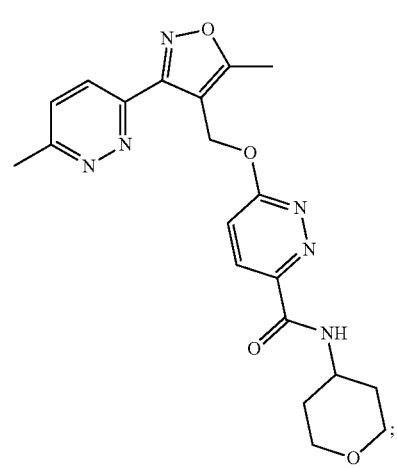
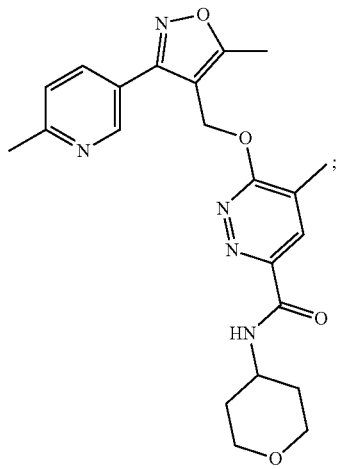
;
or a pharmaceutically acceptable salt thereof.

or a pharmaceutically acceptable salt thereof.

7. The compound or a pharmaceutically acceptable salt thereof.

8. The compound or a pharmaceutically acceptable salt thereof.

9. The compound
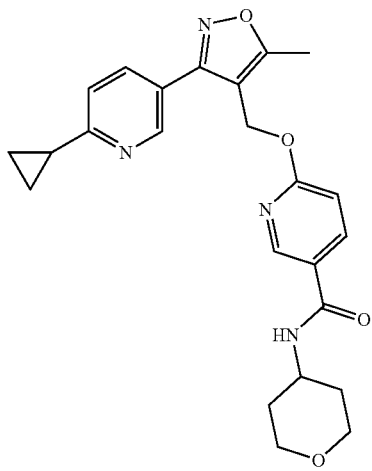 [SMILES: Cc1onc(-c2ccc(C3CC3)nc2)c1COc1ccc(C(=O)NC2CCOCC2)cn1]
or a pharmaceutically acceptable salt thereof.
10. The compound
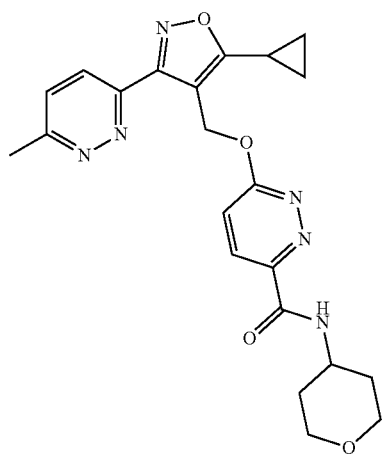 [SMILES: Cc1ccc(-c2noc(C3CC3)c2COc2ccc(C(=O)NC3CCOCC3)nn2)nn1]
or a pharmaceutically acceptable salt thereof.
11. The compound
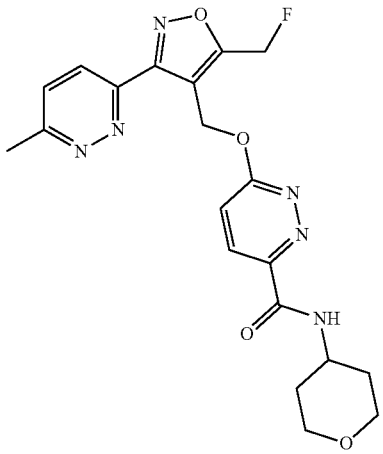 [SMILES: Cc1ccc(-c2noc(CF)c2COc2ccc(C(=O)NC3CCOCC3)nn2)nn1]
or a pharmaceutically acceptable salt thereof.
12. The compound
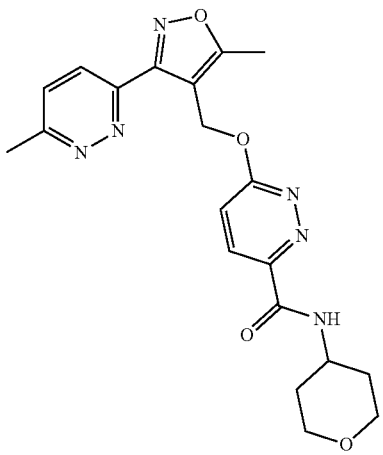 [SMILES: Cc1ccc(-c2noc(C)c2COc2ccc(C(=O)NC3CCOCC3)nn2)nn1]
or a pharmaceutically acceptable salt thereof.
* * * * *